(12) United States Patent
Liu et al.

(10) Patent No.: US 9,617,252 B2
(45) Date of Patent: *Apr. 11, 2017

(54) PROCESSES FOR PREPARING DIHYDROPYRIMIDINE DERIVATIVES AND INTERMEDIATES THEREOF

(71) Applicant: SUNSHINE LAKE PHARMA CO., LTD., Dongguan, Guangdong (CN)

(72) Inventors: Xinchang Liu, Dongguan (CN); Qingyun Ren, Dongguan (CN); Zhifu Zou, Dongguan (CN); Jinsheng Liang, Dongguan (CN); Linjin Tu, Dongguan (CN); Siegfried Goldmann, Wuppertal (DE); Yingjun Zhang, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/023,676

(22) PCT Filed: Nov. 27, 2014

(86) PCT No.: PCT/CN2014/092400
§ 371 (c)(1),
(2) Date: Mar. 21, 2016

(87) PCT Pub. No.: WO2015/078391
PCT Pub. Date: Jun. 4, 2015

(65) Prior Publication Data
US 2016/0264562 A1    Sep. 15, 2016

(30) Foreign Application Priority Data

Nov. 27, 2013 (CN) .......................... 2013 1 0636920
Mar. 27, 2014 (CN) .......................... 2014 1 0121009

(51) Int. Cl.
C07D 417/04    (2006.01)
C07D 417/14    (2006.01)

(52) U.S. Cl.
CPC ......... *C07D 417/04* (2013.01); *C07D 417/14* (2013.01)

(58) Field of Classification Search
CPC ................................................... C07D 417/04
See application file for complete search history.

(56) References Cited

U.S. PATENT DOCUMENTS

| 5,250,531 A | 10/1993 | Cooper |
| 6,057,332 A | 5/2000 | Michne et al. |
| 6,218,538 B1 | 4/2001 | Downs et al. |
| 6,436,943 B1 | 8/2002 | Stoltefuss et al. |
| 6,503,913 B1 | 1/2003 | Goldmann et al. |
| 6,696,451 B1 | 2/2004 | Stoltefuss et al. |
| 7,074,784 B2 | 7/2006 | Goldmann et al. |
| 7,157,461 B2 | 1/2007 | Murugesan et al. |
| 8,106,196 B2 | 1/2012 | Li et al. |
| 8,168,642 B2 | 5/2012 | Li et al. |

(Continued)

FOREIGN PATENT DOCUMENTS

| CN | 101041658 A1 | 9/2007 |
| CN | 101054331 A | 10/2007 |
| CN | 101468986 A | 7/2009 |
| CN | 101468987 A | 7/2009 |
| CN | 101744823 B | 6/2010 |

(Continued)

OTHER PUBLICATIONS

ISR.
Written Opinion.

(Continued)

*Primary Examiner* — Rebecca Anderson
*Assistant Examiner* — Karen Cheng
(74) *Attorney, Agent, or Firm* — Kam W. Law; Squire Patton Boggs (US) LLP

(57) ABSTRACT

The present invention refers to processes for preparing a dihydropyrimidine compound having Formula (I), or a tautomer thereof having Formula (1a), as well as a intermediate thereof. The process of the invention has simple operation, high optical purity of product, high yield and convenient work-up, which is suitable for industrial production.

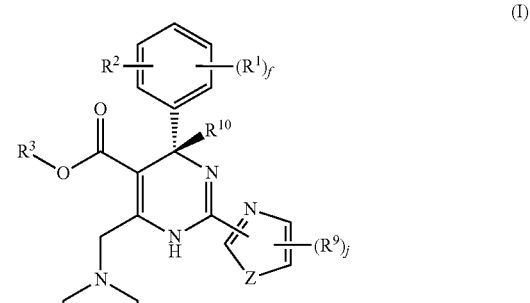

(I)

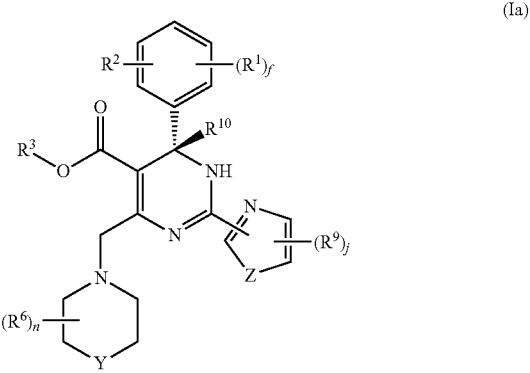

(Ia)

27 Claims, No Drawings

(56) References Cited

U.S. PATENT DOCUMENTS

| | | |
|---|---|---|
| 8,329,902 B2 | 12/2012 | Li et al. |
| RE44,987 E | 7/2014 | Goldmann et al. |
| 8,802,669 B2 | 8/2014 | Li et al. |
| 9,233,933 B2 | 1/2016 | Vandyck et al. |
| 9,233,978 B2 | 1/2016 | Guo et al. |
| 2013/0267517 A1 | 10/2013 | Guo et al. |
| 2014/0343032 A1 | 11/2014 | Guo et al. |
| 2015/0031687 A1 | 1/2015 | Guo et al. |
| 2015/0152096 A1 | 6/2015 | Zhang et al. |
| 2015/0218182 A1 | 8/2015 | Zlotnick et al. |
| 2015/0292045 A1 | 10/2015 | Levrero et al. |

FOREIGN PATENT DOCUMENTS

| | | |
|---|---|---|
| CN | 103664897 A | 3/2014 |
| CN | 103664899 A | 3/2014 |
| CN | 103664925 A | 3/2014 |
| CN | 104650069 A | 5/2015 |
| CN | 104650070 A | 5/2015 |
| EP | 0202654 A2 | 11/1986 |
| WO | WO0058302 A1 | 10/2000 |
| WO | WO0168639 A1 | 9/2001 |
| WO | WO0168641 A1 | 9/2001 |
| WO | WO0168642 A1 | 9/2001 |
| WO | WO0168647 A1 | 9/2001 |
| WO | WO2008154818 A1 | 12/2008 |
| WO | WO2008154819 A1 | 12/2008 |
| WO | WO2008154820 A1 | 12/2008 |
| WO | WO2010069147 A1 | 6/2010 |
| WO | WO2013019967 A1 | 2/2013 |
| WO | WO 2014153459 A2 | 9/2014 |
| WO | WO2015074546 A1 | 5/2015 |
| WO | WO2015144093 A1 | 10/2015 |
| WO | WO2015180631 A1 | 12/2015 |

OTHER PUBLICATIONS

Charushin, Valery N.; Mokrushina, Galina A.; Petrova, Galina M.; Alexandrov, Grigori G.; Chupakhin, Oleg N.,One-step route to fluorinated furo[2,3,-b]quinoxalines, Mendeleev Commun 1998, 8(4), 133-134.

R Mannhold et.al, "Calcium- and calmodulin-antagonism of elnadipine derivatives: comparative SAR", Eur. J. Med. Chem., Dec. 31, 1992, pp. 229-235, vol. 27.

Masayuki Sato et.al, "A Novel Synthetic Method for Tetronic Acids from 1,3-Dioxin-4-ones via Intra- or Intermolecular Ketene Trapping", Chem. Pharm. Bull., Jan. 31, 1990, pp. 94-98, vol. 38, No. 1.

PROCESSES FOR PREPARING DIHYDROPYRIMIDINE DERIVATIVES AND INTERMEDIATES THEREOF

CROSS-REFERENCE TO RELATED APPLICATIONS

This is a U.S. national stage application of the International Patent Application No. PCT/CN2014/092400, filed Nov. 27, 2014, which claims priorities to Chinese Patent Application No. 201310636920.8, filed Nov. 27, 2013, and No. 201410121009.8, filed Mar. 27, 2014, all of which are incorporated herein by reference in their entirety.

FIELD

The invention refers to a chemical medicine field. Specifically, the invention relates to processes for preparation of optically pure dihydropyrimidine derivatives and optically pure dihydropyrimidine intermediates thereof.

BACKGROUND

The hepatitis B virus belongs to the family of hepadnaviridae. It can cause acute and/or persistent or progressive chronic diseases. Many other clinical manifestations in the pathological morphology can also be caused by HBV—in particular chronic hepatitis, cirrhosis and hepatocellular carcinoma. Additionally, coinfection with hepatitis D virus may have adverse effects on the progress of the disease.

The conventional medicaments approved to be used for treating chronic hepatitis are interferon and lamivudine. However, the interferon has just moderate activity but has an adverse side reaction. Although lamivudine has good activity, its resistance develops rapidly during the treatment and relapse effects often appear after the treatment has stopped. The IC50 value of lamivudine (3-TC) is 300 nM (*Science*, 2003, 299, 893-896).

PCT Publication No. WO2008154817 discloses a series of compounds used for preventing, managing, treating or lessening a viral disease in a patient, particularly HBV infection or a related disease. The patent also provides the processes for preparation of specific compounds, such as 4-(R,S)-ethyl 4-(2-bromo-4-fluorophenyl)-6-(morpholinomethyl)-2-(thiazol-2-yl)-1,4-dihydropyrimidine-5-carboxylate as shown in Formula (Ib).

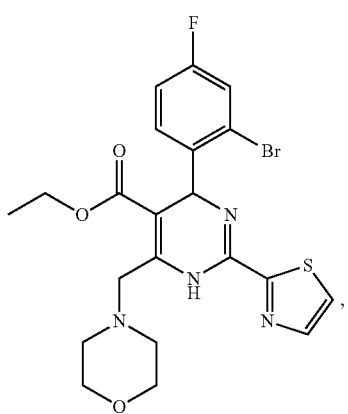

(Ib)

PCT Publication No. WO2008009210 discloses a series of optically pure compounds, which used for preventing, managing, treating or lessening an acute or chronic viral disease in a patient, particularly an acute or chronic HBV disease. The patent also provides the processes for preparation of specific compounds, such as (R)-ethyl 4-(2-chloro-4-fluorophenyl)-6-methyl-2-(thiazol-2-yl)-1,4-dihydropyrimidine-5-carboxylate.

Dihydropyrimidine derivatives can be prepared by several methods described in prior arts, such as patents WO1999054329, WO2008154817, WO2001068641, WO2010069147, and so on. But the process of preparation of optically pure dihydropyrimidine compounds described herein has not been yet be published.

SUMMARY

The invention refers to a process for preparing a dihydropyrimidine compound having Formula (I), or a tautomer thereof having Formula (Ia),

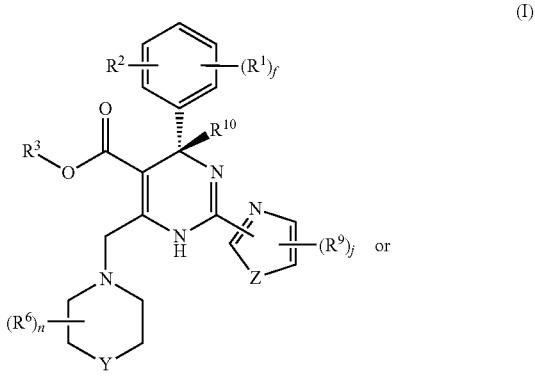

(I)

or

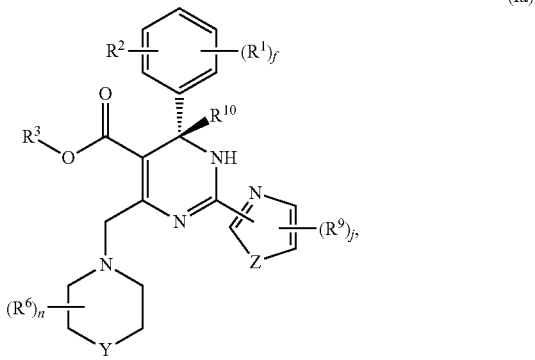

(Ia)

wherein each $R^1$ and $R^2$ is independently F, Cl, or Br; $R^3$ is $C_{1-4}$ alkyl;

Z is —O—, —S—, —S(=O)$_t$, or —N(R$^4$)—;

Y is —O—, —S—, —S(=O)$_t$—, —(CH$_2$)$_q$—, or —N(R$^5$)—;

each t and q is independently 0, 1, or 2;

each of $R^4$ and $R^5$ is independently H or $C_{1-4}$ alkyl;

each $R^6$ is independently H, deuterium, halo, $C_{1-4}$ alkyl, $C_{1-4}$ haloalkyl, amino, $C_{1-4}$ alkylamino, $C_{1-4}$ alkoxy, nitro, triazolyl, tetrazyl, —(CR$^7$R$^{7a}$)$_m$—OH, —S(=O)$_q$OR$^{8a}$, —(CR$^7$R$^{7a}$)$_m$—S(=O)$_q$N(R$^{8a}$)$_2$, —(CR$^7$R$^{7a}$)$_t$—N(R$^{8a}$)$_2$, —(CR$^7$R$^{7a}$)$_m$—C(=O)O—R$^8$, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_m$—C(=O)O—(CR$^7$R$^{7a}$)$_m$—C(=O)O—R$^8$, —(CR$^7$R$^{7a}$)$_m$—OC(=O)—R$^8$ or —(CR$^7$R$^{7a}$)$_m$—C(=O)—N(R$^8$R$^{8a}$);

each $R^{7a}$ and $R^7$ is independently H, halo, $C_{1-4}$ alkyl, $C_{1-4}$ haloalkyl, —(CH$_2$)$_m$—OH, or —(CH$_2$)$_m$—C(=O)O—R$^8$;

or $R^{7a}$ and $R^7$, together with the carbon atom to which they are attached, form a $C_{3-6}$ cycloalkyl group, $C_{2-9}$ heterocyclyl group, or —(C=O)—;

each $R^8$ and $R^{8a}$ is independently H, $C_{1-4}$ alkyl, amino-$C_{1-4}$-alkyl, $C_{1-4}$ alkoxy, $C_{1-6}$ alkyl-S(=O)$_q$—, $C_{6-10}$ aryl, $C_{1-9}$ heteroaryl, $C_{3-6}$ cycloalkyl, $C_{2-9}$ heterocyclyl, $C_{6-10}$ aryl-$C_{1-6}$-alkyl, $C_{1-9}$ heteroaryl-$C_{1-6}$-alkyl, $C_{3-6}$ cycloalkyl-$C_{1-4}$-alkyl, $C_{2-9}$ heterocyclyl-$C_{1-6}$-alkyl, $C_{2-9}$ heterocyclyl-S(=O)$_q$—, $C_{1-9}$ heteroaryl-S(=O)$_q$—, $C_{3-6}$ cycloalkyl-S(=O)$_q$—, $C_{6-10}$ aryl-S(=O)$_q$—, —(CH$_2$)$_m$—OH, —(CH$_2$)$_m$—C(=O)O—(CH$_2$)$_m$—H, or —(CH$_2$)$_m$—OC(=O)—(CH$_2$)$_m$—H;

each $R^9$ is independently H, halo, $C_{1-4}$ alkyl, $C_{1-4}$ haloalkyl, $C_{1-4}$ alkylthio, $C_{3-6}$ cycloalkyl, —(CR$^7$R$^{7a}$)$_m$—C(=O)—N(R$^8$R$^{8a}$), or —(CR$^7$R$^{7a}$)$_m$—C(=O)O—R$^8$;

$R^{10}$ is H or deuterium;

n is 0, 1, 2, 3, 4, or 5; each m is independently 0, 1, 2, 3, or 4; f is 1, 2, 3, or 4; and j is 0, 1, or 2.

Two preparation methods of a dihydropyrimidine compound having Formula (I) or a tautomer thereof having Formula (Ia) are depicted in the following schemes, Scheme 1

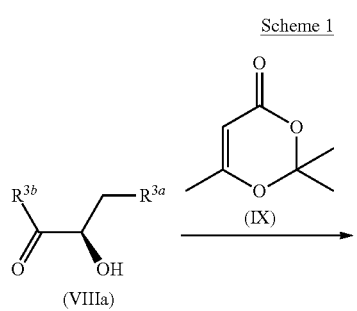

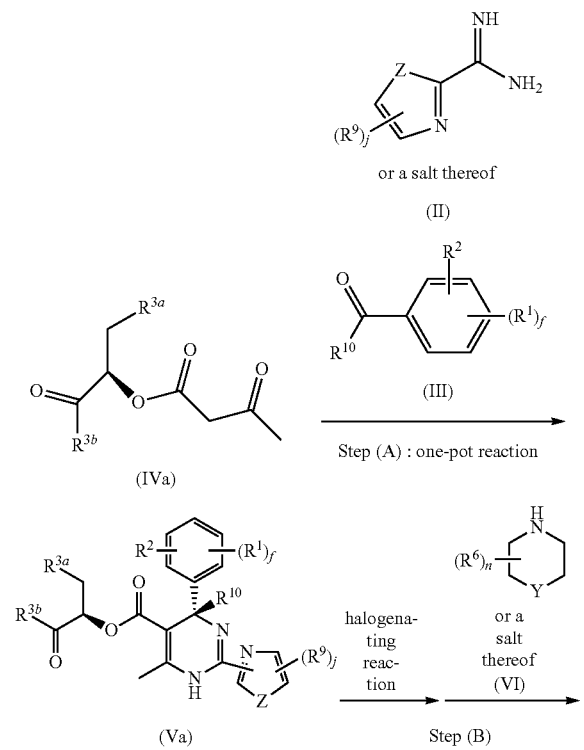

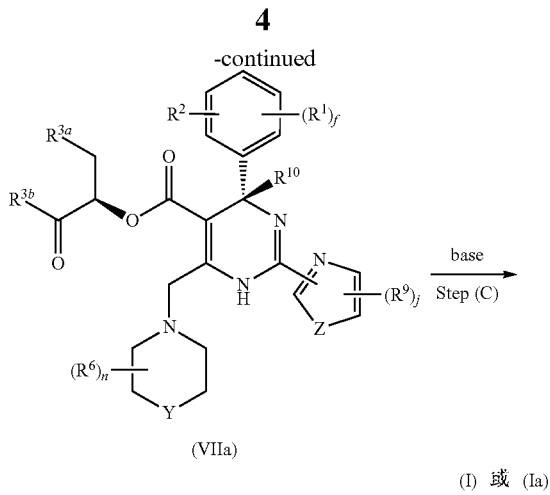

Method One

A dihydropyrimidine compound having Formula (I), or a tautomer thereof having Formula (Ia) can be prepared by a general synthetic procedure illustrated through method one in Scheme 1, wherein $R^1$, $R^2$, Z, $R^9$, j, f, $R^6$, n, Y and $R^{10}$ are as defined herein; wherein $R^{3a}$ is H or $C_{1-3}$ alkyl; $R^{3b}$ is methoxy or ethoxy. The method comprises the following steps of: reacting a compound (VIIIa) with a compound (IX) to obtain a compound (IVa); step (A): reacting a compound (II) or a salt thereof with a compound (III) and the compound (IVa) to obtain a compound (Va) (according to some embodiments of the present invention, the reaction of the step (A) may be an one-pot reaction); step (B): halogenating the compound (Va) to form a halide; and then reacting the halide with a compound (VI), or a salt thereof to obtain a compound (VIIa); step (C): forming a compound (I) or compound (Ia) from the compound (VIIa) in the presence of a base (according to some embodiments of the present invention, the reaction of the step (C) may be a transesterification).

Scheme 2

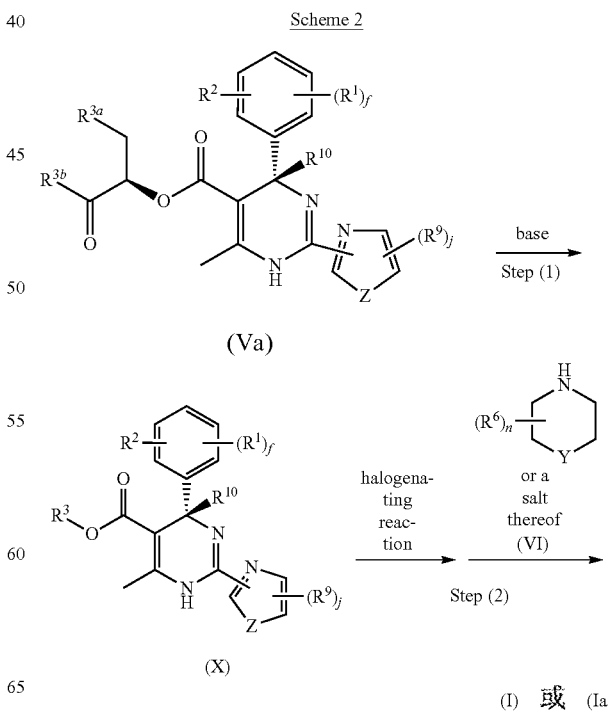

Method Two

A dihydropyrimidine compound having Formula (I), or a tautomer thereof having Formula (Ia) can be prepared by a general synthetic procedure illustrated through method two in Scheme 2, wherein $R^1$, $R^2$, Z, $R^9$, j, f, $R^6$, n, Y, $R^{10}$, $R^{3a}$ and $R^{3b}$ are as defined herein. The method two comprises the following steps of: step (1): reacting the compound (Va) in the presence of a base to obtain a compound (X) (according to some embodiments of the present invention, the reaction of the step (1) may be a transesterification); step (2): halogenating the compound (X) to form a halide; and then reacting the halide with a compound (VI) or a salt thereof to obtain a compound (I) or compound (Ia).

The method one depicted in scheme 1 and the method two depicted in scheme 2 comprises introducing a new chiral center to the mother nucleus of the compound, and splitting the diastereomers based on the difference in the solubility of the diastereomers; at last, removing the new chiral center from the mother nucleus through transesterification, then a compound may be obtained and in some embodiments of the present invention, the obtained compound may be optically pure. These methods have advantages of convenient work-up, high optical purity of product, and high yield. In addition, the processes of the invention have cheap raw material, mild reaction conditions, simplified operational procedure, controlled safely and they are suited for industrial production.

The present invention also refers to an intermediate comprising a dihydropyrimidine compound having Formula (Va), or a tautomer thereof having Formula (Va1), or a salt thereof, or a combination thereof,

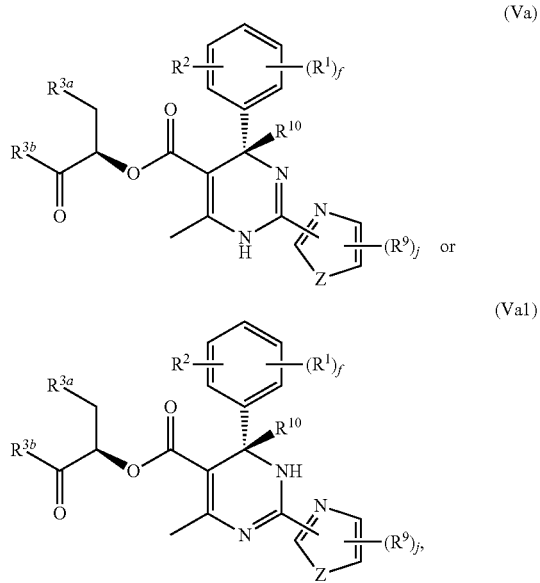

wherein each $R^1$, $R^2$, f, Z, $R^9$, j, $R^{10}$, $R^{3a}$ and $R^{3b}$ is as defined herein.

In one aspect, provided herein is a process for preparing a dihydropyrimidine compound having Formula (I), or a tautomer thereof having Formula (Ia) (such as the method one depicted in scheme 1)

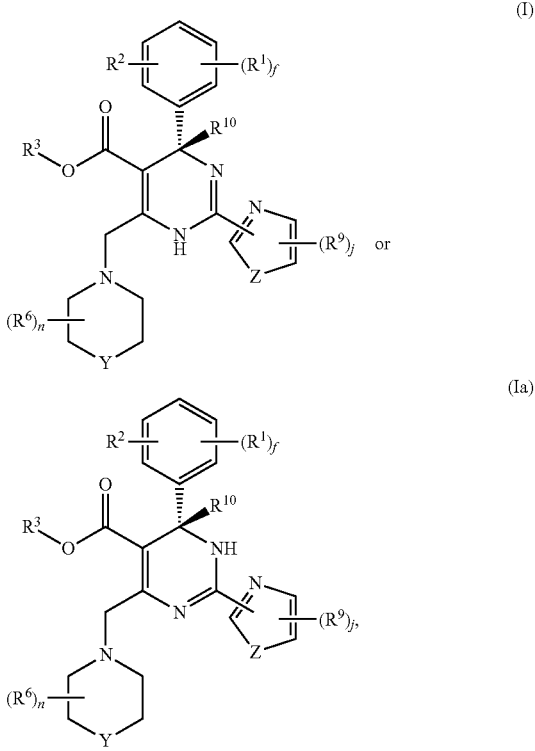

wherein each $R^1$ and $R^2$ is independently F, Cl, or Br;
$R^3$ is $C_{1-4}$ alkyl;
Z is —O—, —S—, —S(=O)$_t$—, or —N($R^4$)—;
Y is —O—, —S—, —S(=O)$_t$—, —(CH$_2$)$_q$—, or —N($R^5$)—;
each t and q is independently 0, 1, or 2;
each of $R^4$ and $R^5$ is independently H, or $C_{1-4}$ alkyl;
each $R^6$ is independently H, deuterium, halo, $C_{1-4}$ alkyl, $C_{1-4}$ haloalkyl, amino, $C_{1-4}$ alkylamino, $C_{1-4}$ alkoxy, nitro, triazolyl, tetrazyl, —(CR$^7$R$^{7a}$)$_m$—OH, —S(=O)$_q$OR$^{8a}$, —(CR$^7$R$^{7a}$)$_m$—S(=O)$_q$N(R$^{8a}$)$_2$, —(CR$^7$R$^{7a}$)$_t$—N(R$^{8a}$)$_2$, —(CR$^7$R$^{7a}$)$_m$—C(=O)O—R$^8$, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_m$—C(=O)O—(CR$^7$R$^{7a}$)$_m$—C(=O)O—R$^8$, —(CR$^7$R$^{7a}$)$_m$—OC(=O)—R$^8$, or —(CR$^7$R$^{7a}$)$_m$—C(=O)—N(R$^8$R$^{8a}$);
each $R^{7a}$ and $R^7$ is independently H, halo, $C_{1-4}$ alkyl, $C_{1-4}$ haloalkyl, —(CH$_2$)$_m$—OH, or —(CH$_2$)$_m$—C(=O)O—R$^8$;
or $R^{7a}$ and $R^7$, together with the carbon atom to which they are attached, form a $C_{3-6}$ cycloalkyl group, $C_{2-9}$ heterocyclyl group, or —(C=O)—;
each $R^8$ and $R^{8a}$ is independently H, $C_{1-4}$ alkyl, amino-$C_{1-4}$-alkyl, $C_{1-4}$ alkoxy, $C_{1-6}$ alkyl-S(=O)$_q$—, $C_{6-10}$ aryl, $C_{1-9}$ heteroaryl, $C_{3-6}$ cycloalkyl, $C_{2-9}$ heterocyclyl, $C_{6-10}$ aryl-$C_{1-6}$-alkyl, $C_{1-9}$ heteroaryl-$C_{1-6}$-alkyl, $C_{3-6}$ cycloalkyl-$C_{1-4}$-alkyl, $C_{2-9}$ heterocyclyl-$C_{1-6}$-alkyl, $C_{2-9}$ heterocyclyl-S(=O)$_q$—, $C_{1-9}$ heteroaryl-S(=O)$_q$—, $C_{3-6}$ cycloalkyl-S(=O)$_q$—, $C_{6-10}$ aryl-S(=O)$_q$—, —(CH$_2$)$_m$—OH, —(CH$_2$)$_m$—C(=O)O—(CH$_2$)$_m$—H, or —(CH$_2$)$_m$—OC(=O)—(CH$_2$)$_m$—H;
each $R^9$ is independently H, halo, $C_{1-4}$ alkyl, $C_{1-4}$ haloalkyl, $C_{1-4}$ alkylthio, $C_{3-6}$ cycloalkyl, —(CR$^7$R$^{7a}$)$_m$—C(=O)—N(R$^8$R$^{8a}$), or —(CR$^7$R$^{7a}$)$_m$—C(=O)O—R$^8$;
$R^{10}$ is H or deuterium;
n is 0, 1, 2, 3, 4, or 5;
each m is independently 0, 1, 2, 3, or 4;

f is 1, 2, 3, or 4;

j is 0, 1, or 2;

wherein the process comprises the steps of:

step (A): reacting an amidine compound of Formula (II), or a salt thereof with an aldehyde compound of Formula (III) and a compound of Formula (IVa) to obtain a compound (Va) (according to some embodiments of the present invention, the reaction of step (A) may be an one-pot reaction),

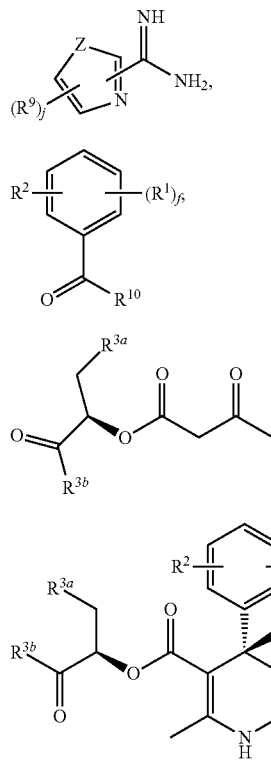

wherein $R^{3b}$ is methoxy or ethoxy; $R^{3a}$ is H or $C_{1-3}$ alkyl;

step (B): halogenating the compound of Formula (Va) to form a halide; and then reacting the halide with a compound of Formula (VI), or a salt thereof to obtain a compound of Formula (VIIa), and step (C): forming the compound of Formula (I) or Formula (Ia) from the compound of Formula (VIIa) by means of a transesterification, and the transesterification may be carried out in the presence of a base.

In some embodiments, the dihydropyrimidine compound having Formula (I-1), or a tautomer thereof having Formula (Ia-1),

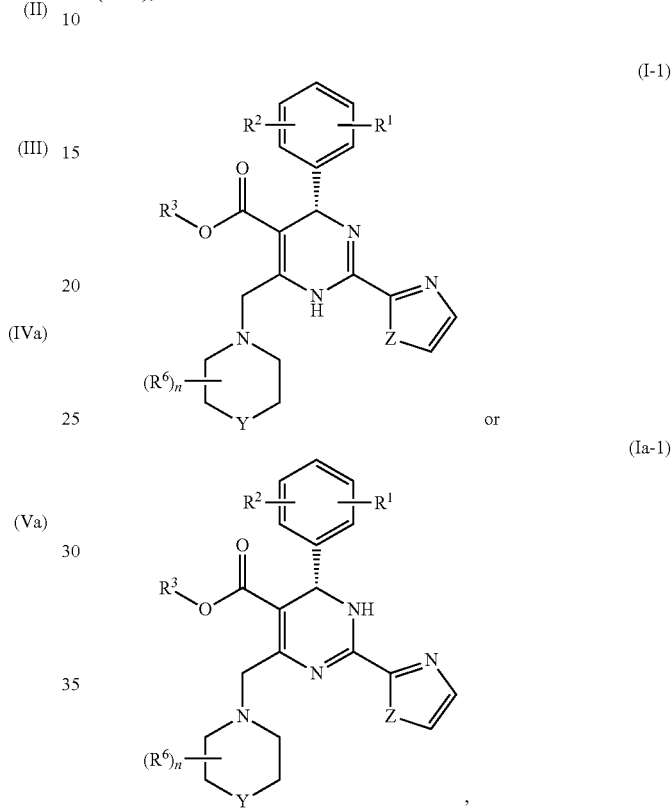

wherein, each $R^6$ is independently H, halo, $C_{1-4}$ alkyl, $C_{1-4}$ haloalkyl, amino, $C_{1-4}$ alkylamino, $C_{1-4}$ alkoxy, nitro, triazolyl, tetrazyl, $-(CR^7R^{7a})_m-OH$, $-S(=O)_qOR^{8a}$, $-(CR^7R^{7a})_m-S(=O)_qN(R^{8a})_2$, $-(CR^7R^{7a})_t-N(R^{8a})_2$, $-(CR^7R^{7a})_m-C(=O)O-R^8$, $-(CR^7R^{7a})_m-C(=O)O-(CR^7R^{7a})_m-OC(=O)O-R^8$, $-(CR^7R^{7a})_m-C(=O)O-(CR^7R^{7a})_m-OC(=O)-R^8$, $-(CR^7R^{7a})_m-C(=O)O-(CR^7R^{7a})_m-C(=O)O-R^8$, $-(CR^7R^{7a})_m-OC(=O)-R^8$, or $-(CR^7R^{7a})_m-C(=O)-N(R^8R^{8a})$;

each $R^{7a}$ and $R^7$ is independently H, $C_{1-4}$ alkyl, $C_{1-4}$ haloalkyl, $-(CH_2)_m-OH$, or $-(CH_2)_m-C(=O)O-R^8$; and each $R^1$, $R^2$, $R^3$, Z, n, Y, m, q, $R^{8a}$, t and $R^8$ is as defined herein;

According to embodiments of present invention, the method one for preparing the dihydropyrimidine compound having Formula (I-1), or a tautomer thereof having Formula (Ia-1) comprises the steps of:

step (A) reacting an amidine compound of Formula (II-1), or a salt thereof with an aldehyde compound of Formula (III-1) and the compound of Formula (IVa) to obtain a compound (Va-1) (according to some embodiments of the present invention, the reaction of the step (A) may be an one-pot reaction).

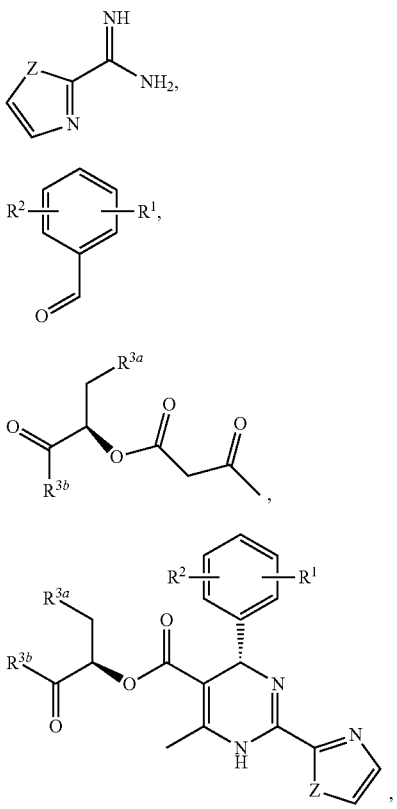

wherein $R^{3a}$ and $R^{3b}$ are as defined in Formula (Va-1) disclosed herein;

step (B): halogenating the compound of Formula (Va-1) to form a halide; and then reacting the halide with a compound of Formula (VI) or a salt thereof to obtain a compound of Formula (VIIa-1),

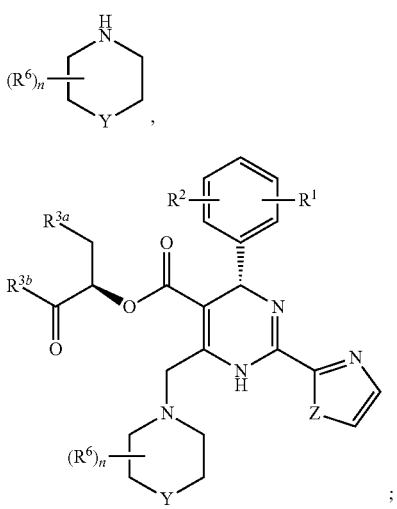

and step (C): forming the compound of Formula (I-1) or Formula (Ia-1) from the compound of Formula (VIIa-1) by means of a transesterification, wherein the transesterification may be carried out in the presence of a base.

In some embodiments, the dihydropyrimidine compound having Formula (I-2), or a tautomer thereof having Formula (Ia-2),

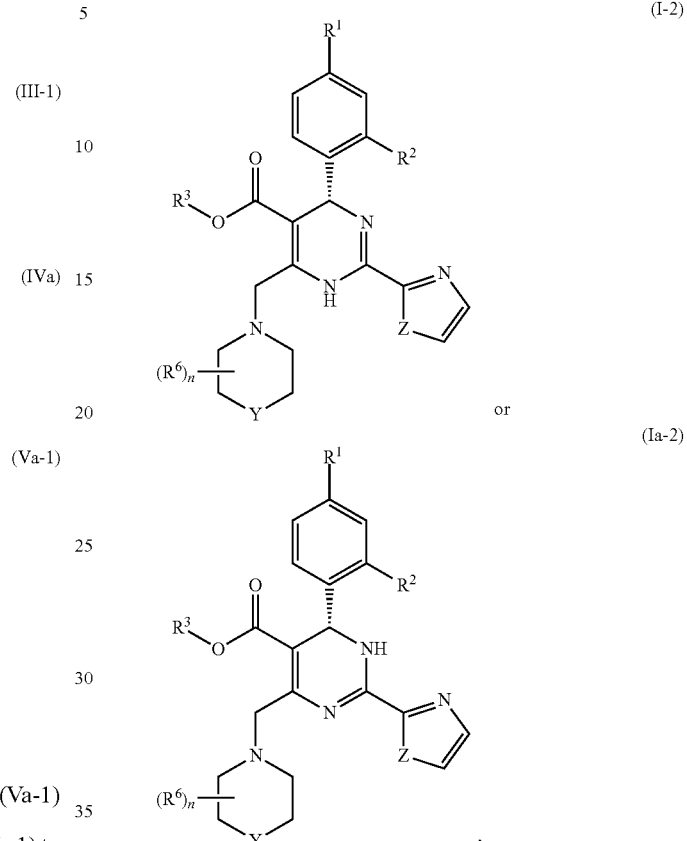

wherein $R^1$ is F or Cl; and $R^2$ is Cl or Br; $R^3$, Z, n, $R^6$ and Y are as defined herein;

According to embodiments of present invention, the method one for preparing the dihydropyrimidine compound having Formula (I-2), or a tautomer thereof having Formula (Ia-2) comprises the steps of:

step (A): reacting an amidine compound of Formula (II-1), or a salt thereof with an aldehyde compound of Formula (III-2) and the compound of Formula (IVa) to obtain a compound (Va-2) (according to some embodiments of the present invention, the reaction of the step (A) may be an one-pot reaction),

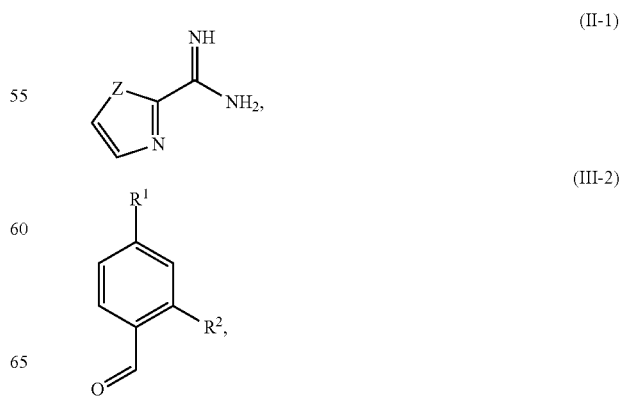

-continued

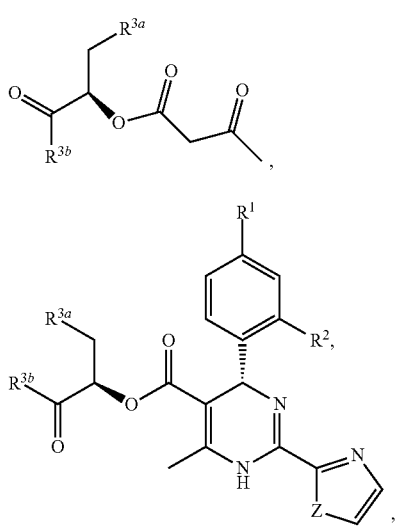
(IVa)

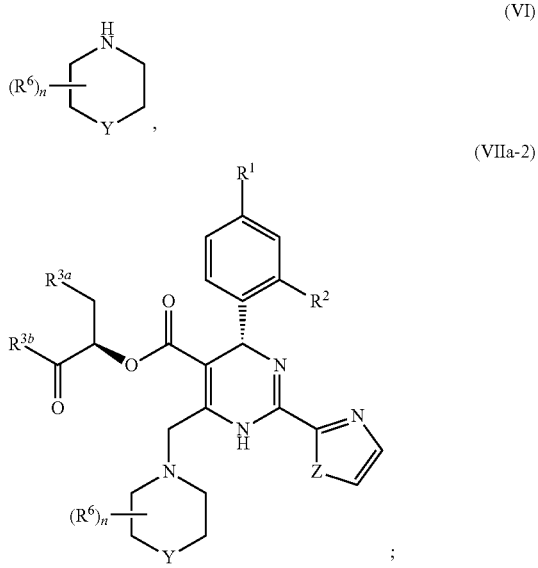
(Va-2)

wherein $R^{3a}$ and $R^{3b}$ are as defined in Formula (Va-1) disclosed herein;

step (B): halogenating the compound of Formula (Va-2) to form a halide; and then reacting the halide with a compound of Formula (VI), or a salt thereof to obtain a compound of Formula (VIIa-2),

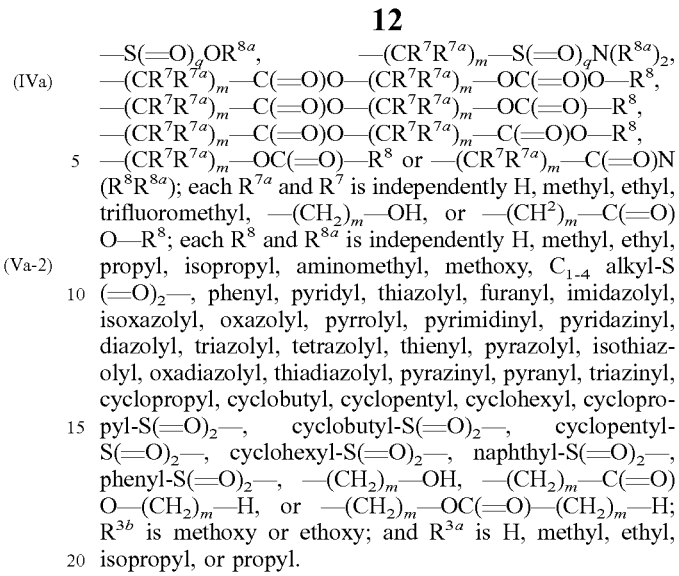
(VI)

(VIIa-2)

and step (C): forming the compound of Formula (I-2) or Formula (Ia-2) from the compound of Formula (VIIa-2) by means of a transesterification, wherein the transesterification may be carried out in the presence of a base.

According to embodiments of present invention, in the method one disclosed herein, in some embodiments, the $R^3$ is methyl, ethyl, propyl, isopropyl, tert-butyl, or butyl; Z is —O—, —S—, or —N(CH$_3$)—; Y is —O—, —S—, —S(=O)$_2$, or —(CH$_2$)$_q$—; each $R^6$ is independently H, halo, $C_{1-4}$ alkyl, $C_{1-4}$ haloalkyl, amino, $C_{1-4}$ alkylamino, $C_{1-4}$ alkoxy, nitro, triazolyl, tetrazyl, —(CR$^7$R$^{7a}$)$_m$—OH, —(CR$^7$R$^{7a}$)$_m$—C(=O)O—R$^8$, —(CR$^7$R$^{7a}$)$_t$—N(R$^{8a}$)$_2$, —S(=O)$_q$OR$^{8a}$, —(CR$^7$R$^{7a}$)$_m$—S(=O)$_q$N(R$^{8a}$)$_2$, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_m$—C(=O)O—(CR$^7$R$^{7a}$)$_m$—C(=O)O—R$^8$, —(CR$^7$R$^{7a}$)$_m$—OC(=O)—R$^8$ or —(CR$^7$R$^{7a}$)$_m$—C(=O)N(R$^8$R$^{8a}$); each $R^{7a}$ and $R^7$ is independently H, methyl, ethyl, trifluoromethyl, —(CH$_2$)$_m$—OH, or —(CH$^2$)$_m$—C(=O)O—R$^8$; each $R^8$ and $R^{8a}$ is independently H, methyl, ethyl, propyl, isopropyl, aminomethyl, methoxy, $C_{1-4}$ alkyl-S(=O)$_2$—, phenyl, pyridyl, thiazolyl, furanyl, imidazolyl, isoxazolyl, oxazolyl, pyrrolyl, pyrimidinyl, pyridazinyl, diazolyl, triazolyl, tetrazolyl, thienyl, pyrazolyl, isothiazolyl, oxadiazolyl, thiadiazolyl, pyrazinyl, pyranyl, triazinyl, cyclopropyl, cyclobutyl, cyclopentyl, cyclohexyl, cyclopropyl-S(=O)$_2$—, cyclobutyl-S(=O)$_2$—, cyclopentyl-S(=O)$_2$—, cyclohexyl-S(=O)$_2$—, naphthyl-S(=O)$_2$—, phenyl-S(=O)$_2$—, —(CH$_2$)$_m$—OH, —(CH$_2$)$_m$—C(=O)O—(CH$_2$)$_m$—H, or —(CH$_2$)$_m$—OC(=O)—(CH$_2$)$_m$—H; $R^{3b}$ is methoxy or ethoxy; and $R^{3a}$ is H, methyl, ethyl, isopropyl, or propyl.

According to some embodiments of the present invention, in the method one disclosed herein, the reaction in step (A) is performed at a temperature from 25° C. to 154° C. In some other embodiments, the reaction in step (A) is performed at a temperature from 60° C. to 100° C.

According to some embodiments of the present invention, in the method one disclosed herein, the one-pot reaction in step (A) is performed at a temperature, in some embodiments, the reaction temperature is from 25° C. to 154° C. In other embodiments, the reaction temperature is from 30° C. to 154° C. In still other embodiments, the reaction temperature is from 60° C. to 100° C. In yet other embodiments, the reaction temperature is 25° C., 30° C., 40° C., 56° C., 60° C., 64° C., 65° C., 77° C., 78° C., 80° C., 82° C., 100° C., 110° C., 120° C., 130° C., 140° C. or 154° C.

According to some embodiments of the present invention, in the method one disclosed herein, the step (A) further comprises a step of cooling the resulting compound of Formula (Va) of step (A) to obtain a solid compound of Formula (Va) at a cooling temperature from −40° C. to 40° C. In some other embodiments, the cooling temperature is from 25° C. to 40° C. In some embodiments, the cooling is performed for a period of from 0 hour to 24 hours. In some other embodiments, the cooling is performed for from 1 minute to 24 hours. In still other embodiments, the cooling is performed for from 1 hour to 8 hours.

According to some embodiments of the present invention, in the method one disclosed herein, the cooling in step (A) is carried out at a temperature, in some embodiments, the cooling temperature is from −50° C. to 60° C. In other embodiments, the cooling temperature is from −40° C. to 40° C. In other embodiments, the cooling temperature is from −30° C. to 40° C. In other embodiments, the cooling temperature is from −20° C. to 40° C. In other embodiments, the cooling temperature is from −10° C. to 40° C. In still other embodiments, the cooling temperature is from 0° C. to 40° C. In yet other embodiments, the cooling temperature is from 25° C. to 40° C. In yet other embodiments, the cooling temperature is −50° C., −40° C., −30° C., −20° C., −15° C., −10° C., −5° C., 0° C., 5° C., 10° C., 15° C., 20° C., 25° C., 30° C., 35° C., 40° C., 50° C. or 60° C.

According to some embodiments of the present invention, in the method one disclosed herein, the cooling temperature in step (A) is kept for a period of time, in some embodiments, the period of time is from 0 hour to 30 hours. In other embodiments, the period of time is from 0 hour to 24 hours. In other embodiments, the period of time is from 1 minute to 24 hours. In other embodiments, the period of time is from 1 hour to 12 hours. In other embodiments, the period of time is from 1 hour to 10 hours. In other embodiments, the period of time is from 1 hour to 8 hours. In still other embodiments, the period of time is from 1 hour to 6 hours. In yet other embodiments, the period of time is 0 hour, 1 minute, 2 hours, 3 hours, 4 hours, 5 hours, 6 hours, 7 hours, 8 hours, 10 hours, 12 hours, 14 hours, 16 hours, 18 hours, 20 hours, 22 hours, 24 hours or 30 hours.

According to some embodiments of the present invention, in the method one disclosed herein, the amidine compound of Formula (II) reacts with the aldehyde compound of Formula (III) and the compound of Formula (IVa) in a first organic solvent. In some embodiments, the first organic solvent is applied in an amount of 0 equivalent to 80 equivalents per 1 equivalent by weight of the amidine compound of Formula (II) or a salt thereof. In some other embodiments, the first organic solvent is applied in an amount of 1 equivalent to 20 equivalents per 1 equivalent by weight of the amidine compound of Formula (II), or a salt thereof.

According to some embodiments of the present invention, in the method one disclosed herein, the first organic solvent in step (A) is applied in an amount, in some embodiments, the amount is 0 equivalent to 80 equivalents per 1 equivalent by weight of an amidine compound of Formula (II), or Formula (II-1), or a salt thereof. In other embodiments, the amount is 1 equivalent to 80 equivalents per 1 equivalent by weight of an amidine compound of Formula (II), or Formula (II-1), or a salt thereof. In other embodiments, the amount is 1 equivalent to 20 equivalents per 1 equivalent by weight of an amidine compound of Formula (II), or Formula (II-1), or a salt thereof. In other embodiments, the amount is 2 equivalents to 20 equivalents per 1 equivalent by weight of an amidine compound of Formula (II), or Formula (II-1), or a salt thereof. In other embodiments, the amount is 1 equivalent to 10 equivalents per 1 equivalent by weight of an amidine compound of Formula (II), or Formula (II-1), or a salt thereof. In still other embodiments, the amount is 3 equivalents to 10 equivalents per 1 equivalent by weight of an amidine compound of Formula (II), or Formula (II-1), or a salt thereof. In yet other embodiments, the amount is 0, 1, 2, 2.5, 3, 4, 4.5, 5, 6, 7, 8, 9, 10, 12, 15, 16, 18, 20, 30, 40, 50, 60, 70 or 80 equivalents per 1 equivalent by weight of an amidine compound of Formula (II), or Formula (II-1), or a salt thereof.

According to some embodiments of the present invention, in the method one disclosed herein, the step (A) further comprises a step of purifying the solid compound of Formula (Va). In some embodiments, the solid compound of Formula (Va) is purified by at least one of the following methods: (1) trituration; (2) recrystallization; (3) washing.

According to some embodiments of the present invention, the purification is carried out in a second organic solvent. In some embodiments, the second organic solvent is applied in an amount of 2 equivalent to 20 equivalents per 1 equivalent by weight of the amidine compound of Formula (II), or a salt thereof.

According to some embodiments of the present invention, in the method one disclosed herein, the trituration is carried out at a temperature from −20° C. to 50° C. In some embodiments, the trituration is carried out at a temperature from 0° C. to 40° C.

According to some embodiments of the present invention, in the method one disclosed herein, the recrystallization comprises a crystallization process at a temperature from −30° C. to 40° C. In some embodiments, the crystallization process is carried out at a temperature from 0° C. to 40° C. In some embodiments, the recrystallization comprises a crystallization process of from 1 hour to 20 hours. In some other embodiments, the recrystallization comprises a crystallization process of from 1 hour to 10 hours.

According to some embodiments of the present invention, in the method one disclosed herein, the washing is performed at a temperature from 0° C. to 30° C.

According to some embodiments of the present invention, in the method one disclosed herein, the compound of Formula (Va), Formula (Va-1), or Formula (Va-2) obtained in step (A) is further purified before step (B). In some embodiments, the compound is further purified by triturating with a second organic solvent. In some embodiments, the trituration is carried out at a temperature from −20° C. to 50° C. In other embodiments, the trituration temperature is from 0° C. to 40° C. In other embodiments, the trituration temperature is from 5° C. to 40° C. In still other embodiments, the trituration temperature is from 25° C. to 40° C. In yet other embodiments, the trituration temperature is −20° C., −10° C., 0° C., 5° C., 10° C., 25° C., 30° C., 35° C., 40° C. or 50° C.

According to some embodiments of the present invention, in the method one disclosed herein, the compound of Formula (Va), Formula (Va-1), or Formula (Va-2) obtained in step (A) is further purified before step (B). In some embodiments, the compound is further purified by recrystallizing from a second organic solvent. In some embodiments, the recrystallization has a crystallization process at a temperature from −30° C. to 50° C. In other embodiments, the crystallization temperature is from −30° C. to 40° C. In other embodiments, the crystallization temperature is from −10° C. to 40° C. In other embodiments, the crystallization temperature is from −10° C. to 30° C. In other embodiments, the crystallization temperature is from 0° C. to 40° C. In other embodiments, the crystallization temperature is from 0° C. to 30° C. In other embodiments, the crystallization temperature is −30° C., −20° C., −10° C., 0° C., 5° C., 10° C., 15° C., 20° C., 25° C., 30° C., 35° C., 40° C. or 50° C. In some embodiments, the recrystallization has a crystallization process taking a period of time from 1 hour to 20 hours. In other embodiments, the period of time is from 2 hours to 18 hours. In still other embodiments, the period of time is from 1 hour to 10 hours. In yet other embodiments, the period of time is 1 hour, 2 hours, 3 hours, 4 hours, 5 hours, 6 hours, 7 hours, 8 hours, 9 hours, 10 hours, 12 hours, 14 hours, 16 hours, 18 hours or 20 hours.

According to some embodiments of the present invention, in the method one disclosed herein, the compound of Formula (Va), Formula (Va-1), or Formula (Va-2) obtained in step (A) is further purified before step (B). In some embodiments, the compound is further purified by washing with a second organic solvent. In some embodiments, the washing is performed at a temperature from 5° C. to 40° C. In other embodiments, the washing temperature is from 0° C. to 30° C. In still other embodiments, the washing temperature is −20° C., −10° C., 0° C., 10° C., 20° C., 25° C., 30° C., 35° C., 40° C. or 50° C.

According to some embodiments of the present invention, in the method one disclosed herein, the second organic solvent used in the further purification before step (B) is applied in an amount, in some embodiments, the amount is about 0 equivalent to 20 equivalents per 1 equivalent by weight of an amidine compound of Formula (II), or Formula (II-1), or a salt thereof. In other embodiments, the amount is about 1 equivalent to 20 equivalents per 1 equivalent by weight of an amidine compound of Formula (II), or Formula (II-1), or a salt thereof. In other embodiments, the amount is about 2 equivalents to 20 equivalents per 1 equivalent by weight of an amidine compound of Formula (II), or Formula (II-1), or a salt thereof. In other embodiments, the amount is about 2 equivalents to 15 equivalents per 1 equivalent by weight of an amidine compound of Formula (II), or Formula (II-1), or a salt thereof. In still other embodiments, the amount is about 2 equivalents to 10 equivalents per 1 equivalent by weight of an amidine compound of Formula (II), or Formula (II-1), or a salt thereof. In yet other embodiments, the amount is about 0, 1, 2, 3, 3.5, 4, 4.5, 5, 6, 7, 7.5, 8, 9, 10, 12, 13, 15, 16, 18, 20, 30, 40, 50, 60, 70 or 80 equivalents per 1 equivalent by weight of an amidine compound of Formula (II), or Formula (II-1), or a salt thereof.

According to some embodiments of the present invention, in the method one disclosed herein, in some embodiments, each of the first organic solvent and the second organic solvent is independently a $C_{1-4}$ alcohol, a $C_{1-4}$ alcohol-water, acetone, diethyl ether, isopropyl ether, petroleum ether, tetrahydrofuran, acetonitrile, cyclopentane, cyclohexane, n-hexane, a $C_{1-4}$ haloalkane, ethyl acetate, trifluoroethanol, 2-methoxyethanol, 1,2-dimethoxyethane, 2-methoxyethyl ether, N,N-dimethyl formamide, N-methylpyrrolidone, or a combination thereof. In other embodiments, each of the first organic solvent and the second organic solvent is independently methanol, ethanol, n-propanol, i-propanol, n-butanol, tert-butanol, an ethanol-water mixture at a volume ratio of from 10:90 to 90:10, an ethanol-water mixture at a volume ratio of 50:50, acetone, tetrahydrofuran, N-methylpyrrolidone, trifluoroethanol, 2-methoxyethanol, 1,2-dimethoxyethane, 2-methoxyethyl ether, ethyl acetate, glycol, N,N-dimethyl formamide, or a combination thereof.

According to some embodiments of the present invention, in the method one disclosed herein, the halogenating in step (B) is carried out in a third organic solvent, in some embodiments, the third organic solvent is one or more $C_{1-4}$ alcohols, one or more $C_{1-4}$ haloalkanes, acetonitrile, isopropyl ether, petroleum ether, toluene, xylene, tetrahydrofuran, ethyl acetate, acetone, or a combination thereof. In other embodiments, the third organic solvent is dichloromethane, chloroform, tetrachloromethane, acetonitrile, isopropyl ether, petroleum ether, tetrahydrofuran, methanol, ethanol, propanol, i-propanol, n-butanol, tert-butanol, ethyl acetate, acetone, or a combination thereof.

According to some embodiments of the present invention, the method one disclosed herein, in some embodiments, the halogenating reaction in step (B) is carried out in the presence of a halogenating agent, and wherein the halogenating agent is N-bromosuccinimide, N-chlorosuccinimide, N-iodosuccinimide, 1,3-dibromo-5,5-dimethylhydantoin, or 1,3-dichloro-5,5-dimethylhydantoin, or a combination thereof.

According to some embodiments of the present invention, the method one disclosed herein, in some embodiments, the base used in step (C) is formed by reacting lithium, sodium, or potassium or a combination thereof with a $C_{1-4}$ alcohol.

According to some embodiments of the present invention, the method one disclosed herein, in some embodiments, the $C_{1-4}$ alcohol for forming the base used in step (C) by reacting with lithium, sodium, or potassium, or a combination thereof is methanol, ethanol, propanol, i-propanol, n-butanol, i-butanol, or tert-butanol.

According to some embodiments of the present invention, the method one disclosed herein, each of the lithium, sodium and potassium or a combination thereof for forming a base used in step (C) by reacting with a $C_{1-4}$ alcohol is independently applied in an amount, in some embodiments, the amount is 0.1 equivalent to 10 equivalents per 1 equivalent by mole of a compound of Formula (VIIa), Formula (VIIa-1), or Formula (VIIa-2). In other embodiments, the amount is 2 equivalents to 6 equivalents per 1 equivalent by mole of a compound of Formula (VIIa), Formula (VIIa-1), or Formula (VIIa-2). In still other embodiments, the amount is 2.5 equivalents to 6 equivalents per 1 equivalent by mole of a compound of Formula (VIIa), Formula (VIIa-1), or Formula (VIIa-2). In yet other embodiments, the amount is 0.1, 0.5, 1, 2, 2.5, 3, 3.5, 4, 5, 6, 7, 8, 9 or 10 equivalents per 1 equivalent by mole of a compound of Formula (VIIa), Formula (VIIa-1), or Formula (VIIa-2).

According to some embodiments of the present invention, the method one disclosed herein, in some embodiments, the compound of Formula (IVa) in step (A) is prepared by a process comprising reacting a compound of Formula (VIIIa) with a compound of Formula (IX),

(VIIIa)

(IX)

wherein $R^{3a}$ and $R^{3b}$ are as defined herein.

In one aspect, provided herein is an intermediate comprising a dihydropyrimidine compound having Formula (Va), or a tautomer thereof having Formula (Va1), or a salt thereof, or a combination thereof,

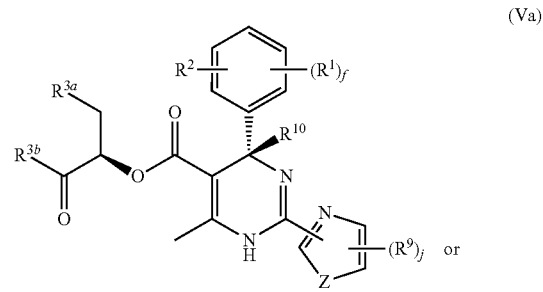
(Va)

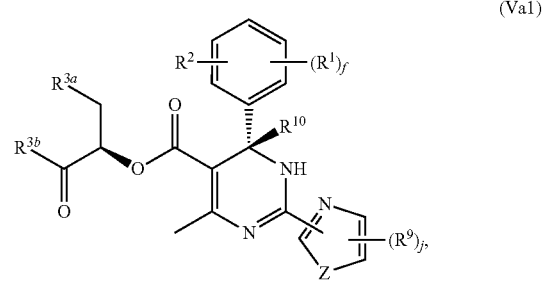
(Va1)

wherein each $R^1$ and $R^2$ is independently F, Cl, or Br;
$R^{3b}$ is methoxy or ethoxy;
$R^{3a}$ is H or $C_{1-3}$ alkyl;
each $R^9$ is independently H, halo, $C_{1-4}$ alkyl, $C_{1-4}$ alkylthio, $C_{1-4}$ haloalkyl, $C_{3-6}$ cycloalkyl, —$(CR^7R^{7a})_m$—C(=O)—N($R^8R^{8a}$), or —$(CR^7R^{7a})_m$—C(=O)O—$R^8$;
each $R^{7a}$ and $R^7$ is independently H, halo, $C_{1-4}$ alkyl, $C_{1-4}$ haloalkyl, —$(CH_2)_m$—OH, or —$(CH_2)_m$—C(=O)O—$R^8$;

or $R^{7a}$ and $R^7$, together with the carbon atom to which they are attached, form a $C_{3-6}$ cycloalkyl group, $C_{2-9}$ heterocyclyl group, or —(C=O)—;

each $R^8$ and $R^{8a}$ is independently H, $C_{1-4}$ alkyl, amino-$C_{1-4}$-alkyl, $C_{1-4}$ alkoxy, $C_{1-6}$ alkyl-S(=O)$_q$—, $C_{6-10}$ aryl, $C_{1-9}$ heteroaryl, $C_{3-6}$ cycloalkyl, $C_{2-9}$ heterocyclyl, $C_{6-10}$ aryl-$C_{1-6}$-alkyl, $C_{1-9}$ heteroaryl-$C_{1-6}$-alkyl, $C_{3-6}$ cycloalkyl-$C_{1-4}$-alkyl, $C_{2-9}$ heterocyclyl-$C_{1-6}$-alkyl, $C_{2-9}$ heterocyclyl-S(=O)$_q$—, $C_{1-9}$ heteroaryl-S(=O)$_q$—, $C_{3-6}$ cycloalkyl-S(=O)$_q$—, $C_{6-10}$ aryl-S(=O)$_q$—, —(CH$_2$)$_m$—OH, —(CH$_2$)$_m$—C(=O)O—(CH$_2$)$_m$—H, or —(CH$_2$)$_m$—OC(=O)—(CH$_2$)$_m$—H;

each m is independently 0, 1, 2, 3, or 4;
$R^{10}$ is H or deuterium;
f is 1, 2, 3, or 4;
j is 0, 1, or 2;
Z is —O—, —S—, —S(=O)$_t$, or —N(R$^4$)—;
t is 0, 1, or 2; and
$R^4$ is H or $C_{1-4}$ alkyl;

In some embodiments, provided herein is the intermediate having Formula (Va-1), or a tautomer thereof having Formula (Va1-1), or a salt thereof, or a combination thereof,

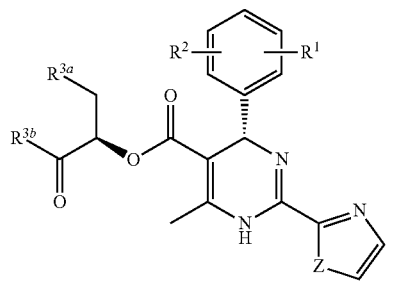

(Va-1)

or

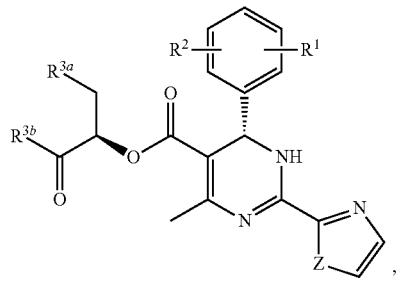

(Va1-1)

wherein $R^{3a}$, $R^{3b}$, $R^1$, $R^2$ and Z are as defined herein.

In some embodiments, provided herein is the intermediate having Formula (Va-2), or a tautomer thereof having Formula (Va1-2), or a salt thereof, or a combination thereof,

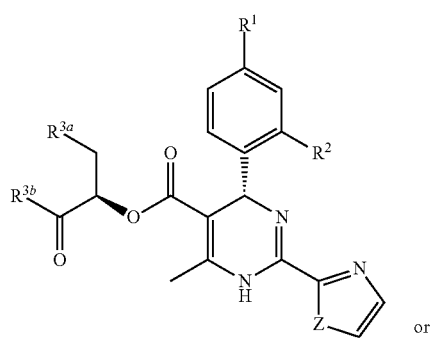

(Va-2)

or

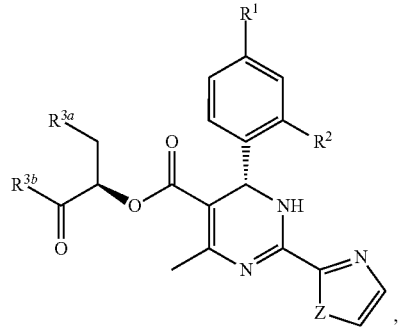

(Va1-2)

wherein $R^1$ is F or Cl; and $R^2$ is Cl or Br;
Z is —O—, —S—, or —N(CH$_3$)—;
$R^{3b}$ is methoxy or ethoxy; and
$R^{3a}$ is H, methyl, ethyl, isopropyl, or propyl.

In other aspect, provided herein is a process for preparing a dihydropyrimidine compound having Formula (I), or a tautomer thereof having Formula (Ia), or a combination thereof, (such as the method two depicted in scheme 2),

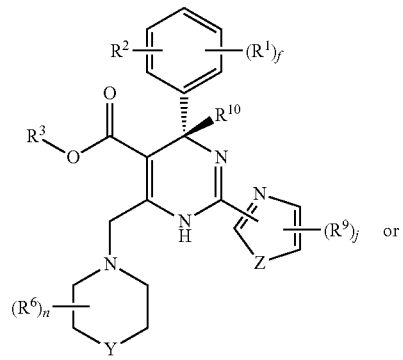

(I)

or

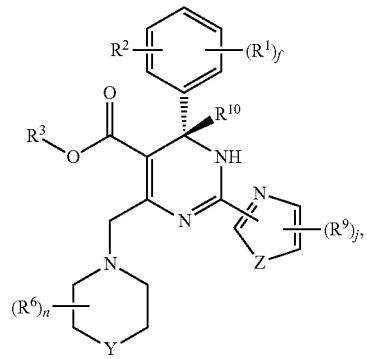

(Ia)

wherein each $R^1$ and $R^2$ is independently F, Cl, or Br;
$R^3$ is $C_{1-4}$ alkyl;
Z is —O—, —S—, —S(=O)$_t$, or —N(R$^4$)—;
Y is —O—, —S—, —S(=O)$_t$, —(CH$_2$)q-, or —N(R$^5$)—;
each t and q is independently 0, 1, or 2;
each of $R^4$ and $R^5$ is independently H, or $C_{1-4}$ alkyl;
each $R^6$ is independently H, deuterium, halo, $C_{1-4}$ alkyl, $C_{1-4}$ haloalkyl, amino, $C_{1-4}$ alkylamino, $C_{1-4}$ alkoxy, nitro, triazolyl, tetrazyl, —(CR$^7$R$^{7a}$)$_m$—OH, —(CR$^7$R$^{7a}$)$_m$—C(=O)O—R$^8$, —(CR$^7$R$^{7a}$)$_t$—N(R$^{8a}$)$_2$, —S(=O)$_q$OR$^{8a}$, —(CR⁷R⁷ᵃ)ₘ—S(=O)_qN(R⁸ᵃ)₂, —(CR⁷R⁷ᵃ)ₘ—C(=O)O—(CR⁷R⁷ᵃ)ₘ—OC(=O)O—R⁸, —(CR⁷R⁷ᵃ)ₘ—C(=O)O—(CR⁷R⁷ᵃ)ₘ—OC(=O)—R⁸, —(CR⁷R⁷ᵃ)ₘ—C(=O)O—(CR⁷R⁷ᵃ)ₘ—C(=O)O—R⁸, —(CR⁷R⁷ᵃ)ₘ—OC(=O)—R⁸, or —(CR⁷R⁷ᵃ)ₘ—C(=O)N(R⁸R⁸ᵃ);

each R⁷ᵃ and R⁷ is independently H, halo, C₁₋₄ alkyl, C₁₋₄ haloalkyl, —(CH₂)ₘ—OH, or —(CH₂)ₘ—C(=O)O—R⁸; or R⁷ᵃ and R⁷, together with the carbon atom to which they are attached, form a C₃₋₆ cycloalkyl group, C₂₋₉ heterocyclyl group, or —(C=O)—;

each R⁸ and R⁸ᵃ is independently H, C₁₋₄ alkyl, amino-C₁₋₄-alkyl, C₁₋₄ alkoxy, C₁₋₆ alkyl-S(=O)_q—, C₆₋₁₀ aryl, C₁₋₉ heteroaryl, C₃₋₆ cycloalkyl, C₂₋₉ heterocyclyl, C₆₋₁₀ aryl-C₁₋₆-alkyl, C₁₋₉ heteroaryl-C₁₋₆-alkyl, C₃₋₆ cycloalkyl-C₁₋₄-alkyl, C₂₋₉ heterocyclyl-C₁₋₆-alkyl, C₂₋₉ heterocyclyl-S(=O)_q—, C₁₋₉ heteroaryl-S(=O)_q—, C₃₋₆ cycloalkyl-S(=O)_q—, C₆₋₁₀ aryl-S(=O)_q—, —(CH₂)ₘ—OH, —(CH₂)ₘ—C(=O)O—(CH₂)ₘ—H, or —(CH₂)ₘ—OC(=O)—(CH₂)ₘ—H;

each R⁹ is independently H, halo, C₁₋₄ alkyl, C₁₋₄ alkylthio, C₁₋₄ haloalkyl, C₃₋₆ cycloalkyl, —(CR⁷R⁷ᵃ)ₘ—C(=O)—N(R⁸R⁸ᵃ), or —(CR⁷R⁷ᵃ)ₘ—C(=O)O—R⁸;

R¹⁰ is H or deuterium;
n is 0, 1, 2, 3, 4, or 5;
each m is independently 0, 1, 2, 3, or 4;
f is 1, 2, 3, or 4; and
j is 0, 1, or 2;
wherein the process comprises the steps of:
step (1): reacting an amidine compound of Formula (II), or a salt thereof with an aldehyde compound of Formula (III) and a compound of Formula (IVa) to obtain a compound of Formula (Va) (according to some embodiments of present invention, the reaction of the step (A) may be, but not limited to an one-pot reaction),

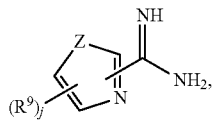

(II)

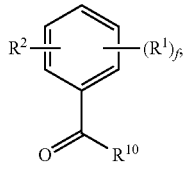

(III)

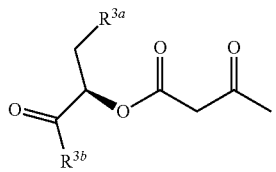

(IVa)

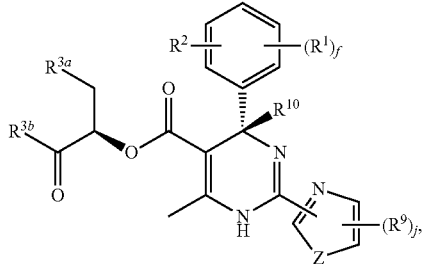

(Va)

step (2): forming a compound of Formula (X) from a compound of Formula (Va) by means of a transesterification, and the transesterification may be carried out in the presence of a base,

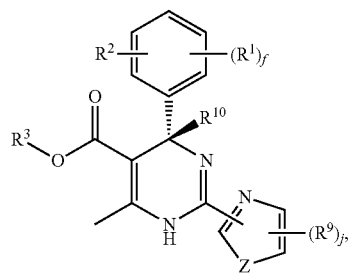

(X)

wherein R³ᵇ is methoxy or ethoxy; and
R³ᵃ is H or C₁₋₃ alkyl;

step (3): halogenating the compound of Formula (X) to form a halide; and then reacting the halide with a compound of Formula (VI), or a salt thereof to obtain a compound of Formula (I) or Formula (Ia).

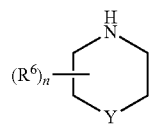

(VI)

In other embodiments, the dihydropyrimidine compound having Formula (I-1), or a tautomer thereof having Formula (Ia-1),

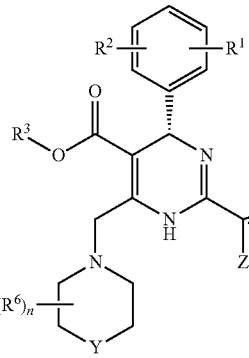

(I-1)

or

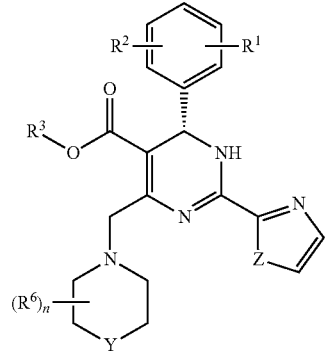

(Ia-1)

wherein each R⁶ is independently H, halo, C₁₋₄ alkyl, C₁₋₄ haloalkyl, amino, C₁₋₄ alkylamino, C₁₋₄ alkoxy, nitro, triazolyl, tetrazyl, —(CR⁷R⁷ᵃ)ₘ—OH, —(CR⁷R⁷ᵃ)ₘ—C(=O)O—R⁸, —(CR⁷R⁷ᵃ)_t—N(R⁸ᵃ)₂, —S(=O)_qOR⁸ᵃ, —(CR⁷R⁷ᵃ)ₘ—S(=O)_qN(R⁸ᵃ)₂, —(CR⁷R⁷ᵃ)ₘ—C(=O)O—(CR⁷R⁷ᵃ)ₘ—OC(=O)O—R⁸, —(CR⁷R⁷ᵃ)ₘ—C(=O)O—(CR⁷R⁷ᵃ)ₘ—OC(=O)—R⁸, —(CR⁷R⁷ᵃ)ₘ—C(=O)

O—(CR$^7$R$^{7a}$)$_m$—C(=O)O—R$^8$, —(CR$^7$R$^{7a}$)$_m$—OC(=O)—R$^8$, or —(CR$^7$R$^{7a}$)$_m$—C(=O)N(R$^8$R$^{8a}$);

each R$^{7a}$ and R$^7$ is independently H, C$_{1-4}$ alkyl, C$_{1-4}$ haloalkyl, —(CH$_2$)$_m$—OH, or —(CH$_2$)$_m$—C(=O)O—R$^8$; and each R$^1$, R$^2$, R$^3$, Z, n, Y, m, q, R$^{8a}$, t and R$^8$ is as defined herein;

According to some embodiments of the present invention, the method two for preparing the optically pure dihydropyrimidine compound having Formula (I-1), or a tautomer thereof having Formula (Ia-1) comprises the steps of:

step (1): reacting an amidine compound of Formula (II-1), or a salt thereof with an aldehyde compound of Formula (III-1) and the compound of Formula (IVa) to obtain a compound (Va-1) (according to some embodiments of present invention, the reaction of the step (A) may be an one-pot reaction).

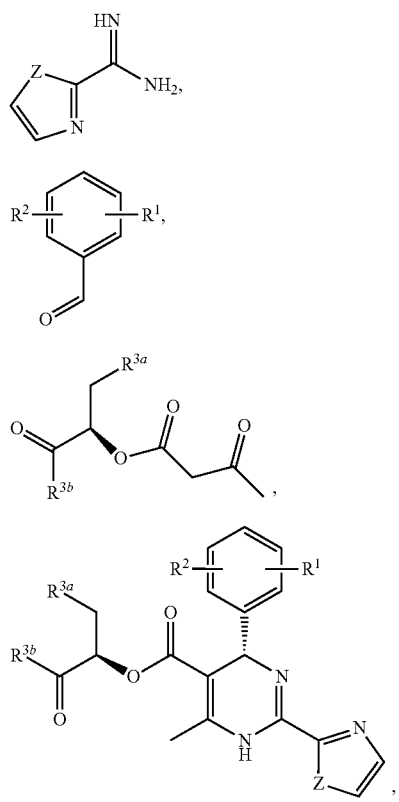

step (2): forming a compound of Formula (X-1) from a compound of Formula (Va-1) by means of a transesterification, wherein the transesterification may be carried out in the presence of a base,

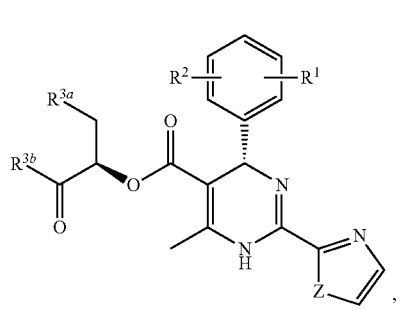

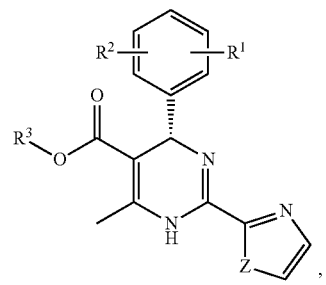

wherein R$^{3a}$ and R$^{3b}$ are as defined herein;

step (3): halogenating the compound of Formula (X-1) to form a halide; and then reacting the intermediate with a compound of Formula (VI), or a salt thereof to obtain a compound of Formula (I-1) or Formula (Ia-1).

In other embodiments, the dihydropyrimidine compound having Formula (I-2), or a tautomer thereof having Formula (Ia-2),

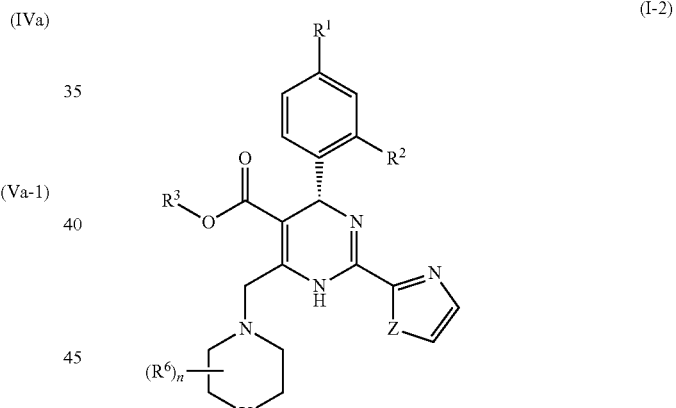

or

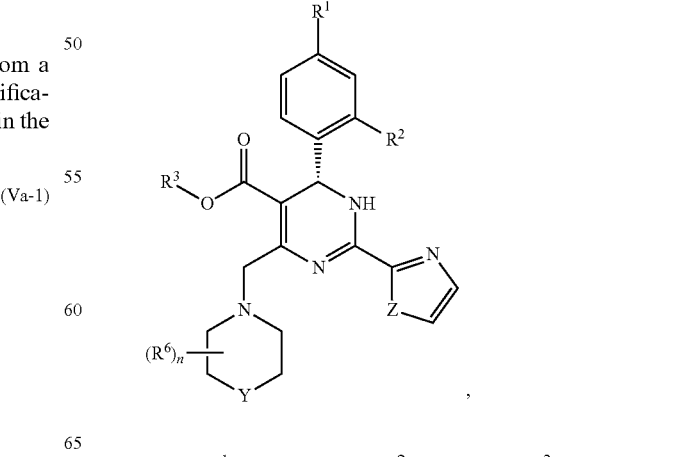

wherein R$^1$ is F or Cl; and R$^2$ is Cl or Br; R$^3$, Z, n, Y and R$^6$ are as defined herein;

According to some embodiments of the present invention, the method two for preparing the dihydropyrimidine compound having Formula (I-2), or a tautomer thereof having Formula (Ia-2) comprises the steps of:

step (1): reacting an amidine compound of Formula (II-1), or a salt thereof with an aldehyde compound of Formula (III-2) and the compound of Formula (IVa) to obtain a compound (Va-2) (according to some embodiments of the present invention, the reaction of the step (A) may be an one-pot reaction),

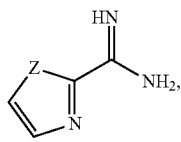
(II-1)

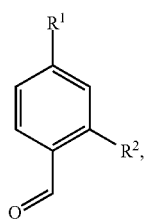
(III-2)

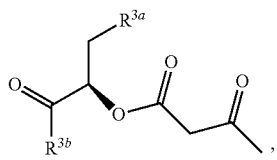
(IVa)

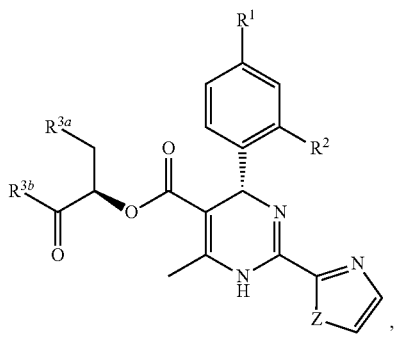
(Va-2)

step (2): forming a compound of Formula (X-2) from a compound of Formula (Va-2) by means of a transesterification, wherein the transesterification may be carried out in the presence of a base,

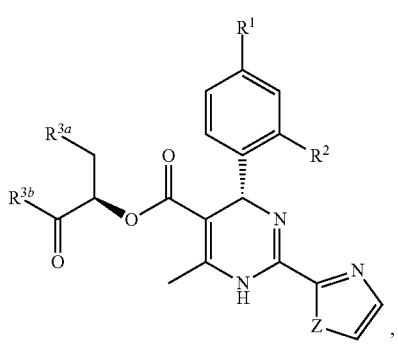
(Va-2)

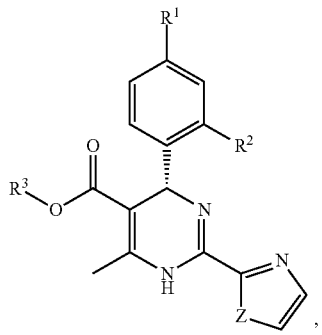
(X-2)

wherein $R^{3a}$ and $R^{3b}$ are as defined herein;

step (3): halogenating the compound of Formula (X-2) to form a halide; and then reacting the halide with a compound of Formula (VI), or a salt thereof to obtain a compound of Formula (I-2) or Formula (Ia-2).

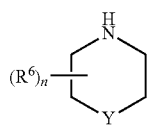
(VI)

According to some embodiments of the present invention, in the method two disclosed herein, in some embodiments, the $R^3$ is methyl, ethyl, propyl, isopropyl, tert-butyl, or butyl; Z is —O—, —S—, or —N(CH$_3$)—; Y is —O—, —S—, —S(=O)$_2$, or —(CH$_2$)$_q$—; each $R^6$ is independently H, halo, $C_{1-4}$ alkyl, $C_{1-4}$ haloalkyl, amino, $C_{1-4}$ alkylamino, $C_{1-4}$ alkoxy, nitro, triazolyl, tetrazyl, —(CR$^7$R$^{7a}$)$_m$—OH, —S(=O)$_q$OR$^{8a}$, —(CR$^7$R$^{7a}$)$_m$—S(=O)$_q$N(R$^{8a}$)$_2$, —(CR$^7$R$^{7a}$)$_t$—N(R$^{8a}$)$_2$, —(CR$^7$R$^{7a}$)$_m$—C(=O)O—R$^8$, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_m$—C(=O)O—(CR$^7$R$^{7a}$)$_m$—C(=O)O—R$^8$, —(CR$^7$R$^{7a}$)$_m$—OC(=O)—R$^8$ or —(CR$^7$R$^{7a}$)$_m$—C(=O)N(R$^8$R$^{8a}$); each $R^{7a}$ and $R^7$ is independently H, methyl, ethyl, trifluoromethyl, —(CH$_2$)$_m$—OH, or —(CH$_2$)$_m$—C(=O)O—R$^8$; each $R^8$ and $R^{8a}$ is independently H, methyl, ethyl, propyl, isopropyl, aminomethyl, methoxy, $C_{1-4}$ alkyl-S(=O)$_2$—, phenyl, pyridyl, thiazolyl, furanyl, imidazolyl, isoxazolyl, oxazolyl, pyrrolyl, pyrimidinyl, pyridazinyl, diazolyl, triazolyl, tetrazolyl, thienyl, pyrazolyl, isothiazolyl, oxadiazolyl, thiadiazolyl, pyrazinyl, pyranyl, triazinyl, cyclopropyl, cyclobutyl, cyclopentyl, cyclohexyl, cyclopropyl-S(=O)$_2$—, cyclobutyl-S(=O)$_2$—, cyclopentyl-S(=O)$_2$—, cyclohexyl-S(=O)$_2$—, naphthyl-S(=O)$_2$—, phenyl-S(=O)$_2$—, —(CH$_2$)$_m$—OH, —(CH$_2$)$_m$—C(=O)O—(CH$_2$)$_m$—H, or —(CH$_2$)$_m$—OC(=O)—(CH$_2$)$_m$—H; $R^{3b}$ is methoxy or ethoxy; and $R^{3a}$ is H, methyl, ethyl, isopropyl, or propyl.

According to some embodiments of the present invention, in the method two disclosed herein, the reaction in step (1) is performed at a temperature from 25° C. to 154° C. In some other embodiments, the reaction in step (1) is performed at a temperature from 60° C. to 100° C.

According to some embodiments of the present invention, in the method two disclosed herein, the step (1) further comprises the step of cooling the resulting compound (Va) of step (1) to obtain a solid compound (Va) at a cooling temperature from −40° C. to 40° C. In other embodiments, the cooling temperature is from 25° C. to 40° C. In some embodiments, the cooling is performed for a period of from 0 hour to 24 hours. In some other embodiments, the cooling is performed for from 1 minute to 24 hours. In still other embodiments, the cooling is performed for from 1 hour to 8 hours.

According to some embodiments of the present invention, in the method two disclosed herein, the amidine compound of Formula (II) reacts with the aldehyde compound of Formula (III) and the compound of Formula (IVa) in a first organic solvent. In some embodiments, the first organic solvent is applied in an amount of 0 equivalent to 80 equivalents per 1 equivalent by weight of the amidine compound of Formula (II), or a salt thereof. In some other embodiments, the first organic solvent is applied in an amount of 1 equivalent to 20 equivalents per 1 equivalent by weight of the amidine compound of Formula (II), or a salt thereof.

According to some embodiments of the present invention, in the method two disclosed herein, step (1) further comprises the step of purifying the solid compound (Va). In some embodiments, the solid compound of Formula (Va) is purified by at least one of the following methods: (1) trituration; (2) recrystallization; (3) washing.

According to some embodiments of the present invention, the purification is carried out in a second organic solvent. In some embodiments, the second organic solvent is applied in an amount of 2 equivalent to 20 equivalents per 1 equivalent by weight of the amidine compound of Formula (II), or a salt thereof.

According to some embodiments of the present invention, in the method two disclosed herein, the trituration is carried out at a temperature from −20° C. to 50° C. In some embodiments, the trituration is carried out at a temperature from 0° C. to 40° C.

According to some embodiments of the present invention, in the method two disclosed herein, the recrystallization comprises a crystallization process at a temperature from −30° C. to 40° C. In some embodiments, the crystallization process is carried out at a temperature from 0° C. to 40° C. In some embodiments, the recrystallization comprises a crystallization process of from 1 hour to 20 hours. In some other embodiments, the recrystallization comprises a crystallization process of from 1 hour to 10 hours.

According to some embodiments of the present invention, in the method two disclosed herein, the washing is performed at a temperature from 0° C. to 30° C.

According to some embodiments of the present invention, in the method two disclosed herein, in some embodiments, each of the first organic solvent and the second organic solvent is independently a $C_{1-4}$ alcohol, a $C_{1-4}$ alcohol-water, acetone, diethyl ether, isopropyl ether, petroleum ether, tetrahydrofuran, acetonitrile, cyclopentane, cyclohexane, n-hexane, $C_{1-4}$ haloalkanes solvent, ethyl acetate, trifluoroethanol, 2-methoxyethanol, 1,2-dimethoxyethane, 2-methoxyethyl ether, N,N-dimethyl formamide, N-methylpyrolidone, or a combination thereof. In some other embodiments, each of the first organic solvent and the second organic solvent is independently methanol, ethanol, n-propanol, i-propanol, n-butanol, tert-butanol, an ethanol-water mixture at a volume ratio from 10:90 to 90:10, an ethanol-water mixture at a volume ratio from 50:50, acetone, tetrahydrofuran, N-methylpyrolidone, trifluoroethanol, 2-methoxyethanol, 1,2-dimethoxyethane, 2-methoxyethyl ether, ethyl acetate, glycol, N,N-dimethyl formamide, or a combination thereof.

According to some embodiments of the present invention, in the method two disclosed herein, in some embodiments, the base used in step (2) is formed by reacting lithium, sodium, or potassium or a combination thereof with a $C_{1-4}$ alcohol.

According to some embodiments of the present invention, in the method two disclosed herein, in some embodiments, the $C_{1-4}$ alcohol for forming the base used in step (2) by reacting with lithium, sodium, or potassium, or a combination thereof is methanol, ethanol, propanol, i-propanol, n-butanol, i-butanol, or tert-butanol.

According to some embodiments of the present invention, in the method two disclosed herein, each of the lithium, sodium and potassium, or a combination thereof for forming the base used in step (2) by reacting with a $C_{1-4}$ alcohol is independently applied in an amount, in some embodiments, the amount is 0.5 equivalent to 10 equivalents per 1 equivalent by mole of a compound of Formula (Va), Formula (Va-1), or Formula (Va-2). In other embodiments, the amount is 2 equivalents to 8 equivalents per 1 equivalent by mole of a compound of Formula (Va), Formula (Va-1), or Formula (Va-2). In still other embodiments, the amount is 2.5 equivalents to 8 equivalents per 1 equivalent by mole of a compound of Formula (Va), Formula (Va-1), or Formula (Va-2). In yet other embodiments, the amount is 0.5, 1, 2.5, 3, 3.5, 4, 5, 6, 7, 8, 9 or 10 equivalents per 1 equivalent by mole of a compound of Formula (Va), Formula (Va-1), or Formula (Va-2).

According to some embodiments of the present invention, in the method two disclosed herein, the halogenating reaction in step (3) is carried out in a forth organic solvent, in some embodiments, the forth organic solvent is one or more $C_{1-4}$ alcohols, one or more $C_{1-4}$ haloalkanes, ethyl acetate, acetonitrile, isopropyl ether, petroleum ether, toluene, xylene, tetrahydrofuran, acetone, or a combination thereof. In other embodiments, the forth organic solvent is dichloromethane, chloroform, tetrachloromethane, acetonitrile, isopropyl ether, petroleum ether, tetrahydrofuran, methanol, ethanol, propanol, i-propanol, n-butanol, tert-butanol, ethyl acetate, acetone, or a combination thereof.

According to some embodiments of the present invention, in the method two disclosed herein, in some embodiments, the halogenating reaction in step (2) is carried out in the presence of a halogenating agent, and wherein the halogenating agent is N-bromosuccinimide, N-chlorosuccinimide, N-iodosuccinimide, 1,3-dibromo-5,5-dimethylhydantoin, or 1,3-dichloro-5,5-dimethylhydantoin, or a combination thereof.

DEFINITIONS AND GENERAL TERMINOLOGY

The term "alkyl" or "alk-" or "alkyl group" as used interchangeably in the context of the present invention, such as in alkyl, aminoalkyl, alkyamino, alkylthio or alkoxy, refers to a saturated linear or branched-chain monovalent hydrocarbon radical of 1 to 10 carbon atoms. Wherein, the alkyl group may be optionally substituted with one or more substituents disclosed herein. In some embodiments, the alkyl group contains 1-10 carbon atoms. In other embodiments, the alkyl group contains 1-6 carbon atoms. In other embodiments, the alkyl group contains 1-4 carbon atoms. In still other embodiments, the alkyl group contains 1-3 carbon atoms.

Some non-limiting examples of the alkyl group include, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH$ (CH$_3$)$_2$), sec-butyl (s-Bu, —CH(CH$_3$)CH$_2$CH$_3$), tert-butyl (t-Bu, —C(CH$_3$)$_3$), n-pentyl (—CH$_2$CH$_2$CH$_2$CH$_2$CH$_3$), 2-pentyl (—CH(CH$_3$)CH$_2$CH$_2$CH$_3$), 3-pentyl (—CH (CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH (CH$_3$)CH$_2$CH$_3$), n-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH (CH$_2$CH$_3$)(CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimethyl-2-butyl (—CH(CH$_3$)C (CH$_3$)$_3$, n-heptyl and n-octyl, etc.

The term "aminoalkyl" refers to a C$_{1-10}$ linear or branched-chain alkyl group substituted with one or more amino groups. In some embodiments, the aminoalkyl group refers to a C$_{1-6}$ aminoalkyl group, wherein the alkyl group is as defined herein. Some non-limiting examples of the aminoalkyl group include aminomethyl, 2-aminoethyl, 2-aminoisopropyl, aminopropyl, aminobutyl and aminohexyl, etc.

The term "alkoxy" refers to an alkyl group attached to the rest part of the molecule through an oxygen atom, wherein the alkyl group is as defined herein. Unless otherwise specified, the alkoxy group contains 1-10 carbon atoms. In some embodiments, the alkoxy group contains 1-6 carbon atoms. In other embodiments, the alkoxy group contains 1-4 carbon atoms. In still other embodiments, the alkoxy group contains 1-3 carbon atoms. Some non-limiting examples of the alkoxy group include methoxy (MeO, —OCH$_3$), ethoxy (EtO, —OCH$_2$CH$_3$), propoxy (n-PrO, n-propoxy, —OCH$_2$CH$_2$CH$_3$), isopropoxy (i-PrO, i-propoxy, —OCH (CH$_3$)$_2$), n-butoxy (n-BuO, —OCH$_2$CH$_2$CH$_2$CH$_3$), 1-methyl-propoxy (s-BuO, s-butoxy, —OCH(CH$_3$) CH$_2$CH$_3$), 2-methyl-1-propoxy (i-BuO, i-butoxy, —OCH$_2$CH(CH$_3$)$_2$), tert-butoxy (t-BuO, t-butoxy, —OC (CH$_3$)$_3$), n-pentoxy (—OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$ CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$) and n-hexyloxy (—OCH$_2$CH$_2$CH$_2$CH$_2$CH$_2$CH$_3$), etc.

The terms "haloalkyl", "haloalkenyl" and "haloalkoxy" respectively refer to alkyl, alkenyl or alkoxy, as the case may be, substituted with one or more halogen atoms. Wherein the alkyl, alkenyl and alkoxy are as defined herein. Some non-limiting examples of these groups include —CF$_3$, —CH$_2$Cl, —CH$_2$CF$_3$, —CH$_2$CH$_2$CF$_3$, —OCF$_3$, —OCHF$_2$, —OCHCl$_2$, —OCH$_2$CHF$_2$, —OCH$_2$CHCl$_2$ and —OCH (CH$_3$)CHF$_2$, etc.

The term "alkylamino" refers to "N-alkylamino" and "N,N-dialkylamino" wherein amino groups are independently substituted with one alkyl radical or two alkyl radicals, respectively. Wherein the amino group and the alkyl group are as defined herein. In some embodiments, the alkylamino radical is "lower alkylamino" radical having one or two C$_{1-6}$ alkyl groups attached to a nitrogen atom. In other embodiments, the alkylamino radical refers to C$_{1-4}$ lower alkylamino group. In still other embodiments, the alkylamino radical refers to C$_{1-3}$ lower alkylamino group. Some non-limiting examples of suitable alkylamino radical include mono or dialkylamino. Some examples include, but are not limited to, methylamino, ethylamino, isopropylamino, propylamino, tert-butylamino, n-butylamino, 1-methylpropylamino, n-pentylamino, n-hexylamino, N,N-dimethylamino and N,N-diethylamino, etc.

The term "alkylthio" refers to a radical containing a linear or branched-alkyl radical of one to ten carbon atoms, attached to a divalent sulfur atom. Wherein the alkyl group is as defined herein. Some non-limiting examples of the alkylthio group include methylthio (CH$_3$S—) and ethylthio, etc.

The term "cycloalkyl" refers to a monovalent or multi-valent saturated ring having 3 to 12 carbon atoms as a monocyclic, bicyclic, or tricyclic ring system. Wherein, the cycloalkyl group may be optionally substituted with one or more substituents disclosed herein. In some embodiments, the cycloalkyl contains 3 to 12 carbon atoms. In still other embodiments, the cycloalkyl contains 3 to 8 carbon atoms. In yet other embodiments, the cycloalkyl contains 3 to 6 carbon atoms. Some examples include, but are not limited to, cyclopropyl, cyclobutyl, cyclopentyl, cyclohexyl, cycloheptyl, cyclooctyl, cyclononyl, cyclodecyl, cyclohendecyl and cyclododecyl, etc.

The term "cycloalkylalkyl" refers to an alkyl radical substituted with one or more cycloalkyl radicals, wherein the cycloalkyl and alkyl are as defined herein. Some non-limiting examples of the cycloalkylalkyl group include cyclopropylmethyl, cyclopropylethyl, cyclopropylpropyl, cyclobutylmethyl, cyclobutylethyl, cyclobutylpropyl, cyclopentylmethyl, cyclopentylethyl, cyclopentylpropyl, cyclohexylmethyl, cyclohexylethyl and cyclohexylpropyl, etc.

The term "cycloalkyloxy" or "cycloalkoxy" refers to a cycloalkyl group, attached to the rest part of the molecule through an oxygen atom. Wherein the cycloalkyl group is as defined herein. Some non-limiting examples of the cycloalkyloxy group include cyclopropoxy, cyclopentyloxy and cyclohexyloxy, etc.

The term "cycloalkylamino" refers to an amino group is substituted with one or two cycloalkyl radicals. Some non-limiting examples of such radical include cyclopropylamino, cyclobutylamino, cyclopentylamino and cyclohexylamino, etc. In some embodiments, the cycloalkyl of cycloalkylamino group may be optionally substituted with one or more substituents disclosed herein.

The term "heterocyclyl" refers to a saturated or unsaturation, nonaromatic, monocyclic, bicyclic or tricyclic ring system in which at least one ring member is selected from nitrogen, sulfur and oxygen. Wherein, the heterocyclyl group may be optionally substituted with one or more substituents disclosed herein. Unless otherwise specified, the heterocyclyl group may be carbon or nitrogen linked, and a —CH$_2$— group can be optionally replaced by a —C(=O)— group. In which, the sulfur can be optionally oxygenized to S-oxide and the nitrogen can be optionally oxygenized to N-oxide. In some embodiments, the heterocyclyl group may be a C$_{2-10}$ heterocyclyl group, which refers to a heterocyclyl group containing 2 to 10 carbon atoms and at least one heteroatom selected from nitrogen, sulfur and oxygen. In other embodiments, the heterocyclyl group may be a C$_{2-9}$ heterocyclyl group, which refers to a heterocyclyl group containing 2 to 9 carbon atoms and at least one heteroatom selected from nitrogen, sulfur and oxygen. In still other embodiments, the heterocyclyl group may be a C$_{2-7}$ heterocyclyl group, which refers to an heterocyclyl group containing 2 to 7 carbon atoms and at least one heteroatom selected from nitrogen, sulfur and oxygen. In yet other embodiments, the heterocyclyl group may be a C$_{2-5}$ heterocyclyl group, which refers to a heterocyclyl group containing 2 to 5 carbon atoms and at least one heteroatom selected from nitrogen, sulfur and oxygen. Some non-limiting examples of the heterocyclyl group include oxiranyl, thietanyl, pyrrolidinyl, pyrazolinyl, pyrazolidinyl, imidazolinyl, imidazolidinyl, oxazolidinyl, tetrahydrofuranyl, dihydrothienyl, dihydropyranyl, piperidinyl, morpholinyl, tetrahydropyrimidinyl, oxazinanyl, thiomorpholinyl and piperazinyl, etc. A —CH$_2$— group of the heterocyclyl group may be substituted with —C(=O), some non-limiting examples of such group include 2-oxopyrrolidinyl, 2-piperidinonyl, 3-morpholinonyl, 3-thiomorpholinonyl and oxotetrahydropyrimidinyl, etc.

The term "heterocyclylalkyl" refers to a heterocyclyl group attached to the rest of the molecule through an alkyl group, wherein the heterocyclyl and alkyl are as defined herein. Some non-limiting examples of such group included pyrrolidinylmethyl, piperidinylmethyl, piperidinylethyl, morpholinylmethyl and morpholinylethyl, etc.

The term "halogen" refers to fluorine (F), chlorine (Cl), bromine (Br) or iodine (I).

The term "aryl" refers to monocyclic, bicyclic and tricyclic carbocyclic ring systems having a total of six to fourteen ring members, or six to twelve ring members, or six to ten ring members, wherein at least one ring in the system is aromatic, wherein each ring in the system contains 3 to 7 ring members and that has a single point or multipoint of attachment to the rest of the molecule. Wherein the aryl may be optionally substituted with the substituent disclosed herein. The term "aryl" and "aromatic ring" can be used interchangeably herein. Some non-limiting examples of the aryl group include phenyl, 2,3-dihydro-1H-indenyl, naphthalenyl and anthracenyl, etc.

The term "arylalkyl" or "aralkyl" refers to an aryl group attached to the rest of the molecule through an alkyl group, wherein the aryl and alkyl are as defined herein. Some non-limiting examples of such group include benzyl, phenylethyl and naphthalenylmethyl, etc.

The term "arylamino" refers to an amino group substituted with one or two aryl groups. Some non-limiting examples of such group included N-phenylamino. In some embodiments, the aryl group of the arylamino may be further substituted.

The term "heteroaryl" refers to monocyclic, bicyclic and tricyclic carbocyclic ring systems having a total of five to twelve ring members, or five to ten ring members, or five to six ring members, wherein at least one ring in the system is aromatic, and in which at least one ring member is selected from nitrogen, sulfur and oxygen, and wherein each ring in the system contains 3 to 7 ring members and that has a single point or multipoint of attachment to the rest of the molecule. The term "heteroaryl" and "heteroaromatic ring" or "heteroaromatic compound" can be used interchangeably herein. In other embodiments, the heteroaryl group may be a $C_{1-9}$ heteroaryl group, which refers to a heteroaryl group containing 1 to 9 carbon atoms and at least one heteroatom selected from nitrogen, sulfur and oxygen. In other embodiments, the heteroaryl group may be a $C_{1-7}$ heteroaryl group, which refers to a heteroaryl group containing 1 to 7 carbon atoms and at least one heteroatom selected from nitrogen, sulfur and oxygen. In still other embodiments, the heteroaryl group may be a $C_{1-6}$ heteroaryl group, which refers to a heteroaryl group containing 1 to 6 carbon atoms and at least one heteroatom selected from nitrogen, sulfur and oxygen. In other embodiments, the heteroaryl group may be a $C_{1-5}$ heteroaryl group, which refers to a heteroaryl group containing 1 to 5 carbon atoms and at least one heteroatom selected from nitrogen, sulfur and oxygen. In still other embodiments, the heteroaryl group may be a $C_{1-4}$ heteroaryl group, which refers to a heteroaryl group containing 1 to 4 carbon atoms and at least one heteroatom selected from nitrogen, sulfur and oxygen. In yet other embodiments, the heteroaryl group may be a $C_{1-3}$ heteroaryl group, which refers to a heteroaryl group containing 1 to 3 carbon atoms and at least one heteroatom selected from nitrogen, sulfur and oxygen. Some non-limiting examples of such group include furanyl, imidazolyl, isoxazolyl, oxazolyl, pyrrolyl, pyrazolyl, pyridyl, pyrimidinyl, pyridazinyl, pyrazinyl, thienyl, diazolyl, triazolyl, tetrazolyl, thiazolyl, isothiazolyl, oxadiazolyl, thiadiazolyl, pyranyl and triazinyl, etc, and also include the following bicycle ring, but are not limited to: benzimidazolyl, benzofuranyl, benzothiophenyl, indolyl, oxoindolyl, indolinyl, imidazopyridyl, pyrazopryridyl, pyrazopyrimidinyl, quinolyl, isoquinolyl and quinazolinyl, etc. The heteroaryl group may be optionally substituted with one or more substituents disclosed herein.

The term "heteroarylalkyl" refers to an heteroaryl group attached to the rest of the molecule through a alkyl group, wherein the heteroaryl and alkyl are as defined herein. The "heteroarylalkyl" group may be optionally substituted with one or more substituents disclosed herein. Some non-limiting examples of such group included pyridylmethyl, pyrrolylethyl and quinolylmethyl, etc.

The term "comprise" is an open expression, it means comprising the contents disclosed herein, but don't exclude other contents.

Furthermore, unless otherwise stated, the phrase "each . . . is independently" is used interchangeably with the phrase "each (of) . . . and . . . is independently". It should be understood broadly that the specific options expressed by the same symbol are independently of each other in different radicals; or the specific options expressed by the same symbol are independently of each other in same radicals. Such as Formula (a), multiple n are independently of each other, multiple $R^6$ are independently of each other,

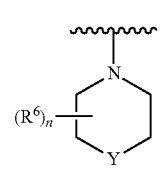

(a)

As described herein, a system containing a group formed by connecting a double bond with a wave bond indicates that it is (Z) or (E) configuration, or a combination thereof.

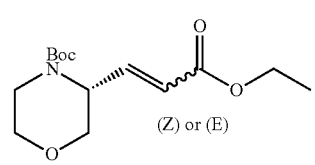

(b)

The solvent used for the reaction of the invention is not particularly restricted, any solvent is contained in the invention so long as it can dissolve the raw materials to a certain extent and doesn't inhibit the reaction. Additionally, many similar modifications in the art, substitutions to same object, or solvent, solvent composition and the solvent composition with different proportions which are equivalent to those described in the invention, all are deemed to be included in the present invention. Wherein the solvent could be alcohols, alcohol-water mixtures, ethers, halohydrocarbons, esters, ketones, aromatic hydrocarbons, alkanes, acetonitrile, trifluoroethanol, N,N-dimethyl formamide (DMF), N-methylpyrolidone (NMP), or a combination thereof. Such as methanol, ethanol, n-propanol, i-propanol, n-butanol, i-butanol, a ethanol-water mixture at a volume ratio of 50:50, trifluoroethanol, tert-butanol, petroleum ether, n-pentane, n-hexane, n-heptane, cyclohexane, isopropyl ether, DMF, tetrahydrofuran, ethyl ether, dioxane, methyl tertiary butyl ether (MTBE), 1,2-dimethoxylethane, NMP, 2-methoxyethanol, 1,2-dimethoxyethane, diethylene glycol dimethyl ether, triethylene glycol dimethyl ether, dichloromethane, 1,2-dichloroethane, chloroform, tetrachloromethane, ethyl acetate, isopropyl acetate, acetone, butanone, benzene, toluene, xylene or a combination thereof.

The amount of water in the solvent is not particularly restricted. So long as the solvent containing a certain amount of water can be used in the reaction disclosed herein, which is deemed to be included in the present invention. The amount of water in the solvent is approximately less than 0.05%, less than 0.1%, less than 0.2%, less than 0.5%, less than 5%, less than 10%, less than 25%, less than 30%, or 0%.

The solvent used for the recrystallization of the invention is not particularly restricted, any solvent is contained in the invention so long as it can dissolve the crude product and the crystal product can precipitate out under certain conditions. Additionally, many similar modifications in the art, substitutions to same object, or solvent, solvent composition and the solvent composition with different proportions which are equivalent to those described in the invention, all are deemed to be included in the present invention. Wherein the solvent could be alcohols, alcohol-water mixtures, ethers, alkanes, halohydrocarbons, esters, ketones, aromatic hydrocarbons, acetonitrile, N,N-dimethyl formamide (DMF), N-methylpyrolidone (NMP), or a combination thereof. Such as methanol, ethanol, n-propanol, i-propanol, n-butanol, i-butanol, tert-butanol, trifluoroethanol, a ethanol-water mixture at a volume ratio of 50:50, petroleum ether, n-pentane, n-hexane, n-heptane, cyclohexane, DMF, tetrahydrofuran, ethyl ether, isopropyl ether, dioxane, methyl tertiary butyl ether (MTBE), 1,2-dimethoxylethane, NMP, 2-methoxyethanol, 1,2-dimethoxyethane, diethylene glycol dimethyl ether, triethylene glycol dimethyl ether, dichloromethane, 1,2-dichloroethane, chloroform, tetrachloromethane, ethyl acetate, isopropyl acetate, acetone, butanone, benzene, toluene, xylene or a combination thereof.

Any temperature is included in the present invention so long as it is applicable for the one-pot reaction. Additionally, many similar modifications in the art, substitutions to same object, or temperature and temperature scope which are equivalent to those described in the invention, all are deemed to be included in the present invention. In some embodiments, the one-pot reaction temperature is from approximately room temperature (usually 25° C.) to 154° C. The reaction is carried out at a low temperature at the beginning or at the earlier stage, after rising of the temperature, the reaction is carried out at a higher temperature, which may be from approximately 25° C. to solvent boiling point, from approximately 30° C. to solvent boiling point, from approximately 25° C. to 154° C., or from approximately 30° C. to 154° C.

Any temperature is included in the present invention so long as it is applicable for the cooling after one-pot reaction. Additionally, many similar modifications in the art, substitutions to same object, or temperature and temperature scope which are equivalent to those described in the invention, all are deemed to be included in the present invention. In some embodiments, the cooling temperature is approximately from −80° C. to 60° C. After the one-pot reaction is complete, the reaction mixture cooling is carried out at a higher temperature, may be from solvent boiling point to 60° C., from solvent boiling point to 40° C., from solvent boiling point to 30° C., from solvent boiling point to 25° C., from solvent boiling point to 0° C., from solvent boiling point to −10° C., from solvent boiling point to −15° C., from solvent boiling point to −20° C., from solvent boiling point to −40° C., from solvent boiling point to −50° C., or solvent boiling point to −80° C., and may be from approximately 60° C. to −20° C., from approximately 50° C. to −20° C., from approximately 40° C. to 10° C., from approximately 30° C. to 10° C., or from approximately room temperature (usually 25° C.) to 10° C. The reaction mixture cooling at the later stage is carried out at a lower temperature, may be from approximately −80° C. to approximately 10° C., from approximately −60° C. to approximately 10° C., from approximately −40° C. to approximately 10° C., from approximately −20° C. to approximately 10° C., or from approximately −10° C. to approximately 10° C., from approximately 0° C. to approximately 10° C.

Any temperature is included in the present invention so long as it can applicable for the crystallization process of recrystallization. Additionally, many similar modifications in the art, substitutions to same object, or temperature and temperature scope which are equivalent to those described in the invention, all are deemed to be included in the present invention. In some embodiments, the crystallization temperature is approximately from −80° C. to 60° C. After all the crude product is dissolved completely, the crystallization is at a higher temperature, may be from solvent boiling point to 60° C., from solvent boiling point to 50° C., from solvent boiling point to 40° C., from solvent boiling point to 30° C., from solvent boiling point to 25° C., from solvent boiling point to 0° C., from solvent boiling point to −10° C., from solvent boiling point to −15° C., from solvent boiling point to −20° C., from solvent boiling point to −30° C., from solvent boiling point to −40° C., from solvent boiling point to −50° C., or solvent boiling point to −80° C., and may be from approximately 60° C. to −20° C., from approximately 50° C. to −20° C., from approximately 40° C. to 10° C., from approximately 30° C. to 10° C., or from approximately room temperature (usually 25° C.) to 10° C. The crystallization at the later stage is at a lower temperature, may be from approximately −80° C. to approximately 10° C., from approximately −60° C. to approximately 10° C., from approximately −40° C. to approximately 10° C., from approximately −20° C. to approximately 10° C., from approximately −10° C. to approximately 10° C., or from approximately 0° C. to approximately 10° C.

Any halogenating agent is included in the present invention so long as it is applicable for the halogenating reaction. For example, N-bromosuccinimide (NBS), N-chlorosuccinimide (NCS), N-iodosuccinimide (NIS), 1,3-dibromo-5,5-dimethylhydantoin, 1,3-dichloro-5,5-dimethylhydantoin, iodomethane, etc, or a combination thereof.

The base used in the present invention may be an organic base or inorganic base. The organic base may be triethylamine, trimethylamine, N,N-diisopropylethylamine, N-methylmorpholine, N-methylpiperidine or a combination thereof; and can also be a base formed by reacting an organic solvent with an alkali metal. The alkali metal comprises lithium, sodium and potassium, or a combination thereof.

The organic solvent can be one or more alcohols, or a combination thereof. The alcohols include, but are not limited to, methanol, ethanol, propanol, i-propanol, n-butanol, i-butanol, tert-butanol and a combination thereof. The inorganic bases include, but are not limited to, alkali metal hydroxide, alkaline earth metal hydroxide, alkali metal alkoxide, alkaline earth metal alkoxide, alkali metal carbonate, alkaline earth metal carbonate and ammonia. In some embodiments, the inorganic base is ammonia, sodium hydroxide, calcium hydroxide, magnesium hydroxide, potassium hydroxide, lithium hydroxide, sodium carbonate, potassium carbonate, lithium carbonate, sodium tert-butoxide, sodium isopropoxide or potassium tert-butoxide.

After the reaction proceeds to a certain extent in the present invention, such as the raw material is consumed more than 20%, more than 30%, more than 40%, more than 50%, more than 70%, more than 80%, more than 90%, more than 95%, or completely by monitoring, the reaction mixture is worked up, such as cooled, collected, drawn, filtered, separated, purified or a combination thereof. The reaction can be monitored by conventional method such as thin-layer chromatography (TLC), high performance liquid chromatography (HPLC), gas chromatography (GC), and the like. The reaction mixture can be worked up by conventional method, for example, the crude product can be collected by concentrating the reaction mixture through vacuum evaporation or conventional distillation and which is used directly in the next operation; or the crude product can be obtained by filtration of the reaction mixture and which is used directly in the next operation; or the crude product can be get by pouring the supernatant liquid of the reaction mixture after standing for a while and which is used directly in the next operation. And the reaction mixture can be purified by suitable methods such as extraction, distillation, crystallization, column chromatography, washing, trituration with suitable organic solvents or a combination thereof.

Unless otherwise stated, structures depicted herein are also meant to include all isomeric (e.g., enantiomeric, diastereomeric, and geometric (or conformeric)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformeric) mixtures of the present compounds are within the scope disclosed herein.

Stereochemical definitions and conventions used herein generally follow Parker et al., *McGraw-Hill Dictionary of Chemical Terms* (1984) McGraw-Hill Book Company, New York and Eliel et al., *Stereochemistry of Organic Compounds*, John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer is referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. If tautomerism could happen (such as in a solvent), the chemical balance between tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. The specific example of keto-enol tautomerisms is hexane-2,4-dione and 4-hydroxyhex-3-en-2-one tautomerism. Another example of tautomerisms is phenol-keto tautomerism. The specific example of phenol-keto tautomerisms is pyridin-4-ol and pyridin-4(3H)-one tautomerism. Unless otherwise stated, all tautomers of the present compounds are within the scope disclosed herein.

General Synthetic Procedures

In the present invention, if the chemical name of the compound doesn't match the corresponding structure, the compound is characterized by the corresponding structure.

Generally, the compounds of Formula (I), Formula (Ia), Formula (I-1), Formula (Ia-1), Formula (I-2) or Formula (Ia-2) disclosed herein may be prepared by methods described herein, wherein the substituents are as defined in Formula (I), Formula (Ia), Formula (I-1), Formula (Ia-1), Formula (I-2) or Formula (Ia-2), except where further noted. The following examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius (° C.). Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Column chromatography was conducted using a silica gel column. Silica gel (200-300 mesh) was purchased from Qingdao Ocean Chemical Factory. 1H NMR spectra were recorded by a Bruker Avance 400 MHz spectrometer or Bruker Avance III HD 600 spectrometer, using $CDCl_3$, $DMSO\text{-}d_6$, $CD_3OD$ or acetone-$d_6$ (reported in ppm) as solvent, and using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets), ddd (doublet of doublet of doublets), ddt (doublet of doublet of triplets), dddd (doublet of doublet of doublet of doublets), td (triplet of doublets), brs (broadened singlet). Coupling constants, when given, are reported in Hertz (Hz).

Low-resolution mass spectral (MS) data were also determined on an Agilent 6320 series LC-MS spectrometer equipped with G1312A binary pumps, a G1316A TCC (Temperature Control of Column, maintained at 30° C.), a G1329A autosampler and a G1315B DAD detector were used in the analysis. An ESI source was used on the LC-MS spectrometer.

Low-resolution mass spectral (MS) data were also determined on an Agilent 6120 series LC-MS spectrometer equipped with G1312A binary pumps, a G1316A TCC (Temperature Control of Column, maintained at 30° C.), a G1329A autosampler and a G1315B DAD detector were used in the analysis. An ESI source was used on the LC-MS spectrometer.

Both LC-MS spectrometers were equipped with an Agilent Zorbax SB-C18, 2.1×30 mm, 5 μm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient condition is shown in Table 1:

TABLE 1

The gradient condition of the mobile phase in Low-resolution mass spectrum analysis

| Time (min) | A (CH$_3$CN, 0.1% HCOOH) | B (H$_2$O, 0.1% HCOOH) |
| --- | --- | --- |
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micron, 10 min, 0.6 mL/min flow rate, 5 to 95% (0.1% formic acid in CH$_3$CN) in (0.1% formic acid in H$_2$O). Column was operated at 40° C.

The following abbreviations are used throughout the specification:
CDCl$_3$ chloroform-d
DMF-d$_6$ N,N-dimethylformamide-d$_6$
DMSO-d$_6$ dimethyl sulfoxide-d$_6$
Acetone-d$_6$ acetone-d$_6$
D$_2$O water-d$_2$
EA, EtOAc ethyl acetate
DMF N,N-dimethylformamide
THF tetrahydrofuran
NMP N-methylpyrrolidone
MeCN, CH$_3$CN acetonitrile
DCM, CH$_2$Cl$_2$ dichloromethane
CHCl$_3$ chloroform
CCl$_4$ tetrachloromethane
PE petroleum ether
CH$_3$OH, MeOH methanol
g gram
c concentration
mol mole
mmol millimole
h hour, hours
min minute, minutes
mL milliliter
v/v. v:v the ratio of volume
DMSO dimethyl sulfoxide
NBS N-bromosuccinimide
NCS N-chlorosuccinimide
NIS N-iodosuccinimide

EXAMPLES

The preparation methods of optically pure dihydropyrimidine compounds disclosed in the examples of the present invention. Skilled in the art can learn from this article to properly improve the process parameters to implement the preparation method. Of particular note is that all similar substitutions and modifications to the skilled person are obvious, and they are deemed to be included in the present invention. The methods disclosed herein were described in the preferred examples. Related person can clearly realize and apply the techniques disclosed herein by making some changes, appropriate alterations or combinations to the methods without departing from spirit, principles and scope of the present disclosure.

In order to further understand the invention, it is detailed below through examples.

Example

Example 1: The Preparation of (R)-ethyl 4-(2-bromo-4-fluorophenyl)-6-(morpholinomethyl)-2-(thiazol-2-yl)-1,4-dihydropyrimidine-5-carboxylate

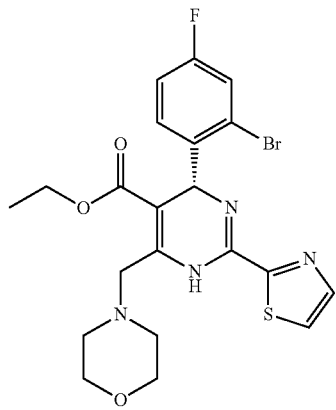

Step 1) (R)-1-ethoxy-1-oxopropan-2-yl 3-oxobutanoate

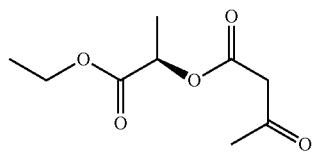

A flask was charged with (D)-ethyl 2-hydroxypropanoate (11.8 g, 10 mmol) and 2,2,6-trimethyl-4H-1,3-dioxin-4-one (14.2 g, 10 mmol) in turn, and then equipped with distillation apparatus or water segregator. The mixture was stirred at 120° C. for 4 hours. After the reaction, the mixture was cooled and concentrated to obtain the title compound as puce liquid (12.9 g, 64%).

MS (ESI, pos.ion) m/z: 203.1 [M+H]$^+$;

Step 2) (R)-(R)-1-ethoxy-1-oxopropan-2-yl 4-(2-bromo-4-fluorophenyl)-6-methyl-2-(thiazol-2-yl)-1,4-dihydropyrimidine-5-carboxylate

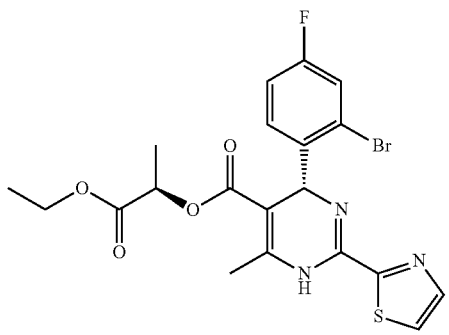

Method One:

To a flask were added 2-thiazolecarboxamidine hydrochloride (16.4 g, 0.1 mol), 2-bromo-4-fluorobenzaldehyde (20.3 g, 0.1 mol), (R)-1-ethoxy-1-oxopropan-2-yl 3-oxobutanoate (20.2 g, 0.1 mol), anhydrous sodium acetate (8.2 g, 0.1 mol) and ethanol (74 g) in turn. The mixture was stirred at 78° C. for 16 hours. After the reaction, the mixture was cooled to 30° C., kept at 30° C. and stirred for 6 hours. The resulting mixture was filtered. The filter cake was washed with water (330 mL) and dried in vacuo at 60° C. for 8 hours to obtain the crude product. To the crude product was added n-propanol (74 g). The mixture was heated until dissolved completely, cooled to 25° C., and then kept at 25° C., stirred and crystallized for 5 hours. The resulting mixture was filtered. The filter cake was dried in vacuo at 60° C. for 8 hours to obtain the product as a yellow solid (13.4 g, 27%).

$[\alpha]_D^{25}$=−122.46 (c=0.3054 g/100 mL, MeOH);

MS (ESI, pos.ion) m/z: 497.7 $[M+H]^+$;

$^1$H NMR (400 MHz, DMSO-$d_6$): δ 10.02 (s, 1H), 7.97 (d, 1H), 7.89 (d, 1H), 7.54 (dd, 1H), 7.36 (dd, 1H), 7.23 (td, 1H), 6.00 (s, 1H), 4.82 (q, 1H), 4.14-4.01 (m, 2H), 2.47 (s, 3H), 1.22 (d, 3H), 1.13 (t, 3H).

The compound 5 can be prepared under the reaction conditions shown in table 2 by using method one described in step 2 of Example 1.

TABLE 2

The reaction conditions

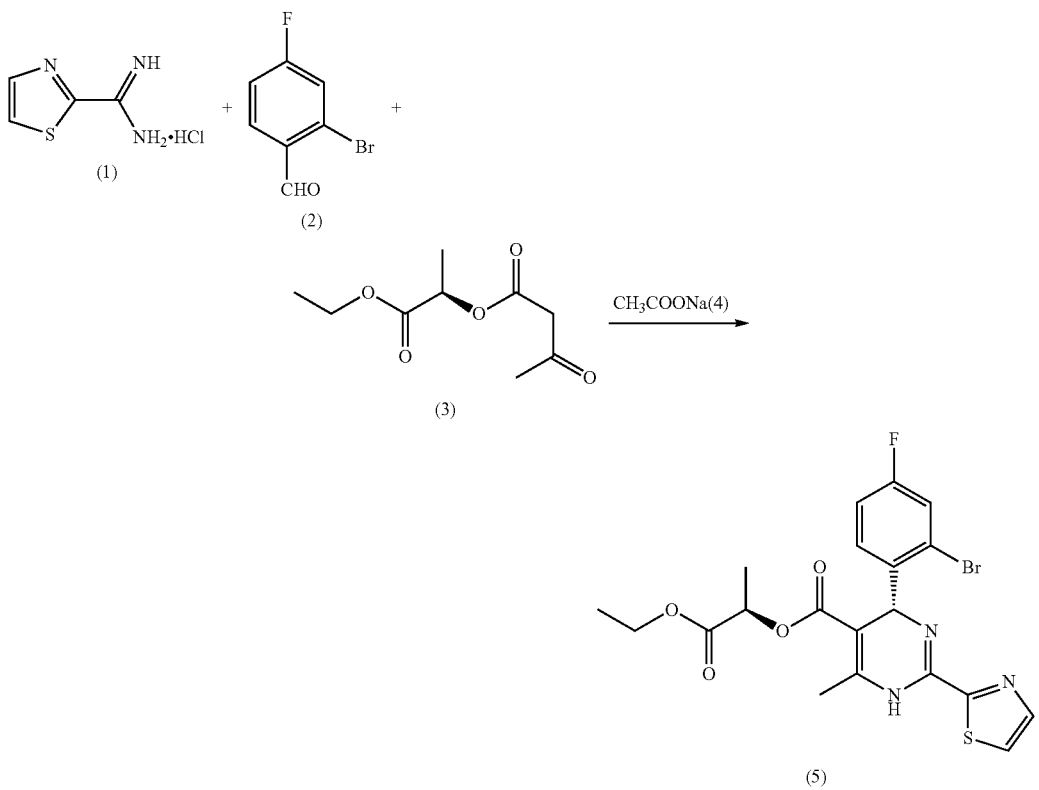

| No. | (1):(2):(3):(4) (mol); the amount of compound (1) is 16.4 g | Reaction solvent | The mass ratio of reaction solvent to compound (1) | Reaction temperature (° C.) | Reaction time (h) | Cooling temperature (° C.) | Cooling time (h) | Recrystallization solvent | The mass ratio of recrystallization solvent to compound (1) | Crystallization temperature (° C.) | Crystallization time (h) | Quality; yield (5) of product |
|---|---|---|---|---|---|---|---|---|---|---|---|---|
| 1 | 1:1:2:1 | — | — | 78 | 12 | 40 | 6 | ethanol | 20 | 0 | 3 | 8.8 g; 17.8 |

TABLE 2-continued

The reaction conditions

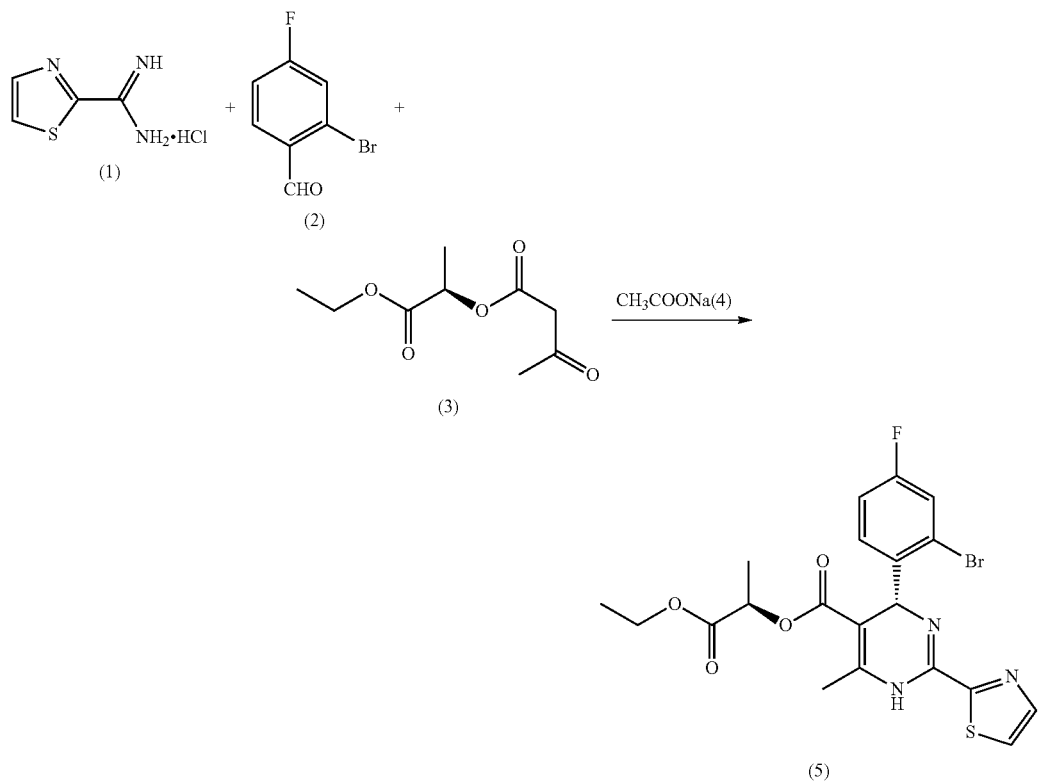

| No. | (1):(2): (3):(4) (mol); the amount of compound (1) is 16.4 g | Reaction solvent | The mass ratio of reaction solvent to compound (1) | Reaction temperature (° C.) | Reaction time (h) | Cooling temperature (° C.) | Cooling time (h) | Recrystallization solvent | The mass ratio of recrystallization solvent to compound (1) | Crystallization temperature (° C.) | Crystallization time (h) | Quality; yield (5) of product |
|---|---|---|---|---|---|---|---|---|---|---|---|---|
| 2 | 1:1:1:1 | ethanol | 1 | 78 | 12 | 40 | 8 | ethanol | 15 | 10 | 6 | 9.6 g; 19.4 |
| 3 | 1:1:1:1 | ethanol | 4.5 | 25 | 72 | 25 | — | ethanol | 4.5 | 5 | 2 | 7.5 g; 15.2 |
| 4 | 1:1:1:1 | ethanol | 4.5 | 78 | 12 | 25 | 6 | ethanol | 3 | 25 | 1 | 12.9 g; 26.1 |
| 5 | 1:1:1:1 | ethanol | 20 | 60 | 24 | −20 | 12 | ethanol | 4.5 | 25 | 6 | 10.1 g; 20.3 |
| 6 | 1:1:1:1 | ethanol | 80 | 78 | 12 | −30 | 24 | ethanol | 5 | 25 | 4 | 7.5 g; 15.1 |
| 7 | 1:1:1:1 | DMF | 4.5 | 154 | 1 | −30 | 6 | n-propanol | 4 | 10 | 4 | 5.9 g; 11.9 |
| 8 | 1:1:1:1 | n-butanol | 5 | 100 | 5 | 0 | 6 | n-butanol | 4 | 25 | 6 | 11.2 g; 22.5 |
| 9 | 1:1:1:1 | n-propanol | 4.5 | 80 | 12 | 25 | 6 | n-propanol | 3.5 | 40 | 10 | 12.4 g; 25.1 |
| 10 | 1:1:1:1 | i-propanol | 4.5 | 82 | 12 | 25 | 1 | i-propanol | 5 | 25 | 4 | 9.6 g; 19.3 |
| 11 | 1:1:1:1 | t-butanol | 4.5 | 82 | 12 | 30 | 12 | i-propanol | 4.5 | 25 | 6 | 10.6 g; 21.4 |
| 12 | 1:1:1:1 | 2-methoxyethanol | 4.5 | 78 | 12 | −10 | 12 | t-propanol | 5 | 25 | 4 | 10.1 g; 20.3 |
| 13 | 1:1:1:1 | 1,2-dimethoxyethane | 4.5 | 78 | 12 | −10 | 12 | n-propanol | 5 | 25 | 4 | 5.9 g; 11.8 |
| 14 | 1:1:1:1 | ethyl acetate | 3 | 77 | 12 | −10 | 12 | t-propanol | 4.5 | 25 | 4 | 7.6 g; 15.4 |

TABLE 2-continued

The reaction conditions

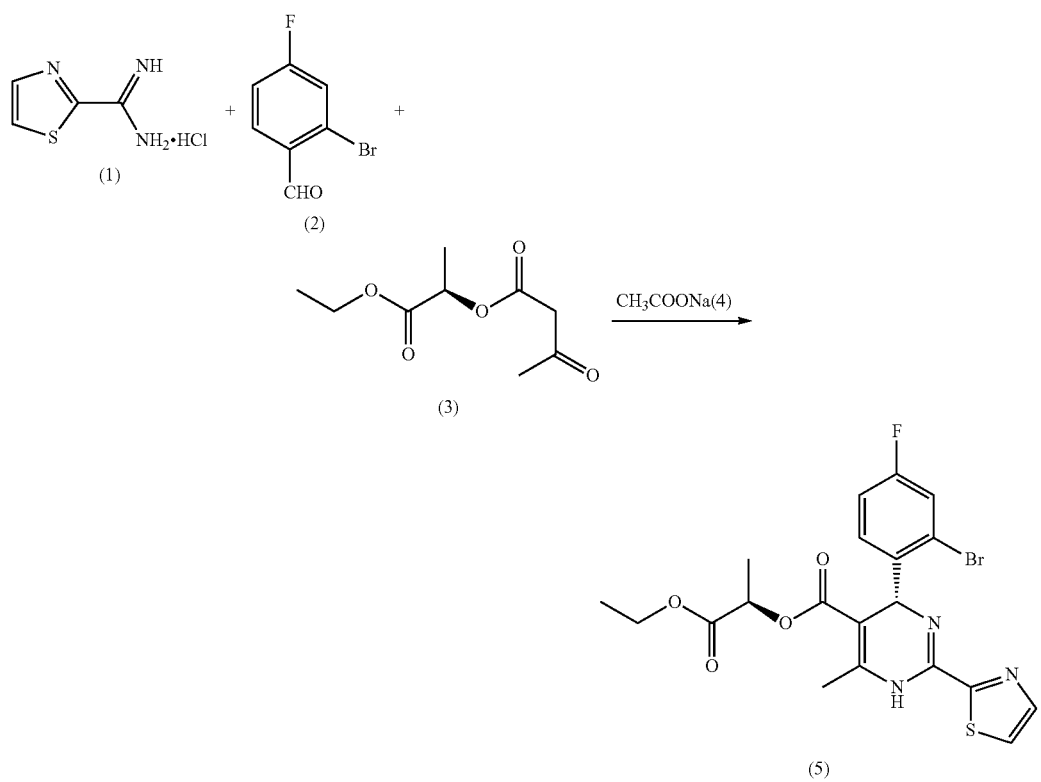

| No. | (1):(2):(3):(4) (mol); the amount of compound (1) is 16.4 g | Reaction solvent | The mass ratio of reaction solvent to compound (1) | Reaction temperature (° C.) | Reaction time (h) | Cooling temperature (° C.) | Cooling time (h) | Recrystallization solvent | The mass ratio of recrystallization solvent to compound (1) | Crystallization temperature (° C.) | Crystallization time (h) | Quality; yield (5) of product |
|---|---|---|---|---|---|---|---|---|---|---|---|---|
| 15 | 1:1:1:1 | acetone | 3 | 56 | 12 | −20 | 12 | t-propanol | 5 | 25 | 4 | 4.2 g; 8.5 |
| 16 | 1:1:1:1 | methanol | 3 | 64 | 12 | 0 | 6 | n-propanol | 5 | 25 | 4 | 7.8 g; 15.8 |
| 17 | 1:1:1:1 | 2-methoxy-ethyl ether | 5 | 78 | 6 | −20 | 12 | n-propanol | 5 | 25 | 6 | 4.8 g; 9.7 |
| 18 | 1:1:1:1 | ethanol | 10 | 78 | 12 | −20 | 12 | ethanol | 4.5 | 30 | 6 | 11.6 g; 23.3 |
| 19 | 1:1:1:1 | ethyl acetate | 3 | 77 | 12 | −10 | 12 | ethyl acetate | 2 | −10 | 4 | 5.7 g; 11.4 |
| 20 | 1:1:1:1 | ethanol | 2 | 78 | 12 | 40 | 8 | ethanol | 15 | 10 | 6 | 9.9 g; 19.9 |
| 21 | 1:1:1:1 | ethanol | 1 | 78 | 12 | 40 | 8 | ethanol | 10 | 10 | 6 | 10.3 g; 20.7 |

Method Two:

To a flask were added 2-thiazolecarboxamidine hydrochloride (16.4 g, 0.1 mol), 2-bromo-4-fluorobenzaldehyde (20.3 g, 0.1 mol), (R)-1-ethoxy-1-oxopropan-2-yl 3-oxobutanoate (20.2 g, 0.1 mol), anhydrous sodium acetate (8.2 g, 0.1 mol) and ethanol (74 g) in turn. The mixture was stirred at 78° C. for 16 hours. After the reaction, the reaction mixture was cooled to 30° C., kept at 30° C. and stirred for 6 hours. The mixture was filtered. The filtrate was washed with ethanol (50 g) and water (330 mL) in turn, and then dried in vacuo at 60° C. for 8 hours to obtain the product as a yellow solid (14.4 g, 29%).

$[\alpha]_D^{25}$=122.46 (c=0.3054 g/100 mL, MeOH);

MS (ESI, pos.ion) m/z: 497.7 [M+H]$^+$;

$^1$H NMR (400 MHz, DMSO-d$_6$): δ 10.02 (s, 1H), 7.97 (d, 1H), 7.89 (d, 1H), 7.54 (dd, 1H), 7.36 (dd, 1H), 7.23 (td, 1H), 6.00 (s, 1H), 4.82 (q, 1H), 4.14-4.01 (m, 2H), 2.47 (s, 3H), 1.22 (d, 3H), 1.13 (t, 3H).

The compound 5 can be prepared under the reaction conditions shown in table 3 by using method two described in step 2 of Example 1.

TABLE 3

The reaction conditions

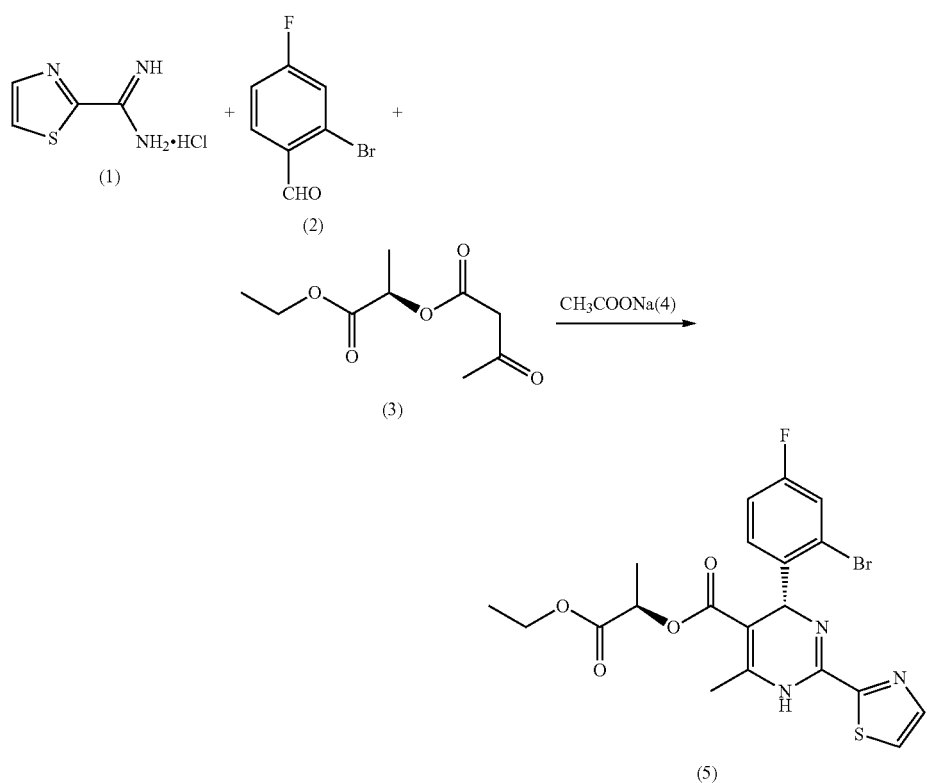

| No. | (1):(2) (3):(4) (mol); the amount of compound (1) is 16.4 g | Reaction solvent | The mass ratio of reaction solvent to compound (1) | Reaction temperature (° C.) | Reaction time (h) | Cooling temperature (° C.) | Cooling time (h) | Washing solvent | The mass ratio of washing solvent to compound (1) | Washing temperature (° C.) | Quality; yield (%) of product |
|---|---|---|---|---|---|---|---|---|---|---|---|
| 1 | 1:1:2:1 | — | — | 78 | 12 | 40 | 6 | ethanol | 15 | 25 | 9.5 g; 19.2 |
| 2 | 1:1:1:1 | ethanol | 1 | 78 | 12 | 40 | 6 | ethanol | 10 | 25 | 10.3 g; 20.8 |
| 3 | 1:1:1:1 | ethanol | 4.5 | 25 | 72 | 25 | — | ethanol | 3 | 25 | 8.5 g; 17.1 |
| 4 | 1:1:1:1 | ethanol | 4.5 | 78 | 12 | 25 | 6 | ethanol | 3.5 | 25 | 13.7 g; 27.6 |
| 5 | 1:1:1:1 | ethanol | 20 | 60 | 24 | −10 | 6 | ethanol | 4.5 | 25 | 11.1 g; 22.4 |
| 6 | 1:1:1:1 | ethanol | 80 | 78 | 12 | −30 | 12 | ethanol | 5 | 25 | 8.4 g; 16.9 |
| 7 | 1:1:1:1 | ethanol | 8 | 78 | 12 | 25 | 6 | — | — | — | 13.1 g; 26.5 |
| 8 | 1:1:1:1 | DMF | 4.5 | 154 | 1 | −30 | 6 | ethanol | 4 | 25 | 6.6 g; 13.3 |
| 9 | 1:1:1:1 | n-butanol | 5 | 100 | 5 | 0 | 6 | n-butanol | 2 | 25 | 12.3 g; 24.7 |
| 10 | 1:1:1:1 | n-propanol | 4.5 | 80 | 12 | 25 | 6 | n-propanol | 3 | 25 | 14.2 g; 28.6 |
| 11 | 1:1:1:1 | i-propanol | 4.5 | 82 | 12 | 25 | 1 | t-propanol | 3 | 25 | 10.7 g; 21.5 |
| 12 | 1:1:1:1 | t-butanol | 4.5 | 82 | 12 | 30 | 12 | t-butanol | 3 | 30 | 11.7 g; 23.6 |
| 13 | 1:1:1:1 | 2-methoxy ethanol | 4.5 | 78 | 12 | −10 | 12 | 2-methoxy-ethanol | 1 | 0 | 10.9 g; 21.9 |
| 14 | 1:1:1:1 | 1,2-dimethoxyethane | 4.5 | 78 | 12 | −10 | 12 | n-propanol | 3 | 25 | 6.6 g; 13.4 |

TABLE 3-continued

The reaction conditions

[Structures shown:
(1) 2-thiazolecarboxamidine hydrochloride
(2) 2-bromo-4-fluorobenzaldehyde
(3) (R)-1-ethoxy-1-oxopropan-2-yl 3-oxobutanoate
+ CH₃COONa (4) →
(5) Product: ethyl (R)-2-((4-(2-bromo-4-fluorophenyl)-6-methyl-2-(thiazol-2-yl)-1,4-dihydropyrimidine-5-carbonyl)oxy)propanoate]

| No. | (1):(2) (3):(4) (mol); the amount of compound (1) is 16.4 g | Reaction solvent | The mass ratio of reaction solvent to compound (1) | Reaction temperature (° C.) | Reaction time (h) | Cooling temperature (° C.) | Cooling time (h) | Washing solvent | The mass ratio of washing solvent to compound (1) | Washing temperature (° C.) | Quality; yield (%) of product |
|---|---|---|---|---|---|---|---|---|---|---|---|
| 15 | 1:1:1:1 | ethyl acetate | 3 | 77 | 12 | −10 | 12 | i-propanol | 3.5 | 25 | 8.33 g; 16.8 |
| 16 | 1:1:1:1 | acetone | 3 | 56 | 12 | −20 | 12 | t-propanol | 3 | 25 | 5.3 g; 10.6 |
| 17 | 1:1:1:1 | methanol | 3 | 64 | 12 | 0 | 6 | n-propanol | 2 | 25 | 8.8 g; 17.7 |
| 18 | 1:1:1:1 | 2-methoxy ethyl ether | 5 | 78 | 6 | −20 | 12 | n-propanol | 2 | 25 | 5.6 g; 11.3 |
| 19 | 1:1:1:1 | n-propanol | 4.5 | 80 | 12 | 25 | 6 | t-propanol | 20 | 0 | 10.4 g; 20.9 |

Method Three:

To a flask were added 2-thiazolecarboxamidine hydrochloride (16.4 g, 0.1 mol), 2-bromo-4-fluorobenzaldehyde (20.3 g, 0.1 mol), (R)-1-ethoxy-1-oxopropan-2-yl 3-oxobutanoate (20.2 g, 0.1 mol), anhydrous sodium acetate (8.2 g, 0.1 mol) and ethanol (74 g) in turn. The mixture was stirred at 78° C. for 16 hours. After the reaction, the mixture was cooled to 30° C., kept at 30° C. and stirred for 6 hours. The resulting mixture was filtered. The filter cake was washed with water (330 mL) and dried in vacuo at 60° C. for 8 hours to obtain the crude product. The crude product was triturated with n-propanol (50 g) at 30° C. for 5 hours and filtered. The filter cake was washed with n-propanol (12.8 g) and dried in vacuo at 60° C. for 8 hours to obtain the product as a yellow solid (13.9 g, 28%).

$[\alpha]_D^{25}=122.46$ (c=0.3054 g/100 mL, MeOH);

MS (ESI, pos.ion) m/z: 497.7 [M+H]$^+$;

$^1$H NMR (400 MHz, DMSO-d$_6$): δ 10.02 (s, 1H), 7.97 (d, 1H), 7.89 (d, 1H), 7.54 (dd, 1H), 7.36 (dd, 1H), 7.23 (td, 1H), 6.00 (s, 1H), 4.82 (q, 1H), 4.14-4.01 (m, 2H), 2.47 (s, 3H), 1.22 (d, 3H), 1.13 (t, 3H).

The compound 5 can be prepared under the reaction conditions shown in table 4 by using method three described in step 2 of Example 1.

TABLE 4

The reaction conditions

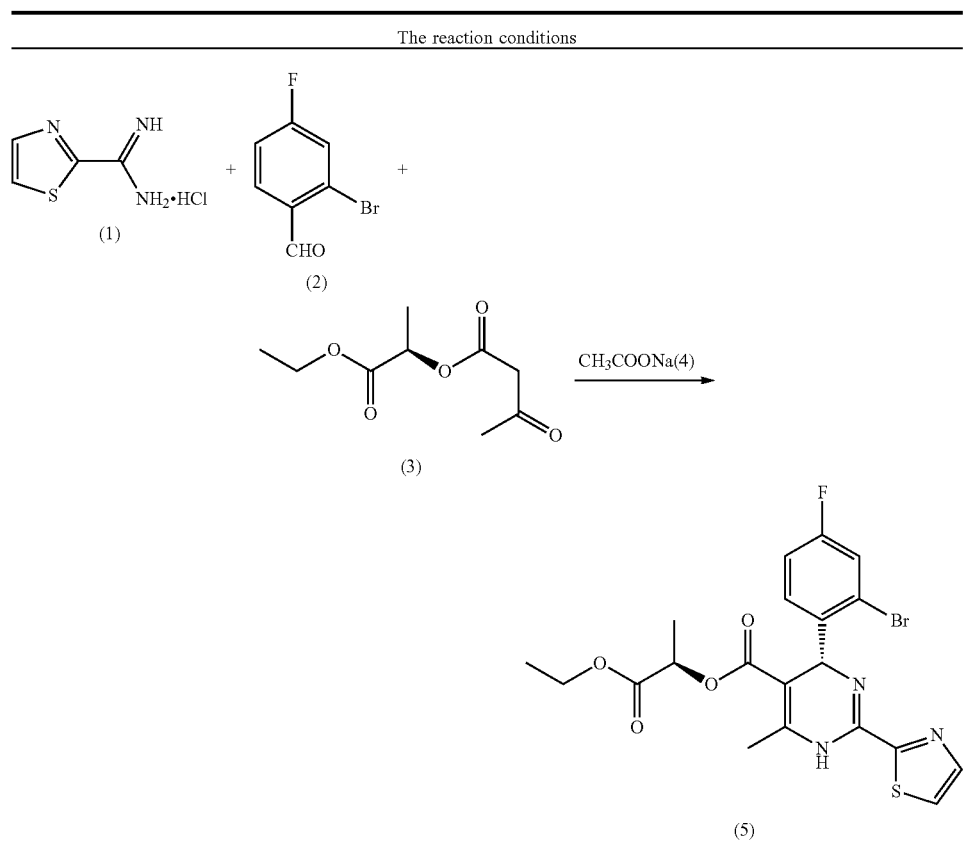

| No. | (1):(2) (3):(4) (mol); the amount of compound (1) is 16.4 g | Reaction solvent | The mass ratio of reaction solvent to compound (1) | Reaction temperature (° C.) | Reaction time (h) | Cooling temperature (° C.) | Cooling time (h) | Trituration solvent | The mass ratio of trituration solvent to compound (1) | Trituration temperature (° C.) | Trituration on time (h) | Quality; yield (%) of product |
|---|---|---|---|---|---|---|---|---|---|---|---|---|
| 1 | 1:1:2:1 | — | — | 78 | 12 | 40 | 6 | ethanol | 13 | 25 | 10 | 9.2 g; 18.6 |
| 2 | 1:1:1:1 | ethanol | 1 | 78 | 12 | 40 | 6 | ethanol | 9 | 25 | 5 | 10 g; 20.2 |
| 3 | 1:1:1:1 | ethanol | 4.5 | 25 | 72 | 25 | — | ethanol | 3 | 25 | 4 | 8.2 g; 16.5 |
| 4 | 1:1:1:1 | ethanol | 4.5 | 78 | 12 | 25 | 6 | ethanol | 6 | 5 | 2 | 13.3 g; 26.8 |
| 5 | 1:1:1:1 | ethanol | 20 | 60 | 24 | −20 | 12 | ethanol | 4 | 25 | 1 | 10.7 g; 21.5 |
| 6 | 1:1:1:1 | ethanol | 80 | 78 | 12 | −30 | 24 | ethanol | 4 | 25 | 5 | 7.9 g; 15.9 |
| 7 | 1:1:1:1 | DMF | 4.5 | 154 | 1 | −30 | 6 | n-propanol | 3.5 | 25 | 6 | 6.3 g; 12.7 |
| 8 | 1:1:1:1 | n-butanol | 5 | 100 | 5 | 0 | 6 | n-butanol | 3.5 | 25 | 4 | 11.6 g; 23.4 |
| 9 | 1:1:1:1 | n-propanol | 4.5 | 80 | 12 | 25 | 6 | n-propanol | 3 | 40 | 8 | 13.7 g; 27.7 |
| 10 | 1:1:1:1 | i-propanol | 4.5 | 82 | 12 | 25 | 1 | i-propanol | 4 | 25 | 3 | 10.1 g; 20.4 |
| 11 | 1:1:1:1 | t-butanol | 4.5 | 82 | 12 | 30 | 12 | i-propanol | 4 | 30 | 5 | 11.2 g; 22.5 |
| 12 | 1:1:1:1 | 2-methoxy ethanol | 4.5 | 78 | 12 | −10 | 12 | i-propanol | 4 | 25 | 5 | 10.5 g; 21.1 |
| 13 | 1:1:1:1 | 1,2-dimethoxyethane | 4.5 | 78 | 12 | −10 | 12 | n-propanol | 3.5 | 25 | 3 | 6.3 g; 12.7 |

TABLE 4-continued

The reaction conditions

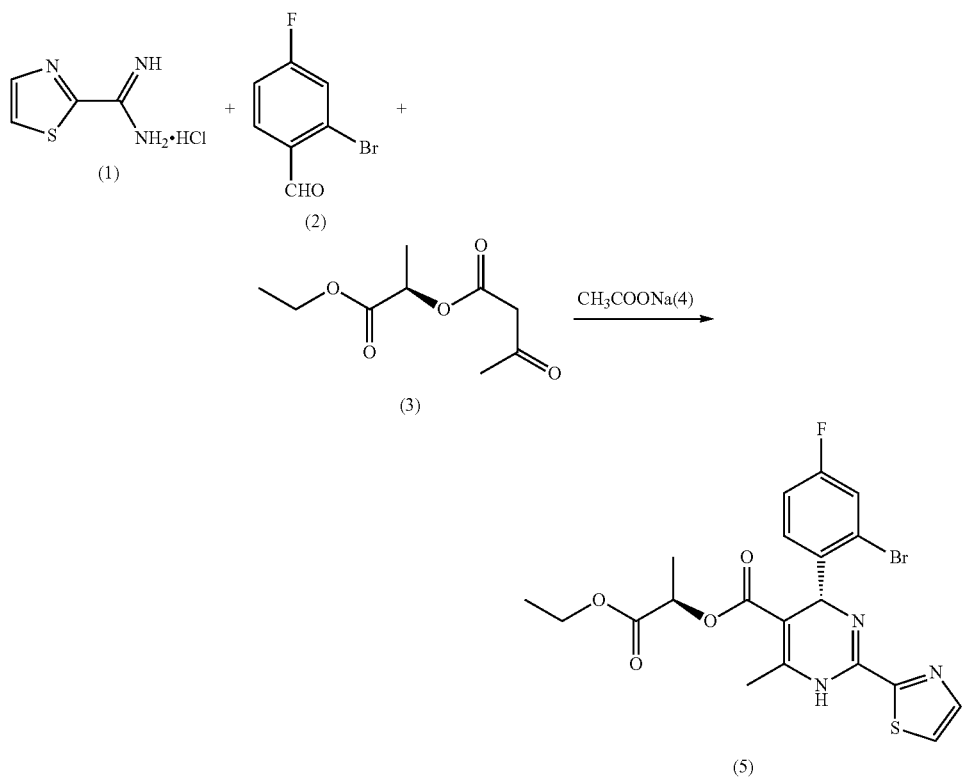

| No. | (1):(2)(3):(4) (mol); the amount of compound (1) is 16.4 g | Reaction solvent | The mass ratio of reaction solvent to compound (1) | Reaction temperature (° C.) | Reaction time (h) | Cooling temperature (° C.) | Cooling time (h) | Trituration solvent | The mass ratio of trituration solvent to compound (1) | Trituration temperature (° C.) | Trituration time (h) | Quality; yield (%) of product |
|---|---|---|---|---|---|---|---|---|---|---|---|---|
| 14 | 1:1:1:1 | ethyl acetate | 3 | 77 | 12 | −10 | 12 | i-propanol | 4 | 25 | 4 | 8 g; 16.2 |
| 15 | 1:1:1:1 | acetone | 3 | 56 | 12 | −20 | 12 | i-propanol | 4 | 25 | 6 | 4.7 g; 9.4 |
| 16 | 1:1:1:1 | methanol | 3 | 64 | 12 | 0 | 6 | n-propanol | 3.5 | 25 | 3 | 8.2 g; 16.5 |
| 17 | 1:1:1:1 | 2-methoxy ethyl ether | 5 | 78 | 6 | −20 | 12 | n-propanol | 3.5 | 25 | 3 | 5.3 g; 10.6 |
| 18 | 1:1:1:1 | ethanol | 1 | 78 | 12 | 40 | 6 | ethanol | 10 | 25 | 5 | 9.4 g; 18.8 |
| 19 | 1:1:1:1 | i-propanol | 4.5 | 82 | 12 | 25 | 1 | i-propanol | 20 | 5 | 3 | 8.9 g; 17.9 |
| 20 | 1:1:1:1 | ethyl acetate | 3 | 77 | 12 | −10 | 12 | ethyl acetate | 2 | −10 | 12 | 6.7 g; 13.5 |
| 21 | 1:1:2:1 | — | — | 78 | 12 | 40 | 6 | ethanol | 15 | 25 | 10 | 9.0 g; 18.1 |

Step 3) (R)-(R)-1-ethoxy-1-oxopropan-2-yl 4-(2-bromo-4-fluorophenyl)-6-bromomethyl-2-(thiazol-2-yl)-1,4-dihydropyrimidine-5-carboxylate

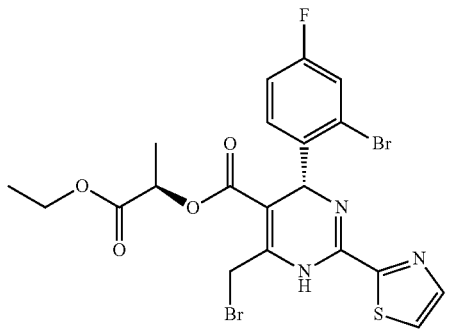

To a flask were added (R)-(R)-1-ethoxy-1-oxopropan-2-yl 4-(2-bromo-4-fluorophenyl)-6-methyl-2-(thiazol-2-yl)-1,4-dihydropyrimidine-5-carboxylate (49.6 g, 0.1 mol) and tetrachloromethane (1000 g). The mixture was heated at 76° C., NBS was added (19.6 g, 0.11 mol), and then the reaction mixture was stirred for 30 min. After the reaction, the reaction mixture was cooled and concentrated. To the residue was added ethanol (250 g). The resulting mixture was cooled to 0° C., kept at 0° C. and stirred. After the solid precipitated out completely, the mixture was filtered. The filter cake was washed with ethanol (50 g) and dried in vacuo at 60° C. for 6 hours to obtain the product as a yellow solid (37.4 g, 65%).

MS (ESI, pos.ion) m/z: 575.8 [M+H]$^+$;

$^1$H NMR (400 MHz, DMSO-d$_6$): δ 8.03 (d, 1H), 7.98 (br, 1H), 7.58 (dd, 2H), 7.43 (dd, 1H), 7.27 (td, 1H), 6.01 (s, 1H), 4.94 (q, 1H), 4.85 (br, 2H), 4.14-4.02 (m, 2H), 1.28 (d, 3H), 1.16 (t, 3H).

The compound A1 can be prepared under the reaction conditions shown in table 5 according to the procedure described in step 3 of Example 1

TABLE 5

The reaction conditions

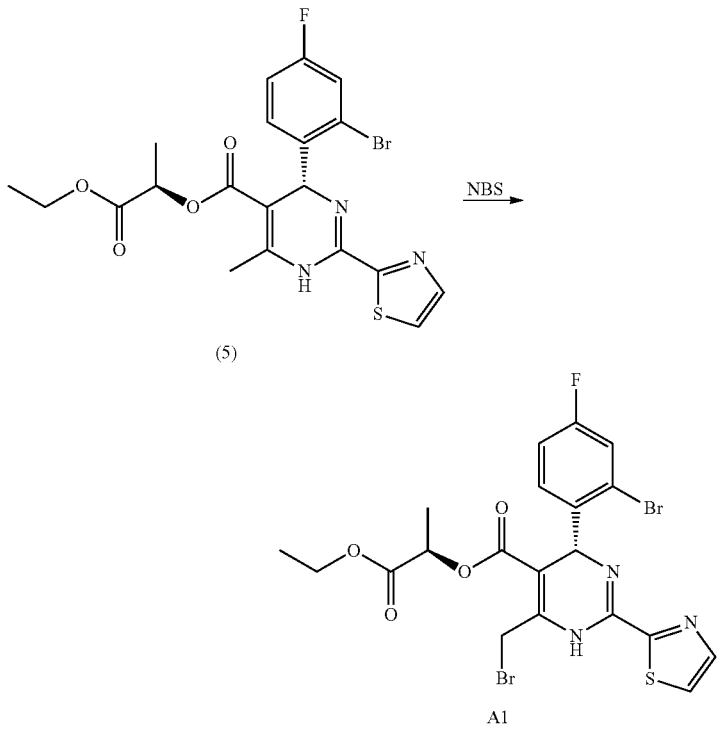

| No. | Compound (5):NBS (mol) the amount of compound (5) is 49.6 | Reaction solvent | The mass ratio of reaction solvent to compound (5) | Reaction temperature (° C.) | The solvent added to the residue | The mass ratio of the additional solvent to compound (5) | Quality; yield (%) of product |
|---|---|---|---|---|---|---|---|
| 1 | 1:1.1, | DCM | 30 | 39 | i-propanol | 7 | 41.4g;72 |
| 2 | 1:1.05, | DCM | 10 | 39 | ethanol | 5 | 38 g; 66 |
| 3 | 1:1.15, | CHCl$_3$ | 20 | 61 | n-propanol | 6 | 42 g; 73 |
| 4 | 1:1.1, | CCl$_4$ | 20 | 76 | ethanol | 5 | 43.1g;75 |

Step 4) (R)-(R)-1-ethoxy-1-oxopropan-2-yl 4-(2-bromo-4-fluorophenyl)-6-(morpholinomethyl)-2-(thiazol-2-yl)-1,4-dihydropyrimidine-5-carboxylate

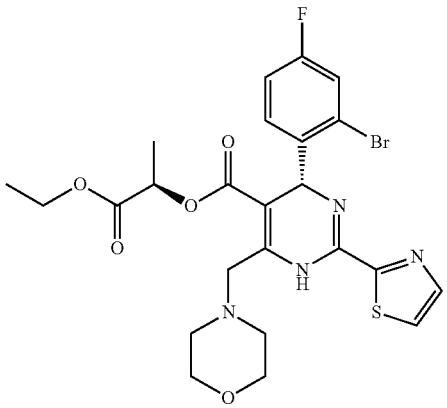 [SMILES: CCOC(=O)[C@@H](C)OC(=O)C1=C(CN2CCOCC2)NC(c2nccs2)=N[C@H]1c1ccc(F)cc1Br]

To a flask were added (R)-(R)-1-ethoxy-1-oxopropan-2-yl 4-(2-bromo-4-fluorophenyl)-6-(bromomethyl)-2-(thiazol-2-yl)-1,4-dihydropyrimidine-5-carboxylate (57.5 g, 0.1 mol), i-propanol (287 g) and morpholine (34.8 g, 0.4 mol). The mixture was stirred at 55° C. for 4 hours. After the reaction, the mixture was cooled to 0° C., kept at this temperature and stirred. After the solid precipitated out completely, the mixture was filtered. The filter cake was washed with i-propanol (58 g) followed by water (575 g), and then dried in vacuo at 60° C. for 8 hours to obtain the product as a yellowish solid (40.1 g, 69%).

MS (ESI, pos.ion) m/z: 581.2 [M+H]$^+$;
$^1$H NMR (600 MHz, DMSO-d$_6$): δ 9.98 (s, 1H), 8.03 (d, 1H), 7.96 (d, 1H), 7.56 (d, 1H), 7.42 (dd, 1H), 7.23 (td, 1H), 6.05 (s, 1H), 4.84 (q, 1H), 4.14-4.05 (m, 2H), 3.92 (dd, 2H), 3.67 (br, 4H), 2.55 (br, 4H), 1.23 (d, 3H), 1.16 (t, 3H).

Step 5) (R)-ethyl 4-(2-bromo-4-fluorophenyl)-6-(morpholinomethyl)-2-(thiazol-2-yl)-1,4-dihydropyrimidine-5-carboxylate

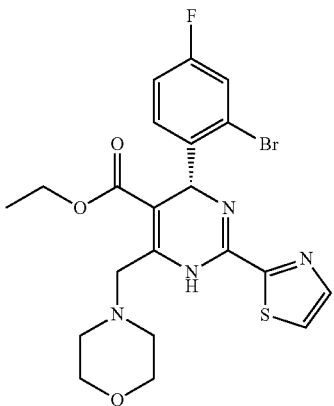

To a flask were added anhydrous ethanol (435 g) and lithium (1.74 g, 0.25 mol) in turn. The mixture was stirred at 43° C. until the lithium was consumed entirely, and then a solution of (R)-(R)-1-ethoxy-1-oxopropan-2-yl 4-(2-bromo-4-fluorophenyl)-6-(morpholinomethyl)-2-(thiazol-2-yl)-1,4-dihydropyrimidine-5-carboxylate (58.1 g, 0.1 mol) in ethanol (435 g) was added. The reaction mixture was stirred at 78° C. for 1.5 hours. After the reaction, the reaction mixture was cooled and concentrated. To the residue was added ethyl acetate (580 g). The mixture was washed with water (250 g×2). The combined organic layers were concentrated to obtain the product as a yellow solid (39.7 g, 78%).

MS (ESI, pos.ion) m/z: 509.1 [M+H]$^+$;
$^1$H NMR (600 MHz, DMSO-d$_6$): δ 9.69 (s, 1H), 8.02 (d, 1H), 7.93 (d, 1H), 7.57 (dd, 1H), 7.40 (dd, 1H), 7.22 (td, 1H), 6.05 (s, 1H), 3.96 (q, 2H), 3.93 (dd, 2H), 3.68 (br, 4H), 2.56 (br, 4H), 1.05 (t, 3H).

Example 2: The Preparation of (R)-methyl 4-(2-bromo-4-fluorophenyl)-6-(morpholinomethyl)-2-(thiazol-2-yl)-1,4-dihydropyrimidine-5-carboxylate

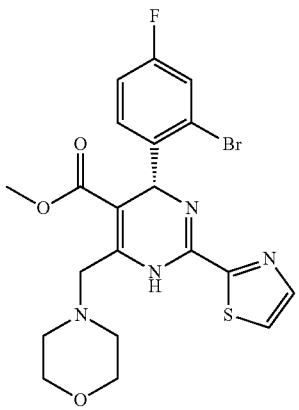

To a flask were added anhydrous methanol (870 g) and lithium (1.74 g, 0.25 mol) in turn. The mixture was stirred at 43° C. until the lithium was consumed entirely, and then (R)-(R)-1-ethoxy-1-oxopropan-2-yl 4-(2-bromo-4-fluorophenyl)-6-(morpholinomethyl)-2-(thiazol-2-yl)-1,4-dihydropyrimidine-5-carboxylate (58.1 g, 0.1 mol) was added. The reaction mixture was allowed to warm up to 60° C. and stirred for 1.5 hours. After the reaction, the reaction mixture was cooled and concentrated. To the residue was added ethyl acetate (580 g). The mixture was washed with water (250 g×2). The combined organic layers were concentrated to obtain the product as yellow thick oil (36.1 g, 73%).

MS (ESI, pos.ion) m/z: 494.7 [M+H]$^+$;
$^1$H NMR (600 MHz, DMSO-d$_6$): δ 9.71 (s, 1H), 8.02 (d, 1H), 7.94 (d, 1H), 7.55 (dd, 1H), 7.37 (dd, 1H), 7.20 (td, 1H), 6.02 (s, 1H), 3.91 (dd, 2H), 3.67 (br, 4H), 3.52 (s, 3H), 2.55 (br, 4H).

Example 3: The Preparation of (R)-3-(morpholin-3-yl)propanoic acid hydrochloride

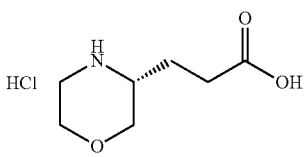 [SMILES: Cl ; O=C(O)CC[C@@H]1COCCN1]

Step 1) (S)-tert-butyl 3-formylmorpholine-4-carboxylate

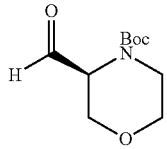 [SMILES: CC(C)(C)OC(=O)N1CCOC[C@H]1C=O]

To a flask were added (R)-tert-butyl 3-(hydroxymethyl)morpholine-4-carboxylate (1.47 g, 6.77 mmol) and DCM (30 mL) in turn, and then Dess-Martin periodinane (3.44 g, 8.12 mmol) was added at 0° C. The mixture was stirred at 0° C. for 1 hour. After the reaction, the mixture was quenched with saturated aqueous sodium bicarbonate (30 mL) and separated. The organic layer was washed with saturated aqueous sodium bicarbonate (30 mL×3) and saturated aqueous sodium chloride (30 mL), dried over anhydrous sodium sulfate and filtered. The filtrate was used directly at next operation.

Step 2) (R)-tert-butyl 3-(3-ethoxy-3-oxoprop-1-en-1-yl)morpholine-4-carboxylate

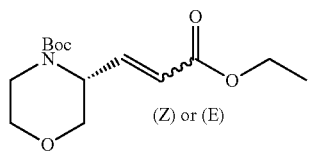 [SMILES: CCOC(=O)C=C[C@@H]1COCCN1C(=O)OC(C)(C)C]

To a flask were added (S)-tert-butyl 3-formylmorpholine-4-carboxylate (1.46 g, 6.77 mmol), DCM (40 mL) and ethyl (triphenylphosphoranylidene)acetate (2.36 g, 6.77 mmol) in turn. The mixture was stirred at 25° C. for 12 hours. After the reaction, the mixture was filtered. The filtrate was concentrated. The residue was purified by silica gel chromatography eluted with PE/EtOAc (V/V)=10/1 to give the product as a colorless oil (1.05 g, 54%).

MS (ESI, pos.ion) m/z: 186.1 [M+H-100]$^+$;

$^1$H NMR (400 MHz, CDCl$_3$): δ 6.69 (dd, 1H), 5.89 (dd, 1H), 4.56 (s, 1H), 4.20-4.12 (m, 2H), 3.94-3.82 (m, 2H), 3.77-3.65 (m, 2H), 3.53-3.43 (m, 1H), 3.27-3.10 (m, 1H), 1.41 (s, 9H), 1.29-1.23 (m, 3H).

Step 3) (R)-tert-butyl 3-(3-ethoxy-3-oxopropyl)morpholine-4-carboxylate

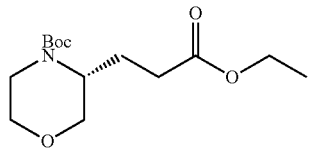 [SMILES: CCOC(=O)CC[C@@H]1COCCN1C(=O)OC(C)(C)C]

To a flask were added (R)-tert-butyl 3-(3-ethoxy-3-oxoprop-1-en-1-yl)morpholine-4-carboxylate (1.05 g, 3.68 mmol), anhydrous ethanol (20 mL) and Pd—C (10%, 0.2 g) in turn. The mixture was stirred at 30° C. under hydrogen atmosphere overnight and filtered. The filtrate was concentrated to give the product as colorless oil (0.96 g, 91%).

MS (ESI, pos.ion) m/z: 188.1 [M+H-100]$^+$;

$^1$H NMR (400 MHz, CDCl$_3$): δ 4.12 (q, 2H), 3.98 (s, 1H), 3.84-3.69 (m, 3H), 3.56 (dd, 1H), 3.42 (td, 1H), 3.12 (t, 1H), 2.37-2.27 (m, 2H), 2.25-2.15 (m, 1H), 1.92-1.83 (m, 1H), 1.45 (s, 9H), 1.25 (t, 3H).

Step 4) (R)-3-(4-(tert-butoxycarbonyl)morpholin-3-yl)propanoic acid

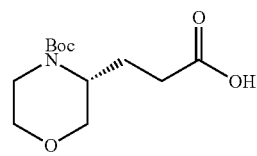 [SMILES: CC(C)(C)OC(=O)N1CCOC[C@H]1CCC(=O)O]

To a flask were added (R)-tert-butyl 3-(3-ethoxy-3-oxopropyl)morpholine-4-carboxylate (0.96 g, 3.34 mmol), anhydrous ethanol (10 mL) and a solution of lithium hydroxide hydrate (1.4 g, 33.4 mmol) in water (10 mL) in turn. The mixture was stirred at 25° C. for 30 min. After the reaction, to the reaction mixture was added ethyl acetate (150 mL) and water (50 mL). The resulting mixture was adjusted to pH 5-6 with concentrated hydrochloric acid at 0° C. After the mixture was partitioned. The organic layer was washed with saturated aqueous sodium chloride (100 mL), dried over anhydrous sodium sulfate and concentrated to give the product as colorless oil (0.85 g, 98%).

MS (ESI, pos.ion) m/z: 160.1 [M+H-100]$^+$;

$^1$H NMR (400 MHz, CDCl$_3$): δ 8.08 (br, 1H), 4.03 (brs, 1H), 3.88-3.72 (m, 3H), 3.58 (dd, 1H), 3.44 (td, 1H), 3.13 (t, 1H), 2.43-2.29 (m, 2H), 2.27-2.20 (m, 1H), 1.94-1.83 (m, 1H), 1.46 (s, 9H).

Step 5) (R)-3-(morpholin-3-yl)propanoic acid hydrochloride

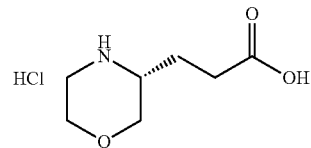 [SMILES: Cl ; O=C(O)CC[C@@H]1COCCN1]

To a flask were added (R)-3-(4-(tert-butoxycarbonyl)morpholin-3-yl)propanoic acid (0.9 g, 3.47 mmol) and a solution of hydrogen chloride in ethyl acetate (4 mol/L, 15 mL) in turn. The mixture was stirred at 25° C. for 4 hours. After the reaction, the mixture was filtered to give the product as a white solid (0.53 g, 78%).

MS (ESI, pos.ion) m/z: 160.1 [M+H]$^+$;

$^1$H NMR (400 MHz, D$_2$O): δ 4.04-3.96 (m, 2H), 3.75-3.68 (m, 1H), 3.52 (dd, 1H), 3.40-3.35 (m, 1H), 3.34-3.29 (m, 1H), 3.22-3.15 (m, 1H), 2.47 (t, 2H), 1.83 (ddd, 2H).

The compound VI hydrochloride can be prepared under the reaction conditions shown in table 6 according to the procedure described in Example 3.

TABLE 6

The reaction conditions for preparation of the compound (VI) hydrochloride (VI) hydrochloride structure: morpholine/pyrrolidine ring with NH, (R⁶)ₙ substituent, and Y position

| Raw material | The amount of raw material | (VI) hydrochloride | Product character | Quality; yield (%) of product |
|---|---|---|---|---|
| (S)-N-Boc-2-(hydroxymethyl)morpholine | 50 g | (S)-3-(morpholin-2-yl)propanoic acid·HCl | white solid | 23 g; 51 |
| (R)-N-Boc-2-(hydroxymethyl)morpholine | 50 g | (R)-3-(morpholin-2-yl)propanoic acid·HCl | white solid | 21.2 g; 47 |
| (S)-N-Boc-3-(hydroxymethyl)morpholine | 50 g | (S)-3-(morpholin-3-yl)propanoic acid·HCl | white solid | 18.5 g; 41 |
| N-Boc-2-methyl-3-(hydroxymethyl)morpholine | 50 g | 3-(2-methylmorpholin-3-yl)propanoic acid·HCl | white solid | 17.8 g; 39 |
| (S)-N-Boc-4,4-difluoro-2-(hydroxymethyl)pyrrolidine | 50 g | (S)-3-(4,4-difluoropyrrolidin-2-yl)propanoic acid·HCl | gray solid | 16.4 g; 36 |
| (R)-N-Boc-4,4-difluoro-2-(hydroxymethyl)pyrrolidine | 50 g | (R)-3-(4,4-difluoropyrrolidin-2-yl)propanoic acid·HCl | gray solid | 17.3 g; 38 |

TABLE 6-1

The NMR and MS datum of the compound (VI) hydrochloride

| (VI) hydrochloride | NMR | MS |
|---|---|---|
| (S)-3-(morpholin-2-yl)propanoic acid·HCl | $^1$H NMR (400 MHz, D$_2$O): δ 4.03 (dd, 1H), 3.78-3.67 (m, 2H), 3.25 (t, 2H), 3.08 (td, 1H), 2.85 (dd, 1H), 2.27-2.23 (m, 2H), 1.73-1.67 (m, 2H). | MS (ESI, neg. ion) m/z: 158.2[M − H]$^-$ |

TABLE 6-1-continued

The NMR and MS datum of the compound (VI) hydrochloride

| (VI) hydrochloride | NMR | MS |
|---|---|---|
| | ¹H NMR (400 MHz, D₂O): δ 4.10-4.02 (m, 1H), 3.80-3.74 (m, 2H), 3.32-3.25 (m, 2H), 3.10 (td, 1H), 2.89 (t, 1H), 2.47-2.43 (m, 2H), 1.88-1.70 (m, 2H). | MS (ESI, pos. ion) m/z: 160.1 [M + H]⁺; |
| | ¹H NMR (400 MHz, D₂O): δ 4.07-3.98 (m, 2H), 3.78-3.71 (m, 1H), 3.55 (dd, 1H), 3.43-3.38 (m, 1H), 3.35 (dt, 1H), 3.24-3.17 (m, 1H), 2.50 (t, 2H), 1.89-1.83 (m, 2H). | MS (ESI, pos. ion) m/z: 160.3 [M + H]⁺; |
| | ¹H NMR (600 MHz, D₂O): δ 4.05 (dd, 1H), 3.84-3.79 (m, 1H), 3.74-3.70 (m, 1H), 3.34 (d, 1H), 3.21 (td, 1H), 3.10 (td, 1H), 2.55 (t, 2H), 2.06-2.03 (m, 1H), 1.82-1.76 (m, 1H), 1.26 (d, 3H). | MS (ESI, pos. ion) m/z: 174.3 [M + H]⁺; |
| | ¹H NMR (600 MHz, DMSO-d₆): δ 10.21 (br, 1H), 3.80-3.73 (m, 2H), 3.66-3.59 (m, 1H), 2.74-2.67 (m, 1H), 2.43-2.40 (m, 2H), 2.33-2.23 (m, 1H), 2.05-1.95 (m, 2H). | MS (ESI, pos. ion) m/z: 180.2 [M + H]⁺; |
| | ¹H NMR (600 MHz, D₂O): δ 4.00-3.94 (m, 1H), 3.82 (dd, 1H), 3.72 (dd, 1H), 2.83-2.76 (m, 1H), 2.57-2.47 (m, 2H), 2.39-2.32 (m, 1H), 2.16-2.03 (m, 2H). | MS (ESI, pos. ion) m/z: 180.2 [M + H]⁺; |

Example 4: The Preparation of (2R,3S)-2-methylmorpholine-3-carboxylic acid

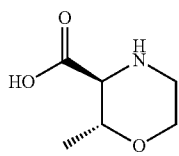

The title compound ((2R,3S)-2-methylmorpholine-3-carboxylic acid) was prepared according to the procedure described in example 34 of patent WO2014029193.

MS (ESI, pos.ion) m/z: 146.2 [M+H]⁺;

¹H NMR (600 MHz, D₂O): δ 4.01-3.98 (m, 1H), 3.82-3.77 (m, 1H), 3.76-3.72 (m, 1H), 3.37 (d, 1H), 3.27-3.24 (m, 1H), 3.19-3.14 (m, 1H), 1.26 (d, 3H).

Example 5: The Preparation of (S)-4-(((R)-6-(2-bromo-4-fluorophenyl)-5-(ethoxycarbonyl)-2-(thiazol-2-yl)-3,6-dihydropyrimidin-4-yl)methyl)morpholine-3-carboxylic acid

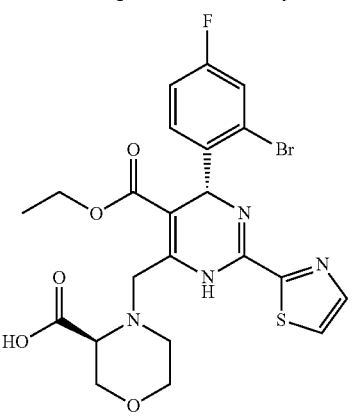

Step 1) (S)-4-(((R)-6-(2-bromo-4-fluorophenyl)-5-((((R)-1-ethoxy-1-oxopropan-2-yl)oxy)carbonyl)-2-(thiazol-2-yl)-3,6-dihydropyrimidin-4-yl)methyl)morpholine-3-carboxylic acid

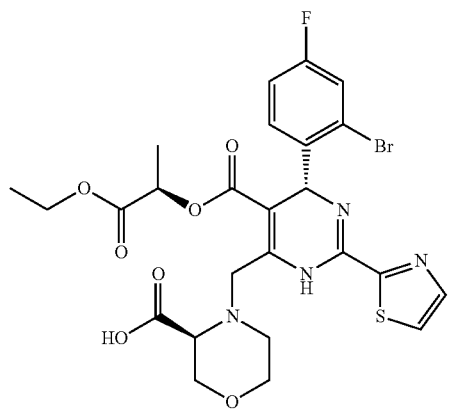

To a flask were added (R)-(R)-1-ethoxy-1-oxopropan-2-yl 4-(2-bromo-4-fluorophenyl)-6-(bromomethyl)-2-(thiazol-2-yl)-1,4-dihydropyrimidine-5-carboxylate (57.5 g, 0.1 mol), ethanol (840 g), (S)-morpholine-3-carboxylic acid (13.1 g, 0.1 mol) and potassium carbonate (27.6 g, 0.2 mol) in turn. The mixture was stirred at 30° C. under nitrogen atmosphere for 12 hours. After the reaction, the mixture was filtered. The filtrate was concentrated. To the residue was added water (840 g), the resulting mixture was extracted with ethyl acetate (840 mL). The organic layer was discarded. To the aqueous layer was added ethyl acetate (900 mL), and the mixture was adjusted to pH 3-6 with concentrated hydrochloric acid. The organic layer was dried over anhydrous sodium sulfate and concentrated to give the product as a yellow solid (46.3 g, 74%).

MS (ESI, pos.ion) m/z: 624.5 [M+H]$^+$;

$^1$H NMR (400 MHz, DMSO-d$_6$): δ 8.03 (d, 1H), 7.94 (d, 1H), 7.56 (dd, 1H), 7.42 (dd, 1H), 7.22 (td, 1H), 6.06 (s, 1H), 4.84 (q, 1H), 4.23-4.13 (m, 1H), 4.12-4.03 (m, 3H), 3.98-3.88 (m, 1H), 3.85 (dd, 1H), 3.73-3.65 (m, 2H), 3.58-3.51 (m, 1H), 3.10-3.04 (m, 1H), 2.42-2.38 (m, 1H), 1.24 (d, 3H), 1.13 (t, 3H).

The compound E can be prepared under the reaction conditions shown in table 7 according to the procedure described in step 1 of Example 5.

TABLE 7

The reaction conditions for preparation of compound E

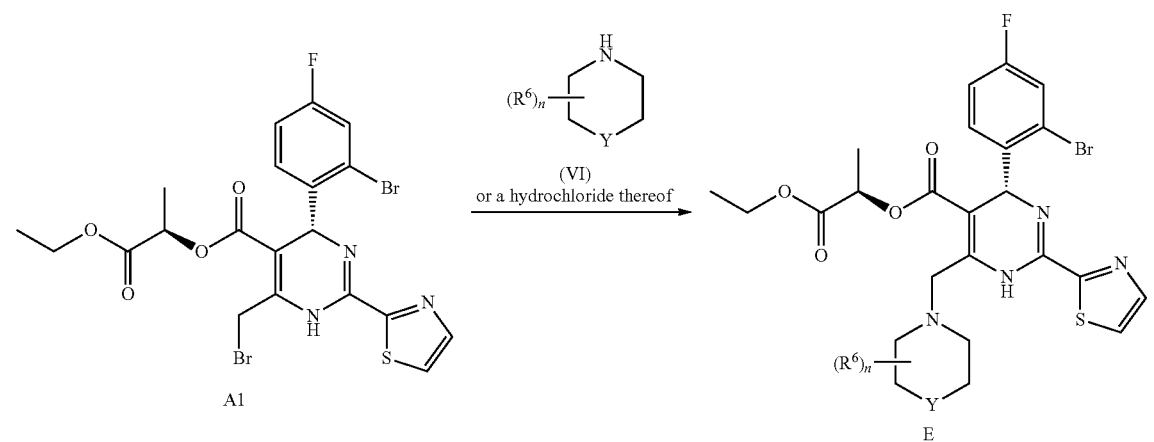

| No. | (VI) or a hydrochloride thereof | CompoundA1:compound(VI) (mol) the amount of compound A1 is 5.75 g | Reaction solvent | Reaction temperature(° C.) | Reaction time(h) | Product character | Quality; yield (%) of product |
|---|---|---|---|---|---|---|---|
| E1 | HO₂C-CH₂CH₂-morpholine·HCl | 1:1 | ethanol | 30 | 12 | yellow solid | 4.58 g; 70 |
| E2 | HO₂C-CH₂CH₂-morpholine·HCl | 1:1 | ethanol | 30 | 12 | yellow solid | 4.32 g; 66 |

TABLE 7-continued

The reaction conditions for preparation of compound E

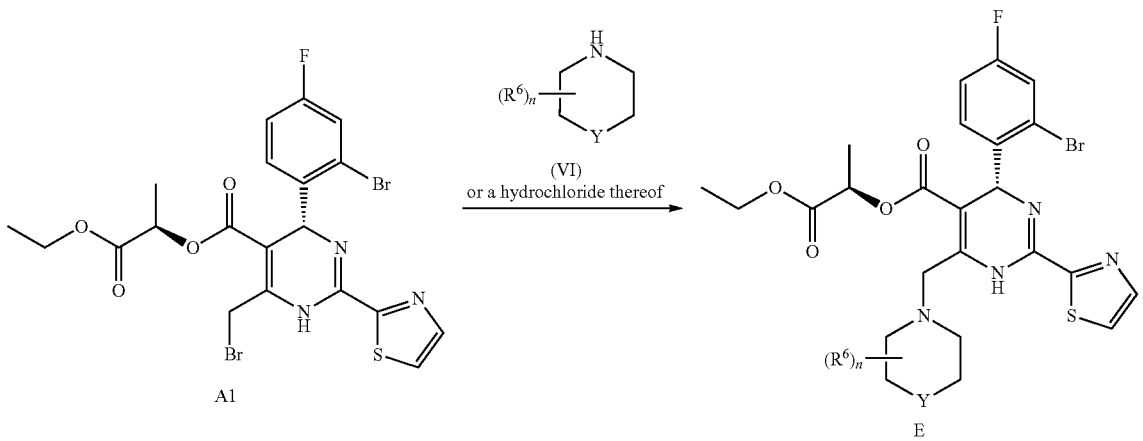

| No. | (VI) or a hydrochloride thereof | CompoundA1: compound(VI) (mol) the amount of compound A1 is 5.75 g | Reaction solvent | Reaction temperature(° C.) | Reaction time(h) | Product character | Quality; yield (%) of product |
|---|---|---|---|---|---|---|---|
| E3 | | 1:1 | ethanol | 30 | 12 | yellow solid | 3.2 g; 49 |
| E4 | | 1:1 | ethanol | 30 | 12 | yellow solid | 5.11 g; 80 |
| E5 | | 1:1 | ethanol | 30 | 12 | yellow solid | 3.41 g; 51 |
| E6 | | 1:1 | ethanol | 30 | 12 | yellow solid | 4.58 g; 71 |
| E7 | | 1:1 | ethanol | 30 | 12 | yellow solid | 3.5 g; 52 |
| E8 | | 1:1 | ethanol | 30 | 12 | yellow solid | 3.3 g; 49 |

TABLE 7-1

The NMR and MS datum of compound E

| No. | $^1$H NMR | MS |
|---|---|---|
| E1 | $^1$H NMR (600 MHz, DMSO-$d_6$): δ 12.02 (br, 1H), 9.74 (s, 1H), 8.02 (d, 1H), 7.95 (d, 1H), 7.56 (dd, 1H), 7.40 (dd, 1H), 7.22 (td, 1H), 6.06 (s, 1H), 4.85 (q, 1H), 4.12-4.05 (m, 2H), 3.92-3.85 (m, 3H), 3.59-3.55 (m, 1H), 3.52-3.48 (m, 1H), 2.79 (t, 2H), 2.35-2.23 (m, 3H), 2.02 (t, 1H), 1.65-1.61 (m, 2H), 1.24 (d, 3H), 1.14 (t, 3H). | MS (ESI, pos.ion) m/z: 652.5 [M + H]$^+$; |
| E2 | $^1$H NMR (600 MHz, DMSO-$d_6$): δ 12.06 (br, 1H), 9.76 (s, 1H), 8.04 (d, 1H), 7.96 (d, 1H), 7.56 (dd, 1H), 7.40 (dd, 1H), 7.23 (td, 1H), 6.04 (s, 1H), 4.86 (q, 1H), 4.14-4.06 (m, 2H), 3.94-3.86 (m, 3H), 3.58-3.53 (m, 1H), 3.51-3.48 (m, 1H), 2.77 (t, 2H), 2.35-2.22 (m, 3H), 2.01 (t, 1H), 1.65-1.62 (m, 2H), 1.25 (d, 3H), 1.12 (t, 3H). | MS (ESI, pos.ion) m/z: 652.5 [M + H]$^+$; |
| E3 | $^1$H NMR (600 MHz, DMSO-$d_6$): δ 12.16 (s, 1H), 9.91 (s, 1H), 8.03 (d, 1H), 7.94 (d, 1H), 7.55 (dd, 1H), 7.40 (dd, 1H), 7.22 (td, 1H), 6.05 (s, 1H), 4.85 (q, 1H), 4.18 (d, 1H), 4.13-4.01 (m, 2H), 3.86 (d, 1H), 3.80 (d, 1H), 3.73-3.71 (m, 1H), 3.62-3.55 (m, 1H), 3.36-3.33 (m, 1H), 2.94-2.73 (m, 1H), 2.56-2.53 (m, 1H), 2.39-2.31 (m, 1H), 2.28-2.22 (m, 1H), 1.88-1.82 (m, 1H), 1.66-1.58 (m, 1H), 1.25 (d, 3H), 1.13 (t, 3H). | MS (ESI, pos.ion) m/z: 653.2 [M + H]$^+$; |
| E4 | $^1$H NMR (600 MHz, DMSO-$d_6$): δ 12.98 (br, 1H), 9.90 (s, 1H), 8.04 (d, 1H), 7.94 (d, 1H), 7.56 (dd, 1H), 7.43 (dd, 1H), 7.21 (td, 1H), 6.04 (s, 1H), 4.86 (q, 1H), 4.14-4.03 (m, 3H), 3.93-3.85 (m, 1H), 3.74-3.67 (m, 2H), 3.65-3.60 (m, 1H), 3.01 (d, 1H), 2.92 (d, 1H), 2.49-2.44 (m, 1H), 1.23 (d, 3H), 1.21 (d, 3H), 1.13 (t, 3H). | MS (ESI, pos.ion) m/z: 639.1 [M + H]$^+$; |
| E5 | $^1$H NMR (400 MHz, DMSO-$d_6$): δ 12.10 (s, 1H), 9.75 (s, 1H), 8.04 (d, 1H), 7.96 (d, 1H), 7.56 (dd, 1H), 7.40 (dd, 1H), 7.20 (td, 1H), 6.05 (s, 1H), 4.87 (q, 1H), 4.15 (d, 1H), 4.11-4.02 (m, 2H), 3.85 (d, 1H), 3.76-3.71 (m, 1H), 3.60-3.55 (m, 1H), 3.53-3.46 (m, 1H), 2.66 (d,1H), 2.46-2.41 (m,1H), 2.37-2.32 (m,3H), 2.07-1.87 (m,1H), 1.79-1.72 (m, 1H), 1.24 (d, 3H), 1.20 (d, 3H), 1.14 (t, 3H). | MS (ESI, pos.ion) m/z: 668.6 [M + H]$^+$; |
| E6 | $^1$H NMR (600 MHz, DMSO-$d_6$): δ 13.05 (br, 1H), 9.79 (s, 1H), 7.98 (d, 1H), 7.92 (d, 1H), 7.57 (dd, 1H), 7.43 (dd, 1H), 7.23 (td, 1H), 6.04 (s, 1H), 4.85 (q, 1H), 4.31 (d, 1H), 4.13-4.05 (m, 3H), 3.92 (t, 1H), 3.55-3.49 (m, 1H), 3.18-3.12 (m, 1H), 2.82-2.72 (m, 1H), 2.48-2.43 (m, 1H), 1.24 (d, 3H), 1.16 (t, 3H). | MS (ESI, pos.ion) m/z: 644.5 [M + H]$^+$; |
| E7 | $^1$H NMR (600 MHz, DMSO-$d_6$): δ 9.56 (s, 1H), 8.04 (d, 1H), 7.96(d, 1H), 7.57 (d, 1H), 7.43 (dd, 1H), 7.24(td,1H), 6.04 (s, 1H), 4.86 (q, 1H), 4.12-4.03 (m, 4H), 3.51-3.44 (m, 1H), 3.08-2.94 (m, 2H), 2.48-2.44 (m, 1H), 2.37-2.19 (m, 2H), 2.13-2.01 (m, 1H), 1.98-1.91(m, 1H), 1.58-1.52 (m, 1H), 1.24 (d, 3H), 1.16 (t, 3H). | MS (ESI, pos.ion) m/z: 673.1 [M + H]$^+$; |
| E8 | $^1$H NMR (600 MHz, DMSO-$d_6$): δ 9.52 (br, 1H), 9.79 (s, 1H), 8.02 (d, 1H), 7.94 (d, 1H), 7.56 (dd, 1H), 7.40 (dd, 1H), 7.23 (td, 1H), 6.03 (s, 1H), 4.87 (q, 1H), 4.14 (d, 1H), 3.47-3.42 (m, 3H), 3.02 (t, 1H), 2.60-2.52 (m, 1H), 2.41-2.21 (m, 1H), 2.12-1.98 (m, 1H), 1.61-1.59 (m, 1H), 1.24 (d, 3H), 1.14 (t, 3H). | MS (ESI, pos.ion) m/z: 672.7 [M + H]$^+$; |

Step 2) (S)-4-(((R)-6-(2-bromo-4-fluorophenyl)-5-(ethoxycarbonyl)-2-(thiazol-2-yl)-3,6-dihydropyrimidin-4-yl)methyl)morpholine-3-carboxylic acid

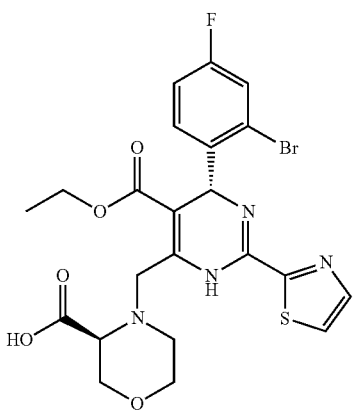 [SMILES: CCOC(=O)C1=C(CN2CCOC[C@H]2C(=O)O)NC(c2nccs2)=N[C@H]1c1ccc(F)cc1Br]

To a flask were added anhydrous ethanol (940 g) and lithium (2.43 g, 0.35 mol) in turn. The mixture was stirred at 43° C. until the lithium was consumed entirely, and then (S)-4-(((R)-6-(2-bromo-4-fluorophenyl)-5-((((R)-1-ethoxy-1-oxopropan-2-yl)oxy)carbonyl)-2-(thiazol-2-yl)-3,6-dihydropyrimidin-4-yl)methyl)morpholine-3-carboxylic acid (62.5 g, 0.1 mol) was added. The reaction mixture was allowed to warm up to 78° C. and stirred for 12 hours. After the reaction, the mixture was cooled and concentrated. To the residue was added water (1200 g), the resulting mixture was extracted with ethyl acetate (1000 mL). The organic layer was discarded. To the aqueous layer was added ethyl acetate (1280 mL), the mixture was adjusted to pH 3-6 with concentrated hydrochloric acid. The organic layer was dried over anhydrous sodium sulfate and concentrated to give the product as a yellow solid (37.1 g, 67%).

MS (ESI, pos.ion) m/z: 553.2 [M+H]$^+$;
$^1$H NMR (400 MHz, DMSO-$d_6$): δ 12.85 (br, 1H), 9.80 (s, 1H), 8.00 (d, 1H), 7.91 (d, 1H), 7.54 (dd, 1H), 7.39 (dd, 1H), 7.19 (td, 1H), 6.01 (s, 1H), 4.25 (d, 1H), 4.02 (d, 1H), 3.97-3.91 (m, 3H), 3.81 (dd, 1H), 3.72-3.69 (m, 1H), 3.66-3.63 (m, 1H), 3.61-3.58 (m, 1H), 3.10-3.03 (m, 1H), 2.42-2.35 (m, 1H), 1.04 (t, 3H).

The compound F can be prepared under the reaction conditions shown in table 8 according to the procedure described in step 2 of Example 5.

TABLE 8

The reaction conditions for preparation of compound F

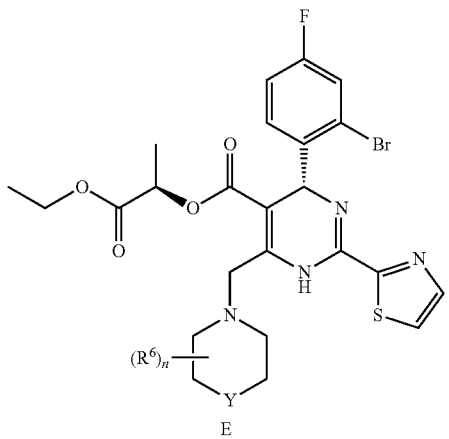

| No. | R³ | (R⁶)ₙ-[ring]-Y | The mole ratio of Lithium to compound E; the amount of compound E | Reaction solvent | Reaction temperature(° C.) | Reaction time(h) | Product character | Quality; yield (%) of product |
|---|---|---|---|---|---|---|---|---|
| F1 | ethyl |  | 6; 6.4 g | ethanol | 78 | 2 | yellow solid | 3.78 g; 65 |
| F2 | ethyl | 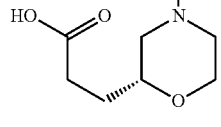 | 5; 6.4 g | ethanol | 78 | 2 | yellow solid | 3.66 g; 63 |
| F3 | ethyl | 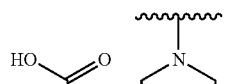 | 5; 6.4 g | ethanol | 78 | 2 | yellow solid | 3.02 g; 52 |
| F4 | ethyl | 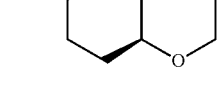 | 5; 6.26 g | ethanol | 78 | 12 | yellow solid | 3.97 g; 70 |
| F5 | ethyl | 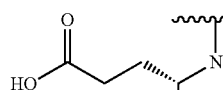 | 5; 6.54 g | ethanol | 78 | 2 | yellow solid | 2.86 g; 48 |
| F6 | ethyl |  | 5; 6.3 g | ethanol | 78 | 12 | yellow solid | 3.5 g; 61 |

TABLE 8-continued

The reaction conditions for preparation of compound F

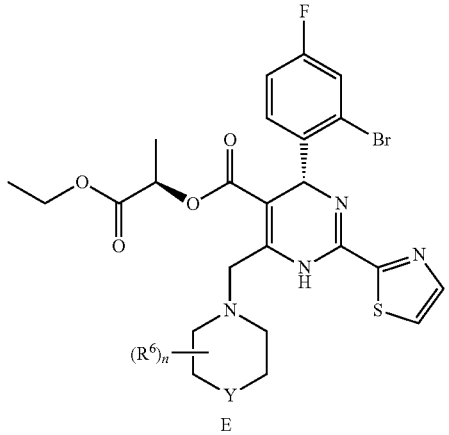

| No. | R³ | (R⁶)ₙ group | The mole ratio of Lithium to compound E; the amount of compound E | Reaction solvent | Reaction temperature(° C.) | Reaction time(h) | Product character | Quality; yield (%) of product |
|---|---|---|---|---|---|---|---|---|
| F7 | ethyl | 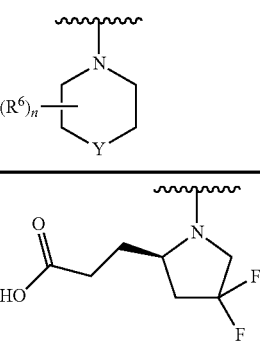 | 5; 6.6 g | ethanol | 78 | 2 | yellow solid | 3.13 g; 52 |
| F8 | ethyl | 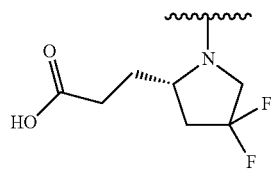 [SMILES: *N1CC(F)(F)C[C@@H]1CCC(=O)O] | 5; 6.6 g | ethanol | 78 | 2 | yellow solid | 3 g; 50 |
| F9 | methyl | 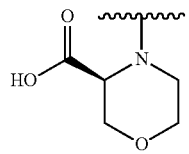 | 2; 6.1 g | methanol | 64 | 18 | yellow solid | 3.61 g; 67 |
| F10 | methyl | 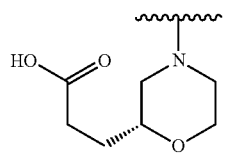 [SMILES: *N1CCO[C@H](CCC(=O)O)C1] | 5; 6.4 g | methanol | 64 | 6 | yellow solid | 3.52 g; 62 |
| F11 | methyl | 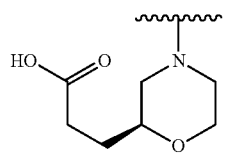 [SMILES: *N1CCO[C@@H](CCC(=O)O)C1] | 5; 6.4 g | methanol | 64 | 4 | yellow solid | 3.4 g; 60 |
| F12 | methyl | 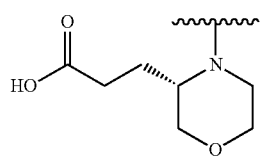 [SMILES: *N1CCOC[C@@H]1CCC(=O)O] | 5; 6.4 g | methanol | 64 | 8 | yellow solid | 2.72 g; 48 |

TABLE 8-continued

The reaction conditions for preparation of compound F

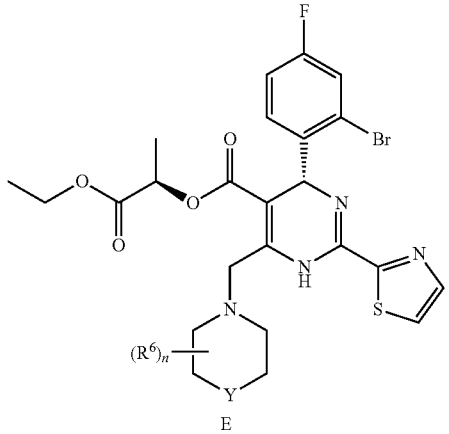

| No. | R³ | 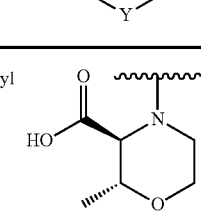 | The mole ratio of Lithium to compound E; the amount of compound E | Reaction solvent | Reaction temperature(° C.) | Reaction time(h) | Product character | Quality; yield (%) of product |
|---|---|---|---|---|---|---|---|---|
| F13 | methyl | 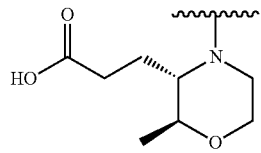 [SMILES: *N1CCO[C@@H](C)[C@@H]1CCC(=O)O] | 5; 6.26 g | methanol | 64 | 18 | yellow solid | 3.87 g; 70 |
| F14 | methyl | 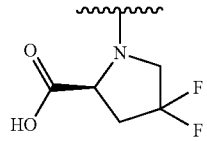 | 5; 6.54 g | methanol | 64 | 5 | yellow solid | 2.73 g; 47 |
| F15 | methyl | 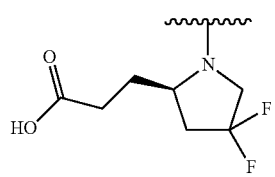 [SMILES: *N1CC(F)(F)C[C@H]1CCC(=O)O] | 5; 6.3 g | methanol | 64 | 12 | yellow solid | 3.75 g; 67 |
| F16 | methyl | 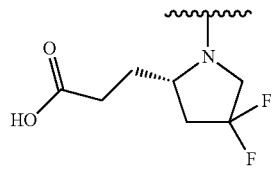 [SMILES: *N1CC(F)(F)C[C@@H]1CCC(=O)O] | 5; 6.87 g | methanol | 64 | 6 | yellow solid | 2.88 g; 49 |
| F17 | methyl |  | 5; 6.87 g | methanol | 64 | 6 | yellow solid | 2.82 g; 48 |

TABLE 8-1

| | The NMR and MS datum of compound F | |
|---|---|---|
| No. | ¹H NMR | MS |
| F1 | ¹H NMR (400 MHz, DMSO-$d_6$): δ 12.06 (s, 1H), 9.65 (s, 1H), 8.02 (d, 1H), 7.94 (d, 1H), 7.57 (dd, 1H), 7.39 (dd, 1H), 7.22 (td, 1H), 6.03 (s, 1H), 3.96 (q, 2H), 3.89-3.85 (m, 3H), 3.61-3.47 (m, 2H), 2.81-2.75 (m, 2H), 2.38-2.21 (m, 3H), 2.04-2.02 (m, 1H), 1.65-1.60 (m, 2H), 1.06 (t, 3H). | MS (ESI, pos.ion) m/z: 581.2 [M + H]⁺; |
| F2 | ¹H NMR (400 MHz, DMSO-$d_6$): δ 12.06 (s, 1H), 9.66 (s, 1H), 8.02 (d, 1H), 7.95 (d, 1H), 7.56 (dd, 1H), 7.41 (dd, 1H), 7.20 (td, 1H), 6.03 (s, 1H), 3.97 (q, 2H), 3.93-3.83 (m, 3H), 3.57-3.46 (m, 2H), 2.88 (d, 1H), 2.63 (d, 1H), 2.37-2.22 (m, 3H), 2.13-2.08 (m, 1H), 1.75-1.65 (m, 2H), 1.06 (t, 3H). | MS (ESI, pos.ion) m/z: 580.9 [M + H]⁺; |
| F3 | ¹H NMR (400 MHz, DMSO-$d_6$): δ 12.14 (br, 1H), 9.82 (s, 1H), 8.02 (d, 1H), 7.92 (d, 1H), 7.54 (dd, 1H), 7.40 (dd, 1H), 7.22 (td, 1H), 6.03 (s, 1H), 4.18 (d, 1H), 3.96 (q, 2H), 3.91 (d, 1H), 3.82-3.79 (m, 1H), 3.74-3.71 (m, 1H), 3.61-3.57 (m, 1H), 3.37-3.32 (m, 1H), 2.78-2.75 (m, 1H), 2.57-2.53 (m, 1H), 2.49-2.47 (m, 1H), 2.38-2.32 (m, 2H), 1.89-1.84 (m, 1H), 1.68-1.58 (m, 1H), 1.06 (t, 3H). | MS (ESI, pos.ion) m/z: 580.9 [M + H]⁺; |
| F4 | ¹H NMR (400 MHz, DMSO-$d_6$): δ 13.02 (s, 1H), 9.78 (s, 1H), 8.03 (d, 1H), 7.93 (d, 1H), 7.56 (dd, 1H), 7.39 (dd, 1H), 7.22 (td, 1H), 6.00 (s, 1H), 4.10 (d, 1H), 3.95 (q, 2H), 3.90-3.87 (m, 1H), 3.76-3.60 (m, 3H), 3.46-3.42 (m, 1H), 2.98 (d, 1H), 2.93 (d, 1H), 1.21 (d, 3H), 1.05 (t, 3H). | MS (ESI, pos.ion) m/z: 567.1 [M + H]⁺; |
| F5 | ¹H NMR (400 MHz, DMSO-$d_6$): δ 12.11 (s, 1H), 9.74 (s, 1H), 8.02 (d, 1H), 7.95 (d, 1H), 7.56 (dd, 1H), 7.39 (dd, 1H), 7.19 (td, 1H), 6.04 (s, 1H), 4.16 (d, 1H), 4.00-3.93 (m, 2H), 3.86 (d, 1H), 3.77-3.72 (m, 1H), 3.59-3.53 (m, 1H), 3.51-3.45 (m, 1H), 2.66 (d, 1H), 2.46-2.40 (m, 1H), 2.37-2.30 (m, 3H), 2.03 -1.91 (m, 1H), 1.80-1.73 (m, 1H), 1.20 (d, 3H), 1.06 (t, 3H). | MS (ESI, pos.ion) m/z: 594.6 [M + H]⁺ |
| F6 | ¹H NMR (600 MHz, DMSO-$d_6$): δ 9.98 (br, 1H), 8.03 (d, 1H), 8.00 (d, 1H), 7.61 (dd, 1H), 7.48 (dd, 1H), 7.28 (td, 1H), 6.02 (s, 1H), 4.35 (d, 1H), 4.13 (d, 1H), 4.01-3.94 (m, 3H), 3.61-3.51 (m, 1H), 3.25-3.19 (m, 1H), 3.10-3.04 (m, 1H), 2.86-2.68 (m, 1H), 1.20 (t, 3H). | MS (ESI, pos.ion) m/z: 573.0 [M + H]⁺; |
| F7 | ¹H NMR (600 MHz, DMSO-$d_6$): δ 12.08 (s, 1H), 9.51 (s, 1H), 8.01 (d, 1H), 7.93 (d, 1H), 7.57 (dd, 1H), 7.41 (dd, 1H), 7.24 (td, 1H), 6.01 (s, 1H), 4.12 (dd, 2H), 3.97 (q, 2H), 3.61-3.52 (m, 1H), 3.04-2.96 (m, 2H), 2.58-2.56 (m, 1H), 2.35-2.20 (m, 2H), 2.12-1.98 (m, 1H), 1.93-1.90 (m, 1H), 1.56-1.48 (m, 1H), 1.06 (t, 3H). | MS (ESI, pos.ion) m/z: 601.1 [M + H]⁺; |
| F8 | ¹H NMR (400 MHz, CDCl₃): δ 12.19 (br, 1H), 9.46 (s, 1H), 7.86 (d, 1H), 7.50 (d, 1H), 7.37-7.33 (m, 2H), 7.00 (td, 1H), 6.19 (s, 1H), 4.52 (d, 1H), 4.14-4.03 (m, 2H), 3.65 (d, 1H), 3.31-3.23 (m, 2H), 3.02-2.91 (m, 1H), 2.57-2.25 (m, 5H), 1.79-1.74 (m, 1H), 1.16 (t, 3H). | MS (ESI, pos.ion) m/z: 601.2 [M + H]⁺; |
| F9 | ¹H NMR (600 MHz, DMSO-$d_6$): δ 12.88 (br, 1H), 10.07 (br, 1H), 8.02 (d, 1H), 7.93 (d, 1H), 7.56 (dd, 1H), 7.39 (dd, 1H), 7.23 (td, 1H), 6.01 (s, 1H), 4.25 (d, 1H), 4.04 (d, 1H), 3.99 (dd, 1H), 3.84 (dd, 1H), 3.73-3.70 (m, 1H), 3.69-3.65 (m, 1H), 3.62-3.58 (m, 1H), 3.51 (s, 3H), 3.10-3.07 (m, 1H), 2.41-2.39 (m, 1H). | MS (ESI, pos.ion) m/z: 539.1 [M + H]⁺; |
| F10 | ¹H NMR (400 MHz, DMSO-$d_6$): δ 12.03 (s, 1H), 9.69 (s, 1H), 8.01 (d, 1H), 7.93 (d, 1H), 7.56 (dd, 1H), 7.38 (dd, 1H), 7.23 (td, 1H), 6.01 (s, 1H), 3.93-3.83 (m, 3H), 3.60-3.53 (m, 2H), 3.52 (s, 3H), 2.77 (dd, 2H), 2.38-2.25 (m, 3H), 2.05-1.99 (m, 1H), 1.65-1.59 (m, 2H). | MS (ESI, pos.ion) m/z: 567.2 [M + H]⁺; |
| F11 | ¹H NMR (600 MHz, DMSO-$d_6$): δ 12.06 (s, 1H), 9.70 (s, 1H), 8.03 (d, 1H), 7.94 (d, 1H), 7.57 (dd, 1H), 7.39 (dd, 1H), 7.23 (td, 1H), 6.02 (s, 1H), 3.95 (d, 1H), 3.86-3.80 (m, 2H), 3.56-3.54 (m, 1H), 3.53 (s, 3H), 3.52-3.49 (m, 1H), 2.88 (d, 1H), 2.62 (d, 1H), 2.37-2.21 (m, 3H), 2.15-2.08 (m, 1H), 1.72-1.64 (m, 2H). | MS (ESI, pos.ion) m/z: 567.2 [M + H]⁺; |
| F12 | ¹H NMR (400 MHz, DMSO-d6): δ 9.87 (s, 1H), 8.03 (d, 1H), 7.94 (d, 1H), 7.56 (dd, 1H), 7.38 (dd, 1H), 7.23 (td, 1H), 6.01 (s, 1H), 4.18 (d, 1H), 3.91 (d, 1H), 3.83-3.79 (m, 1H), 3.75-3.70 (m, 1H), 3.61-3.56 (m, 1H), 3.53 (s, 3H), 3.47-3.40 (m, 1H), 3.04-2.86 (m, 1H), 2.77-2.75 (m, 1H), 2.58-2.54 (m, 1H), 2.37-2.22 (m, 2H), 1.88-1.84 (m, 1H), 1.65-1.58 (m, 1H). | MS (ESI, pos.ion) m/z: 567.2 [M + H]⁺; |

TABLE 8-1-continued

The NMR and MS datum of compound F

| No. | $^1$H NMR | MS |
|---|---|---|
| F13 | $^1$H NMR (400 MHz, DMSO-$d_6$): δ 13.02 (s, 1H), 9.83 (s, 1H), 8.02 (d, 1H), 7.94 (d, 1H), 7.56 (dd, 1H), 7.38 (dd, 1H), 7.22 (td, 1H), 5.99 (s, 1H), 4.05 (d, 1H), 3.90-3.85 (m, 1H), 3.75-3.60 (m, 3H), 3.52 (s, 3H), 3.47-3.42 (m, 1H), 3.00 (d, 1H), 2.92 (d, 1H), 1.21 (d, 3H). | MS (ESI, pos.ion) m/z: 553.0 [M + H]$^+$; |
| F14 | $^1$H NMR (400 MHz, DMSO-$d_6$): δ 12.10 (s, 1H), 9.75 (s, 1H), 8.01 (d, 1H), 7.96 (d, 1H), 7.54 (dd, 1H), 7.40 (dd, 1H), 7.20 (td, 1H), 6.02 (s, 1H), 4.18 (d, 1H), 3.88 (d, 1H), 3.78-3.73 (m, 1H), 3.60-3.54 (m, 1H), 3.52 (s, 3H), 3.50-3.45 (m, 1H), 2.68 (d, 1H), 2.47-2.41 (m, 1H), 2.36-2.30 (m, 3H), 2.04-1.92 (m, 1H), 1.81-1.73 (m, 1H), 1.21 (d, 3H). | MS (ESI, pos.ion) m/z: 581.2 [M + H]$^+$; |
| F15 | $^1$H NMR (600 MHz, DMSO-$d_6$): δ 9.71 (br, 1H), 7.98 (d, 1H), 7.91 (d, 1H), 7.56 (dd, 1H), 7.40 (dd, 1H), 7.23 (td, 1H), 5.99 (s, 1H), 4.33 (d, 1H), 4.09 (d, 1H), 3.93-3.88 (m, 1H), 3.52 (s, 3H), 3.49-3.45 (m, 1H), 3.22-3.08 (m, 2H), 2.82-2.74 (m, 1H). | MS (ESI, pos.ion) m/z: 558.6 [M + H]$^+$; |
| F16 | $^1$H NMR (400 MHz, DMSO-$d_6$): δ 11.03 (s, 1H), 9.57 (s, 1H), 7.99 (d, 1H), 7.92 (d, 1H), 7.55 (dd, 1H), 7.39 (dd, 1H), 7.23 (td, 1H), 6.00 (s, 1H), 4.14 (dd, 2H), 3.62-3.54 (m, 1H), 3.53 (s, 3H), 3.05-2.96 (m, 2H), 2.57-2.56 (m, 1H), 2.36-2.20 (m, 2H), 2.13-1.98 (m, 1H), 1.95-1.90 (m, 1H), 1.56-1.46 (m, 1H). | MS (ESI, pos.ion) m/z: 587.2 [M + H]$^+$; |
| F17 | $^1$H NMR (400 MHz, CDCl$_3$): δ 12.15 (br, 1H), 9.47 (s, 1H), 7.85 (d, 1H), 7.51 (d, 1H), 7.38-7.33 (m, 2H), 7.01 (td, 1H), 6.17 (s, 1H), 4.50 (d, 1H), 3.66 (d, 1H), 3.55 (s, 3H), 3.33-3.23 (m, 2H), 3.04-2.92 (m, 1H), 2.58-2.25 (m, 5H), 1.78-1.74 (m, 1H). | MS (ESI, pos.ion) m/z: 587.2 [M + H]$^+$; |

Example 6: The Preparation of (R)-ethyl 4-(2-bromo-4-fluorophenyl)-6-(morpholinomethyl)-2-(thiazol-2-yl)-1,4-dihydropyrimidine-5-carboxylate

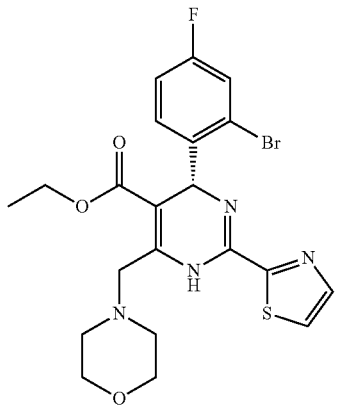

Step 1) (R)-ethyl 4-(2-bromo-4-fluorophenyl)-6-methyl-2-(thiazol-2-yl)-1,4-dihydropyrimidine-5-carboxylate

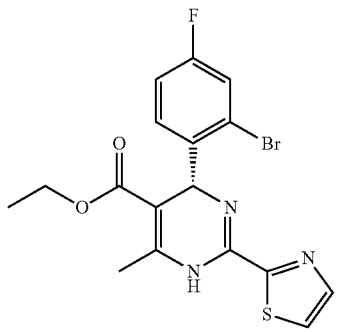

To a flask were added anhydrous ethanol (500 g) and lithium (2.43 g, 0.35 mol) in turn. The mixture was stirred at 43° C. until the lithium was consumed entirely, and then (R)-(R)-1-ethoxy-1-oxopropan-2-yl 4-(2-bromo-4-fluorophenyl)-6-methyl-2-(thiazol-2-yl)-1,4-dihydropyrimidine-5-carboxylate (49.6 g, 0.1 mol) was added. The reaction mixture was stirred at 78° C. for 6 hours. After the reaction, the reaction mixture was cooled to 10° C., kept at 10° C. and stirred for 8 hours. The mixture was filtered. The filter cake was washed with anhydrous ethanol (50 g) and water (500 g) in turn, and then dried in vacuo at 60° C. for 8 hours to obtain the product as a yellowish solid (31.8 g, 75%).

$[α]_D^{25}$=80.71 (c=0.3023 g/100 mL, MeOH);

MS (ESI, pos.ion) m/z: 424.0 [M+H]$^+$;

$^1$H NMR (400 MHz, DMSO-$d_6$): δ 9.88 (s, 1H), 7.97 (d, 1H), 7.89 (d, 1H), 7.54 (dd, 1H), 7.35 (dd, 1H), 7.23 (td, 1H), 5.96 (s, 1H), 3.93 (q, 2H), 2.46 (s, 3H), 1.03 (t, 3H).

The compound G can be prepared under the reaction conditions shown in table 9 according to the procedure described in step 1 of Example 6.

TABLE 9

The reaction conditions for preparation of compound G

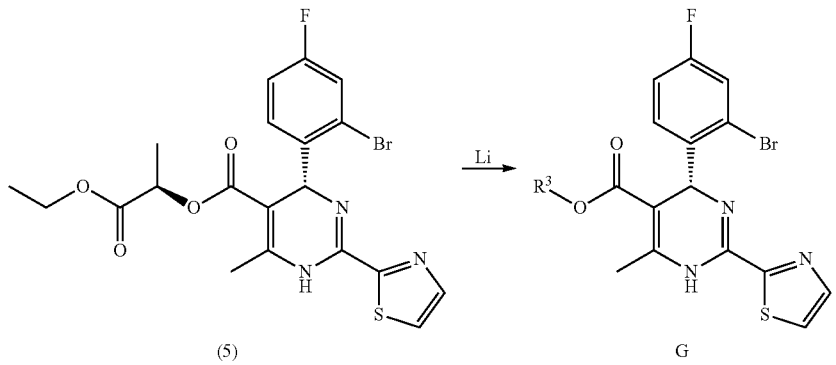

| No. | $R^3$ | The mole ratio of Lithium to compound (5); the amount of compound (5) is 49.6 g | Reaction solvent | The mass ratio of reaction solvent to compound (5) | Reaction temperature (° C.) | Reaction time(h) | Product character | Quality; yield (%) of product |
|---|---|---|---|---|---|---|---|---|
| G1 | ethyl | 2.5 | ethanol | 10 | 78 | 12 | yellow solid | 19.5 g; 46 |
| G1 | ethyl | 3 | ethanol | 6 | 78 | 8 | yellow solid | 31.8 g; 75 |
| G1 | ethyl | 4 | ethanol | 10 | 78 | 4 | yellow solid | 29.7 g; 70 |
| G1 | ethyl | 5 | ethanol | 20 | 78 | 24 | yellow solid | 24.2 g; 57 |
| G1 | ethyl | 6 | ethanol | 30 | 78 | 12 | yellow solid | 20.4 g; 48 |
| G1 | ethyl | 8 | ethanol | 20 | 78 | 12 | yellow solid | 25.4 g; 60 |
| G2 | methyl | 3 | methanol | 3 | 64 | 20 | yellow solid | 25.4 g; 62 |
| G2 | methyl | 3 | methanol | 4 | 64 | 6 | yellow solid | 18.5 g; 45 |
| G2 | methyl | 4 | methanol | 6 | 64 | 8 | yellow solid | 15.6 g; 38 |

TABLE 9-1

The NMR, MS and specific rotation datum of the compound G

| No. | $^1$H NMR | MS | specific rotation |
|---|---|---|---|
| G1 | $^1$H NMR (400 MHz, DMSO-$d_6$): δ 9.88 (s, 1H), 7.97 (d, 1H), 7.89 (d, 1H), 7.54 (dd, 1H), 7.35 (dd, 1H), 7.23 (td, 1H), 5.96 (s, 1H), 3.93 (q, 2H), 2.46 (s, 3H), 1.03 (t, 3H). | MS (ESI, pos.ion) m/z: 424.0 [M + H]$^+$; | $[a]_D^{25}$ = −80.71 (c = 0.3023 g/100 mL, MeOH); |
| G2 | $^1$H NMR (400 MHz, DMSO-$d_6$): δ 7.79 (d, 1H), 7.67 (d, 1H), 7.42 (dd, 2H), 7.36 (dd, 1H), 7.15 (td, 1H), 5.85 (s, 1H), 3.40 (s, 3H), 2.33 (s, 3H). | MS (ESI, pos.ion) m/z: 410.0 [M + H]$^+$; | $[a]_D^{25}$ = −86.04 (c = 0.3022 g/100 mL, MeOH); |

Step 2) (R)-ethyl 4-(2-bromo-4-fluorophenyl)-6-bromomethyl-2-(thiazol-2-yl)-1,4-dihydropyrimidine-5-carboxylate

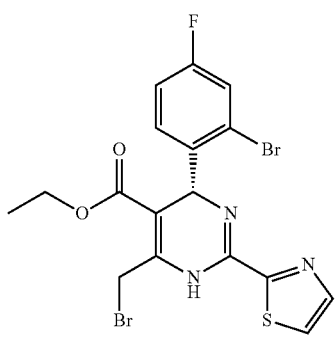

To a flask were added (R)-ethyl 4-(2-bromo-4-fluorophenyl)-6-methyl-2-(thiazol-2-yl)-1,4-dihydropyrimidine-5-carboxylate (42.4 g, 0.1 mol) and $CCl_4$ (800 mL), followed by NBS (19.6 g, 0.11 mol) at 70° C. The mixture was stirred for 30 min. After the reaction, the mixture was cooled and filtered. The filtrate was concentrated to obtain the product as a yellow solid (34.2 g, 68%).

MS (ESI, pos.ion) m/z: 503.9 [M+H]$^+$;

$^1$H NMR (600 MHz, DMSO-$d_6$): δ 10.23 (s, 1H), 8.01 (d, 1H), 7.98 (d, 1H), 7.62 (dd, 1H), 7.42 (dd, 1H), 7.29 (td, 1H), 6.01 (s, 1H), 4.79 (br, 2H), 4.01 (q, 2H), 1.08 (t, 3H).

The compound J can be prepared under the reaction conditions shown in table 10 according to the procedure described in step 2 of Example 6.

TABLE 10

The reaction conditions for preparation of compound J

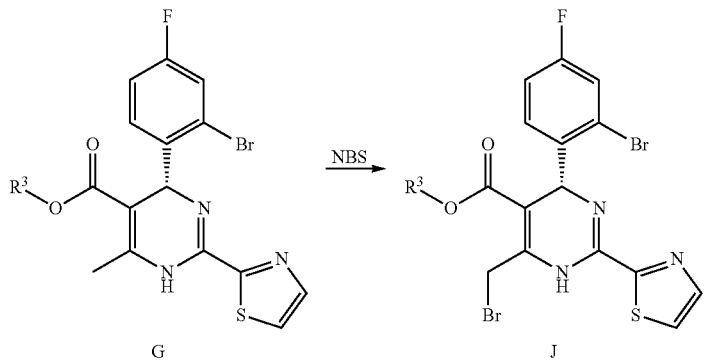

| No. | R³ | The mole ratio of NBS to compound G; the amount of compound G | Reaction solvent | The mass ratio of reaction solvent to compound G | Reaction temperature (° C.) | Product character | Quality; yield (%) of product |
|---|---|---|---|---|---|---|---|
| J1 | ethyl | 1.0; 42.4 g | DCM | 10 | 39 | yellow solid | 35.2 g; 70 |
| J1 | ethyl | 1.0; 42.4 g | CHCl₃ | 20 | 61 | yellow solid | 36.3 g; 72 |
| J1 | ethyl | 1.1; 42.4 g | CCl₄ | 30 | 76 | yellow solid | 44.3 g; 88 |
| J2 | methyl | 1.0; 41 g | DCM | 10 | 39 | yellow solid | 29.9 g; 73 |
| J2 | methyl | 1.1; 41 g | CHCl₃ | 20 | 61 | yellow solid | 30.8 g; 75 |
| J2 | methyl | 1.1; 41 g | CCl₄ | 30 | 76 | yellow solid | 34.9 g; 85 |

TABLE 10-1

The NMR and MS datum of compound J

| No. | ¹H NMR | MS |
|---|---|---|
| J1 | ¹H NMR (600 MHz, DMSO-d₆): δ 10.23 (s, 1H), 8.01 (d, 1H), 7.98 (d, 1H), 7.62 (dd, 1H), 7.42 (dd, 1H), 7.29 (td, 1H), 6.01 (s, 1H), 4.79 (br, 2H), 4.01 (q, 2H), 1.08 (t, 3H). | MS (ESI, pos.ion) m/z: 503.9 [M + H]⁺; |
| J2 | ¹H NMR (400 MHz, CDCl₃): δ 8.87 (d, 1H), 7.54 (d, 1H), 7.4(dd, 1H), 7.35 (dd, 1H), 7.03 (td, 1H), 6.11 (s, 1H), 4.97 (d, 1H), 4.64 (d, 1H), 3.69 (s, 3H). | MS (ESI, pos.ion) m/z: 489.9 [M + H]⁺; |

Step 3) (R)-ethyl 4-(2-bromo-4-fluorophenyl)-6-(morpholinomethyl)-2-(thiazol-2-yl)-1,4-dihydropyrimidine-5-carboxylate

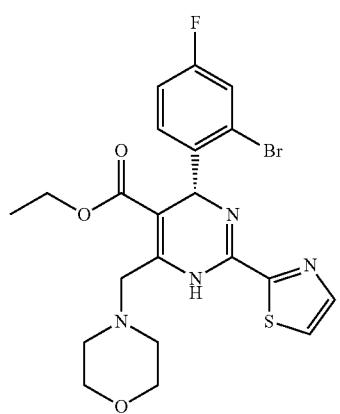

To a flask were added (R)-ethyl 4-(2-bromo-4-fluorophenyl)-6-(bromomethyl)-2-(thiazol-2-yl)-1,4-dihydropyrimidine-5-carboxylate (50.3 g, 0.1 mol), anhydrous ethanol (302 g) and morpholine (34.8 g, 0.4 mol). The mixture was stirred at 25° C. under nitrogen atmosphere for 6 hours. After the reaction, the mixture was concentrated. To the residue was added ethyl acetate (500 g), the resulting mixture was washed with water (250 mL×2). The organic layer was concentrated to give the product as tawny oil (37.7 g, 74%)

MS (ESI, pos.ion) m/z: 509.1 [M+H]⁺;

¹H NMR (600 MHz, DMSO-d₆): δ 9.69 (s, 1H), 8.02 (d, 1H), 7.93 (d, 1H), 7.57 (dd, 1H), 7.40 (dd, 1H), 7.22 (td, 1H), 6.05 (s, 1H), 3.96 (q, 4H), 3.93 (dd, 2H), 3.68 (br, 4H), 2.56 (br, 4H), 1.05 (t, 3H).

The compound L can be prepared under the reaction conditions shown in table 11 according to the procedure described in step 3 of Example 6.

TABLE 11

The reaction conditions for preparation of compound L

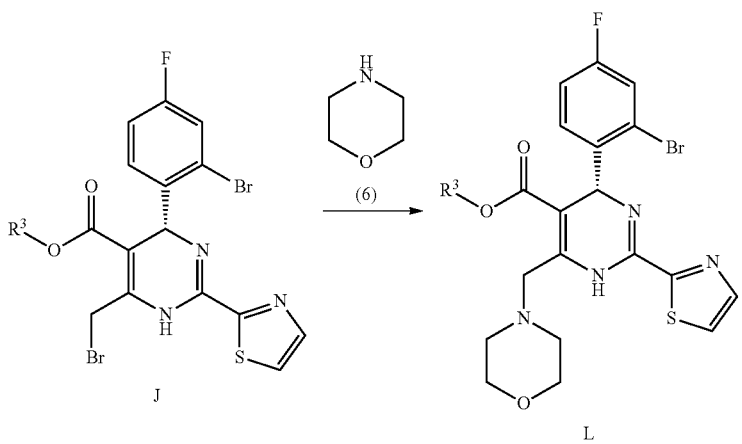

| No. | $R^3$ | The mole ratio of compound (6) to compound (J); the amount of compound J | Reaction solvent | The mass ratio of reaction solvent to compound (J) | Reaction temperature (° C.) | Reaction time(h) | Product character | Quality; yield (%) of product |
|---|---|---|---|---|---|---|---|---|
| L1 | ethyl | 2; 50.3 g | ethanol | 20 | 25 | 2 | tawny oil | 38.2 g; 75 |
| L1 | ethyl | 3; 50.3 g | acetone | 10 | 40 | 10 | tawny oil | 40.8 g; 80 |
| L1 | ethyl | 4; 50.3 g | methanol | 10 | 30 | 6 | tawny oil | 38.7 g; 76 |
| L1 | ethyl | 5; 50.3 g | ethyl acetate | 20 | 50 | 24 | tawny oil | 35.7 g; 70 |
| L1 | ethyl | 6; 50.3 g | DCM | 8 | 39 | 6 | tawny oil | 36.2 g; 71 |
| L1 | ethyl | 3; 50.3 g | DMF | 4 | 60 | 1 | tawny oil | 36.7 g; 72 |
| L1 | ethyl | 4; 50.3 g | THF | 6 | 50 | 8 | tawny oil | 38.2 g; 75 |
| L2 | methyl | 2; 48.9 g | ethanol | 20 | 25 | 2 | tawny oil | 36.2 g; 73 |
| L2 | methyl | 3; 48.9 g | acetone | 10 | 40 | 10 | tawny oil | 37.6 g; 76 |
| L2 | methyl | 4; 48.9 g | methanol | 10 | 30 | 6 | tawny oil | 39.6 g; 80 |
| L2 | methyl | 5; 48.9 g | ethyl acetate | 20 | 50 | 24 | tawny oil | 38.6 g; 78 |
| L2 | methyl | 6; 48.9 g | DCM | 8 | 39 | 6 | tawny oil | 35.2 g; 71 |
| L2 | methyl | 3; 48.9 g | DMF | 4 | 60 | 1 | tawny oil | 36.2 g; 73 |
| L2 | methyl | 4; 48.9 g | THF | 6 | 50 | 8 | tawny oil | 35.7 g; 72 |

TABLE 11-1

The NMR and MS datum of compound L

| No. | $^1$H NMR | MS |
|---|---|---|
| L1 | $^1$H NMR (600 MHz, DMSO-$d_6$): δ 9.69 (s, 1H), 8.02 (d, 1H), 7.93 (d, 1H), 7.57 (dd, 1H), 7.40 (dd, 1H), 7.22 (td, 1H), 6.05 (s, 1H), 3.96 (q, 4H), 3.93 (dd, 2H), 3.68 (br, 4H), 2.56 (br, 4H), 1.05 (t, 3H). | MS (ESI, pos. ion) m/z: 509.1 [M + H]$^+$; |
| L2 | $^1$H NMR (600 MHz, DMSO-$d_6$): δ 9.71 (s, 1H), 8.02 (d, 1H), 7.94 (d, 1H), 7.55 (dd, 1H), 7.37 (dd, 1H), 7.20 (td, 1H), 6.02 (s, 1H), 3.91 (dd, 2H), 3.67 (br, 4H), 3.52 (s, 3H), 2.55 (br, 4H). | MS (ESI, pos. ion) m/z: 494.7 [M + H]$^+$; |

Example 7: The Preparation of (S)-4-(((R)-6-(2-bromo-4-fluorophenyl)-5-(ethoxycarbonyl)-2-(thiazol-2-yl)-3,6-dihydropyrimidin-4-yl)methyl)morpholine-3-carboxylic acid

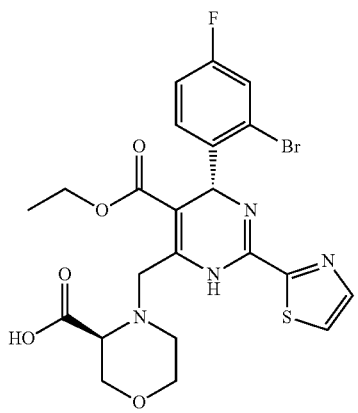

To a flask were added (R)-ethyl 4-(2-bromo-4-fluorophenyl)-6-(bromomethyl)-2-(thiazol-2-yl)-1,4-dihydropyrimidine-5-carboxylate (5.03 g, 10 mmol), (S)-morpholine-3-carboxylic acid (1.31 g, 10 mmol), potassium carbonate (2.76 g, 20 mmol) and ethanol (100 mL). The mixture was stirred at 30° C. under nitrogen atmosphere for 12 hours. After the reaction, the mixture was filtered. The filtrate was concentrated. To the residue was added water (100 mL), the resulting mixture was extracted with ethyl acetate (100 mL). The organic layer was discarded. To the aqueous layer was added ethyl acetate (100 mL), the mixture was adjusted to pH 3-6 with concentrated hydrochloric acid. The organic layer was dried over anhydrous sodium sulfate and concentrated to give the product as a yellow solid (4.4 g, 80%).

MS (ESI, pos.ion) m/z: 553.2 [M+H]$^+$;

$^1$H NMR (400 MHz, DMSO-$d_6$): δ 12.85 (br, 1H), 9.80 (s, 1H), 8.00 (d, 1H), 7.91 (d, 1H), 7.54 (dd, 1H), 7.39 (dd, 1H), 7.19 (td, 1H), 6.01 (s, 1H), 4.25 (d, 1H), 4.02 (d, 1H), 3.97-3.91 (m, 3H), 3.81 (dd, 1H), 3.72-3.69 (m, 1H), 3.66-3.63 (m, 1H), 3.61-3.58 (m, 1H), 3.10-3.03 (m, 1H), 2.42-2.35 (m, 1H), 1.04 (t, 3H).

The compound F can be prepared under the reaction conditions shown in table 12 according to the procedure described in Example 7.

TABLE 12

The reaction conditions for preparation of compound F

| No. | $R^3$ | (VI) or a hydrochloride thereof | The mole ratio of compound (J) to compound (VI); the amount of compound (J) | Reaction solvent | The mass ratio of reaction solvent to compound (J) | Reaction temperature (° C.) | Reaction time(h) | Product character | Quality; yield (%) of product |
|---|---|---|---|---|---|---|---|---|---|
| F1 | ethyl | | 1; 5.03 g | ethanol | 8 | 30 | 4 | yellow solid | 4.07 g; 70 |
| F2 | ethyl | | 1; 5.03 g | ethanol | 4 | 30 | 8 | yellow solid | 4.12 g; 71 |

TABLE 12-continued

The reaction conditions for preparation of compound F

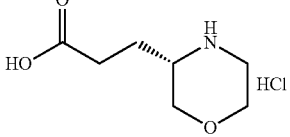

| No. | R³ | (VI) or a hydrochloride thereof | The mole ratio of compound (J) to compound (VI); the amount of compound (J) | Reaction solvent | The mass ratio of reaction solvent to compound (J) | Reaction temperature (° C.) | Reaction time(h) | Product character | Quality; yield (%) of product |
|---|---|---|---|---|---|---|---|---|---|
| F3 | ethyl | 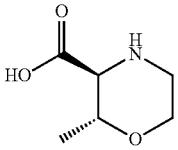 | 1; 5.03 g | ethanol | 20 | 30 | 24 | yellow solid | 2.61 g; 45 |
| F4 | ethyl | 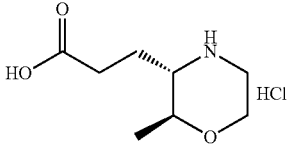 | 1; 5.03 g | ethanol | 30 | 30 | 6 | yellow solid | 4.54 g; 80 |
| F5 | ethyl | 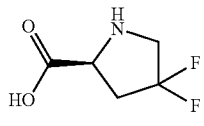 | 1; 5.03 g | ethanol | 15 | 30 | 24 | yellow solid | 3.04 g; 51 |
| F6 | ethyl | 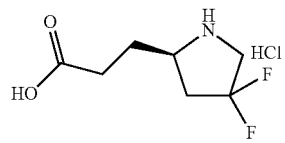 [SMILES: O=C(O)CC[C@@H]1CC(F)(F)CN1 ; Cl] | 1; 5.03 g | ethanol | 20 | 30 | 6 | yellow solid | 4.47 g; 78 |
| F7 | ethyl | 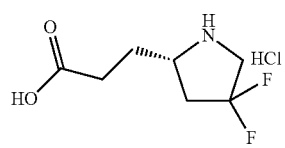 [SMILES: O=C(O)CC[C@H]1CC(F)(F)CN1 ; Cl] | 1; 5.03 g | ethanol | 25 | 30 | 12 | yellow solid | 3.91 g; 65 |
| F8 | ethyl |  | 1; 5.03 g | ethanol | 14 | 30 | 12 | yellow solid | 4.09 g; 68 |

TABLE 12-continued

The reaction conditions for preparation of compound F

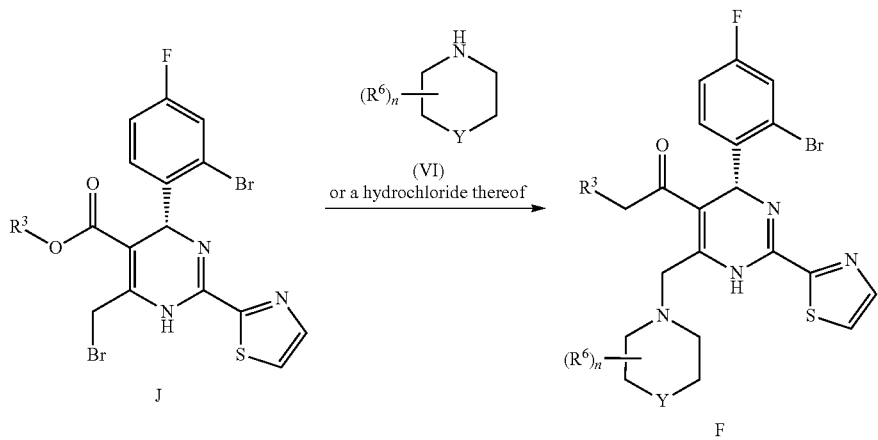

| No. | R³ | (VI) or a hydrochloride thereof | The mole ratio of compound (J) to compound (VI); the amount of compound (J) | Reaction solvent | The mass ratio of reaction solvent to compound (J) | Reaction temperature (° C.) | Reaction time(h) | Product character | Quality; yield (%) of product |
|---|---|---|---|---|---|---|---|---|---|
| F9 | methyl | (S)-morpholine-3-carboxylic acid | 1; 4.89 g | ethanol | 8 | 30 | 4 | yellow solid | 3.83 g; 71 |
| F10 | methyl | 3-((S)-morpholin-2-yl)propanoic acid·HCl | 1; 4.89 g | ethanol | 4 | 30 | 8 | yellow solid | 3.85 g; 68 |
| F11 | methyl | 3-((R)-morpholin-2-yl)propanoic acid·HCl | 1; 4.89 g | ethanol | 10 | 30 | 12 | yellow solid | 3.74 g; 66 |
| F12 | methyl | 3-((R)-morpholin-3-yl)propanoic acid·HCl | 1; 4.89 g | ethanol | 30 | 30 | 6 | yellow solid | 2.50 g; 44 |
| F13 | methyl | (2S,3S)-2-methylmorpholine-3-carboxylic acid | 1; 4.89 g | ethanol | 8 | 30 | 12 | yellow solid | 4.32 g; 78 |
| F14 | methyl | 3-((2S,3S)-2-methylmorpholin-3-yl)propanoic acid·HCl | 1; 4.89 g | ethanol | 20 | 30 | 6 | yellow solid | 2.79 g; 48 |

TABLE 12-continued

The reaction conditions for preparation of compound F

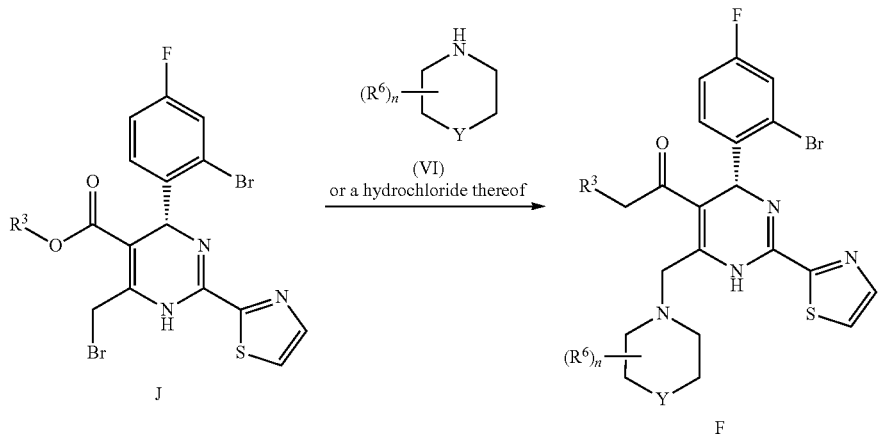

| No. | R³ | (VI) or a hydrochloride thereof | The mole ratio of compound (J) to compound (VI); the amount of compound (J) | Reaction solvent | The mass ratio of reaction solvent to compound (J) | Reaction temperature (° C.) | Reaction time(h) | Product character | Quality; yield (%) of product |
|---|---|---|---|---|---|---|---|---|---|
| F15 | methyl | (pyrrolidine-2-carboxylic acid with 4,4-difluoro) | 1; 4.89 g | ethanol | 25 | 30 | 12 | yellow solid | 4.14 g; 74 |
| F16 | methyl | (4,4-difluoropyrrolidin-2-yl propanoic acid HCl) | 1; 4.89 g | ethanol | 14 | 30 | 12 | yellow solid | 3.64 g; 62 |
| F17 | methyl | (4,4-difluoropyrrolidin-2-yl propanoic acid HCl) | 1; 4.89 g | ethanol | 15 | 30 | 24 | yellow solid | 3.7 g; 63 |

TABLE 12-1

The NMR and MS datum of compound L

| No. | ¹H NMR | MS |
|---|---|---|
| F1 | ¹H NMR (400 MHz, DMSO-$d_6$): δ 12.06 (s, 1H), 9.65 (s, 1H), 8.02 (d, 1H), 7.94 (d, 1H), 7.57 (dd, 1H), 7.39 (dd, 1H), 7.22 (td, 1H), 6.03 (s, 1H), 3.96 (q, 2H), 3.89-3.85 (m, 3H), 3.61-3.47 (m, 2H), 2.81-2.75 (m, 2H), 2.38-2.21 (m, 3H), 2.04-2.02 (m, 1H), 1.65-1.60 (m, 2H), 1.06 (t, 3H). | MS (ESI, pos. ion) m/z: 581.2 [M + H]⁺; |
| F2 | ¹H NMR (400 MHz, DMSO-$d_6$): δ 12.06 (s, 1H), 9.66 (s, 1H), 8.02 (d, 1H), 7.95 (d, 1H), 7.56 (dd, 1H), 7.41 (dd, 1H), 7.20 (td, 1H), 6.03 (s, 1H), 3.97 (q, 2H), 3.93-3.83 (m, 3H), 3.57-3.46 (m, 2H), 2.88 (d, 1H), 2.63 (d, 1H), 2.37-2.22 (m, 3H), 2.13-2.08 (m, 1H), 1.75-1.65 (m, 2H), 1.06 (t, 3H). | MS (ESI, pos. ion) m/z: 580.9 [M + H]⁺; |
| F3 | ¹H NMR (400 MHz, DMSO-$d_6$): δ 12.14 (br, 1H), 9.82 (s, 1H), 8.02 (d, 1H), 7.92 (d, 1H), 7.54( dd, 1H), 7.40 (dd, 1H), 7.22 (td, 1H), 6.03 (s, 1H), 4.18 (d, 1H), 3.96 (q, 2H), 3.91 (d, 1H), 3.82-3.79 (m, 1H), 3.74-3.71 (m, 1H), 3.61-3.57 (m, 1H), 3.37-3.32 (m, 1H), 2.78-2.75 (m, 1H), 2.57-2.53 (m, 1H), 2.49-2.47 (m, 1H), 2.38-2.32 (m, 2H), 1.89-1.84 (m, 1H), 1.68-1.58 (m, 1H), 1.06 (t, 3H). | MS (ESI, pos. ion) m/z: 580.9 [M + H]⁺; |

TABLE 12-1-continued

The NMR and MS datum of compound L

| No. | ¹H NMR | MS |
|---|---|---|
| F4 | ¹H NMR (400 MHz, DMSO-$d_6$): δ 13.02 (s, 1H), 9.78 (s, 1H), 8.03 (d, 1H), 7.93 (d, 1H), 7.56 (dd, 1H), 7.39 (dd, 1H), 7.22 (td, 1H), 6.00 (s, 1H), 4.10 (d, 1H), 3.95 (q, 2H), 3.90-3.87 (m, 1H), 3.76-3.60 (m, 3H), 3.46-3.42 (m, 1H), 2.98 (d, 1H), 2.93 (d, 1H), 1.21 (d, 3H), 1.05 (t, 3H). | MS (ESI, pos. ion) m/z: 567.1 [M + H]⁺; |
| F5 | ¹H NMR (400 MHz, DMSO-$d_6$): δ 12.11 (s, 1H), 9.74 (s, 1H), 8.02 (d, 1H), 7.95 (d, 1H), 7.56 (dd, 1H), 7.39 (dd, 1H), 7.19 (td, 1H), 6.04 (s, 1H), 4.16 (d, 1H), 4.00-3.93 (m, 2H), 3.86 (d, 1H), 3.77-3.72 (m, 1H), 3.59-3.53 (m, 1H), 3.51-3.45 (m, 1H), 2.66 (d, 1H), 2.46-2.40 (m, 1H), 2.37-2.30 (m, 3H), 2.03 -1.91 (m, 1H), 1.80-1.73 (m, 1H), 1.20 (d, 3H), 1.06 (t, 3H). | MS (ESI, pos. ion) m/z: 594.6 [M + H]⁺; |
| F6 | ¹H NMR (600 MHz, DMSO-$d_6$): δ 9.98 (br, 1H), 8.03 (d, 1H), 8.00 (d, 1H), 7.61 (dd, 1H), 7.48 (dd, 1H), 7.28 (td, 1H), 6.02 (s, 1H), 4.35 (d, 1H), 4.13 (d, 1H), 4.01-3.94 (m, 3H), 3.61-3.51 (m, 1H), 3.25-3.19 (m, 1H), 3.10-3.04 (m, 1H), 2.86-2.68 (m, 1H), 1.20 (t, 3H). | MS (ESI, pos. ion) m/z: 573.0 [M + H]⁺; |
| F7 | ¹H NMR (600 MHz, DMSO-$d_6$): δ 12.08 (s, 1H), 9.51 (s, 1H), 8.01 (d, 1H), 7.93 (d, 1H), 7.57 (dd, 1H), 7.41 (dd, 1H), 7.24 (td, 1H), 6.01 (s, 1H), 4.12 (dd, 2H), 3.97 (q, 2H), 3.61-3.52 (m, 1H), 3.04-2.96 (m, 2H), 2.58-2.56 (m, 1H), 2.35-2.20 (m, 2H), 2.12-1.98 (m, 1H), 1.93-1.90 (m, 1H), 1.56-1.48 (m, 1H), 1.06 (t, 3H). | MS (ESI, pos. ion) m/z: 601.1 [M + H]⁺; |
| F8 | ¹H NMR (400 MHz, CDCl₃): δ 12.19 (br, 1H), 9.46 (s, 1H), 7.86 (d, 1H), 7.50 (d, 1H), 7.37-7.33 (m, 2H), 7.00 (td, 1H), 6.19 (s, 1H), 4.52 (d, 1H), 4.14-4.03(m, 2H), 3.65(d, 1H), 3.31-3.23 (m, 2H), 3.02-2.91 (m, 1H), 2.57-2.25 (m, 5H), 1.79-1.74 (m, 1H), 1.16 (t, 3H). | MS (ESI, pos. ion) m/z: 601.2 [M + H]⁺; |
| F9 | ¹H NMR (600 MHz, DMSO-$d_6$): δ 12.88 (br, 1H), 10.07 (br, 1H), 8.02 (d, 1H), 7.93 (d, 1H), 7.56 (dd, 1H), 7.39 (dd, 1H), 7.23 (td, 1H), 6.01 (s, 1H), 4.25 (d, 1H), 4.04 (d, 1H), 3.99 (dd, 1H), 3.84 (dd, 1H), 3.73-3.70 (m, 1H), 3.69-3.65 (m, 1H), 3.62-3.58 (m, 1H), 3.51 (s, 3H), 3.10-3.07 (m, 1H), 2.41-2.39 (m, 1H). | MS (ESI, pos. ion) m/z: 539.1 [M + H]⁺; |
| F10 | ¹H NMR (400 MHz, DMSO-$d_6$): δ 12.03 (s, 1H), 9.69 (s, 1H), 8.01 (d, 1H), 7.93 (d, 1H), 7.56 (dd, 1H), 7.38 (dd, 1H), 7.23 (td, 1H), 6.01 (s, 1H), 3.93-3.83 (m, 3H), 3.60-3.53 (m, 2H) 3.52 (s, 3H), 2.77 (dd, 2H), 2.38-2.25 (m, 3H), 2.05-1.99 (m, 1H), 1.65-1.59 (m, 2H). | MS (ESI, pos. ion) m/z: 567.2 [M + H]⁺; |
| F11 | ¹H NMR (600 MHz, DMSO-$d_6$): δ 12.06 (s, 1H), 9.70 (s, 1H), 8.03 (d, 1H), 7.94 (d, 1H), 7.57 (dd, 1H), 7.39 (dd, 1H), 7.23 (td, 1H), 6.02 (s, 1H), 3.95 (d, 1H), 3.86-3.80 (m, 2H), 3.56-3.54 (m, 1H), 3.53 (s, 3H), 3.52-3.49 (m, 1H), 2.88 (d, 1H), 2.62 (d, 1H), 2.37-2.21 (m, 3H), 2.15-2.08 (m, 1H), 1.72-1.64 (m, 2H). | MS (ESI, pos. ion) m/z: 567.2 [M + H]⁺; |
| F12 | ¹H NMR (400 MHz, DMSO-$d_6$): δ 9.87 (s, 1H), 8.03 (d, 1H), 7.94 (d, 1H), 7.56 (dd, 1H), 7.38 (dd, 1H), 7.23 (td, 1H), 6.01 (s, 1H), 4.18 (d, 1H), 3.91 (d, 1H), 3.83-3.79 (m, 1H), 3.75-3.70 (m, 1H), 3.61-3.56 (m, 1H), 3.53 (s, 3H), 3.47-3.40 (m, 1H), 3.04-2.86 (m, 1H), 2.77-2.75 (m, 1H), 2.58-2.54 (m, 1H), 2.37-2.22 (m, 2H), 1.88-1.84 (m, 1H), 1.65-1.58 (m, 1H). | MS (ESI, pos. ion) m/z: 567.2 [M + H]⁺; |
| F13 | ¹H NMR (400 MHz, DMSO-$d_6$): δ 13.02 (s, 1H), 9.83 (s, 1H), 8.02 (d, 1H), 7.94 (d, 1H), 7.56 (dd, 1H), 7.38 (dd, 1H), 7.22 (td, 1H), 5.99 (s, 1H), 4.05 (d, 1H), 3.90-3.85 (m, 1H), 3.75-3.60 (m, 3H), 3.52 (s, 3H), 3.47-3.42 (m, 1H), 3.00 (d, 1H), 2.92 (d, 1H), 1.21 (d, 3H). | MS (ESI, pos. ion) m/z: 553.0 [M + H]⁺; |
| F14 | ¹H NMR (400 MHz, DMSO-$d_6$): δ 12.10 (s, 1H), 9.75 (s, 1H), 8.01 (d, 1H), 7.96 (d, 1H), 7.54 (dd, 1H), 7.40 (dd, 1H), 7.20 (td, 1H), 6.02 (s, 1H), 4.18 (d, 1H), 3.88 (d, 1H), 3.78-3.73 (m, 1H), 3.60-3.54 (m, 1H), 3.52 (s, 3H), 3.50-3.45 (m, 1H), 2.68 (d, 1H), 2.47-2.41 (m, 1H), 2.36-2.30 (m, 3H), 2.04-1.92 (m, 1H), 1.81-1.73 (m, 1H), 1.21 (d, 3H). | MS (ESI, pos. ion) m/z: 581.2 [M + H]⁺; |

TABLE 12-1-continued

The NMR and MS datum of compound L

| No. | $^1$H NMR | MS |
|---|---|---|
| F15 | $^1$H NMR (600 MHz, DMSO-$d_6$): δ 9.71 (br, 1H), 7.98 (d, 1H), 7.91 (d, 1H), 7.56 (dd, 1H), 7.40 (dd, 1H), 7.23 (td, 1H), 5.99 (s, 1H), 4.33 (d, 1H), 4.09 (d, 1H), 3.93-3.88 (m, 1H), 3.52 (s, 3H), 3.49-3.45 (m, 1H), 3.22-3.08 (m, 2H), 2.82-2.74 (m, 1H). | MS (ESI, pos. ion) m/z: 558.6 [M + H]$^+$; |
| F16 | $^1$H NMR (400 MHz, DMSO-$d_6$): δ 11.03 (s, 1H), 9.57 (s, 1H), 7.99 (d, 1H), 7.92 (d, 1H), 7.55 (dd, 1H), 7.39 (dd, 1H), 7.23 (td, 1H), 6.00 (s, 1H), 4.14 (dd, 2H), 3.62-3.54 (m, 1H), 3.53 (s, 3H), 3.05-2.96 (m, 2H), 2.57-2.56 (m, 1H), 2.36-2.20 (m, 2H), 2.13-1.98 (m, 1H), 1.95-1.90 (m, 1H), 1.56-1.46 (m, 1H). | MS (ESI, pos. ion) m/z: 587.2 [M + H]$^+$; |
| F17 | $^1$H NMR (400 MHz, CDCl$_3$): δ 12.15 (br, 1H), 9.47 (s, 1H), 7.85 (d, 1H), 7.51 (d, 1H), 7.38-7.33 (m, 2H), 7.01 (td, 1H), 6.17 (s, 1H), 4.50 (d, 1H), 3.66 (d, 1H) 3.55 (s, 3H), 3.33-3.23 (m, 2H), 3.04-2.92 (m, 1H), 2.58-2.25 (m, 5H), 1.78-1.74 (m, 1H). | MS (ESI, pos. ion) m/z: 587.2 [M + H]$^+$; |

Example 8: The Preparation of (R)-ethyl 4-(2-chloro-4-fluorophenyl)-6-(morpholinomethyl)-2-(thiazol-2-yl)-1,4-dihydropyrimidine-5-carboxylate

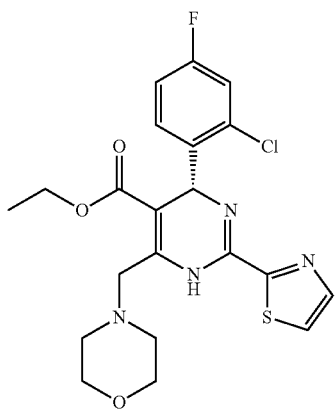

Step 1) (R)-(R)-1-ethoxy-1-oxopropan-2-yl 4-(2-chloro-4-fluorophenyl)-6-methyl-2-(thiazol-2-yl)-1,4-dihydropyrimidine-5-carboxylate

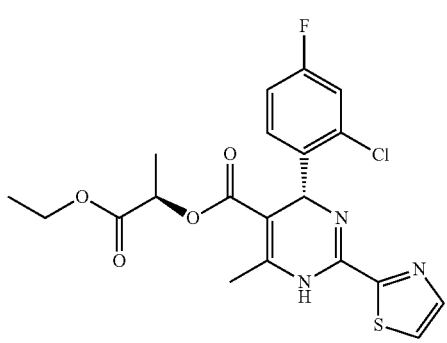

Method One:

To a flask were added 2-thiazolecarboxamidine hydrochloride (16.4 g, 0.1 mol), 2-chloro-4-fluorobenzaldehyde (15.9 g, 0.1 mol), (R)-1-ethoxy-1-oxopropan-2-yl 3-oxobutanoate (20.2 g, 0.1 mol), anhydrous sodium acetate (8.2 g, 0.1 mol) and ethanol (74 g) in turn. The mixture was stirred at 78° C. for 16 hours. After the reaction, the mixture was cooled to 30° C., kept at 30° C. and stirred for 6 hours. The resulting mixture was filtered. The filter cake was washed with water (330 mL) and dried in vacuo at 60° C. for 8 hours to obtain the crude product. To the crude product was added n-propanol (50 g). The mixture was heated until dissolved completely, cooled to 30° C., and then kept at 30° C., stirred and crystallized for 8 hours. The resulting mixture was filtered. The filter cake was dried in vacuo at 60° C. for 8 hours to obtain the product as a yellow solid (10.4 g, 23%).

$[α]_D^{25}$=−91.47 (c=0.3083 g/100 mL, MeOH);

MS (ESI, pos.ion) m/z: 452.2 [M+H]$^+$;

$^1$H NMR (400 MHz, DMSO-$d_6$): δ 10.05 (s, 1H), 7.98 (d, 1H), 7.91 (d, 1H), 7.42-7.37 (m, 2H), 7.20 (td, 1H), 6.03 (s, 1H), 4.84 (q, 1H), 4.12-4.04 (m, 2H), 2.47 (s, 3H), 1.22 (d, 3H), 1.14 (t, 3H).

The compound 8 can be prepared under the reaction conditions shown in table 13 by using method one described in step 1 of Example 8.

TABLE 13

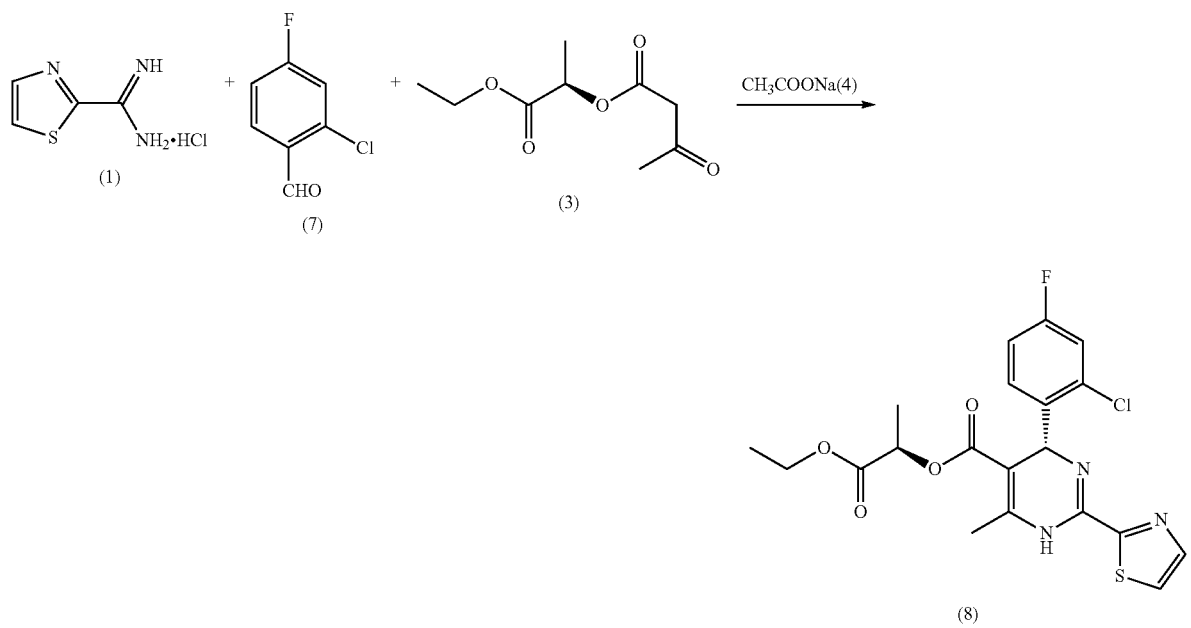

| No. | (1):(7):(3):(4): (mol); the amount of compound (1) is 16.4 g | Reaction sovent | The mass ratio of reaction solvent to compound (1) | Reaction temperature (° C.) | Reaction time (h) | Cooling temperature (° C.) | Cooling time (h) | Recrystallization solvent | The mass ratio of recrystallization solvent to compound (1) | Crystallization temperature (° C.) | Crystallization time (h) | Quality; yield (%) of product |
|---|---|---|---|---|---|---|---|---|---|---|---|---|
| 1 | 1:1:2:1 | — | — | 78 | 12 | 40 | 6 | ethanol | 20 | 0 | 3 | 7.9 g; 17.5 |
| 2 | 1:1:1:1 | ethanol | 1 | 78 | 12 | 40 | 6 | ethanol | 15 | 25 | 10 | 8.5 g; 18.8 |
| 3 | 1:1:1:1 | ethanol | 4.5 | 25 | 72 | 25 | — | ethanol | 4 | 5 | 8 | 9.1 g; 20.2 |
| 4 | 1:1:1:1 | ethanol | 5 | 78 | 12 | 25 | 6 | ethanol | 3 | 15 | 5 | 10.2 g; 22.5 |
| 5 | 1:1:1:1 | ethanol | 20 | 60 | 24 | −20 | 12 | ethanol | 3 | 25 | 6 | 8.9 g; 19.6 |
| 6 | 1:1:1:1 | ethanol | 80 | 78 | 12 | −40 | 24 | ethanol | 5 | 25 | 4 | 7.6 g; 16.9 |
| 7 | 1:1:1:1 | n-butanol | 4.5 | 100 | 5 | 25 | 6 | n-butanol | 4 | 25 | 6 | 10.4 g; 23.1 |
| 8 | 1:1:1:1 | n-propanol | 4.5 | 80 | 12 | 25 | 6 | n-propanol | 3 | 25 | 6 | 11.8 g; 26.2 |
| 9 | 1:1:1:1 | i-propanol | 4.5 | 82 | 12 | 25 | 2 | i-propanol | 3 | 30 | 6 | 11.4 g; 25.3 |
| 10 | 1:1:1:1 | t-butanol | 4.5 | 82 | 12 | 30 | 12 | t-butanol | 4 | 25 | 6 | 11 g; 24.4 |
| 11 | 1:1:1:1 | 2-methoxy-ethanol | 4.5 | 78 | 12 | −10 | 12 | i-propanol | 3.5 | 25 | 4 | 9 g; 20 |
| 12 | 1:1:1:1 | 1,2-dimethoxy-ethane | 4.5 | 78 | 12 | −15 | 12 | i-propanol | 3.5 | 25 | 6 | 8.6 g; 19.1 |

Method Two

To a flask were added 2-thiazolecarboxamidine hydrochloride (16.4 g, 0.1 mol), 2-chloro-4-fluorobenzaldehyde (15.9 g, 0.1 mol), (R)-1-ethoxy-1-oxopropan-2-yl 3-oxobutanoate (20.2 g, 0.1 mol), anhydrous sodium acetate (8.2 g, 0.1 mol) and ethanol (74 g) in turn. The mixture was stirred at 78° C. for 16 hours. After the reaction, the reaction mixture was cooled to 30° C., kept at 30° C. and stirred for 6 hours. The mixture was filtered. The filtrate was washed with ethanol (16.4 g) and water (330 mL) in turn, and then dried in vacuo at 60° C. for 8 hours to obtain the product as a yellow solid (12.2 g, 27%).

$[\alpha]_D^{25}$=−91.47 (c=0.3083 g/100 mL, MeOH);
MS (ESI, pos.ion) m/z: 452.2 [M+H]$^+$;
$^1$H NMR (400 MHz, DMSO-d$_6$): δ 10.05 (s, 1H), 7.98 (d, 1H), 7.91 (d, 1H), 7.42-7.37 (m, 2H), 7.20 (td, 1H), 6.03 (s, 1H), 4.84 (q, 1H), 4.12-4.04 (m, 2H), 2.47 (s, 3H), 1.22 (d, 3H), 1.14 (t, 3H).

The compound 8 can be prepared under the reaction conditions shown in table 14 by using method two described in step 1 of Example 8.

TABLE 14

The reaction conditions

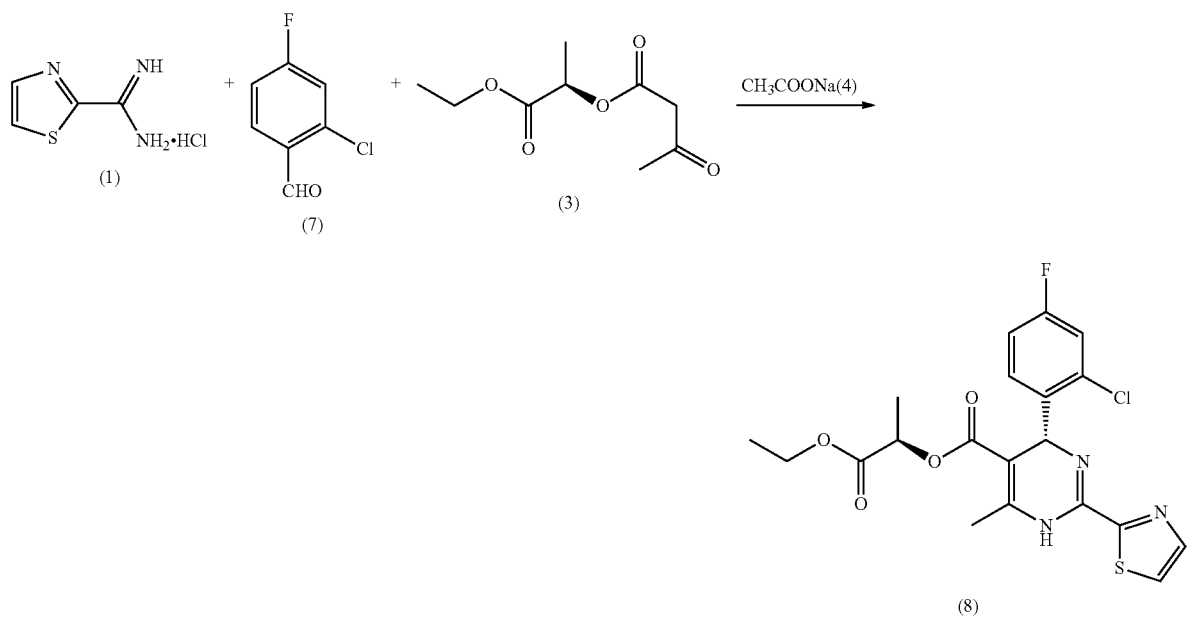

| No. | (1):(7):(3):(4): (mol); the amount of compound (1) is 16.4 g | Reaction sovent | The mass ratio of reaction solvent to compound (1) | Reaction temperature | Reaction time(h) | Cooling temperature(° C.) | Cooling time(h) | Washing solvent | The mass ratio of washing solvent to compound (1) | Washing temperature (° C.) | Quality; yield (%) of product |
|---|---|---|---|---|---|---|---|---|---|---|---|
| 1 | 1:1:2:1 | — | — | 78 | 12 | 40 | 6 | ethanol | 10 | 25 | 8.8 g; 19.4 |
| 2 | 1:1:1:1 | ethanol | 1 | 78 | 12 | 40 | 6 | ethanol | 7.5 | 25 | 9.3 g; 20.5 |
| 3 | 1:1:1:1 | ethanol | 4.5 | 25 | 72 | 25 | — | ethanol | 2 | 25 | 10 g; 22.2 |
| 4 | 1:1:1:1 | ethanol | 5 | 78 | 12 | 25 | 6 | ethanol | 3 | 25 | 11.1 g; 24.6 |
| 5 | 1:1:1:1 | n-propanol | 6 | 80 | 12 | 25 | 6 | — | — | — | 13.1 g; 28.9 |
| 6 | 1:1:1:1 | ethanol | 20 | 60 | 24 | −20 | 6 | ethanol | 3 | 25 | 9.6 g; 21.3 |
| 7 | 1:1:1:1 | ethanol | 80 | 78 | 12 | −30 | 24 | ethanol | 5 | 25 | 9.3 g; 18.8 |
| 8 | 1:1:1:1 | n-butanol | 4.5 | 100 | 5 | 25 | 6 | n-butanol | 3 | 25 | 11.4 g; 25.2 |
| 9 | 1:1:1:1 | n-propanol | 4.5 | 80 | 12 | 25 | 6 | n-propanol | 2 | 25 | 12.8 g; 28.4 |
| 10 | 1:1:1:1 | i-propanol | 4.5 | 82 | 12 | 25 | 2 | i-propanol | 2 | 30 | 12.6 g; 27.8 |
| 11 | 1:1:1:1 | t-butanol | 4.5 | 82 | 12 | 30 | 12 | t-butanol | 3 | 25 | 12 g; 26.5 |
| 12 | 1:1:1:1 | 2-methoxy-ethanol | 4.5 | 78 | 12 | −10 | 12 | 2-methoxy-ethanol | 1 | 0 | 9.9 g; 21.8 |

TABLE 14-continued

| 13 | 1:1:1:1 | 1,2-dimethoxyethane | 4.5 | 78 | 12 | −15 | 12 | i-propanol | 2 | 25 | 9.6 g; 21.3 |

Method Three:

To a flask were added 2-thiazolecarboxamidine hydrochloride (16.4 g, 0.1 mol), 2-chloro-4-fluorobenzaldehyde (15.9 g, 0.1 mol), (R)-1-ethoxy-1-oxopropan-2-yl 3-oxobutanoate (20.2 g, 0.1 mol), anhydrous sodium acetate (8.2 g, 0.1 mol) and ethanol (74 g) in turn. The mixture was stirred at 78° C. for 16 hours. After the reaction, the mixture was cooled to 30° C., kept at 30° C. and stirred for 6 hours. The resulting mixture was filtered. The filter cake was washed with water (330 mL) and dried in vacuo at 60° C. for 8 hours to obtain the crude product. The crude product was triturated with n-propanol (50 g) at 30° C. for 5 hours and filtered. The filter cake was dried in vacuo at 60° C. for 8 hours to obtain the product as a yellow solid (11.3 g, 25%).

$[a]_D^{25}$=−91.47 (c=0.3083 g/100 mL, MeOH);

MS (ESI, pos.ion) m/z: 452.2 [M+H]$^+$;

$^1$H NMR (400 MHz, DMSO-d$_6$): δ 10.05 (s, 1H), 7.98 (d, 1H), 7.91 (d, 1H), 7.42-7.37 (m, 2H), 7.20 (td, 1H), 6.03 (s, 1H), 4.84 (q, 1H), 4.12-4.04 (m, 2H), 2.47 (s, 3H), 1.22 (d, 3H), 1.14 (t, 3H).

The compound 8 can be prepared under the reaction conditions shown in table 15 by using method three described in step 1 of Example 8.

TABLE 15

The reaction conditions

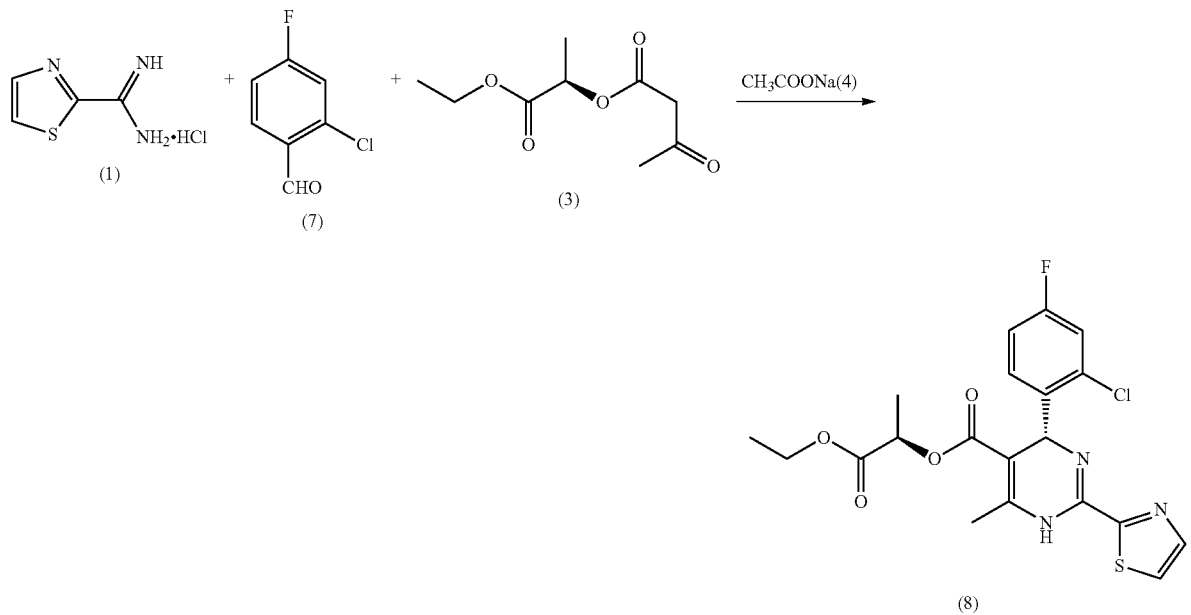

| No. | (1):(7):(3):(4): (mol); the amount of compound (1) is 16.4 g | Reaction sovent | The mass ratio of reaction solvent to compound (1) | Reaction temperature (° C.) | Reaction time(h) | Cooling temperature (° C.) | Cooling time(h) | Trituration solvent | The mass ratio of trituration solvent to compound (1) | Trituration temperature (° C.) | Trituration time(h) | Quality; yield (%) of product |
|---|---|---|---|---|---|---|---|---|---|---|---|---|
| 1 | 1:1:2:1 | — | — | 78 | 12 | 40 | 6 | ethanol | 8 | 25 | 10 | 8.4 g; 18.6 |
| 2 | 1:1:1:1 | ethanol | 1 | 78 | 12 | 40 | 6 | ethanol | 7 | 25 | 5 | 8.8 g; 19.5 |
| 3 | 1:1:1:1 | ethanol | 4.5 | 25 | 72 | 25 | — | ethanol | 3 | 25 | 3 | 9.6 g; 21.3 |
| 4 | 1:1:1:1 | ethanol | 5 | 78 | 12 | 25 | 6 | ethanol | 4 | 5 | 1 | 10.5 g; 23.2 |
| 5 | 1:1:1:1 | ethanol | 20 | 60 | 24 | −20 | 12 | ethanol | 3 | 25 | 4 | 9.3 g; 20.6 |
| 6 | 1:1:1:1 | ethanol | 80 | 78 | 12 | −40 | 24 | ethanol | 5 | 25 | 2 | 8.1 g; 17.8 |
| 7 | 1:1:1:1 | n-butanol | 4.5 | 100 | 5 | 25 | 6 | n-butanol | 4 | 25 | 3 | 10.9 g; 24.1 |

TABLE 15-continued

| | | | | | | | | | | | |
|---|---|---|---|---|---|---|---|---|---|---|---|
| 8 | 1:1:1:1 | n-propanol | 4.5 | 80 | 12 | 25 | 6 | n-propanol | 3 | 25 | 4 | 12.4 g; 27.5 |
| 9 | 1:1:1:1 | i-propanol | 4.5 | 82 | 12 | 25 | 2 | i-propanol | 3 | 30 | 2 | 12.1 g; 26.7 |
| 10 | 1:1:1:1 | t-butanol | 4.5 | 82 | 12 | 30 | 12 | t-butanol | 4 | 25 | 4 | 11.4 g; 25.3 |
| 11 | 1:1:1:1 | 2-methoxy-ethanol | 4.5 | 78 | 12 | −10 | 12 | i-propanol | 3 | 25 | 3 | 9.4 g; 20.9 |
| 12 | 1:1:1:1 | 1,2-di-methoxy-ethane | 4.5 | 78 | 12 | −15 | 12 | i-propanol | 3 | 25 | 2 | 9.2 g; 20.4 |

Step 2) (R)-(R)-1-ethoxy-1-oxopropan-2-yl 4-(2-chloro-4-fluorophenyl)-6-bromomethyl-2-(thiazol-2-yl)-1,4-dihydropyrimidine-5-carboxylate

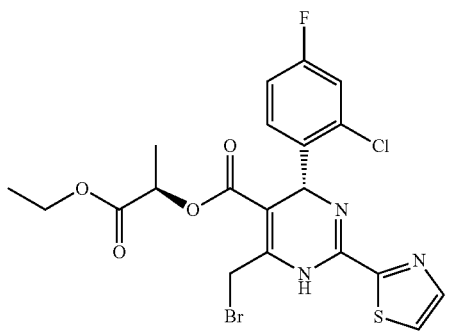 [SMILES: CCOC(=O)[C@@H](C)OC(=O)C1=C(CBr)NC(c2nccs2)=N[C@H]1c1ccc(F)cc1Cl]

To a flask were added (R)-(R)-1-ethoxy-1-oxopropan-2-yl 4-(2-chloro-4-fluorophenyl)-6-methyl-2-(thiazol-2-yl)-1,4-dihydropyrimidine-5-carboxylate (45.2 g, 0.1 mol) and tetrachloromethane (900 g). The mixture was heated at 76° C., NBS was added (19.6 g, 0.11 mol), and then the reaction mixture was stirred for 30 min. After the reaction, the reaction mixture was cooled and concentrated. To the residue was added ethanol (226 g). The resulting mixture was cooled to 0° C., kept at 0° C. and stirred. After the solid precipitated out completely, the mixture was filtered. The filter cake was washed with ethanol (45 g) and dried in vacuo at 60° C. for 6 hours to obtain the product as a yellow solid (31.3 g, 59%).

MS (ESI, pos.ion) m/z: 531.6 [M+H]$^+$;

$^1$H NMR (400 MHz, DMSO-d$_6$): δ 10.37 (s, 1H), 8.03 (d, 1H), 8.00 (d, 1H), 7.47-7.42 (m, 2H), 7.23 (td, 1H), 6.01 (s, 1H), 4.94 (q, 1H), 4.87-4.78 (m, 2H), 4.16-4.04 (m, 2H), 1.27 (d, 3H), 1.15 (t, 3H).

The compound A2 can be prepared under the reaction conditions shown in table 16 according to the procedure described in step 2 of Example 8.

TABLE 16

The reaction conditions

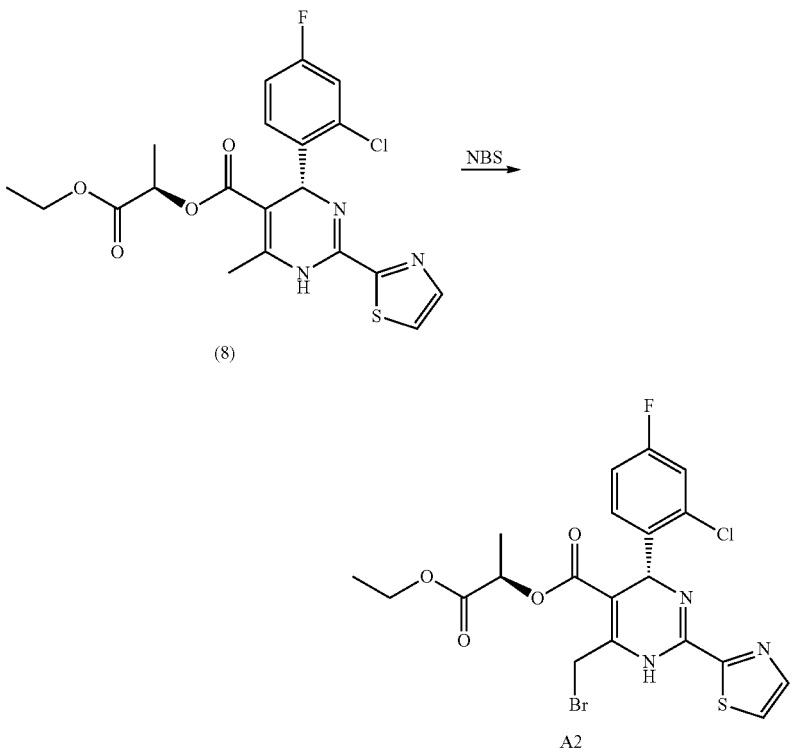

TABLE 16-continued

| No. | Compound (8):NBS(mol) the amount of compound (8) is 45.2 g | Reaction solvent | The mass ratio of reaction solvent to compound (8) | Reaction temperature (° C.) | The solvent added to the residue | The mass ratio of the additional solvent to compound (8) | Quality; yield (%) of product |
|---|---|---|---|---|---|---|---|
| 1 | 1:1.1, | DCM | 30 | 39 | i-propanol | 7 | 33.5 g; 63% |
| 2 | 1:1.05, | DCM | 10 | 39 | ethanol | 5 | 31.9 g; 60% |
| 3 | 1:1.15, | CHCl₃ | 20 | 61 | n-propanol | 6 | 34.5 g; 65% |
| 4 | 1:1.1, | CCl₄ | 20 | 76 | ethanol | 5 | 36.1 g; 68% |

Step 3) (R)-(R)-1-ethoxy-1-oxopropan-2-yl 4-(2-chloro-4-fluorophenyl)-6-morpholinomethyl-2-(thiazol-2-yl)-1,4-dihydropyrimidine-5-carboxylate

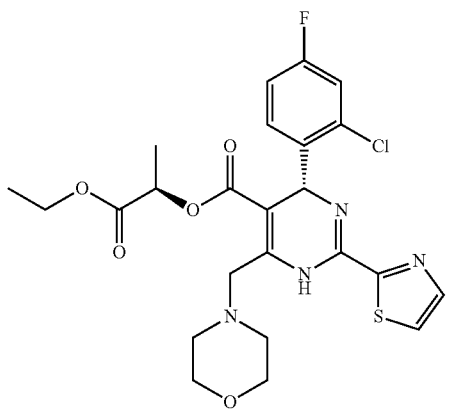

To a flask were added (R)-(R)-1-ethoxy-1-oxopropan-2-yl 4-(2-chloro-4-fluorophenyl)-6-(bromomethyl)-2-(thiazol-2-yl)-1,4-dihydropyrimidine-5-carboxylate (53.1 g, 0.1 mol), i-propanol (287 g) and morpholine (34.8 g, 0.4 mol). The mixture was stirred at 55° C. for 4 hours. After the reaction, the mixture was cooled to 0° C., kept at this temperature and stirred. After the solid precipitated out completely, the mixture was filtered. The filter cake was washed with i-propanol (53 g) followed by water (530 g), and then dried in vacuo at 60° C. for 8 hours to obtain the product as a yellowish solid (34.4 g, 64%).

MS (ESI, pos.ion) m/z: 537.2 [M+H]⁺;

¹H NMR (600 MHz, DMSO-d₆): δ 9.77 (s, 1H), 8.04 (d, 1H), 7.95 (d, 1H), 7.44-7.41 (m, 2H), 7.18 (td, 1H), 6.09 (s, 1H), 4.86 (q, 1H), 4.12-4.04 (m, 2H), 3.90 (dd, 2H), 3.68 (t, 4H), 2.56 (br, 4H), 1.25 (d, 3H), 1.14 (t, 3H).

Step 4) (R)-ethyl 4-(2-chloro-4-fluorophenyl)-6-(morpholinomethyl)-2-(thiazol-2-yl)-1,4-dihydropyrimidine-5-carboxylate

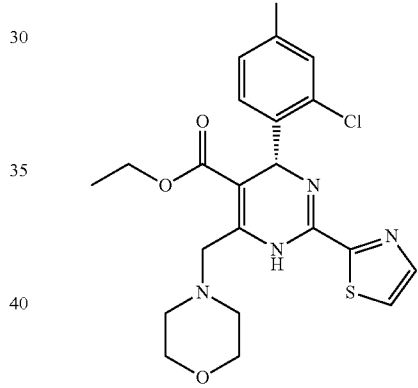

To a flask were added anhydrous ethanol (403 g) and lithium (1.74 g, 0.25 mol) in turn. The mixture was stirred at 43° C. until the lithium was consumed entirely, and then a solution of (R)-(R)-1-ethoxy-1-oxopropan-2-yl 4-(2-chloro-4-fluorophenyl)-6-(morpholinomethyl)-2-(thiazol-2-yl)-1,4-dihydropyrimidine-5-carboxylate (53.7 g, 0.1 mol) in ethanol (403 g) was added. The reaction mixture was stirred at 78° C. for 1.5 hours. After the reaction, the reaction mixture was cooled and concentrated. To the residue was added ethyl acetate (540 g). The mixture was washed with water (250 g×2). The organic layer was concentrated to obtain the product as yellow thick oil (34.9 g, 75%).

MS (ESI, pos.ion) m/z: 465.2 [M+H]⁺;

¹H NMR (400 MHz, DMSO-d₆): δ 9.65 (s, 1H), 8.00 (d, 1H), 7.91 (d, 1H), 7.40-7.37 (m, 2H), 7.15 (td, 1H), 6.03 (s, 1H), 3.94 (q, 2H), 3.88 (dd, 2H), 3.65 (br, 4H), 2.56 (br, 4H), 1.05 (t, 3H).

Example 9: The Preparation of (R)-methyl 4-(2-chloro-4-fluorophenyl)-6-(morpholinomethyl)-2-(thiazol-2-yl)-1,4-dihydropyrimidine-5-carboxylate

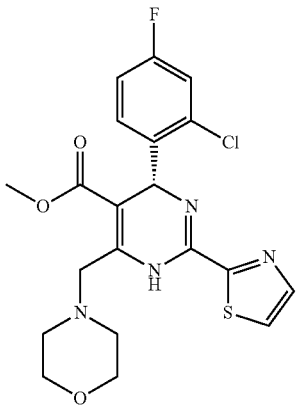 [SMILES: COC(=O)C1=C(CN2CCOCC2)NC(c2nccs2)=N[C@H]1c1ccc(F)cc1Cl]

To a flask were added anhydrous methanol (806 g) and lithium (1.74 g, 0.25 mol) in turn. The mixture was stirred at 43° C. until the lithium was consumed entirely, and then (R)-(R)-1-ethoxy-1-oxopropan-2-yl 4-(2-chloro-4-fluorophenyl)-6-(morpholinomethyl)-2-(thiazol-2-yl)-1,4-dihydropyrimidine-5-carboxylate (53.7 g, 0.1 mol) was added. The reaction mixture was allowed to warm up to 60° C. and stirred for 1.5 hours. After the reaction, the reaction mixture was cooled and concentrated. To the residue was added ethyl acetate (540 g). The mixture was washed with water (250 g×2). The organic layer was concentrated to obtain the product as yellow thick oil (32.9 g, 73%).

MS (ESI, pos.ion) m/z: 450.8 [M+H]$^+$;

$^1$H NMR (600 MHz, DMSO-d$_6$): δ 9.72 (s, 1H), 8.03 (d, 1H), 7.94 (d, 1H), 7.43-7.38 (m, 2H), 7.17 (td, 1H), 6.05 (s, 1H), 3.93 (dd, 2H), 3.68 (br, 4H), 3.53 (s, 3H), 2.56 (br, 4H).

Example 10: The Preparation of (S)-4-(((R)-6-(2-chloro-4-fluorophenyl)-5-(ethoxycarbonyl)-2-(thiazol-2-yl)-3,6-dihydropyrimidin-4-yl)methyl)morpholine-3-carboxylic acid

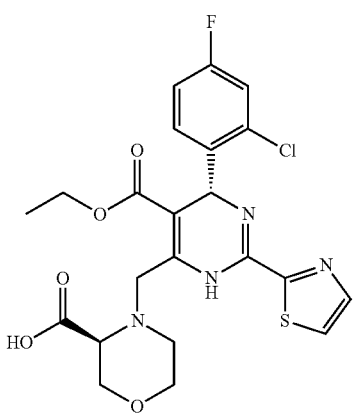 [SMILES: CCOC(=O)C1=C(CN2CCOC[C@H]2C(=O)O)NC(c2nccs2)=N[C@H]1c1ccc(F)cc1Cl]

Step 1) (S)-4-(((R)-6-(2-chloro-4-fluorophenyl)-5-((((R)-1-ethoxy-1-oxopropan-2-yl)oxy)carbonyl)-2-(thiazol-2-yl)-3,6-dihydropyrimidin-4-yl)methyl)morpholine-3-carboxylic acid

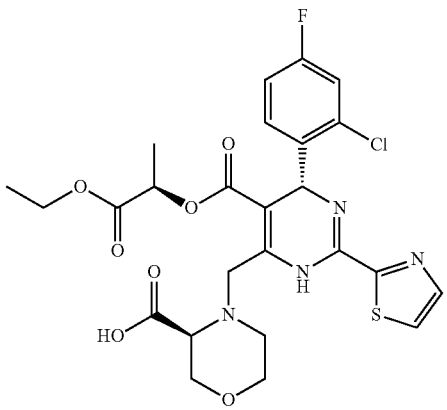 [SMILES: CCOC(=O)[C@@H](C)OC(=O)C1=C(CN2CCOC[C@H]2C(=O)O)NC(c2nccs2)=N[C@H]1c1ccc(F)cc1Cl]

To a flask were added (R)-(R)-1-ethoxy-1-oxopropan-2-yl 4-(2-chloro-4-fluorophenyl)-6-(bromomethyl)-2-(thiazol-2-yl)-1,4-dihydropyrimidine-5-carboxylate (53.1 g, 0.1 mol), ethanol (800 g), (S)-morpholine-3-carboxylic acid (13.1 g, 0.1 mol) and potassium carbonate (27.6 g, 0.2 mol) in turn. The mixture was stirred at 30° C. for 12 hours. After the reaction, the mixture was filtered. The filtrate was concentrated. To the residue was added water (840 g), the resulting mixture was extracted with ethyl acetate (840 mL), the organic layer was discarded. To the aqueous layer was added ethyl acetate (900 mL), the mixture was adjusted to pH 3-6 with concentrated hydrochloric acid. The organic layer was dried over anhydrous sodium sulfate and concentrated to give the product as a yellow solid (41.8 g, 72%).

MS (ESI, pos.ion) m/z: 581.1 [M+H]$^+$;

$^1$H NMR (400 MHz, DMSO-d$_6$): δ 8.01 (d, 1H), 7.96 (d, 1H), 7.43-7.39 (m, 2H), 7.18 (td, 1H), 6.04 (s, 1H), 4.86 (q, 1H), 4.25-4.14 (m, 1H), 4.11-4.02 (m, 3H), 3.99-3.87 (m, 1H), 3.84 (dd, 1H), 3.74-3.65 (m, 2H), 3.57-3.51 (m, 1H), 3.11-3.04 (m, 1H), 2.43-2.38 (m, 1H), 1.22 (d, 3H), 1.14 (t, 3H).

The compound Q can be prepared under the reaction conditions shown in table 17 according to the procedure described in step 1 of Example 10.

TABLE 17

The reaction conditions for preparation of compound Q

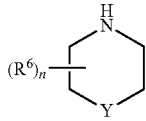

| No. | (VI) or a hydrochloride thereof | compound A2: compound(VI)(mol); the amount of compound A1 is 5.31 g | Reaction solvent | Reaction temperature (° C.) | Reaction time(h) | Product character | Quality; yield (%) of product |
|---|---|---|---|---|---|---|---|
| Q1 | 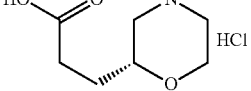 | 1:1 | ethanol | 30 | 12 | yellow solid | 4.14 g; 68 |
| Q2 | 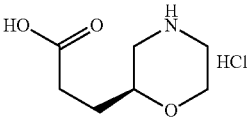 | 1:1 | ethanol | 30 | 12 | yellow solid | 4.08 g; 67 |
| Q3 | 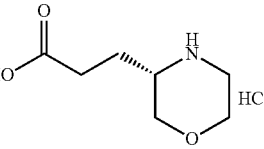 | 1:1 | ethanol | 30 | 12 | yellow solid | 2.68 g; 44 |
| Q4 | 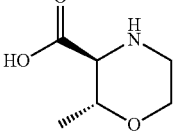 | 1:1 | ethanol | 30 | 12 | yellow solid | 4.22 g; 71 |
| Q5 | 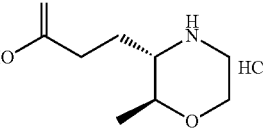 | 1:1 | ethanol | 30 | 12 | yellow solid | 2.68 g; 43 |
| Q6 | 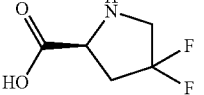 | 1:1 | ethanol | 30 | 12 | yellow solid | 4.09 g; 68 |

TABLE 17-continued

The reaction conditions for preparation of compound Q

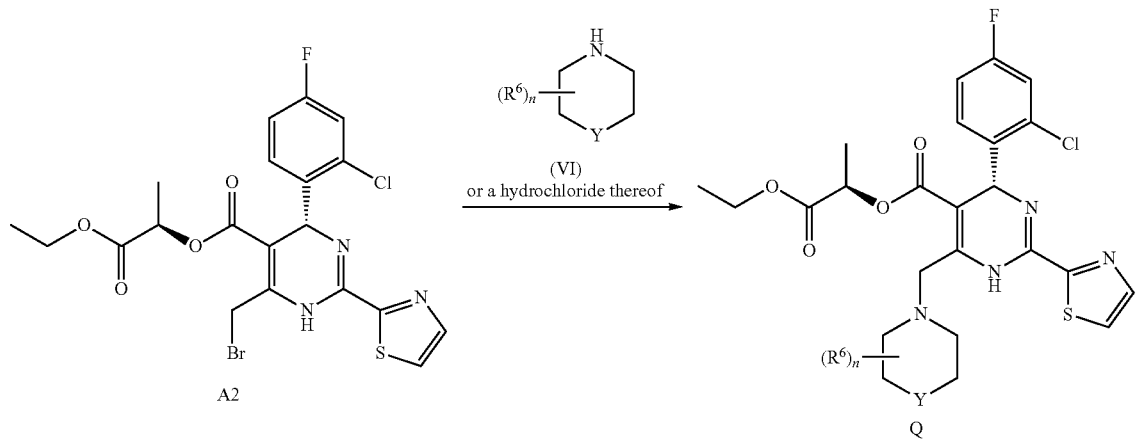

| No. | (VI) or a hydrochloride thereof | compound A2: compound(VI)(mol); the amount of compound A1 is 5.31 g | Reaction solvent | Reaction temperature (° C.) | Reaction time(h) | Product character | Quality; yield (%) of product |
|---|---|---|---|---|---|---|---|
| Q7 | (structure with pyrrolidine, F, F, HCl, COOH) | 1:1 | ethanol | 30 | 12 | yellow solid | 3.4 g; 54 |
| Q8 | (structure with pyrrolidine, F, F, HCl, COOH) | 1:1 | ethanol | 30 | 12 | yellow solid | 3.2 g; 51 |

TABLE 17-1

The NMR and MS datum of compound Q

| No. | $^1$H NMR | MS |
|---|---|---|
| Q1 | $^1$H NMR (600 MHz, DMSO-$d_6$): δ 12.03 (br, 1H), 9.76 (s, 1H), 8.02 (d, 1H), 7.95 (d, 1H), 7.44-7.39 (m, 2H), 7.20 (td, 1H), 6.05 (s, 1H), 4.86 (q, 1H), 4.13-4.05 (m, 2H), 3.93-3.85 (m, 3H), 3.59-3.56 (m, 1H), 3.53-3.48 (m, 1H), 2.78 (t, 2H), 2.36-2.23 (m, 3H), 2.01 (t, 1H), 1.65-1.62 (m, 2H), 1.24 (d, 3H), 1.13 (t, 3H). | MS (ESI, pos. ion) m/z: 609.1 [M + H]$^+$; |
| Q2 | $^1$H NMR (600 MHz, DMSO-$d_6$): δ 12.06 (br, 1H), 9.72 (s, 1H), 8.04 (d, 1H), 7.96 (d, 1H), 7.43-7.39 (m, 2H), 7.19 (td, 1H), 6.04 (s, 1H), 4.84 (q, 1H), 4.14-4.06 (m, 2H), 3.94-3.86 (m, 3H), 3.58-3.55 (m, 1H), 3.52-3.48 (m, 1H), 2.77 (t, 2H), 2.37-2.23 (m, 3H), 2.02 (t, 1H), 1.66-1.62 (m, 2H), 1.24 (d, 3H), 1.14 (t, 3H). | MS (ESI, pos. ion) m/z: 608.7 [M + H]$^+$; |
| Q3 | $^1$H NMR (600 MHz, DMSO-$d_6$): δ 9.78 (s, 1H), 8.04 (d, 1H), 7.96 (d, 1H), 7.44-7.40 (m, 2H), 7.20 (td, 1H), 6.03 (s, 1H), 4.84 (q, 1H), 4.16 (d, 1H), 4.12-4.02 (m, 2H), 3.86 (d, 1H), 3.81 (d, 1H), 3.74-3.72 (m, 1H), 3.62-3.54 (m, 1H), 3.35-3.33 (m, 1H), 2.93-2.73 (m, 1H), 2.57-2.54 (m, 1H), 2.39-2.32 (m, 1H), 2.29-2.23 (m, 1H), 1.89-1.82 (m, 1H), 1.67-1.58 (m, 1H), 1.25 (d, 3H), 1.12 (t, 3H). | MS (ESI, pos. ion) m/z: 609.2 [M + H]$^+$; |

TABLE 17-1-continued

The NMR and MS datum of compound Q

| No. | $^1$H NMR | MS |
|---|---|---|
| Q4 | $^1$H NMR (600 MHz, DMSO-d$_6$): δ 9.91 (s, 1H), 8.04 (d, 1H), 7.94 (d, 1H), 7.44-7.41 (m, 2H), 7.18 (td, 1H), 6.06 (s, 1H), 4.85 (q, 1H), 4.13-4.04 (m, 3H), 3.92-3.86 (m, 1H), 3.73-3.68 (m, 2H), 3.64-3.61 (m, 1H), 3.00 (d, 1H), 2.91 (d, 1H), 2.49-2.45 (m, 1H), 1.24 (d, 3H), 1.22 (d, 3H), 1.14 (t, 3H). | MS (ESI, pos. ion) m/z: 595.2 [M + H]$^+$; |
| Q5 | $^1$H NMR (400 MHz, DMSO-d$_6$): δ 12.12 (s, 1H), 9.76 (s, 1H), 8.03 (d, 1H), 7.96 (d, 1H), 7.40-7.36 (m, 2H), 7.18 (td, 2H), 6.05 (s, 1H), 4.86 (q, 1H), 4.15 (d, 1H), 4.10-4.01 (m, 2H), 3.84 (d, 1H), 3.76-3.72 (m, 1H), 3.61-3.56 (m, 1H), 3.55-3.46 (m, 1H), 2.68 (d, 1H), 2.46-2.41 (m, 1H), 2.38-2.32 (m, 3H), 2.08-1.87 (m, 1H), 1.79-1.71 (m, 1H), 1.24 (d, 3H), 1.21 (d, 3H), 1.16 (t, 3H). | MS (ESI, pos. ion) m/z: 623.2 [M + H]$^+$; |
| Q6 | $^1$H NMR (600 MHz, DMSO-d$_6$): δ 9.78 (s, 1H), 7.98 (d, 1H), 7.92 (d, 1H), 7.46-7.41 (m, 2H), 7.21-7.18 (m, 1H), 6.06 (s, 1H), 4.87-4.77 (m, 1H), 4.33 (dd, 1H), 4.11-4.04 (m, 3H), 3.94-3.91 (m, 1H), 3.52-3.50 (m, 1H), 3.17-3.11 (m, 1H), 2.80-2.73 (m, 1H), 2.47-2.42 (m, 1H), 1.24 (d, 3H), 1.14 (t, 3H). | MS (ESI, pos. ion) m/z: 601.2 [M + H]$^+$; |
| Q7 | $^1$H NMR (600 MHz, DMSO-d$_6$): δ 12.06 (s, 1H), 9.58 (s, 1H), 8.01 (d, 1H), 7.94 (d, 1H), 7.46-7.41 (m, 2H), 7.20 (td, 1H), 6.08 (s, 1H), 4.87 (q, 1H), 4.17-4.05 (m, 4H), 3.58-3.52 (m, 1H), 3.03-2.93 (m, 2H), 2.63-2.53 (m, 1H), 2.36-2.19 (m, 2H), 2.12-2.01 (m, 1H), 1.95-1.88 (m, 1H), 1.59-1.52 (m, 1H), 1.25 (d, 3H), 1.14 (t, 3H). | MS (ESI, pos. ion) m/z: 629.2 [M + H]$^+$; |
| Q8 | $^1$H NMR (600 MHz, DMSO-d$_6$): δ 12.15 (s, 1H), 9.55 (s, 1H), 8.01 (d, 1H), 7.95 (d, 1H), 7.47 (dd, 1H), 7.43 (dd, 1H), 7.19 (td, 1H), 6.09 (s, 1H), 4.86 (q, 1H), 4.17-4.05 (m, 4H), 3.48-3.43 (m, 1H), 3.01-2.91 (m, 2H), 2.59-2.52 (m, 1H), 2.40-2.23 (m, 2H), 2.14-1.97 (m, 2H), 1.63-1.60 (m, 1H), 1.26 (d, 3H), 1.14 (t, 3H). | MS (ESI, pos. ion) m/z: 629.2 [M + H]$^+$; |

Step 2) (S)-4-(((R)-6-(2-chloro-4-fluorophenyl)-5-(ethoxycarbonyl)-2-(thiazol-2-yl)-3,6-dihydropyrimidin-4-yl)methyl)morpholine-3-carboxylic acid

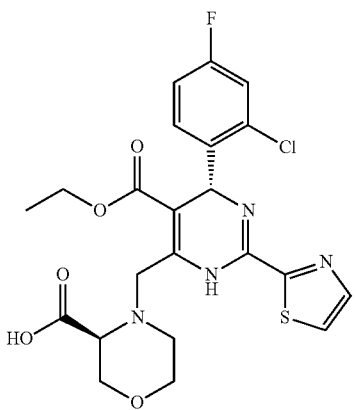 [SMILES: CCOC(=O)C1=C(CN2CCOC[C@H]2C(=O)O)NC(c2nccs2)=N[C@H]1c1ccc(F)cc1Cl]

To a flask were added anhydrous ethanol (870 g) and lithium (2.43 g, 0.35 mol) in turn. The mixture was stirred at 43° C. until the lithium was consumed entirely, and then (S)-4-(((R)-6-(2-chloro-4-fluorophenyl)-5-((((R)-1-ethoxy-1-oxopropan-2-yl)oxy)carbonyl)-2-(thiazol-2-yl)-3,6-dihydropyrimidin-4-yl)methyl)morpholine-3-carboxylic acid (58.1 g, 0.1 mol) was added. The reaction mixture was allowed to warm up to 78° C. and stirred for 12 hours. After the reaction, the mixture was cooled and concentrated. To the residue was added water (1100 g), the resulting mixture was extracted with ethyl acetate (1000 mL). The organic layer was discarded. To the aqueous layer was added ethyl acetate (1280 mL), the mixture was adjusted to pH 3-6 with concentrated hydrochloric acid. The organic layer was dried over anhydrous sodium sulfate and concentrated to give the product as a yellow solid (33.1 g, 65%).

MS (ESI, pos.ion) m/z: 509.2 [M+H]$^+$;

$^1$H NMR (400 MHz, DMSO-d$_6$): δ 13.00 (br, 1H), 9.95 (s, 1H), 8.02 (d, 1H), 7.93 (d, 1H), 7.46-7.38 (m, 2H), 7.17 (td, 1H), 6.05 (s, 1H), 4.20 (d, 1H), 4.05-4.02 (m, 1H), 3.97-3.91 (m, 3H), 3.81 (dd, 1H), 3.72-3.63 (m, 2H), 3.58-3.53 (m, 1H), 3.08-3.05 (m, 1H), 2.42-2.38 (m, 1H), 1.06 (t, 3H).

The compound X can be prepared under the reaction conditions shown in table 18 according to the procedure described in step 2 of Example 10.

TABLE 18

The reaction conditions for preparation of compound X

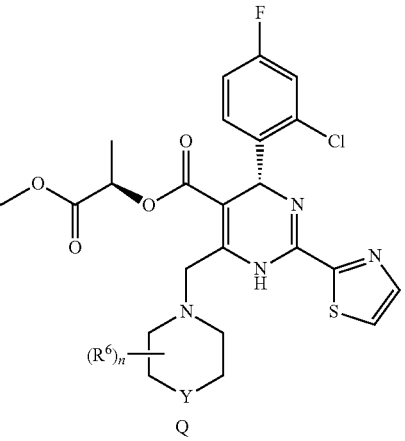

| No. | R³ | (R⁶)ₙ structure | The mole ratio of Lithium to compound Q; the amount of compound Q | Reaction solvent | Reaction temperature (° C.) | Reaction time(h) | Product character | Quality; yield (%) of product |
|---|---|---|---|---|---|---|---|---|
| X1 | ethyl | 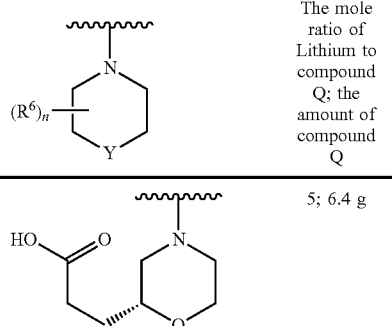 | 5; 6.4 g | ethanol | 78 | 2 | yellow solid | 3.38 g; 63 |
| X2 | ethyl | 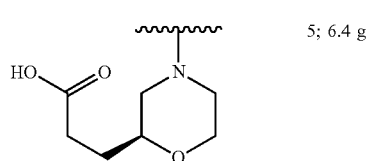 | 5; 6.4 g | ethanol | 78 | 2 | yellow solid | 3.33 g; 62 |
| X3 | ethyl | 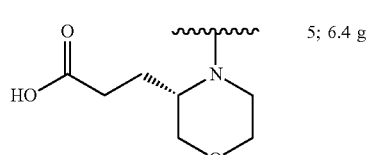 | 5; 6.4 g | ethanol | 78 | 2 | yellow solid | 2.63 g; 49 |
| X4 | ethyl | 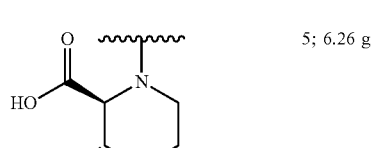 | 5; 6.26 g | ethanol | 78 | 12 | yellow solid | 3.77 g; 72 |
| X5 | ethyl | 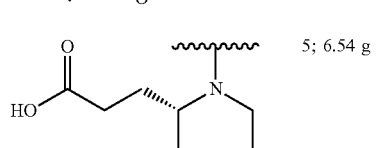 | 5; 6.54 g | ethanol | 78 | 2 | yellow solid | 2.48 g; 45 |
| X6 | ethyl | 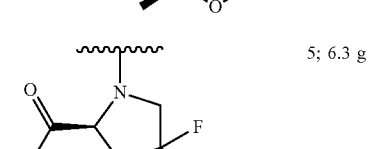 | 5; 6.3 g | ethanol | 78 | 12 | yellow solid | 3.07 g; 58 |

TABLE 18-continued

The reaction conditions for preparation of compound X

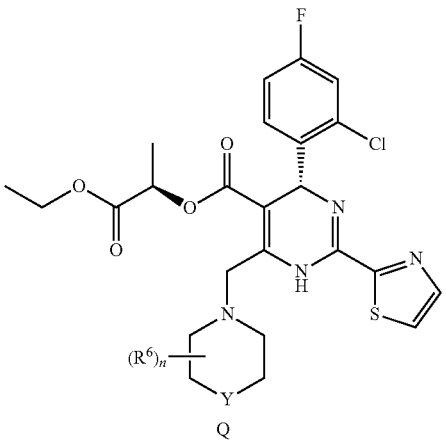

| No. | R³ | (R⁶)ₙ— with Y ring | The mole ratio of Lithium to compound Q; the amount of compound Q | Reaction solvent | Reaction temperature (° C.) | Reaction time(h) | Product character | Quality; yield (%) of product |
|---|---|---|---|---|---|---|---|---|
| X7 | ethyl | 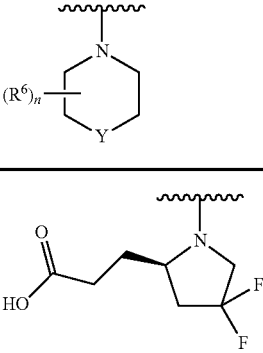 | 5; 6.6 g | ethanol | 78 | 2 | yellow solid | 2.73 g; 49 |
| X8 | ethyl | 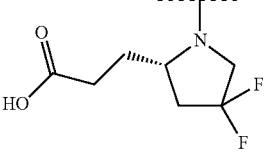 | 5; 6.6 g | ethanol | 78 | 2 | yellow solid | 2.9 g; 52 |
| X9 | methyl | 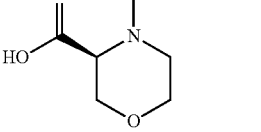 | 5; 6.1 g | methanol | 64 | 18 | yellow solid | 3.47 g; 70 |
| X10 | methyl | 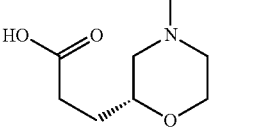 | 5; 6.4 g | methanol | 64 | 6 | yellow solid | 3.14 g; 60 |
| X11 | methyl | 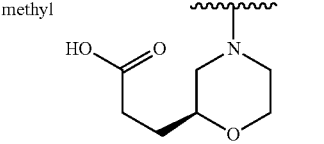 | 5; 6.4 g | methanol | 64 | 4 | yellow solid | 3.09 g; 59 |

TABLE 18-continued

The reaction conditions for preparation of compound X

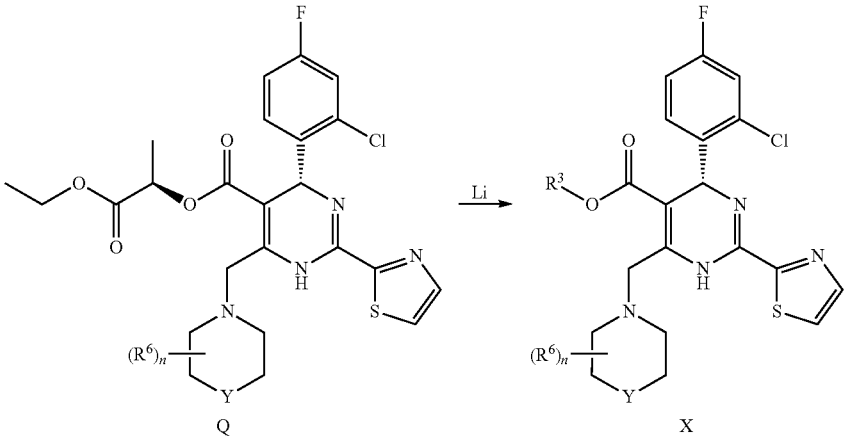

| No. | R³ | 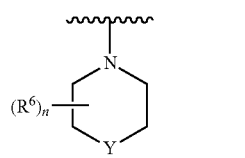 (R⁶)ₙ | The mole ratio of Lithium to compound Q; the amount of compound Q | Reaction solvent | Reaction temperature (° C.) | Reaction time(h) | Product character | Quality; yield (%) of product |
|---|---|---|---|---|---|---|---|---|
| X12 | methyl | 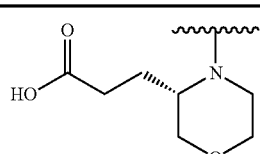 | 5; 6.4 g | methanol | 64 | 8 | yellow solid | 2.41 g; 46 |
| X13 | methyl | 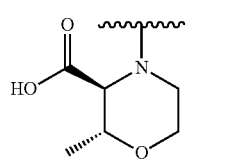 | 5; 6.26 g | methanol | 64 | 18 | yellow solid | 3.51 g; 69 |
| X14 | methyl | 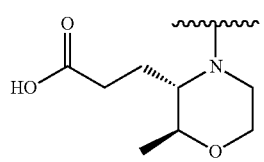 [SMILES: *N1CCO[C@@H](C)[C@@H]1CCC(=O)O] | 5; 6.54 g | methanol | 64 | 5 | yellow solid | 2.31 g; 43 |
| X15 | methyl | 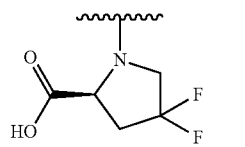 [SMILES: *N1CC(F)(F)C[C@H]1C(=O)O] | 5; 6.3 g | methanol | 64 | 12 | yellow solid | 2.83 g; 55 |
| X16 | methyl | 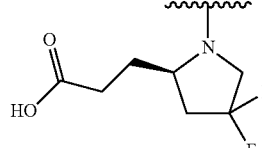 | 5; 6.87 g | methanol | 64 | 6 | yellow solid | 2.55 g; 47 |

TABLE 18-continued

The reaction conditions for preparation of compound X

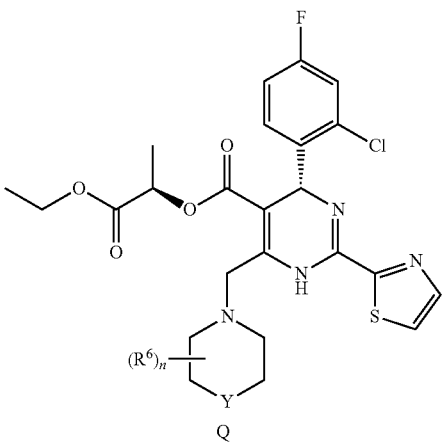

| No. | R³ | (R⁶)ₙ group | The mole ratio of Lithium to compound Q; the amount of compound Q | Reaction solvent | Reaction temperature (° C.) | Reaction time(h) | Product character | Quality; yield (%) of product |
|---|---|---|---|---|---|---|---|---|
| X17 | methyl | (pyrrolidine with difluoro and propanoic acid substituent) | 5; 6.87 g | methanol | 64 | 6 | yellow solid | 2.66 g; 49 |

TABLE 18-1

The NMR and MS datum of compound X

| No. | ¹H NMR | MS |
|---|---|---|
| X1 | ¹H NMR (400 MHz, DMSO-$d_6$): δ 9.65 (s, 1H), 8.02 (d, 1H), 7.94 (d, 1H), 7.44-7.38 (m, 2H), 7.18 (td, 1H), 6.05 (s, 1H), 3.96 (q, 2H), 3.89-3.85 (m, 3H), 3.59-3.46 (m, 2H), 2.80-2.74 (m, 2H), 2.36-2.21 (m, 3H), 2.03-1.98 (m, 1H), 1.64-1.59 (m, 2H), 1.06 (t, 3H). | MS (ESI, pos. ion) m/z: 537.3 [M + H]⁺; |
| X2 | ¹H NMR (400 MHz, DMSO-$d_6$): δ 12.07 (s, 1H), 9.65 (s, 1H), 8.02 (d, 1H), 7.94 (d, 1H), 7.44-7.40 (m, 2H), 7.19 (td, 1H), 6.06 (s, 1H), 3.97 (q, 2H), 3.92-3.82 (m, 3H), 3.58-3.46 (m, 2H), 2.88 (d, 1H), 2.63 (d, 1H), 2.37-2.22 (m, 3H), 2.08-1.99 (m, 1H), 1.72-1.65 (m, 2H), 1.05 (t, 3H). | MS (ESI, pos. ion) m/z: 536.9 [M + H]⁺; |
| X3 | ¹H NMR (400 MHz, DMSO-$d_6$): δ 12.13 (br, 1H), 9.81 (s, 1H), 8.02 (d, 1H), 7.94 (d, 1H), 7.44-7.38 (m, 2H), 7.18 (td, 1H), 6.02 (s, 1H), 4.20 (d, 1H), 3.98 (q, 2H), 3.92 (d, 1H), 3.83-3.78 (m, 1H), 3.75-3.72 (m, 1H), 3.62-3.58 (m, 1H), 3.37-3.33 (m, 1H), 2.79-2.75 (m, 1H), 2.58-2.53 (m, 1H), 2.49-2.46 (m, 1H), 2.39-2.32 (m, 2H), 1.89-1.83 (m, 1H), 1.66-1.58 (m, 1H), 1.06 (t, 3H). | MS (ESI, pos. ion) m/z: 537.2 [M + H]⁺; |
| X4 | ¹H NMR (600 MHz, DMSO-$d_6$): δ 13.00 (s, 1H), 9.78 (s, 1H), 8.03 (d, 1H), 7.93 (d, 1H), 7.43-7.30 (m, 2H), 7.18 (td, 1H), 6.03 (s, 1H), 4.06 (d, 1H), 3.95 (q, 2H), 3.90 (d, 1H), 3.74-3.69 (m, 2H), 3.65-3.60 (m, 1H), 2.98 (d, 1H), 2.89 (d, 1H), 2.49-2.45 (m, 1H), 1.21 (d, 3H), 1.04 (t, 3H). | MS (ESI, pos. ion) m/z: 523.2 [M + H]⁺; |
| X5 | ¹H NMR (400 MHz, DMSO-$d_6$): δ 12.12 (s, 1H), 9.75 (s, 1H), 8.02 (d, 1H), 7.95 (d, 1H), 7.42-7.36 (m, 2H), 7.15 (td, 1H), 6.06 (s, 1H), 4.15 (d, 1H), 4.02-3.91 (m, 2H), 3.86 (d, 1H), 3.75-3.73 (m, 1H), 3.59-3.54 (m, 1H), 3.51-3.45 (m, 1H), 2.66 (d, 1H), 2.46-2.40 (m, 1H), 2.37-2.30 (m, 3H), 2.03-1.92 (m, 1H), 1.80-1.74 (m, 1H), 1.20 (d, 3H), 1.06 (t, 3H). | MS (ESI, pos. ion) m/z: 551.2 [M + H]⁺; |

TABLE 18-1-continued

The NMR and MS datum of compound X

| No. | ¹H NMR | MS |
|---|---|---|
| X6 | ¹H NMR (600 MHz, DMSO-$d_6$): δ 13.01 (br, 1H), 9.66 (s, 1H), 7.98 (d, 1H), 7.91 (d, 1H), 7.45-7.41 (m, 2H), 7.19 (td, 1H), 6.04 (s, 1H), 4.33 (d, 1H), 4.08 (d, 1H), 4.05-4.02 (m, 1H), 3.97 (q, 2H), 3.92-3.89 (m, 1H), 3.53-3.48 (m, 1H), 3.19-3.12 (m, 1H), 2.82-2.72 (m, 1H), 1.05 (t, 3H). | MS (ESI, pos. ion) m/z: 529.1 [M + H]⁺; |
| X7 | ¹H NMR (400 MHz, DMSO-$d_6$): δ 12.08 (s, 1H), 9.52 (s, 1H), 7.99 (d, 1H), 7.92 (d, 1H), 7.44-7.40 (m, 2H), 7.19 (td, 1H), 6.03 (s, 1H), 4.13 (dd, 2H), 3.97 (q, 2H), 3.60-3.52 (m, 1H), 3.06-2.96 (m, 2H), 2.59-2.56 (m, 1H), 2.36-2.20 (m, 2H), 2.13-1.99 (m, 1H), 1.93-1.88 (m, 1H), 1.57-1.44 (m, 1H), 1.05 (t, 3H). | MS (ESI, pos. ion) m/z: 556.9 [M + H]⁺; |
| X8 | ¹H NMR (400 MHz, DMSO-$d_6$): δ 12.16 (br, 1H), 9.45 (s, 1H), 8.00 (d, 1H), 7.94 (d, 1H), 7.47-7.41 (m, 2H), 7.18 (td, 1H), 6.06 (s, 1H), 4.12 (dd, 2H), 4.00-3.93 (m, 2H), 3.46-3.38 (m, 1H), 3.01-2.85 (m, 2H), 2.60-2.53 (m, 1H), 2.40-2.23 (m, 2H), 2.15-1.99 (m, 2H), 1.66-1.56 (m, 1H), 1.05 (t, 3H). | MS (ESI, pos. ion) m/z: 557.2 [M + H]⁺; |
| X9 | ¹H NMR (400 MHz, DMSO-$d_6$): δ 12.52 (br, 1H), 9.86 (s, 1H), 8.03 (d, 1H), 7.94 (d, 1H), 7.43-7.38 (m, 2H), 7.16 (td, 1H), 6.04 (s, 1H), 4.24 (d, 1H), 4.06-3.97 (m, 2H), 3.84 (dd, 1H), 3.73-3.66 (m, 2H), 3.64-3.59 (m, 1H), 3.51 (s, 3H), 3.10-3.06 (m, 1H), 2.43-2.39 (m, 1H). | MS (ESI, pos. ion) m/z: 494.9 [M + H]⁺; |
| X10 | ¹H NMR (400 MHz, DMSO-$d_6$): δ 12.12 (s, 1H), 9.71 (s, 1H), 8.03 (d, 1H), 7.96 (d, 1H), 7.44-7.38 (m, 2H), 7.18 (td, 1H), 6.02 (s, 1H), 3.94-3.82 (m, 3H), 3.62-3.54 (m, 2H), 3.53 (s, 3H), 2.78 (dd, 2H), 2.38-2.26 (m, 3H), 2.06-1.99 (m, 1H), 1.66-1.59 (m, 2H). | MS (ESI, pos. ion) m/z: 522.9 [M + H]⁺; |
| X11 | ¹H NMR (400 MHz, DMSO-$d_6$): δ 12.09 (br, 1H), 9.70 (s, 1H), 8.03 (d, 1H), 7.94 (d, 1H), 7.44-7.38 (m, 2H), 7.18 (td, 1H), 6.04 (s, 1H), 3.95 (d, 1H), 3.86-3.81 (m, 2H), 3.57-3.54 (m, 1H), 3.52 (s, 3H), 3.50-3.47 (m, 1H), 2.87 (d, 1H), 2.62 (d, 1H), 2.35-2.19 (m, 3H), 2.14-2.08 (m, 1H), 1.73-1.61 (m, 2H). | MS (ESI, pos. ion) m/z: 523.2 [M + H]⁺; |
| X12 | ¹H NMR (400 MHz, DMSO-$d_6$): δ 9.87 (s, 1H), 8.03 (d, 1H), 7.94 (d, 1H), 7.44-7.40 (m, 2H), 7.16 (td, 1H), 6.02 (s, 1H), 4.20 (d, 1H), 3.93 (d, 1H), 3.84-3.79 (m, 1H), 3.75-3.71 (m, 1H), 3.62-3.56 (m, 1H), 3.52 (s, 3H), 3.48-3.41 (m, 1H), 3.05-2.87 (m, 1H), 2.78-2.75 (m, 1H), 2.58-2.56 (m, 1H), 2.38-2.23 (m, 2H), 1.87-1.84 (m, 1H), 1.66-1.58 (m, 1H). | MS (ESI, pos. ion) m/z: 523.1 [M + H]; |
| X13 | ¹H NMR (600 MHz, DMSO-$d_6$): δ 13.01 (s, 1H), 9.83 (s, 1H), 8.02 (d, 1H), 7.93 (d, 1H), 7.42-7.38 (m, 2H), 7.17 (td, 1H), 6.02 (s, 1H), 4.07 (d, 1H), 3.89 (d, 1H), 3.76-3.62 (m, 3H), 3.51 (s, 3H), 3.47-3.43 (m, 1H), 2.98 (d, 1H), 2.89 (d, 1H), 1.20 (d, 3H). | MS (ESI, pos. ion) m/z: 508.7 [M + H]⁺; |
| X14 | ¹H NMR (400 MHz, DMSO-$d_6$): δ 12.11 (s, 1H), 9.76 (s, 1H), 8.02 (d, 1H), 7.96 (d, 1H), 7.44-7.40 (m, 2H), 7.16 (td, 1H), 6.01 (s, 1H), 4.16 (d, 1H), 3.88 (d, 1H), 3.78-3.74 (m, 1H), 3.60-3.55 (m, 1H), 3.53 (s, 3H), 3.50-3.46 (m, 1H), 2.68 (d, 1H), 2.48-2.42 (m, 1H), 2.36-2.31 (m, 3H), 2.04-1.93 (m, 1H), 1.82-1.73 (m, 1H), 1.21 (d, 3H). | MS (ESI, pos. ion) m/z: 537.1 [M + H]⁺; |

TABLE 18-1-continued

The NMR and MS datum of compound X

| No. | ¹H NMR | MS |
|---|---|---|
| X15 | ¹H NMR (600 MHz, DMSO-$d_6$): δ 9.70 (br, 1H), 8.01 (d, 1H), 7.92 (d, 1H), 7.44-7.38 (m, 2H), 7.18 (td, 1H), 6.01 (s, 1H), 4.31 (d, 1H), 4.09 (d, 1H), 3.94-3.89(m, 1H), 3.53 (s, 3H), 3.48-3.44 (m, 1H), 3.23-3.07 (m, 2H), 2.84-2.75 (m, 1H). | MS (ESI, pos. ion) m/z: 515.1 [M + H]⁺; |
| X16 | ¹H NMR (400 MHz, DMSO-$d_6$): δ 12.07 (br, 1H), 9.55 (s, 1H), 7.99 (d, 1H), 7.92 (d, 1H), 7.43-7.39 (m, 2H), 7.18 (td, 1H), 6.03 (s, 1H), 4.15 (d, 1H), 4.09 (d, 1H), 3.56-3.54 (m, 1H), 3.53 (s, 3H), 3.05-2.95 (m, 2H), 2.48-2.46 (m, 1H), 2.36-2.17 (m, 2H), 2.15-2.02 (m, 1H), 1.97-1.85 (m, 1H), 1.59-1.50 (m, 1H). | MS (ESI, pos. ion) m/z: 543.0 [M + H]⁺; |
| X17 | ¹H NMR (400 MHz, DMSO-$d_6$): δ 12.06 (br, 1H), 9.56 (s, 1H), 8.01 (d, 1H), 7.94 (d, 1H), 7.44-7.40 (m, 2H), 7.16 (td, 1H), 6.05 (s, 1H), 4.13 (d, 1H), 4.09 (d, 1H), 3.57-3.54 (m, 1H), 3.52 (s, 3H), 3.06-2.96 (m, 2H), 2.47-2.45 (m, 1H), 2.37-2.17 (m, 2H), 2.16-2.02 (m, 1H), 1.98-1.85 (m, 1H), 1.60-1.51 (m, 1H). | MS (ESI, pos. ion) m/z: 543.0 [M + H]⁺; |

Example 11: The Preparation of (R)-ethyl 4-(2-chloro-4-fluorophenyl)-6-(morpholinomethyl)-2-(thiazol-2-yl)-1,4-dihydropyrimidine-5-carboxylate

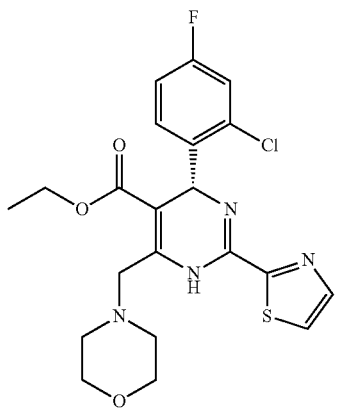

Step 1) (R)-ethyl 4-(2-chloro-4-fluorophenyl)-6-methyl-2-(thiazol-2-yl)-1,4-dihydropyrimidine-5-carboxylate

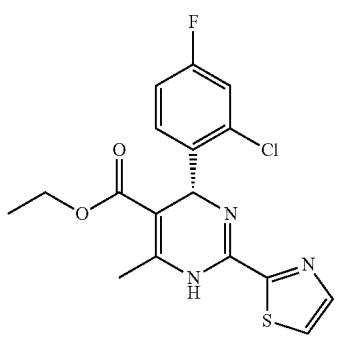 [SMILES: CCOC(=O)C1=C(C)NC(c2nccs2)=N[C@H]1c1ccc(F)cc1Cl]

To a flask were added anhydrous ethanol (360 g) and lithium (2.43 g, 0.35 mol) in turn. The mixture was stirred at 43° C. until the lithium was consumed entirely, and then (R)-(R)-1-ethoxy-1-oxopropan-2-yl 4-(2-chloro-4-fluorophenyl)-6-methyl-2-(thiazol-2-yl)-1,4-dihydropyrimidine-5-carboxylate (45.2 g, 0.1 mol) was added. The reaction mixture was stirred at 78° C. for 6 hours. After the reaction, the reaction mixture was cooled to 10° C., kept at 10° C. and stirred for 8 hours. The mixture was filtered. The filtrate was washed with anhydrous ethanol (45 g) and water (500 g) in turn, and then dried in vacuo at 60° C. for 8 hours to obtain the product as a yellow solid (23.6 g, 62%).

$[\alpha]_D^{25}$=−59.6 (c=0.3020 g/100 mL, MeOH);

MS (ESI, pos.ion) m/z: 380.2 [M+H]⁺;

¹H NMR (600 MHz, DMSO-$d_6$): δ 9.92 (s, 1H), 7.97 (d, 1H), 7.90 (d, 1H), 7.41 (dd, 1H), 7.37 (dd, 1H), 7.19 (td, 1H), 6.00 (s, 1H), 3.93 (q, 2H), 2.46 (s, 3H), 1.03 (t, 3H).

The compound T can be prepared under the reaction conditions shown in table 19 according to the procedure described in step 1 of Example 11.

TABLE 19

The reaction conditions for preparation of compound T

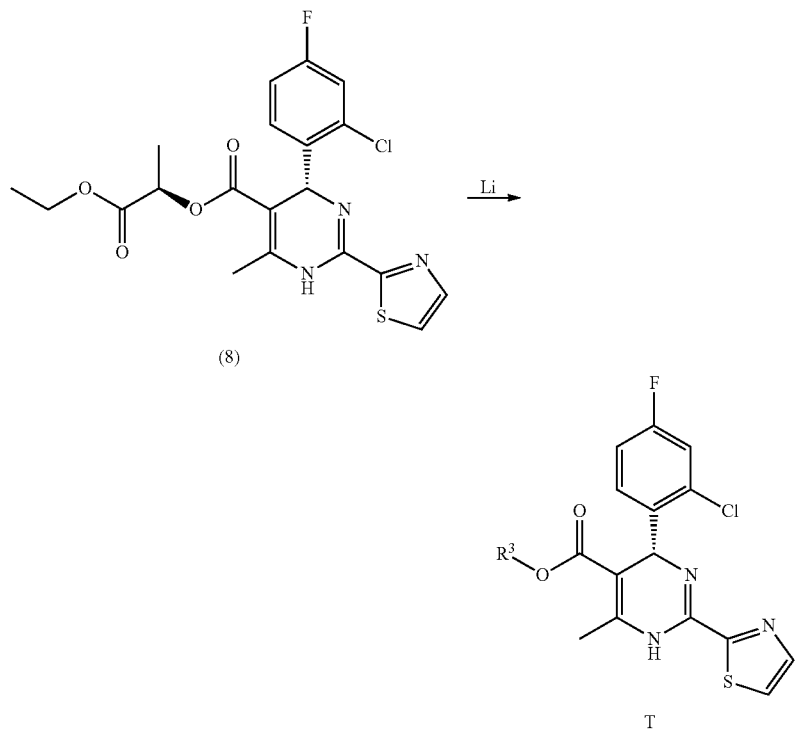

| No. | R³ | The mole ratio of Lithium to compound (8); the amount of compound (8) is 49.6 g | Reaction solvent | The mass ratio of reaction solvent to compound (8) | Reaction temperature (° C.) | Reaction time (h) | Product character | Quality; yield (%) of product |
|---|---|---|---|---|---|---|---|---|
| T1 | ethyl | 2.5 | ethanol | 10 | 78 | 12 | yellow solid | 15.2 g; 40 |
| T1 | ethyl | 3 | ethanol | 6 | 78 | 8 | yellow solid | 26.6 g; 70 |
| T1 | ethyl | 4 | ethanol | 10 | 78 | 4 | yellow solid | 22 g; 58 |
| T1 | ethyl | 5 | ethanol | 20 | 78 | 24 | yellow solid | 17.1 g; 45 |
| T1 | ethyl | 6 | ethanol | 30 | 78 | 12 | yellow solid | 14.1 g; 37 |
| T1 | ethyl | 8 | ethanol | 20 | 78 | 12 | yellow solid | 17.9 g; 47 |
| T2 | methyl | 3 | methanol | 3 | 64 | 20 | yellow solid | 20.9 g; 57 |
| T2 | methyl | 3 | methanol | 4 | 64 | 6 | yellow solid | 17.9 g; 49 |
| T2 | methyl | 4 | methanol | 6 | 64 | 8 | yellow solid | 11.7 g; 32 |

TABLE 19-1

The NMR, MS and specific rotation datum of the compound T

| No. | ¹H NMR | MS | specific rotation |
|---|---|---|---|
| T1 | ¹H NMR (600 MHz, DMSO-d₆): δ 9.92 (s, 1H), 7.97 (d, 1H), 7.90 (d, 1H), 7.41 (dd, 1H), 7.37 (dd, 1H), 7.19 (td, 1H), 6.00 (s, 1H), 3.93 (q, 2H), 2.46 (s, 3H), 1.03 (t, 3H). | MS (ESI, pos. ion) m/z: 380.2 [M + H]⁺; | $[\alpha]_D^{25}$ = −59.6 (c = 0.3020 g/100 mL, MeOH); |

TABLE 19-1-continued

The NMR, MS and specific rotation datum of the compound T

| No. | ¹H NMR | MS | specific rotation |
|---|---|---|---|
| T2 | ¹H NMR (400 MHz, DMSO-d₆): δ 7.81 (d, 1H), 7.68 (d, 1H), 7.36 (dd, 1H), 7.29 (dd, 1H), 7.11 (td, 1H), 5.90 (s, 1H), 3.41 (s, 3H), 2.34 (s, 3H). | MS (ESI, pos. ion) m/z: 366.1 [M + H]⁺; | $[\alpha]_D^{25} = -81.49$ (c = 0.5031 g/100 mL, MeOH); |

Step 2) (R)-ethyl 4-(2-chloro-4-fluorophenyl)-6-bromomethyl-2-(thiazol-2-yl)-1,4-dihydropyrimidine-5-carboxylate

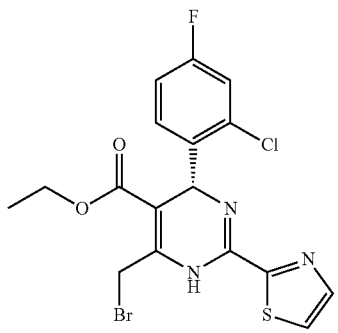 [SMILES: CCOC(=O)C1=C(CBr)NC(c2nccs2)=N[C@H]1c1ccc(F)cc1Cl]

To a dry flask were added (R)-ethyl 4-(2-chloro-4-fluorophenyl)-6-methyl-2-(thiazol-2-yl)-1,4-dihydropyrimidine-5-carboxylate (38 g, 0.1 mol) and CCl₄ (760 g), followed by NBS (19.6 g, 0.11 mol) at 70° C. The mixture was stirred for 30 min and cooled, and then filtered. The filtrate was concentrated to obtain a yellow solid (37.6 g, 82%).

MS (ESI, pos.ion) m/z: 457.9 [M+H]⁺;

¹H NMR (400 MHz, DMSO-d₆): δ 9.67 (s, 1H), 8.01 (d, 1H), 7.97 (br, 1H), 7.44-7.41 (m, 2H), 7.22 (td, 1H), 5.99 (s, 1H), 4.83 (br, 2H), 4.02 (q, 2H), 1.07 (t, 3H).

The compound W can be prepared under the reaction conditions shown in table 20 according to the procedure described in step 2 of Example 11.

TABLE 20

The reaction conditions for preparation of compound W

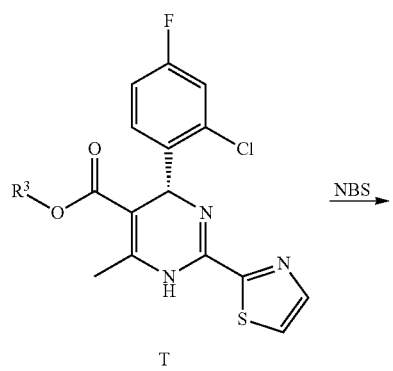

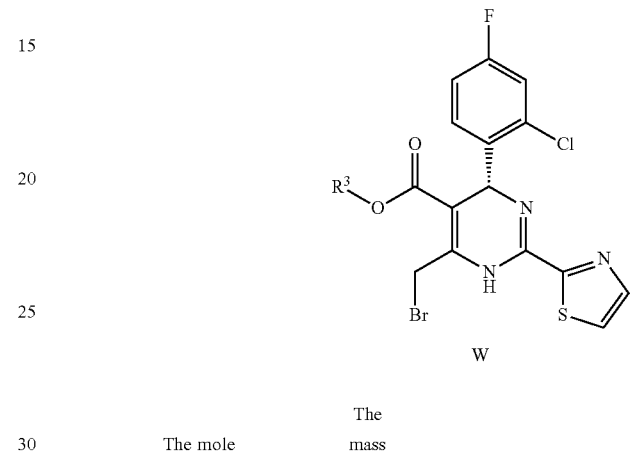

| No. | R³ | The mole ratio of NBS to compound T; the amount of compound T | Reaction solvent | The mass ratio of reaction solvent to compound (W) | Reaction temperature (° C.) | Product character | Quality; yield (%) of product |
|---|---|---|---|---|---|---|---|
| W1 | ethyl | 1.0; 38 g | DCM | 10 | 39 | yellow solid | 37.2 g; 81 |
| W1 | ethyl | 1.0; 38 g | CHCl₃ | 20 | 61 | yellow solid | 35.8 g; 78 |
| W1 | ethyl | 1.1; 38 g | CCl₄ | 30 | 76 | yellow solid | 38.6 g; 84 |
| W2 | methyl | 1.0; 36.6 g | DCM | 10 | 39 | yellow solid | 32 g; 72 |
| W2 | methyl | 1.1; 36.6 g | CHCl₃ | 20 | 61 | yellow solid | 32.5 g; 73 |
| W2 | methyl | 1.1; 36.6 g | CCl₄ | 30 | 76 | yellow solid | 36.5 g; 82 |

TABLE 20-1

| | The NMR and MS datum of compound W | |
|---|---|---|
| No. | $^1$H NMR | MS |
| W1 | $^1$H NMR (400 MHz, DMSO-$d_6$): δ 9.62 (s, 1H), 8.01 (d, 1H), 7.92 (d, 1H), 7.44-7.38 (m, 2H), 7.18 (td, 1H), 6.04 (s, 1H), 4.94 (d, 1H), 4.62 (d, 1H), 4.15 (q, 2H), 1.12 (t, 3H). | MS (ESI, pos. ion) m/z: 457.9 [M + H]$^+$; |
| W2 | $^1$H NMR (600 MHz, DMSO-$d_6$): δ 8.02 (d, 1H), 7.96 (br, 1H), 7.46-7.40 (m, 2H), 7.22 (td, 1H), 5.98 (s, 1H), 4.83 (br, 2H), 3.57 (s, 3H). | MS (ESI, pos. ion) m/z: 445.6 [M + H]$^+$; |

Step 3) (R)-ethyl 4-(2-chloro-4-fluorophenyl)-6-(morpholinomethyl)-2-(thiazol-2-yl)-1,4-dihydropyrimidine-5-carboxylate

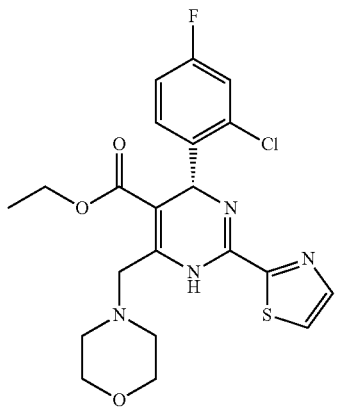 [SMILES: CCOC(=O)C1=C(CN2CCOCC2)NC(c2nccs2)=N[C@H]1c1ccc(F)cc1Cl]

To a flask were added (R)-ethyl 4-(2-chloro-4-fluorophenyl)-6-(bromomethyl)-2-(thiazol-2-yl)-1,4-dihydropyrimidine-5-carboxylate (45.9 g, 0.1 mol), anhydrous ethanol (275 g) and morpholine (34.8 g, 0.4 mol). The mixture was stirred at 25° C. under nitrogen atmosphere for 6 hours. After the reaction, the mixture was concentrated. To the residue was added ethyl acetate (500 g), the resulting mixture was washed with water (250 mL×2). The organic layer was concentrated to give the product as tawny oil (35.8 g, 77%)

MS (ESI, pos.ion) m/z: 465.2 [M+H]$^+$;

$^1$H NMR (400 MHz, DMSO-$d_6$): δ 9.65 (s, 1H), 8.00 (d, 1H), 7.91 (d, 1H), 7.40-7.37 (m, 2H), 7.15 (td, 1H), 6.03 (s, 1H), 3.94 (q, 2H), 3.88 (dd, 2H), 3.65 (br, 4H), 2.56 (br, 4H), 1.05 (t, 3H).

The compound U can be prepared under the reaction conditions shown in table 21 according to the procedure described in step 3 of Example 11.

TABLE 21

The reaction conditions for preparation of compound U

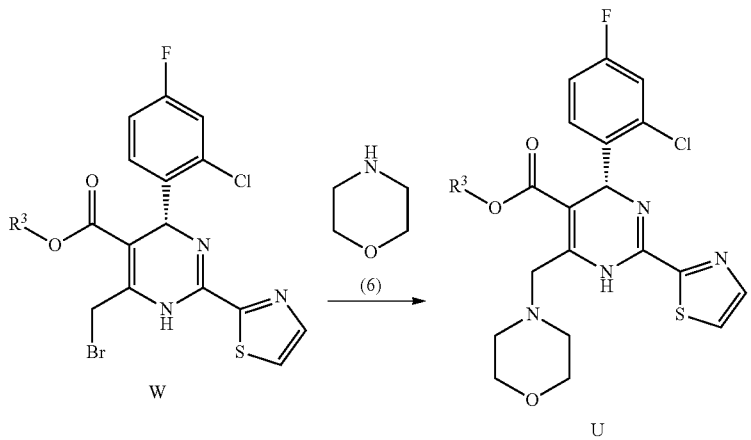

| No. | R$^3$ | The mole ratio of compound (6) to compound W; the amount of compound W | Reaction solvent | The mass ratio of reaction solvent to compound (J) | Reaction temperature (° C.) | Reaction time (h) | Product character | Quality; yield (%) of product |
|---|---|---|---|---|---|---|---|---|
| U1 | ethyl | 2; 45.9 g | ethanol | 20 | 25 | 2 | tawny oil | 34 g; 73 |
| U1 | ethyl | 3; 45.9 g | acetone | 10 | 40 | 10 | tawny oil | 36.3 g; 78 |

TABLE 21-continued

| U1 | ethyl | 4; 45.9 g | methanol | 10 | 30 | 6 | tawny oil 33.5 g; 72 |
| U1 | ethyl | 5; 45.9 g | ethyl acetate | 20 | 50 | 24 | tawny oil 34.4 g; 74 |
| U1 | ethyl | 6; 45.9 g | DCM | 8 | 39 | 6 | tawny oil 33 g; 71 |
| U1 | ethyl | 3; 45.9 g | DMF | 4 | 60 | 1 | tawny oil 31.6 g; 68 |
| U1 | ethyl | 4; 45.9 g | THF | 6 | 50 | 8 | tawny oil 33.5 g; 72 |
| U2 | methyl | 2; 44.5 g | ethanol | 20 | 25 | 2 | tawny oil 33.8 g; 75 |
| U2 | methyl | 3; 44.5 g | acetone | 10 | 40 | 10 | tawny oil 32.4 g; 72 |
| U2 | methyl | 4; 44.5 g | methanol | 10 | 30 | 6 | tawny oil 34.6 g; 77 |
| U2 | methyl | 5; 44.5 g | ethyl acetate | 20 | 50 | 24 | tawny oil 33.3 g; 74 |
| U2 | methyl | 6; 44.5 g | DCM | 8 | 39 | 6 | tawny oil 30.2 g; 67 |
| U2 | methyl | 3; 44.5 g | DMF | 4 | 60 | 1 | tawny oil 32 g; 71 |
| U2 | methyl | 4; 44.5 g | THF | 6 | 50 | 8 | tawny oil 30.6 g; 68 |

TABLE 21-1

The NMR and MS datum of compound U

| No. | $^1$H NMR | MS |
|---|---|---|
| U1 | $^1$H NMR (400 MHz, DMSO-$d_6$): δ 9.65 (s, 1H), 8.00 (d, 1H), 7.91 (d, 1H), 7.40-7.37 (m, 2H), 7.15 (td, 1H), 6.03 (s, 1H), 3.94 (q, 2H), 3.88 (dd, 2H), 3.65 (br, 4H), 2.56 (br, 4H), 1.05 (t, 3H). | MS (ESI, pos. ion) m/z: 465.2 [M + H]$^+$; |
| U2 | $^1$H NMR (600 MHz, DMSO-$d_6$): δ 9.72 (s, 1H), 8.03 (d, 1H), 7.94 (d, 1H), 7.43-7.38 (m, 2H), 7.17 (td, 1H), 6.05 (s, 1H), 3.93 (dd, 2H), 3.68 (br, 4H), 3.53 (s, 3H), 2.56 (br, 4H). | MS (ESI, pos. ion) m/z: 450.8 [M + H]$^+$; |

Example 12: The Preparation of (S)-4-(((R)-6-(2-chloro-4-fluorophenyl)-5-(ethoxycarbonyl)-2-(thiazol-2-yl)-3,6-dihydropyrimidin-4-yl)methyl)morpholine-3-carboxylic acid

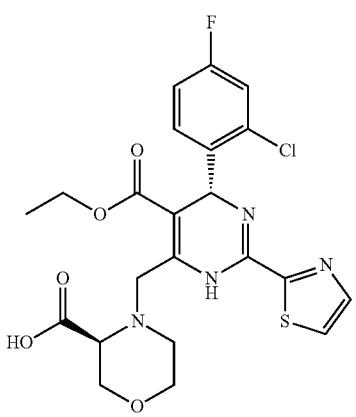

To a flask were added (R)-ethyl 4-(2-chloro-4-fluorophenyl)-6-(bromomethyl)-2-(thiazol-2-yl)-1,4-dihydropyrimidine-5-carboxylate (4.59 g, 10 mmol), (S)-morpholine-3-carboxylic acid (1.31 g, 10 mmol), potassium carbonate (2.76 g, 20 mmol) and ethanol (90 mL). The mixture was stirred at 30° C. under nitrogen atmosphere for 12 hours. After the reaction, the mixture was filtered. The filtrate was concentrated. To the residue was added water (100 mL), the resulting mixture was extracted with ethyl acetate (100 mL). The organic layer was discarded. To the aqueous layer was added ethyl acetate (100 mL), and the mixture was adjusted to pH 3-6 with concentrated hydrochloric acid. The organic layer was dried over anhydrous sodium sulfate and concentrated to give the product as a yellow solid (3.96 g, 78%).

MS (ESI, pos.ion) m/z: 509.2 [M+H]$^+$;

$^1$H NMR (400 MHz, DMSO-$d_6$): δ 13.00 (br, 1H), 9.95 (s, 1H), 8.02 (d, 1H), 7.93 (d, 1H), 7.46-7.38 (m, 2H), 7.17 (td, 1H), 6.05 (s, 1H), 4.20 (d, 1H), 4.05-4.02 (m, 1H), 3.97-3.91 (m, 3H), 3.81 (dd, 1H), 3.72-3.63 (m, 2H), 3.58-3.53 (m, 1H), 3.08-3.05 (m, 1H), 2.42-2.38 (m, 1H), 1.06 (t, 3H).

The compound X can be prepared under the reaction conditions shown in table 22 according to the procedure described Example 12.

TABLE 22

The reaction conditions for preparation of compound X

| No. | R³ | (VI) or a hydrochloride thereof | The mole ratio of compound W to compound (VI); the amount of compound W | Reaction solvent | The mass ratio of reaction solvent to compound (W) | Reaction temperature (° C.) | Reaction time (h) | Product character | Quality; yield (%) of product |
|---|---|---|---|---|---|---|---|---|---|
| X1 | ethyl | (structure) HCl | 1; 4.59 g | ethanol | 20 | 30 | 4 | yellow solid | 3.65 g; 68 |
| X2 | ethyl | (structure) HCl | 1; 4.59 g | ethanol | 15 | 30 | 6 | yellow solid | 3.6 g; 67 |
| X3 | ethyl | (structure) HCl | 1; 4.59 g | ethanol | 10 | 30 | 12 | yellow solid | 2.31 g; 43 |
| X4 | ethyl | (structure) | 1; 4.59 g | ethanol | 4 | 30 | 24 | yellow solid | 4.1 g; 78 |
| X5 | ethyl | (structure) HCl | 1; 4.59 g | ethanol | 12 | 30 | 16 | yellow solid | 2.76 g; 50 |
| X6 | ethyl | (structure) | 1; 4.59 g | ethanol | 20 | 30 | 24 | yellow solid | 3.97 g; 75 |

TABLE 22-continued

The reaction conditions for preparation of compound X

| No. | R[3] | (VI) or a hydrochloride thereof | The mole ratio of compound W to compound (VI); the amount of compound W | Reaction solvent | The mass ratio of reaction solvent to compound (W) | Reaction temperature (° C.) | Reaction time (h) | Product character | Quality; yield (%) of product |
|---|---|---|---|---|---|---|---|---|---|
| X7 | ethyl | (4,4-difluoropyrrolidine propanoic acid)·HCl | 1; 4.59 g | ethanol | 10 | 30 | 12 | yellow solid | 3.45 g; 62 |
| X8 | ethyl | (4,4-difluoropyrrolidine propanoic acid)·HCl | 1; 4.59 g | ethanol | 15 | 30 | 18 | yellow solid | 3.4 g; 61 |
| X9 | methyl | (morpholine-3-carboxylic acid) | 1; 4.45 g | ethanol | 6 | 30 | 24 | yellow solid | 3.47 g; 70 |
| X10 | methyl | (morpholine propanoic acid)·HCl | 1; 4.45 g | ethanol | 10 | 30 | 12 | yellow solid | 3.45 g; 66 |
| X11 | methyl | (morpholine propanoic acid)·HCl | 1; 4.45 g | ethanol | 20 | 30 | 16 | yellow solid | 3.29 g; 63 |
| X12 | methyl | (morpholine propanoic acid)·HCl | 1; 4.45 g | ethanol | 15 | 30 | 20 | yellow solid | 2.2 g; 42 |

TABLE 22-continued

The reaction conditions for preparation of compound X

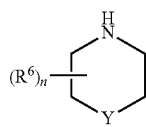

| No. | R³ | (VI) or a hydrochloride thereof | The mole ratio of compound W to compound (VI); the amount of compound W | Reaction solvent | The mass ratio of reaction solvent to compound (W) | Reaction temperature (° C.) | Reaction time (h) | Product character | Quality; yield (%) of product |
|---|---|---|---|---|---|---|---|---|---|
| X13 | methyl | 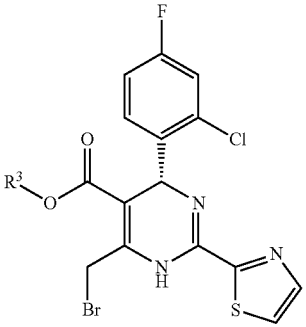 | 1; 4.45 g | ethanol | 30 | 30 | 2 | yellow solid | 3.82 g; 75 |
| X14 | methyl | 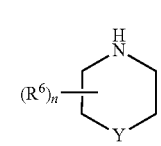 | 1; 4.45 g | ethanol | 8 | 30 | 10 | yellow solid | 2.47 g; 46 |
| X15 | methyl | 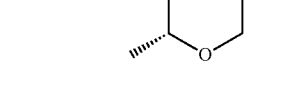 | 1; 4.45 g | ethanol | 15 | 30 | 16 | yellow solid | 3.71 g; 72 |
| X16 | methyl | 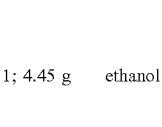 | 1; 4.45 g | ethanol | 10 | 30 | 8 | yellow solid | 3.2 g; 59 |
| X17 | methyl | 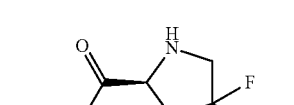 | 1; 4.45 g | ethanol | 20 | 30 | 8 | yellow solid | 3.15 g; 58 |

TABLE 22-1

The NMR and MS datum of compound X

| No. | $^1$H NMR | MS |
|---|---|---|
| X1 | $^1$H NMR (400 MHz, DMSO-d$_6$): δ 9.65 (s, 1H), 8.02 (d, 1H), 7.94 (d, 1H), 7.44-7.38 (m, 2H), 7.18 (td, 1H), 6.05 (s, 1H), 3.96 (q, 2H), 3.89-3.85 (m, 3H), 3.59-3.46 (m, 2H), 2.80-2.74 (m, 2H), 2.36-2.21 (m, 3H), 2.03-1.98 (m, 1H), 1.64-1.59 (m, 2H), 1.06 (t, 3H). | MS (ESI, pos. ion) m/z: 537.3 [M + H]$^+$; |
| X2 | $^1$H NMR (400 MHz, DMSO-d$_6$): δ 12.07 (s, 1H), 9.65 (s, 1H), 8.02 (d, 1H), 7.94 (d, 1H), 7.44-7.40 (m, 2H), 7.19 (td, 1H), 6.06 (s, 1H), 3.97 (q, 2H), 3.92-3.82 (m, 3H), 3.58-3.46 (m, 2H), 2.88 (d, 1H), 2.63 (d, 1H), 2.37-2.22 (m, 3H), 2.08-1.99 (m, 1H), 1.72-1.65 (m, 2H), 1.05 (t, 3H). | MS (ESI, pos. ion) m/z: 536.9 [M + H]$^+$; |
| X3 | $^1$H NMR (400 MHz, DMSO-d$_6$): δ 12.13 (br, 1H), 9.81 (s, 1H), 8.02 (d, 1H), 7.94 (d, 1H), 7.44-7.38 (m, 2H), 7.18 (td, 1H), 6.02 (s, 1H), 4.20 (d, 1H), 3.98 (q, 2H), 3.92 (d, 1H), 3.83-3.78 (m, 1H), 3.75-3.72 (m, 1H), 3.62-3.58 (m, 1H), 3.37-3.33 (m, 1H), 2.79-2.75 (m, 1H), 2.58-2.53 (m, 1H), 2.49-2.46 (m, 1H), 2.39-2.32 (m, 2H), 1.89-1.83 (m, 1H), 1.66-1.58 (m, 1H), 1.06 (t, 3H). | MS (ESI, pos. ion) m/z: 537.2 [M + H]$^+$; |
| X4 | $^1$H NMR (600 MHz, DMSO-d$_6$): δ 13.00 (s, 1H), 9.78 (s, 1H), 8.03 (d, 1H), 7.93 (d, 1H), 7.43-7.30 (m, 2H), 7.18 (td, 1H), 6.03 (s, 1H), 4.06 (d, 1H), 3.95 (q, 2H), 3.90 (d, 1H), 3.74-3.69 (m, 2H), 3.65-3.60 (m, 1H), 2.98 (d, 1H), 2.89 (d, 1H), 2.49-2.45 (m, 1H), 1.21 (d, 3H), 1.04 (t, 3H). | MS (ESI, pos. ion) m/z: 523.2 [M + H]$^+$; |
| X5 | $^1$H NMR (400 MHz, DMSO-d$_6$): δ 12.12 (s, 1H), 9.75 (s, 1H), 8.02 (d, 1H), 7.95 (d, 1H), 7.42-7.36 (m, 2H), 7.15 (td, 1H), 6.06 (s, 1H), 4.15 (d, 1H), 4.02-3.91 (m, 2H), 3.86 (d, 1H), 3.75-3.73 (m, 1H), 3.59-3.54 (m, 1H), 3.51-3.45 (m, 1H), 2.66 (d, 1H), 2.46-2.40 (m, 1H), 2.37-2.30 (m, 3H), 2.03-1.92 (m, 1H), 1.80-1.74 (m, 1H), 1.20 (d, 3H), 1.06 (t, 3H). | MS (ESI, pos. ion) m/z: 551.2 [M + H]$^+$; |
| X6 | $^1$H NMR (600 MHz, DMSO-d$_6$): δ 13.01 (br, 1H), 9.66 (s, 1H), 7.98 (d, 1H), 7.91 (d, 1H), 7.45-7.41 (m, 2H), 7.19 (td, 1H), 6.04 (s, 1H), 4.33 (d, 1H), 4.08 (d, 1H), 4.05-4.02 (m, 1H), 3.97 (q, 2H), 3.92-3.89 (m, 1H), 3.53-3.48 (m, 1H), 3.19-3.12 (m, 1H), 2.82-2.72 (m, 1H), 1.05 (t, 3H). | MS (ESI, pos. ion) m/z: 529.1 [M + H]$^+$; |
| X7 | $^1$H NMR (400 MHz, DMSO-d$_6$): δ 12.08 (s, 1H), 9.52 (s, 1H), 7.99 (d, 1H), 7.92 (d, 1H), 7.44-7.40 (m, 2H), 7.19 (td, 1H), 6.03 (s, 1H), 4.13 (dd, 2H), 3.97 (q, 2H), 3.60-3.52 (m, 1H), 3.06-2.96 (m, 2H), 2.59-2.56 (m, 1H), 2.36-2.20 (m, 2H), 2.13-1.99 (m, 1H), 1.93-1.88 (m, 1H), 1.57-1.44 (m, 1H), 1.05 (t, 3H). | MS (ESI, pos. ion) m/z: 556.9 [M + H]$^+$; |
| X8 | $^1$H NMR (400 MHz, DMSO-d$_6$): δ 12.16 (br, 1H), 9.45 (s, 1H), 8.00 (d, 1H), 7.94 (d, 1H), 7.47-7.41 (m, 2H), 7.18 (td, 1H), 6.06 (s, 1H), 4.12 (dd, 2H), 4.00-3.93 (m, 2H), 3.46-3.38 (m, 1H), 3.01-2.85 (m, 2H), 2.60-2.53 (m, 1H), 2.40-2.23 (m, 2H), 2.15-1.99 (m, 2H), 1.66-1.56 (m, 1H), 1.05 (t, 3H). | MS (ESI, pos. ion) m/z: 557.2 [M + H]$^+$; |
| X9 | $^1$H NMR (400 MHz, DMSO-d$_6$): δ 12.52 (br, 1H), 9.86 (s, 1H), 8.03 (d, 1H), 7.94 (d, 1H), 7.43-7.38 (m, 2H), 7.16 (td, 1H), 6.04 (s, 1H), 4.24 (d, 1H), 4.06-3.97 (m, 2H), 3.84 (dd, 1H), 3.73-3.66 (m, 2H), 3.64-3.59 (m, 1H), 3.51 (s, 3H), 3.10-3.06 (m, 1H), 2.43-2.39 (m, 1H). | MS (ESI, pos. ion) m/z: 494.9 [M + H]$^+$; |
| X10 | $^1$H NMR (400 MHz, DMSO-d$_6$): δ 12.12 (s, 1H), 9.71 (s, 1H), 8.03 (d, 1H), 7.96 (d, 1H), 7.44-7.38 (m, 2H), 7.18 (td, 1H), 6.02 (s, 1H), 3.94-3.82 (m, 3H), 3.62-3.54 (m, 2H), 3.53 (s, 3H), 2.78 (dd, 2H), 2.38-2.26 (m, 3H), 2.06-1.99 (m, 1H), 1.66-1.59 (m, 2H). | MS (ESI, pos. ion) m/z: 522.9 [M + H]$^+$; |
| X11 | $^1$H NMR (400 MHz, DMSO-d$_6$): δ 12.09 (br, 1H), 9.70 (s, 1H), 8.03 (d, 1H), 7.94 (d, 1H), 7.44-7.38 (m, 2H), 7.18 (td, 1H), 6.04 (s, 1H), 3.95 (d, 1H), 3.86-3.81 (m, 2H), 3.57-3.54 (m, 1H), 3.52 (s, 3H), 3.50-3.47 (m, 1H), 2.87 (d, 1H), 2.62 (d, 1H), 2.35-2.19 (m, 3H), 2.14-2.08 (m, 1H), 1.73-1.61 (m, 2H). | MS (ESI, pos. ion) m/z: 523.2 [M + H]$^+$; |
| X12 | $^1$H NMR (400 MHz, DMSO-d$_6$): δ 9.87 (s, 1H), 8.03 (d, 1H), 7.94 (d, 1H), 7.44-7.40 (m, 2H), 7.16 (td, 1H), 6.02 (s, 1H), 4.20 (d, 1H), 3.93 (d, 1H), 3.84-3.79 (m, 1H), 3.75-3.71 (m, 1H), 3.62-3.56 (m, 1H), 3.52 (s, 3H), 3.48-3.41 (m, 1H), 3.05-2.87 (m, 1H), 2.78-2.75 (m, 1H), 2.58-2.56 (m, 1H), 2.38-2.23 (m, 2H), 1.87-1.84 (m, 1H), 1.66-1.58 (m, 1H). | MS (ESI, pos. ion) m/z: 523.1 [M + H]$^+$; |
| X13 | $^1$H NMR (600 MHz, DMSO-d$_6$): δ 13.01 (s, 1H), 9.83 (s, 1H), 8.02 (d, 1H), 7.93 (d, 1H), 7.42-7.38 (m, 2H), 7.17 (td, 1H), 6.02 (s, 1H), 4.07 (d, 1H), 3.89 (d, 1H), 3.76-3.62 (m, 3H), 3.51 (s, 3H), 3.47-3.43 (m, 1H), 2.98 (d, 1H), 2.89 (d, 1H), 1.20 (d, 3H). | MS (ESI, pos. ion) m/z: 508.7 [M + H]$^+$; |
| X14 | $^1$H NMR (400 MHz, DMSO-d$_6$): δ 12.11 (s, 1H), 9.76 (s, 1H), 8.02 (d, 1H), 7.96 (d, 1H), 7.44-7.40 (m, 2H), 7.16 (td, 1H), 6.01 (s, 1H), 4.16 (d, 1H), 3.88 (d, 1H), 3.78-3.74 (m, 1H), 3.60-3.55 (m, 1H), 3.53 (s, 3H), 3.50-3.46 (m, 1H), 2.68 (d, 1H), 2.48-2.42 (m, 1H), 2.36-2.31 (m, 3H), 2.04-1.93 (m, 1H), 1.82-1.73 (m, 1H), 1.21 (d, 3H). | MS (ESI, pos. ion) m/z: 537.1 [M + H]$^+$; |

TABLE 22-1-continued

The NMR and MS datum of compound X

| No. | $^1$H NMR | MS |
|---|---|---|
| X15 | $^1$H NMR (600 MHz, DMSO-d$_6$): δ 9.70 (br, 1H), 8.01 (d, 1H), 7.92 (d, 1H), 7.44-7.38 (m, 2H), 7.18 (td, 1H), 6.01 (s, 1H), 4.31 (d, 1H), 4.09 (d, 1H), 3.94-3.89 (m, 1H), 3.53 (s, 3H), 3.48-3.44 (m, 1H), 3.23-3.07 (m, 2H), 2.84-2.75 (m, 1H). | MS (ESI, pos. ion) m/z: 515.1 [M + H]$^+$; |
| X16 | $^1$H NMR (400 MHz, DMSO-d$_6$): δ 12.07 (br, 1H), 9.55 (s, 1H), 7.99 (d, 1H), 7.92 (d, 1H), 7.43-7.39 (m, 2H), 7.18 (td, 1H), 6.03 (s, 1H), 4.15 (d, 1H), 4.09 (d, 1H), 3.56-3.54 (m, 1H), 3.53 (s, 3H), 3.05-2.95 (m, 2H), 2.48-2.46 (m, 1H), 2.36-2.17 (m, 2H), 2.15-2.02 (m, 1H), 1.97-1.85 (m, 1H), 1.59-1.50 (m, 1H). | MS (ESI, pos. ion) m/z: 543.0 [M + H]$^+$; |
| X17 | $^1$H NMR (400 MHz, DMSO-d$_6$): δ 12.06 (br, 1H), 9.56 (s, 1H), 8.01 (d, 1H), 7.94 (d, 1H), 7.44-7.40 (m, 2H), 7.16 (td, 1H), 6.05 (s, 1H), 4.13 (d, 1H), 4.09 (d, 1H), 3.57-3.54 (m, 1H), 3.52 (s, 3H), 3.06-2.96 (m, 2H), 2.47-2.45 (m, 1H), 2.37-2.17 (m, 2H), 2.16-2.02 (m, 1H), 1.98-1.85 (m, 1H), 1.60-1.51 (m, 1H). | MS (ESI, pos. ion) m/z: 543.0 [M + H]$^+$; |

Example 13: The Preparation of (R)-ethyl 4-(2,4-dichlorophenyl)-6-(morpholinomethyl)-2-(thiazol-2-yl)-1,4-dihydropyrimidine-5-carboxylate

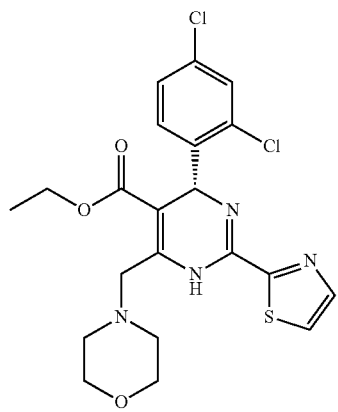 [SMILES: CCOC(=O)C1=C(CN2CCOCC2)NC(c2nccs2)=N[C@H]1c1ccc(Cl)cc1Cl]

Step 1) (R)-(R)-1-ethoxy-1-oxopropan-2-yl 4-(2,4-dichlorophenyl)-6-methyl-2-(thiazol-2-yl)-1,4-dihydropyrimidine-5-carboxylate

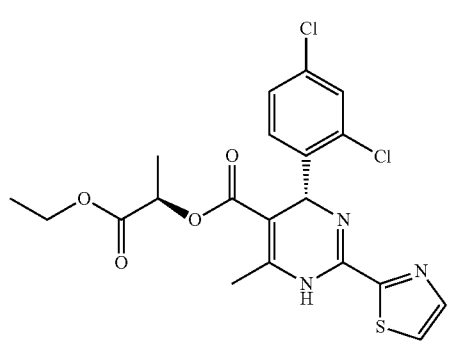

Method One:

To a flask were added 2-thiazolecarboxamidine hydrochloride (16.4 g, 0.1 mol), 2,4-dichlorobenzaldehyde (17.5 g, 0.1 mol), (R)-1-ethoxy-1-oxopropan-2-yl 3-oxobutanoate (20.2 g, 0.1 mol), anhydrous sodium acetate (8.2 g, 0.1 mol) and ethanol (107 g) in turn. The mixture was stirred at 78° C. for 16 hours. After the reaction, the mixture was cooled to 30° C., kept at 30° C. and stirred for 6 hours. The resulting mixture was filtered. The filter cake was washed with water (330 mL) and dried in vacuo at 60° C. for 8 hours to obtain the crude product. To the crude product was added n-propanol (82 g). The mixture was heated until dissolved completely, cooled to 30° C., and then kept at 30° C., stirred and crystallized for 5 hours. The resulting mixture was filtered. The filter cake was dried in vacuo at 60° C. for 8 hours to obtain the product as a yellow solid (12.1 g, 25.9%).

$[α]_D^{25}$=−74.42 (c=0.3037 g/100 mL, MeOH);

MS (ESI, pos.ion) m/z: 467.7 [M+H]$^+$;

$^1$H NMR (400 MHz, DMSO-d$_6$): δ 10.07 (s, 1H), 7.98 (d, 1H), 7.91 (d, 1H), 7.59 (d, 1H), 7.41 (dd, 1H), 7.36 (d, H), 6.03 (s, 1H), 4.83 (q, 1H), 4.12-4.03 (m, 2H), 2.47 (s, 3H), 1.22 (d, 3H), 1.13 (t, 3H).

The compound 10 can be prepared under the reaction conditions shown in table 23 by using method one described in step 1 of Example 13.

TABLE 23

The reaction conditions

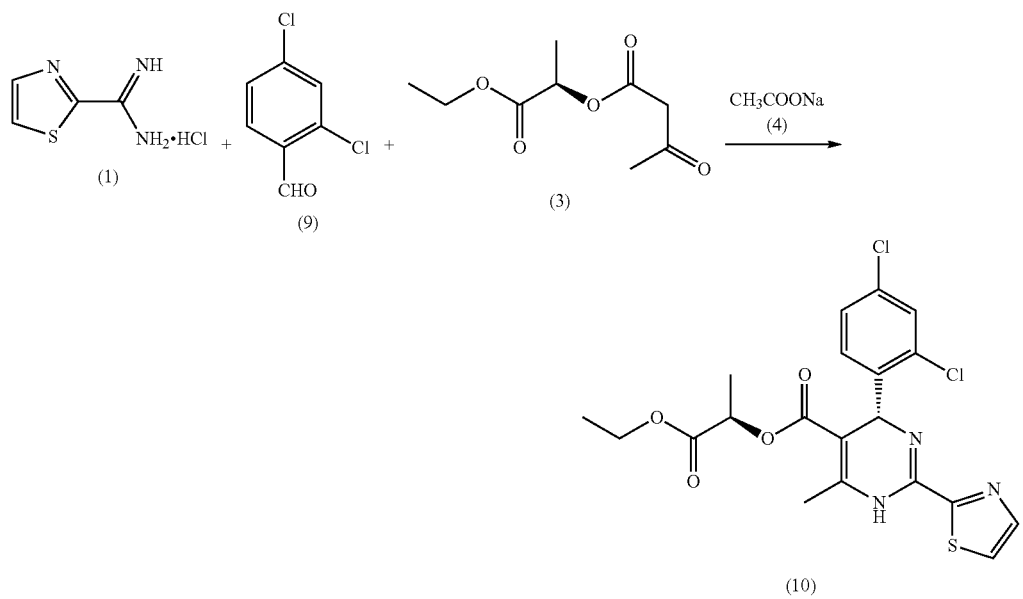

| No. | (1):(9):(3):(4) (mol); the amount of compound (1) is 16.4 g | Reaction solvent | The mass ratio of reaction solvent to compound (1) | Reaction temperature (° C.) | Reaction time (h) | Cooling temperature (° C.) | Cooling time (h) | Recrystallization solvent | The mass ratio of recrystallization solvent to compound (1) | Crystallization temperature (° C.) | Crystallization time (h) | Quality; yield (%) of product |
|---|---|---|---|---|---|---|---|---|---|---|---|---|
| 1 | 1:1:2:1 | — | — | 78 | 12 | 40 | 6 | ethanol | 20 | 5 | 6 | 9.8 g; 20.9 |
| 2 | 1:1:1:1 | ethanol | 1 | 78 | 12 | 40 | 6 | ethanol | 15 | 15 | 8 | 10.6 g; 22.6 |
| 3 | 1:1:1:1 | ethanol | 4.5 | 25 | 72 | 25 | — | ethanol | 5 | 0 | 6 | 9.3 g; 19.8 |
| 4 | 1:1:1:1 | ethanol | 20 | 60 | 24 | −10 | 12 | ethanol | 6 | 25 | 4 | 11.1 g; 23.7 |
| 5 | 1:1:1:1 | ethanol | 80 | 78 | 12 | −40 | 24 | ethanol | 6 | 25 | 6 | 10.7 g; 22.8 |
| 6 | 1:1:1:1 | DMF | 4.5 | 154 | 1 | −20 | 6 | i-propanol | 6 | 20 | 4 | 7.3 g; 15.7 |
| 7 | 1:1:1:1 | n-butanol | 4.5 | 100 | 2 | −5 | 10 | n-propanol | 4.5 | 25 | 4 | 9.1 g; 19.4 |
| 8 | 1:1:1:1 | n-propanol | 4.5 | 80 | 12 | 30 | 6 | n-propanol | 4 | 40 | 10 | 12.8 g; 27.4 |
| 9 | 1:1:1:1 | i-propanol | 4.5 | 82 | 12 | 25 | 1 | i-propanol | 5 | 25 | 1 | 13.2 g; 28.3 |
| 10 | 1:1:1:1 | t-butanol | 5 | 82 | 12 | 30 | 6 | t-butanol | 5 | 25 | 6 | 13.3 g; 28.5 |

Method Two

To a flask were added 2-thiazolecarboxamidine hydrochloride (16.4 g, 0.1 mol), 2,4-dichlorobenzaldehyde (17.5 g, 0.1 mol), (R)-1-ethoxy-1-oxopropan-2-yl 3-oxobutanoate (20.2 g, 0.1 mol), anhydrous sodium acetate (8.2 g, 0.1 mol) and ethanol (107 g) in turn. The mixture was stirred at 78° C. for 16 hours. After the reaction, the reaction mixture was cooled to 30° C., kept at 30° C. and stirred for 3 hours. The mixture was filtered. The filtrate was washed with ethanol (50 g) and water (330 mL) in turn, and then dried in vacuo at 60° C. for 8 hours to obtain the product as a yellow solid (14.4 g, 30.8%).

$[\alpha]_D^{25} = -74.42$ (c=0.3037 g/100 mL, MeOH);

MS (ESI, pos.ion) m/z: 467.7 [M+H]$^+$;

$^1$H NMR (400 MHz, DMSO-d$_6$): δ 10.07 (s, 1H), 7.98 (d, 1H), 7.91 (d, 1H), 7.59 (d, 1H), 7.41 (dd, 1H), 7.36 (d, 1H), 6.03 (s, 1H), 4.83 (q, 1H), 4.12-4.03 (m, 2H), 2.47 (s, 3H), 1.22 (d, 3H), 1.13 (t, 3H).

The compound 10 can be prepared under the reaction conditions shown in table 24 by using method two described in step 1 of Example 13.

TABLE 24

The reaction conditions

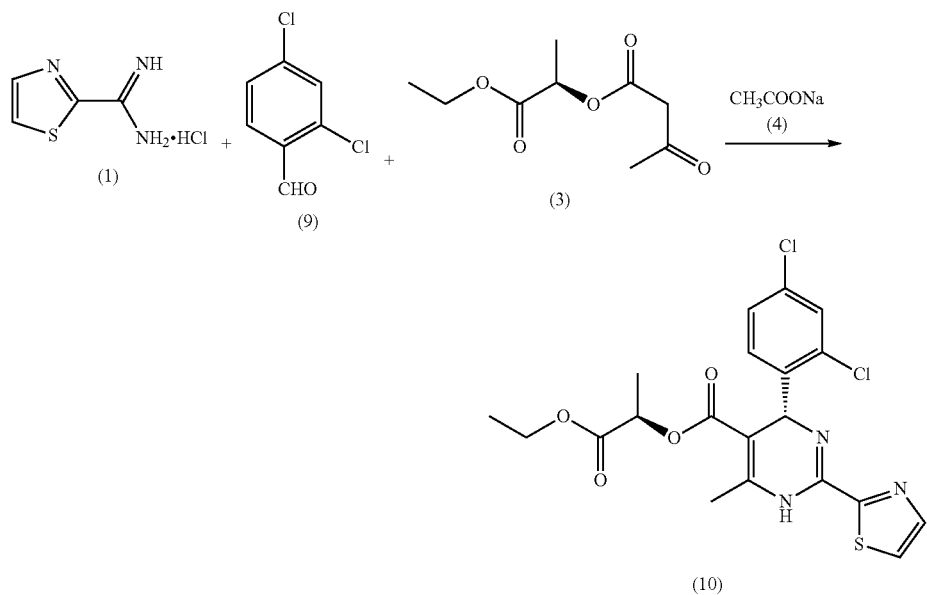

| No. | (1):(9):(3):(4) (mol); the amount of compound (1) is 16.4 g | Reaction solvent | The mass ratio of reaction solvent to compound (1) | Reaction temperature (° C.) | Reaction time (h) | Cooling temperature (° C.) | Cooling time (h) | Washing solvent | The mass ratio of washing solvent to compound (1) | Washing temperature (° C.) | Quality; yield (%) of product |
|---|---|---|---|---|---|---|---|---|---|---|---|
| 1 | 1:1:2:1 | — | — | 78 | 12 | 40 | 6 | ethanol | 10 | 25 | 10.9 g; 23.3 |
| 2 | 1:1:1:1 | ethanol | 1 | 78 | 12 | 40 | 6 | ethanol | 8 | 25 | 11.6 g; 24.7 |
| 3 | 1:1:1:1 | ethanol | 5 | 25 | 72 | 25 | — | ethanol | 1 | 25 | 10.2 g; 21.8 |
| 4 | 1:1:1:1 | ethanol | 9 | 78 | 12 | 25 | 4 | — | — | — | 12.4 g; 26.6 |
| 5 | 1:1:1:1 | ethanol | 20 | 60 | 24 | −10 | 6 | ethanol | 3.5 | 25 | 11.7 g; 24.9 |
| 6 | 1:1:1:1 | ethanol | 80 | 78 | 12 | −30 | 24 | ethanol | 5 | 25 | 11.6 g; 24.7 |
| 7 | 1:1:1:1 | DMF | 4.5 | 154 | 1 | −20 | 6 | i-propanol | 3 | 0 | 7.9 g; 16.9 |
| 8 | 1:1:1:1 | n-butanol | 4.5 | 100 | 2 | −5 | 7 | n-butanol | 3.5 | 25 | 10 g; 21.4 |
| 9 | 1:1:1:1 | n-propanol | 4.5 | 80 | 12 | 30 | 6 | n-propanol | 3 | 25 | 13.9 g; 29.6 |
| 10 | 1:1:1:1 | i-propanol | 4.5 | 82 | 12 | 25 | 1 | i-propanol | 2 | 30 | 14.3 g; 30.5 |
| 11 | 1:1:1:1 | t-butanol | 5 | 82 | 12 | 30 | 6 | t-butanol | 3.5 | 25 | 13.9 g; 29.8 |

Method Three:

To a flask were added 2-thiazolecarboxamidine hydrochloride (16.4 g, 0.1 mol), 2,4-dichlorobenzaldehyde (17.5 g, 0.1 mol), (R)-1-ethoxy-1-oxopropan-2-yl 3-oxobutanoate (20.2 g, 0.1 mol), anhydrous sodium acetate (8.2 g, 0.1 mol) and ethanol (107 g) in turn. The mixture was stirred at 78° C. for 16 hours. After the reaction, the mixture was cooled to 30° C., kept at 30° C. and stirred for 3 hours. The resulting mixture was filtered. The filter cake was washed with water (330 mL) and dried in vacuo at 60° C. for 8 hours to obtain the crude product. The crude product was triturated with i-propanol (82 g) at 30° C. for 5 hours and filtered. The filter cake was dried in vacuo at 60° C. for 8 hours to obtain the product as a yellow solid (12.9 g, 27.5%).

$[a]_D^{25}$=−74.42 (c=0.3037 g/100 mL, MeOH);

MS (ESI, pos.ion) m/z: 467.7 [M+H]$^+$;

$^1$H NMR (400 MHz, DMSO-$d_6$): δ 10.07 (s, 1H), 7.98 (d, 1H), 7.91 (d, 1H), 7.59 (d, 1H), 7.41 (dd, 1H), 7.36 (d, 1H), 6.03 (s, 1H), 4.83 (q, 1H), 4.12-4.03 (m, 2H), 2.47 (s, 3H), 1.22 (d, 3H), 1.13 (t, 3H).

The compound 10 can be prepared under the reaction conditions shown in table 25 by using method three described in step 1 of Example 13.

TABLE 25

The reaction conditions

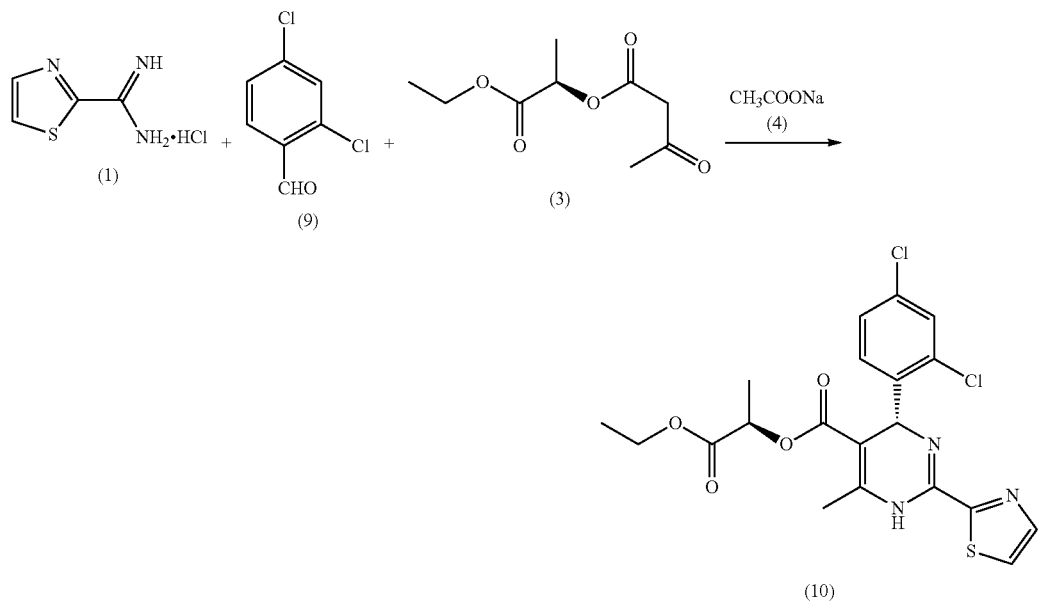

| No. | (1):(9):(3):(4) (mol); the amount of compound (1) is 16.4 g | Reaction solvent | The mass ratio of reaction solvent to compound (1) | Reaction temperature (° C.) | Reaction time (h) | Cooling temperature (° C.) | Cooling time (h) | Trituration solvent | The mass ratio of trituration solvent to compound (1) | Trituration temperature (° C.) | Trituration time (h) | Quality; yield (%) of product |
|---|---|---|---|---|---|---|---|---|---|---|---|---|
| 1 | 1:1:2:1 | — | — | 78 | 12 | 40 | 6 | ethanol | 12 | 25 | 10 | 10.5 g; 22.4 |
| 2 | 1:1:1:1 | ethanol | 1 | 78 | 12 | 40 | 6 | ethanol | 8 | 25 | 4 | 11 g; 23.5 |
| 3 | 1:1:1:1 | ethanol | 5 | 25 | 72 | 25 | — | ethanol | 3 | 40 | 3 | 9.8 g; 20.9 |
| 4 | 1:1:1:1 | ethanol | 20 | 60 | 24 | −10 | 12 | ethanol | 5 | 25 | 2 | 11.4 g; 24.3 |
| 5 | 1:1:1:1 | ethanol | 80 | 78 | 12 | −40 | 24 | ethanol | 4 | 25 | 3 | 10.7 g; 22.9 |
| 6 | 1:1:1:1 | DMF | 4.5 | 154 | 1 | −20 | 6 | i-propanol | 4.5 | 25 | 2 | 7.6 g; 16.3 |
| 7 | 1:1:1:1 | n-butanol | 4.5 | 100 | 2 | −5 | 10 | n-butanol | 4 | 25 | 3 | 9.6 g; 20.6 |

TABLE 25-continued

| 8 | 1:1:1:1 | n-propanol | 4.5 | 80 | 12 | 30 | 6 | n-propanol | 5 | 0 | 2 | 13.3 g; 28.5 |
| 9 | 1:1:1:1 | i-propanol | 4.5 | 82 | 12 | 25 | 1 | i-propanol | 6 | 5 | 4 | 13.7 g; 29.2 |
| 10 | 1:1:1:1 | t-butanol | 5 | 82 | 12 | 30 | 6 | t-butanol | 4 | 25 | 4 | 13.6 g; 29.1 |

Step 2) (R)-(R)-1-ethoxy-1-oxopropan-2-yl 4-(2,4-dichlorophenyl)-6-bromomethyl-2-(thiazol-2-yl)-1,4-dihydropyrimidine-5-carboxylate

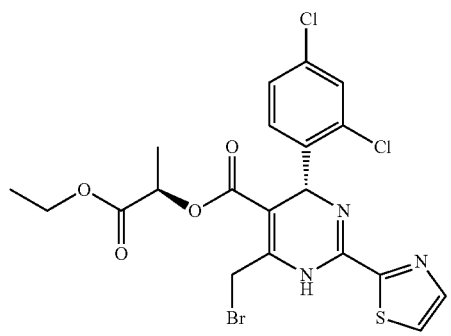 [SMILES: CCOC(=O)[C@@H](C)OC(=O)C1=C(CBr)NC(c2nccs2)=N[C@H]1c1ccc(Cl)cc1Cl]

To a flask were added (R)-(R)-1-ethoxy-1-oxopropan-2-yl 4-(2,4-dichlorophenyl)-6-methyl-2-(thiazol-2-yl)-1,4-dihydropyrimidine-5-carboxylate (46.8 g, 0.1 mol) and tetrachloromethane (936 g). The mixture was heated at 76° C., NBS was added (19.6 g, 0.11 mol), and then the reaction mixture was stirred for 30 min. After the reaction, the reaction mixture was cooled and concentrated. To the residue was added ethanol (234 g). The resulting mixture was cooled to 0° C., kept at 0° C. and stirred. After solid was precipitated out completely, the mixture was filtered. The filter cake was washed with ethanol (47 g) and dried in vacuo at 60° C. for 6 hours to obtain the product as a yellow solid (30.1 g, 55%).

MS (ESI, pos.ion) m/z: 548.0 [M+H]$^+$;

$^1$H NMR (400 MHz, DMSO-d$_6$): δ 9.81 (s, 1H), 8.01 (d, 1H), 7.96 (d, 1H), 7.59 (br, 2H), 7.39 (br, 2H), 6.01 (s, 1H), 4.96 (q, 1H), 4.88-4.79 (m, 2H), 4.14-4.03 (m, 2H), 1.26 (d, 3H), 1.12 (t, 3H).

The compound A3 can be prepared under the reaction conditions shown in table 26 according to the procedure described in step 2 of Example 13

TABLE 26

The reaction conditions

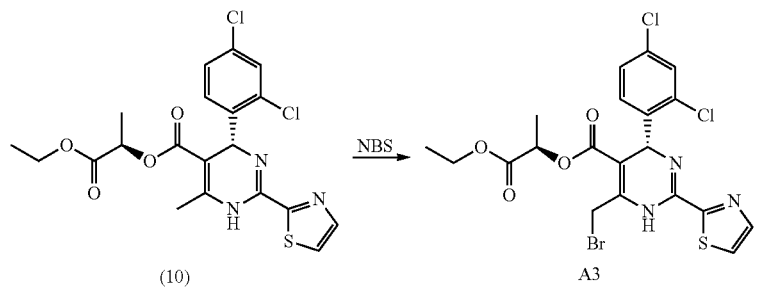

| No. | Compound (10)/NBS(mol) the amount of compound (10) is 46.8 g | Reaction solvent | The mass ratio of reaction solvent to compound (10) | Reaction temperature (° C.) | The solvent added to the residue | The mass ratio of the additional solvent to compound (10) | Quality; yield (%) of product |
|---|---|---|---|---|---|---|---|
| 1 | 1/1.1 | DCM | 30 | 39 | i-propanol | 7 | 28.9 g; 53 |
| 2 | 1/1.05 | DCM | 10 | 39 | ethanol | 5 | 31.2 g; 57 |
| 3 | 1/1.15 | CHCl$_3$ | 20 | 61 | n-propanol | 6 | 30.6 g; 56 |
| 4 | 1/1.1 | CCl$_4$ | 20 | 76 | ethanol | 5 | 32.3 g; 59 |

Step 3) (R)-(R)-1-ethoxy-1-oxopropan-2-yl 4-(2,4-dichlorophenyl)-6-(morpholinomethyl)-2-(thiazol-2-yl)-1,4-dihydropyrimidine-5-carboxylate

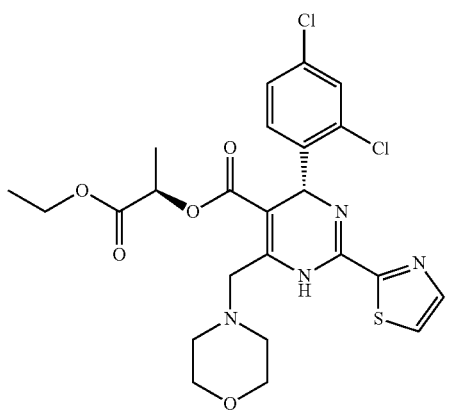

To a flask were added (R)-(R)-1-ethoxy-1-oxopropan-2-yl 4-(2,4-dichlorophenyl)-6-(bromomethyl)-2-(thiazol-2-yl)-1,4-dihydropyrimidine-5-carboxylate (54.7 g, 0.1 mol), i-propanol (273 g) and morpholine (34.8 g, 0.4 mol). The mixture was stirred at 55° C. for 4 hours. After the reaction, the mixture was cooled to 0° C., kept at this temperature and stirred. After the solid precipitated out completely, the mixture was filtered. The filter cake was washed with i-propanol (55 g) followed by water (550 g), and then dried in vacuo at 60° C. for 8 hours to obtain the product as a yellowish solid (33.7 g, 61%).

MS (ESI, pos.ion) m/z: 553.1 [M+H]+;

$^1$H NMR (600 MHz, DMSO-d$_6$): δ 9.87 (s, 1H), 8.01 (d, 1H), 7.96 (d, 1H), 7.59 (br, 1H), 7.38 (br, 2H), 6.05 (s, 1H), 4.86 (q, 1H), 4.14-4.06 (m, 2H), 3.92 (dd, 2H), 3.67 (br, 4H), 2.56 (br, 4H), 1.24 (d, 3H), 1.13 (t, 3H).

Step 4) (R)-ethyl 4-(2,4-dichlorophenyl)-6-(morpholinomethyl)-2-(thiazol-2-yl)-1,4-dihydropyrimidine-5-carboxylate

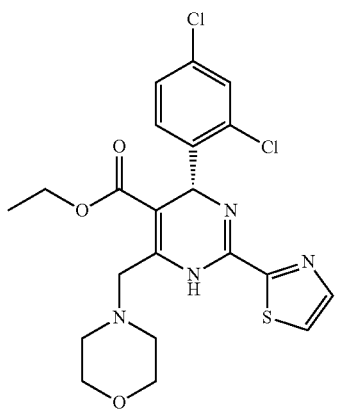

To a flask were added anhydrous ethanol (415 g) and lithium (1.74 g, 0.25 mol) in turn. The mixture was stirred at 43° C. until the lithium was consumed entirely, and then a solution of (R)-(R)-1-ethoxy-1-oxopropan-2-yl 4-(2,4-dichlorophenyl)-6-(morpholinomethyl)-2-(thiazol-2-yl)-1,4-dihydropyrimidine-5-carboxylate (55.3 g, 0.1 mol) in ethanol (415 g) was added. The reaction mixture was stirred at 78° C. for 1.5 hours. After the reaction, the reaction mixture was cooled and concentrated. To the residue was added ethyl acetate (540 g). The mixture was washed with water (250 g×2). The organic layer was concentrated to obtain the product as yellow thick oil (34.6 g, 72%).

MS (ESI, pos.ion) m/z: 480.7 [M+H]+;

$^1$H NMR (600 MHz, DMSO-d$_6$): δ 9.69 (s, 1H), 8.03 (d, 1H), 7.94 (d, 1H), 7.60 (s, 1H), 7.39 (s, 2H), 6.06 (s, 1H), 3.97 (q, 2H), 3.92 (dd, 2H), 3.67 (br, 4H), 2.56 (br, 4H), 1.06 (t, 3H).

Example 14: The Preparation of (R)-methyl 4-(2,4-dichlorophenyl)-6-(morpholinomethyl)-2-(thiazol-2-yl)-1,4-dihydropyrimidine-5-carboxylate

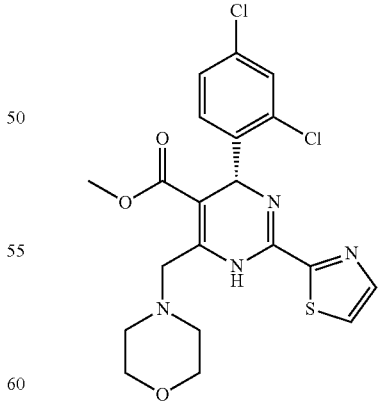

To a flask were added anhydrous methanol (830 g) and lithium (1.74 g, 0.25 mol) in turn. The mixture was stirred at 43° C. until the lithium was consumed entirely, and then (R)-(R)-1-ethoxy-1-oxopropan-2-yl 4-(2,4-dichlorophenyl)-6-(morpholinomethyl)-2-(thiazol-2-yl)-1,4-dihydropyrimidine-5-carboxylate (55.3 g, 0.1 mol) was added. The reaction mixture was stirred at 60° C. for 1.5 hours. After the reaction, the reaction mixture was cooled and concentrated. To the residue was added ethyl acetate (550 g). The mixture was washed with water (250 g×2). The combined organic layers were concentrated to obtain the product as yellow thick oil (32.2 g, 69%).

MS (ESI, pos.ion) m/z: 467.1 [M+H]$^+$;

$^1$H NMR (400 MHz, CDCl$_3$): δ 9.73 (s, 1H), 7.87 (d, 1H), 7.47 (d, 1H), 7.42 (d, 1H), 7.24 (d, 1H), 7.18 (dd, 1H), 6.21 (s, 1H), 4.02 (d, 1H), 3.89 (d, 1H), 3.85 (t, 4H), 3.62 (s, 3H), 2.65 (t, 4H).

Example 15: The Preparation of (S)-4-(((R)-6-(2,4-dichlorophenyl)-5-(ethoxycarbonyl)-2-(thiazol-2-yl)-3,6-dihydropyrimidin-4-yl)methyl)morpholine-3-carboxylic acid

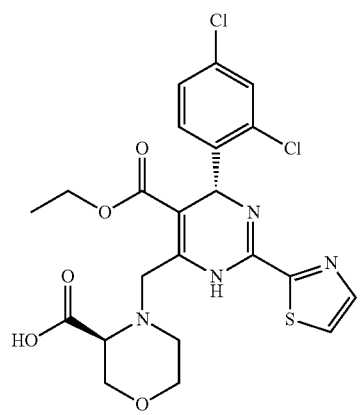

Step 1) (S)-4-(((R)-6-(2,4-dichlorophenyl)-5-((((R)-1-ethoxy-1-oxopropan-2-yl)oxy)carbonyl)-2-(thiazol-2-yl)-3,6-dihydropyrimidin-4-yl)methyl)morpholine-3-carboxylic acid

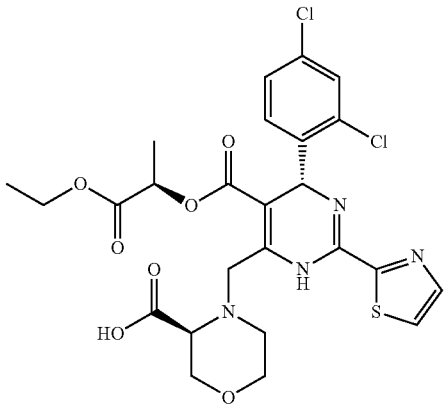 [SMILES: CCOC(=O)[C@@H](C)OC(=O)C1=C(CN2CCOC[C@H]2C(=O)O)NC(c2nccs2)=N[C@H]1c1ccc(Cl)cc1Cl]

To a flask were added (R)-(R)-1-ethoxy-1-oxopropan-2-yl 4-(2,4-dichlorophenyl)-6-(bromomethyl)-2-(thiazol-2-yl)-1,4-dihydropyrimidine-5-carboxylate (54.7 g, 0.1 mol), ethanol (820 g), (S)-morpholine-3-carboxylic acid (13.1 g, 0.1 mol) and potassium carbonate (27.6 g, 0.2 mol) in turn. The mixture was stirred at 30° C. for 12 hours. After the reaction, the mixture was filtered. The filtrate was concentrated. To the residue was added water (820 g), the resulting mixture was extracted with ethyl acetate (820 mL). The organic layer was discarded. To the aqueous layer was added ethyl acetate (900 mL), the mixture was adjusted to pH 3-6 with concentrated hydrochloric acid. The organic layer was dried over anhydrous sodium sulfate and concentrated to give the product as a yellow solid (43.6 g, 73%).

MS (ESI, pos.ion) m/z: 596.6 [M+H]$^+$;

$^1$H NMR (400 MHz, DMSO-d$_6$): δ 12.87 (br, 1H), 9.93 (s, 1H), 8.04 (d, 1H), 7.96 (d, 1H), 7.60 (d, 1H), 7.43-7.37 (m, 2H), 6.09 (s, 1H), 4.85 (q, 1H), 4.22 (d, 1H), 4.13-3.99 (m, 4H), 3.85 (dd, 1H), 3.74-3.61 (m, 3H), 3.12-3.04 (m, 1H), 2.43-2.38 (m, 1H), 1.24 (d, 3H), 1.13 (t, 3H).

The compound H can be prepared under the reaction conditions shown in table 27 according to the procedure described in step 1 of Example 15.

TABLE 27
The reaction conditions for preparation of compound H
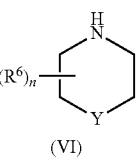
| No. | (VI) or a hydrochloride thereof | compound A3: compound (VI) (mol); the amount of compound A3 is 5.47 g | Reaction solvent | Reaction temperature (° C.) | Reaction time (h) | Product character | Quality; yield (%) of product |
|---|---|---|---|---|---|---|---|
| H1 | 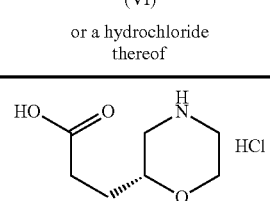 | 1:1 | ethanol | 30 | 12 | yellow solid | 4.44 g; 71 |
| H2 | 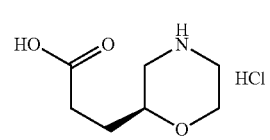 [SMILES: O=C(O)CC[C@H]1CNCCO1 ; Cl] | 1:1 | ethanol | 30 | 12 | yellow solid | 4.32 g; 69 |
| H3 | 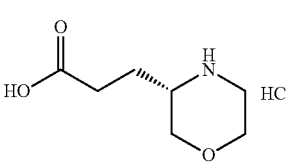 | 1:1 | ethanol | 30 | 12 | yellow solid | 2.63 g; 42 |
| H4 | 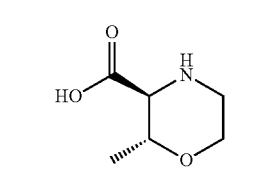 | 1:1 | ethanol | 30 | 12 | yellow solid | 4.52 g; 74 |

TABLE 27-continued
The reaction conditions for preparation of compound H
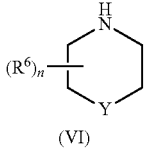
| No. | (VI) or a hydrochloride thereof | compound A3: compound (VI) (mol); the amount of compound A3 is 5.47 g | Reaction solvent | Reaction temperature (° C.) | Reaction time (h) | Product character | Quality; yield (%) of product |
|---|---|---|---|---|---|---|---|
| H5 | 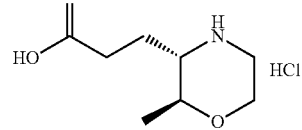 | 1:1 | ethanol | 30 | 12 | yellow solid | 2.56 g; 40 |
| H6 | 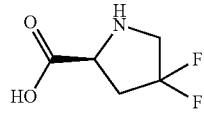 | 1:1 | ethanol | 30 | 12 | yellow solid | 4.89 g; 63 |
| H7 | 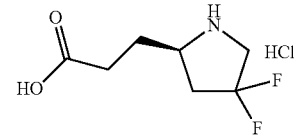 [SMILES: O=C(O)CC[C@@H]1CC(F)(F)CN1 ; Cl] | 1:1 | ethanol | 30 | 12 | yellow solid | 3.23 g; 50 |
| H8 | 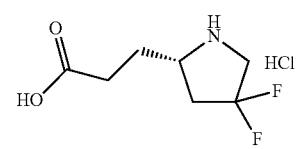 [SMILES: O=C(O)CC[C@H]1CC(F)(F)CN1 ; Cl] | 1:1 | ethanol | 30 | 12 | yellow solid | 3.04 g; 47 |

TABLE 27-1

The NMR and MS datum of compound H

| No. | $^1$H NMR | MS |
|---|---|---|
| H1 | $^1$H NMR (600 MHz, DMSO-d$_6$): δ 12.08 (br, 1H), 9.75 (s, 1H), 8.04 (d, 1H), 7.96 (d, 1H), 7.62 (br, 1H), 7.41 (br, 2H), 6.07 (s, 1H), 4.86 (q, 1H), 4.15-4.06 (m, 2H), 3.98-3.86 (m, 3H), 3.58-3.47 (m, 2H), 2.85-2.75 (m, 2H), 2.35-2.25 (m, 3H), 2.02 (br, 1H), 1.67-1.62 (m, 2H), 1.25 (d, 3H), 1.09 (t, 3H). | MS (ESI, pos. ion) m/z: 624.6 [M + H]$^+$; |
| H2 | $^1$H NMR (600 MHz, DMSO-d$_6$): δ 9.83 (s, 1H), 8.03 (d, 1H), 7.94 (d, 1H), 7.60 (br, 1H), 7.39 (br, 2H), 6.03 (s, 1H), 4.87 (q, 1H), 4.16-4.06 (m, 2H), 3.97-3.86 (m, 3H), 3.59-3.57 (m, 1H), 3.54-3.48 (m, 1H), 2.79 (t, 2H), 2.37-2.24 (m, 3H), 2.01 (t, 1H), 1.68-1.63 (m, 2H), 1.22 (d, 3H), 1.12 (t, 3H). | MS (ESI pos. ion) m/z: 624.6 [M + H]$^+$; |
| H3 | $^1$H NMR (600 MHz, DMSO-d$_6$): δ 9.79 (s, 1H), 8.02 (d, 1H), 7.96 (d, 1H), 7.58 (br, 1H), 7.39 (br, 2H), 6.05 (s, 1H), 4.86 (q, 1H), 4.17 (d, 1H), 4.13-4.03 (m, 2H), 3.87 (d, 1H), 3.82 (d, 1H), 3.76-3.72 (m, 1H), 3.62-3.56 (m, 1H), 3.37-3.33 (m, 1H), 2.94-2.73 (m, 1H), 2.58-2.54 (m, 1H), 2.38-2.31 (m, 1H), 2.29-2.21 (m, 1H), 1.89-1.84 (m, 1H), 1.68-1.59 (m, 1H), 1.24 (d, 3H), 1.14 (t, 3H). | MS (ESI, pos. ion) m/z: 625.1 [M + H]$^+$; |
| H4 | $^1$H NMR (600 MHz, DMSO-d$_6$): δ 9.81 (s, 1H), 8.03 (d, 1H), 7.94 (d, 1H), 7.59 (br, 1H), 7.40 (br, 2H), 6.04 (s, 1H), 4.85 (q, 1H), 4.12-4.03 (m, 3H), 3.93-3.86 (m, 1H), 3.74-3.68 (m, 2H), 3.65-3.61 (m, 1H), 2.99 (d, 1H), 2.92 (d, 1H), 2.48-2.44 (m, 1H), 1.24 (d, 3H), 1.21 (d, 3H), 1.12 (t, 3H). | MS (ESI pos. ion) m/z: 611.1 [M + H]$^+$; |
| H5 | $^1$H NMR (400 MHz, DMSO-d$_6$): δ 12.14 (s, 1H), 9.87 (s, 1H), 8.04 (d, 1H), 7.96 (d, 1H), 7.61 (br, 1H), 7.38 (br, 2H), 6.09 (s, 1H), 4.87 (q, 1H), 4.16 (d, 1H), 4.12-4.02 (m, 2H), 3.83 (d, 1H), 3.77-3.74 (m, 1H), 3.60-3.55 (m, 1H), 3.50-3.46 (m, 1H), 2.69 (d, 1H), 2.45-2.41 (m, 1H), 2.36-2.31(m, 3H), 2.08-1.88 (m, 1H), 1.79-1.72 (m, 1H), 1.25 (d, 3H), 1.20 (d, 3H), 1.14 (t, 3H). | MS (ESI, pos. ion) m/z: 639.2 [M + H]$^+$; |
| H6 | $^1$H NMR (600 MHz, DMSO-d$_6$): δ 9.69 (s, 1H), 7.98 (d, 1H), 7.94 (d, 1H), 7.59 (br, 1H), 7.40 (br, 2H), 6.04 (s, 1H), 4.86-4.81 (m, 1H), 4.31 (d, 1H), 4.10-4.03 (m, 3H), 3.93-3.90 (m, 1H), 3.52-3.49 (m, 1H), 3.18-3.13 (m, 1H), 2.81-2.75 (m, 1H), 2.48-2.43 (m, 1H), 1.23 (d, 3H), 1.12 (t, 3H). | MS (ESI pos. ion) m/z: 617.1 [M + H]$^+$; |
| H7 | $^1$H NMR (600 MHz, DMSO-d$_6$): δ 12.05 (s, 1H), 9.58 (s, 1H), 8.04 (d, 1H), 7.96 (d, 1H), 7.60 (br, 1H), 7.39 (br, 2H), 6.07 (s, 1H), 4.86 (q, 1H), 4.15-4.04 (m, 4H), 3.56-3.51 (m, 1H), 3.05-2.94 (m, 2H), 2.63-2.54 (m, 1H), 2.37-2.21 (m, 2H), 2.13-2.01 (m, 1H), 1.96-1.89 (m, 1H), 1.58-1.52 (m, 1H), 1.24 (d, 3H), 1.12 (t, 3H). | MS (ESI, pos. ion) m/z: 645.1 [M + H]$^+$; |
| H8 | $^1$H NMR (600 MHz, DMSO-d$_6$): δ 12.14 (s, 1H), 9.51 (s, 1H), 8.01 (d, 1H), 7.95 (d, 1H), 7.59 (br, 1H), 7.40 (br, 2H), 6.09 (s, 1H), 4.87 (q, 1H), 4.16-4.05 (m, 4H), 3.51-3.47 (m, 1H), 3.03-2.92 (m, 2H), 2.61-2.58 (m, 1H), 2.41-2.23 (m, 2H), 2.14-1.99 (m, 2H), 1.61-1.54 (m, 1H), 1.26 (d, 3H), 1.16 (t, 3H). | MS (ESI, pos. ion) m/z: 645.1 [M + H]$^+$; |

Step 2) (S)-4-(((R)-6-(2,4-dichlorophenyl)-5-(ethoxycarbonyl)-2-(thiazol-2-yl)-3,6-dihydropyrimidin-4-yl)methyl)morpholine-3-carboxylic acid

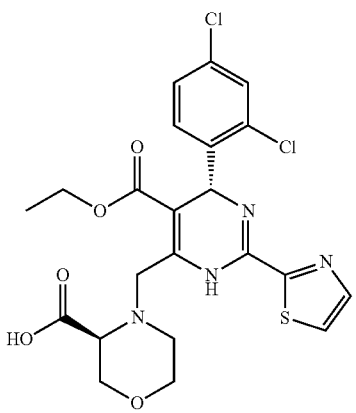 [SMILES: CCOC(=O)C1=C(CN2CCOC[C@H]2C(=O)O)NC(c2nccs2)=N[C@H]1c1ccc(Cl)cc1Cl]

To a flask were added anhydrous ethanol (870 g) and lithium (2.43 g, 0.35 mol) in turn. The mixture was stirred at 43° C. until the lithium was consumed entirely, and then (S)-4-(((R)-6-(2,4-dichlorophenyl)-5-((((R)-1-ethoxy-1-oxopropan-2-yl)oxy)carbonyl)-2-(thiazol-2-yl)-3,6-dihydropyrimidin-4-yl)methyl)morpholine-3-carboxylic acid (59.7 g, 0.1 mol) was added. The reaction mixture was allowed to warm up to 78° C. and stirred for 12 hours. After the reaction, the mixture was cooled and concentrated. To the residue was added water (1200 g), the resulting mixture was extracted with ethyl acetate (1200 mL) The organic layer was discarded. To the aqueous layer was added ethyl acetate (1280 mL), and the mixture was adjusted to pH 3-6 with concentrated hydrochloric acid. The organic layer was dried over anhydrous sodium sulfate and concentrated to give the product as a yellow solid (35.7 g, 68%).

MS (ESI, pos.ion) m/z: 524.7 [M+H]$^+$;

$^1$H NMR (400 MHz, DMSO-d$_6$): δ 12.86 (br, 1H), 9.84 (s, 1H), 8.03 (d, 1H), 7.94 (d, 1H), 7.60 (br, 1H), 7.42-7.36 (m, 2H), 6.05 (s, 1H), 4.25 (d, 1H), 4.09-3.91 (m, 4H), 3.83 (dd, 1H), 3.75-3.58 (m, 3H), 3.12-3.03 (m, 1H), 2.43-2.36 (m, 1H), 1.06 (t, 3H).

The compound XX can be prepared under the reaction conditions shown in table 28 according to the procedure described in step 2 of Example 15.

TABLE 28

The reaction conditions for preparation of compound XX

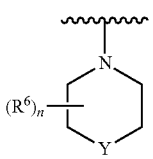

| No. | R³ | (R⁶)ₙ—[N-Y ring] | The mole ratio of Lithium to compound Q; the amount of compound Q | Reaction solvent | Reaction temperature (° C.) | Reaction time (h) | Product character | Quality; yield (%) of product |
|---|---|---|---|---|---|---|---|---|
| XX1 | ethyl | 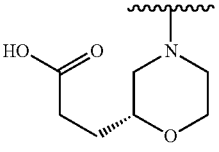 [SMILES: *N1CCO[C@H](CCC(=O)O)C1] | 5; 6.25 g | ethanol | 78 | 2 | yellow solid | 3.33 g; 60 |
| XX2 | ethyl | 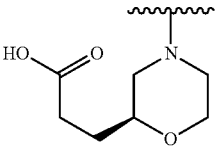 [SMILES: *N1CCO[C@@H](CCC(=O)O)C1] | 5; 6.25 g | ethanol | 78 | 2 | yellow solid | 3.21 g; 58 |
| XX3 | ethyl | 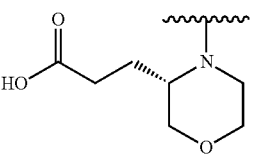 | 5; 6.25 g | ethanol | 78 | 2 | yellow solid | 2.38 g; 43 |
| XX4 | ethyl | 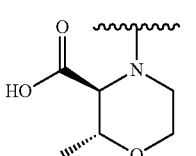 | 5; 6.11 g | ethanol | 78 | 12 | yellow solid | 3.61 g; 67 |
| XX5 | ethyl | 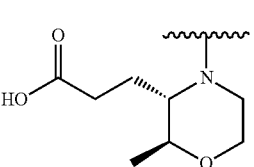 | 5; 6.39 g | ethanol | 78 | 2 | yellow solid | 2.38 g; 42 |
| XX6 | ethyl | 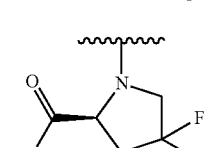 | 5; 6.17 g | ethanol | 78 | 12 | yellow solid | 2.83 g; 52 |

TABLE 28-continued

The reaction conditions for preparation of compound XX

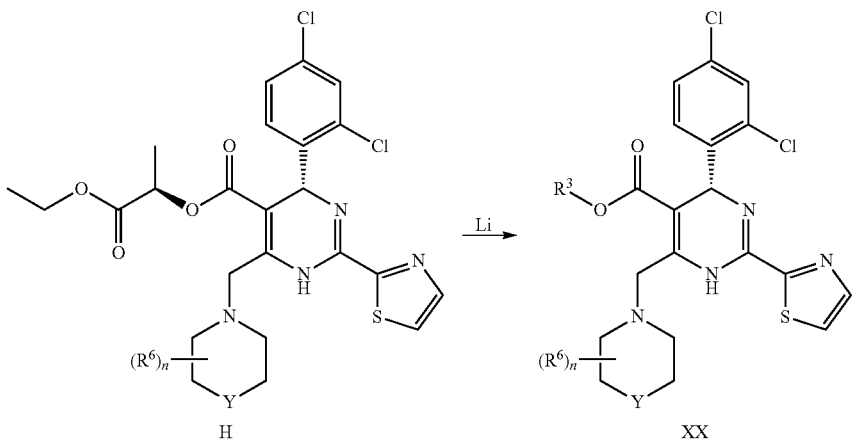

| No. | R³ | (R⁶)ₙ—[N-Y ring] | The mole ratio of Lithium to compound Q; the amount of compound Q | Reaction solvent | Reaction temperature (° C.) | Reaction time (h) | Product character | Quality; yield (%) of product |
|---|---|---|---|---|---|---|---|---|
| XX7 | ethyl | pyrrolidine with CH2CH2COOH and gem-difluoro | 5; 6.46 g | ethanol | 78 | 2 | yellow solid | 2.58 g; 45 |
| XX8 | ethyl | pyrrolidine with CH2CH2COOH and gem-difluoro (stereoisomer) | 5; 6.46 g | ethanol | 78 | 2 | yellow solid | 2.87 g; 50 |
| XX9 | methyl | morpholine with COOH | 5; 5.97 g | methanol | 64 | 18 | yellow solid | 3.53 g; 69 |
| XX10 | methyl | morpholine with CH2CH2COOH | 5; 6.25 g | methanol | 64 | 6 | yellow solid | 3.13 g; 58 |
| XX11 | methyl | morpholine with CH2CH2COOH (stereoisomer) | 5; 6.25 g | methanol | 64 | 4 | yellow solid | 3.02 g; 56 |
| XX12 | methyl | morpholine with CH2CH2COOH | 5; 6.25 g | methanol | 64 | 8 | yellow solid | 2.21 g; 41 |

TABLE 28-continued

The reaction conditions for preparation of compound XX

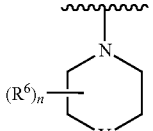

| No. | R³ | (R⁶)ₙ-[morpholine/pyrrolidine]-Y | The mole ratio of Lithium to compound Q; the amount of compound Q | Reaction solvent | Reaction temperature (° C.) | Reaction time (h) | Product character | Quality; yield (%) of product |
|---|---|---|---|---|---|---|---|---|
| XX13 | methyl | 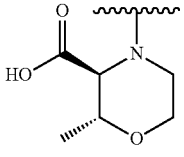 [SMILES: *N1CCO[C@H](C)[C@H]1C(=O)O] | 5; 6.11 g | methanol | 64 | 18 | yellow solid | 3.36 g; 64 |
| XX14 | methyl | 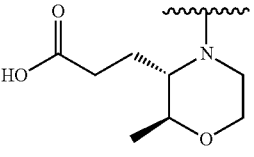 | 5; 6.39 g | methanol | 64 | 5 | yellow solid | 2.21 g; 40 |
| XX15 | methyl | 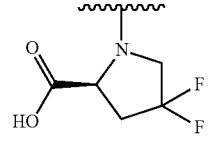 [SMILES: *N1CC(F)(F)C[C@H]1C(=O)O] | 5; 6.17 g | methanol | 64 | 12 | yellow solid | 2.6 g; 49 |
| XX16 | methyl | 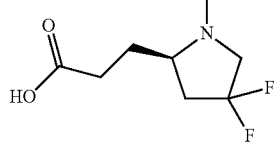 | 5; 6.87 g | methanol | 64 | 6 | yellow solid | 2.57 g; 46 |
| XX17 | methyl | 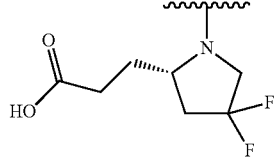 [SMILES: *N1CC(F)(F)C[C@@H]1CCC(=O)O] | 5; 6.46 g | methanol | 64 | 6 | yellow solid | 2.63 g; 47 |

TABLE 28-1

| No. | $^1$H NMR | MS |
|---|---|---|
| XX1 | $^1$H NMR (400 MHz, DMSO-$d_6$): δ 12.04 (s, 1H), 9.66 (s, 1H), 8.02 (d, 1H), 7.95 (d, 1H), 7.61 (br, 1H), 7.38 (br, 2H), 6.05 (s, 1H), 3.96 (q, 2H), 3.89-3.86 (m, 3H), 3.61-3.46 (m, 2H), 2.77 (t, 2H), 2.36-2.23 (m, 3H), 2.02 (t, 1H), 1.63 (dd, 2H), 1.05 (t, 3H). | MS (ESI, pos. ion) m/z: 553.2 [M + H]$^+$; |
| XX2 | $^1$H NMR (400 MHz, DMSO-$d_6$): δ 12.08 (s, 1H), 9.66 (s, 1H), 8.03 (d, 1H), 7.95 (d, 1H), 7.61 (br, 1H), 7.40 (br, 2H), 6.06 (s, 1H), 3.98-3.93 (m, H), 3.86-3.82 (m, 2H), 3.58-3.48 (m, 2H), 2.87 (d, 1H), 2.63 (d, 1H), 2.36-2.23 (m, 3H), 2.10 (t, 1H), 1.72-1.63 (m, 2H), 1.06 (t, 3H). | MS (ESI, pos. ion) m/z: 552.9 [M + H]$^+$; |
| XX3 | $^1$H NMR (400 MHz, DMSO-$d_6$): δ 9.84 (s, 1H), 8.03 (d, 1H), 7.95 (d, 1H), 7.60 (br, 1H), 7.40 (br, 2H), 6.05 (s, 1H), 4.18 (d, 1H), 3.97 (q, 2H), 3.90 (d, 1H), 3.82-3.80 (m, 1H), 3.74-3.72 (m, 1H), 3.61-3.55 (m, 1H), 3.37-3.35 (m, 1H), 2.78-2.76 (m, 1H), 2.56-2.54 (m, 1H), 2.49-2.46 (m, 1H), 2.35-2.20 (m, 2H), 1.88-1.83 (m, 1H), 1.64-1.54 (m, 1H), 1.07 (t, 3H). | MS (ESI, pos. ion) m/z: 552.9 [M + H]$^+$; |
| XX4 | $^1$H NMR (400 MHz, DMSO-$d_6$): δ 13.12 (s, 1H), 9.79 (s, 1H), 8.02 (d, 1H), 7.94 (d, 1H), 7.60 (br, 1H), 7.39 (br, 2H), 6.03 (s, 1H), 4.06 (d, 1H), 3.96 (q, 2H), 3.90-3.87 (m, 1H), 3.74-3.59 (m, 3H), 3.47-3.43 (m, 1H), 2.98 (d, 1H), 2.90 (d, 1H), 1.20 (d, 3H), 1.04 (t, 3H). | MS (ESI, pos. ion) m/z: 539.2 [M + H]$^+$; |
| XX5 | $^1$H NMR (400 MHz, DMSO-$d_6$): δ 12.09 (s, 1H), 9.76 (s, 1H), 8.03 (d, 1H), 7.96 (d, 1H), 7.59 (br, 1H), 7.38 (br, 2H), 6.06 (s, 1H), 4.15 (d, 1H), 4.02-3.93 (m, 2H), 3.87 (d, 1H), 3.78-3.73 (m, 1H), 3.60-3.54 (m, 1H), 3.51-3.46 (m, 1H), 2.67 (d, 1H), 2.45-2.41 (m, 1H), 2.38-2.30 (m, 3H), 2.04-1.92 (m, 1H), 1.81-1.73 (m, 1H), 1.21 (d, 3H), 1.08 (t, 3H). | MS (ESI, pos. ion) m/z: 567.1 [M + H]$^+$; |
| XX6 | $^1$H NMR (600 MHz, DMSO-$d_6$): δ 12.90 (s, 1H), 9.67 (s, 1H), 7.98 (d, 1H), 7.92 (d, 1H), 7.60 (br, 1H), 7.42 (br, 2H), 6.03 (s, 1H), 4.33 (d, 1H), 4.08 (d, 1H), 3.96 (q, 2H), 3.92-3.89 (m, 1H), 3.53-3.48 (m, 1H), 3.19-3.13 (m, 1H), 2.79-2.73 (m, 1H), 2.47-2.45 (m, 1H), 1.06 (t, 3H). | MS (ESI, pos. ion) m/z: 545.1 [M + H]$^+$; |
| XX7 | $^1$H NMR (400 MHz, DMSO-$d_6$): δ 12.05 (s, 1H), 9.52 (s, 1H), 8.00 (d, 1H), 7.94 (d, 1H), 7.60 (br, 1H), 7.41 (br, 2H), 6.04 (s, 1H), 4.14 (dd, 2H), 3.97 (q, 2H), 3.57-3.49 (m, 1H), 3.07-2.97 (m, 2H), 2.58-2.54 (m, 1H), 2.34-2.21 (m, 2H), 2.18-2.03 (m, 2H), 1.95-1.91 (m, 1H), 1.60-1.49 (m, 1H), 1.06 (t, 3H). | MS (ESI, pos. ion) m/z: 573.3 [M + H]$^+$; |
| XX8 | $^1$H NMR (400 MHz, DMSO-$d_6$): δ 12.17 (s, 1H), 9.47 (s, 1H), 8.00 (d, 1H), 7.94 (d, 1H), 7.60 (br, 1H), 7.45-7.37 (m, 2H), 6.06 (s, 1H), 4.15 (dd, 2H), 3.96 (q, 2H), 3.47-3.39 (m, 1H), 3.01-2.86 (m, 2H), 2.59-2.53 (m, 1H), 2.38-2.25 (m, 2H), 2.15-2.01 (m, 2H), 1.65-1.55 (m, 1H), 1.05 (t, 3H). | MS (ESI, pos. ion) m/z: 573.2 [M + H]$^+$; |
| XX9 | $^1$H NMR (400 MHz, CDCl$_3$): δ 8.42 (s, 1H), 7.87 (d, 1H), 7.50 (d, 1H), 7.42 (d, 1H), 7.28 (br, 1H), 7.20 (dd, 1H), 6.20 (s, 1H), 4.23-4.15 (m, 2H), 4.13-4.05 (m, 2H), 3.90-3.80 (m, 2H), 3.61 (s, 3H), 3.59-3.57 (m, 1H), 3.27-3.23 (m, 1H), 2.62-2.54 (m, 1H). | MS (ESI, pos. ion) m/z: 511.1 [M + H]$^+$; |
| XX10 | $^1$H NMR (400 MHz, DMSO-$d_6$): δ 12.03 (s, 1H), 9.70 (s, 1H), 8.01 (d, 1H), 7.94 (d, 1H), 7.59 (br, 1H), 7.37 (br, 2H), 6.04 (s, 1H), 3.89-3.86 (m, 3H), 3.63-3.57 (m, 1H), 3.52 (s, 3H), 3.49-3.47 (m, 1H), 2.76 (t, 2H), 2.39-2.24 (m, 3H), 2.04 (t, 1H), 1.63 (dd, 2H). | MS (ESI, pos. ion) m/z: 538.8 [M + H]$^+$; |
| XX11 | $^1$H NMR (600 MHz, DMSO-$d_6$): δ 12.06 (s, 1H), 9.70 (s, 1H), 8.03 (d, 1H), 7.94 (d, 1H), 7.59 (br, 1H), 7.40 (br, 2H), 6.03 (s, 1H), 3.96 (d, 1H), 3.85-3.80 (m, 2H), 3.57-3.55 (m, 1H), 3.52 (s, 3H), 3.51-3.48 (m, 1H), 2.88 (d, 1H), 2.61 (d, 1H), 2.38-2.21 (m, 3H), 2.16-2.09 (m, 1H), 1.72-1.65 (m, 2H). | MS (ESI, pos. ion) m/z: 539.1 [M + H]$^+$; |
| XX12 | $^1$H NMR (400 MHz, DMSO-$d_6$): δ 12.17 (s, 1H), 9.89 (s, 1H), 8.04 (d, 1H), 7.95 (d, 1H), 7.60 (br, 1H), 7.42-7.37 (m, 2H), 6.04 (s, 1H), 4.18 (d, 1H), 3.90 (d, 1H), 3.84-3.80 (m, 1H), 3.76-3.72 (m, 1H), 3.61-3.56 (m, 1H), 3.53 (s, 3H), 3.46-3.42 (m, 1H), 3.30-3.26 (m, 1H), 2.80-2.75 (m, 1H), 2.56-2.53 (m, 1H), 2.37-2.22 (m, 2H), 1.93-1.83 (m, 1H), 1.62-1.58 (m, 1H). | MS (ESI, pos. ion) m/z: 538.9 [M + H]$^+$; |
| XX13 | $^1$H NMR (600 MHz, DMSO-$d_6$): δ 13.00 (s, 1H), 9.83 (s, 1H), 8.03 (d, 1H), 7.94 (d, 1H), 7.60 (br, 1H), 7.39-7.36 (m, 2H), 6.02 (s, 1H), 4.05 (d, 1H), 3.90-3.86 (m, 1H), 3.74 (d, 1H), 3.70-3.68 (m, 1H), 3.65-3.60 (m, 1H), 3.51 (s, 3H), 3.42-3.36 (m, 1H), 2.99 (d, 1H), 2.89 (d, 1H), 1.20 (d, 3H). | MS (ESI, pos. ion) m/z: 524.7 [M + H]$^+$; |

TABLE 28-1-continued

The NMR and MS datum of compound XX

| No. | $^1$H NMR | MS |
|---|---|---|
| XX14 | $^1$H NMR (400 MHz, DMSO-d$_6$): δ 12.09 (s, 1H), 9.76 (s, 1H), 8.03 (d, 1H), 7.94 (d, 1H), 7.59 (br, 1H), 7.39 (br, 1H), 6.03 (s, 1H), 4.17 (d, 1H), 3.89 (d, 1H), 3.78-3.74 (m, 1H), 3.61-3.55 (m, 1H), 3.53 (s, 3H), 3.50-3.46 (m, 1H), 2.67 (d, 1H), 2.48-2.42 (m, 1H), 2.37-2.31 (m, 3H), 2.03-1.93 (m, 1H), 1.82-1.73 (m, 1H), 1.21 (d, 3H). | MS (ESI, pos. ion) m/z: 553.1 [M + H]$^+$; |
| XX15 | $^1$H NMR (400 MHz, CDCl$_3$): δ 8.19 (s, 1H), 7.88 (d, 1H), 7.57 (d, 1H), 7.45 (br, 1H), 7.28 (br, 2H), 6.15 (s, 1H), 4.67 (d, 1H), 3.98-3.93 (m, 2H), 3.76 (d, 1H), 3.64 (s, 3H), 3.60-3.55 (m, 1H), 3.34-3.24 (m, 1H), 2.86-2.76 (m, 1H), 2.68-2.54 (m, 1H). | MS (ESI, pos. ion) m/z: 531.1 [M + H]$^+$; |
| XX16 | $^1$H NMR (400 MHz, DMSO-d$_6$): δ 11.07 (br, 1H), 9.56 (s, 1H), 7.99 (d, 1H), 7.92 (d, 1H), 7.60 (br, 1H), 7.39 (br, 2H), 6.02 (s, 1H), 4.14 (dd, 2H), 3.52 (s, 3H), 3.08-2.94 (m, 3H), 2.55-2.53 (m, 1H), 2.30-2.19 (m, 2H), 2.12-1.99 (m, 1H), 1.95-1.84 (m, 1H), 1.60-1.46 (m, 1H). | MS (ESI, pos. ion) m/z: 559.0 [M + H]$^+$; |
| XX17 | $^1$H NMR (400 MHz, DMSO-d$_6$): δ 12.15 (s, 1H), 9.52 (s, 1H), 8.00 (d, 1H), 7.94 (d, 1H), 7.60 (s, 1H), 7.41 (br, 2H), 6.05 (s, 1H), 4.13 (dd, 2H), 3.52 (s, 3H), 3.47-3.39 (m, 1H), 3.01-2.87 (m, 2H), 2.59-2.53 (m, 1H), 2.37-2.25 (m, 2H), 2.15-2.02 (m, 2H), 1.64-1.55 (m, 1H). | MS (ESI, pos. ion) m/z: 558.6 [M + H]$^+$; |

Example 16: The Preparation of (R)-ethyl 4-(2,4-dichlorophenyl)-6-(morpholinomethyl)-2-(thiazol-2-yl)-1,4-dihydropyrimidine-5-carboxylate

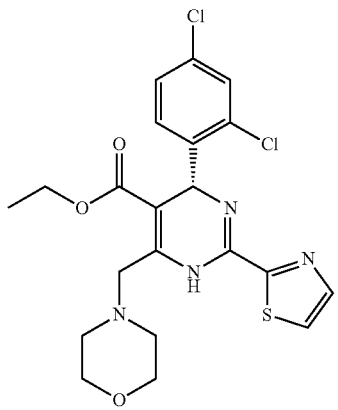

Step 1) (R)-ethyl 4-(2,4-dichlorophenyl)-6-methyl-2-(thiazol-2-yl)-1,4-dihydropyrimidine-5-carboxylate

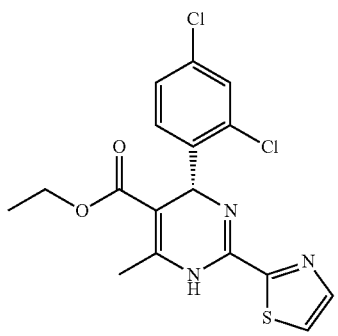

To a flask were added anhydrous ethanol (374 g) and lithium (2.43 g, 0.35 mol) in turn. The mixture was stirred at 43° C. until the lithium was consumed entirely, and then (R)-(R)-1-ethoxy-1-oxopropan-2-yl 4-(2,4-dichlorophenyl)-6-methyl-2-(thiazol-2-yl)-1,4-dihydropyrimidine-5-carboxylate (46.8 g, 0.1 mol) was added. The reaction mixture was stirred at 78° C. for 6 hours. After the reaction, the reaction mixture was cooled to 10° C., kept at 10° C. and stirred for 8 hours. The mixture was filtered. The filter cake was washed with anhydrous ethanol (47 g) and water (500 g) in turn, and then dried in vacuo at 60° C. for 8 hours to obtain the product as a yellow solid (28.1 g, 71%).

$[a]_D^{25}$=−39.07 (c=0.3032 g/100 mL, MeOH);

MS (ESI, pos.ion) m/z: 396.1 [M+H]$^+$;

$^1$H NMR (400 MHz, DMSO-d$_6$): δ 9.93 (s, 1H), 7.97 (d, 1H), 7.90 (d, 1H), 7.58 (d, 1H), 7.41 (dd, 1H), 7.35 (d, 1H), 6.00 (s, 1H), 3.93 (q, 2H), 2.46 (s, 3H), 1.03 (t, 3H).

The compound TT can be prepared under the reaction conditions shown in table 29 according to the procedure described in step 1 of Example 16.

TABLE 29

The reaction conditions for preparation of compound TT

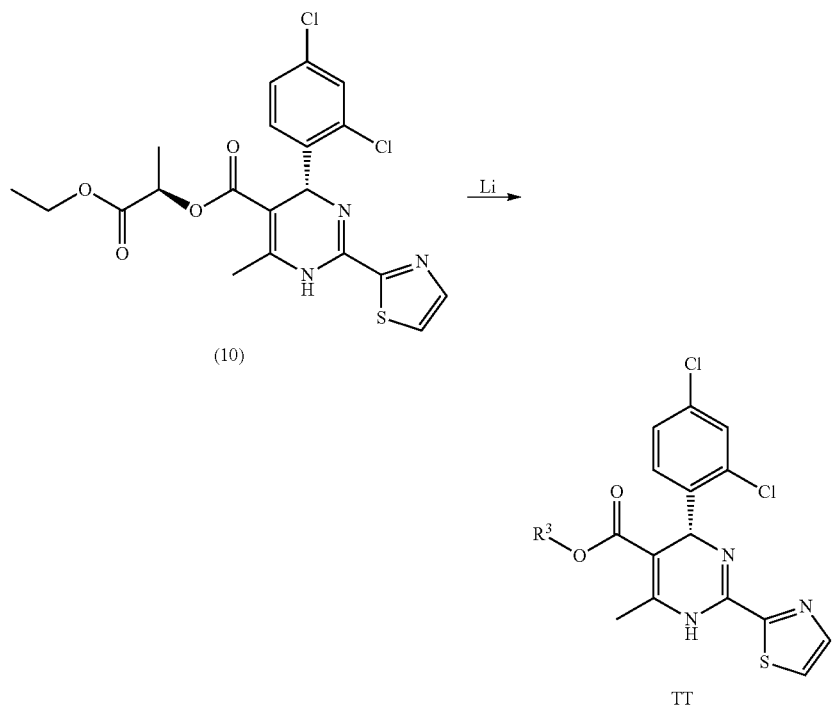

| No. | R³ | The mole ratio of Lithium to compound (10); the amount of compound (10) is 46.8 g | Reaction solvent | The mass ratio of reaction solvent to compound (10) | Reaction temperature (° C.) | Reaction time (h) | Product character | Quality; yield (%) of product |
|---|---|---|---|---|---|---|---|---|
| TT1 | ethyl | 2.5 | ethanol | 10 | 78 | 12 | yellow solid | 17 g; 43 |
| TT1 | ethyl | 3 | ethanol | 6 | 78 | 8 | yellow solid | 28.5 g; 72 |
| TT1 | ethyl | 4 | ethanol | 10 | 78 | 4 | yellow solid | 21.4 g; 54 |
| TT1 | ethyl | 5 | ethanol | 20 | 78 | 24 | yellow solid | 18.6 g; 47 |
| TT1 | ethyl | 6 | ethanol | 30 | 78 | 12 | yellow solid | 15.4 g; 39 |
| TT1 | ethyl | 8 | ethanol | 20 | 78 | 12 | yellow solid | 17.9 g; 45 |
| TT2 | methyl | 3 | methanol | 3 | 64 | 20 | yellow solid | 22.9 g; 60% |
| TT2 | methyl | 3 | methanol | 4 | 64 | 6 | yellow solid | 17.6 g; 46 |
| TT2 | methyl | 4 | methanol | 6 | 64 | 8 | yellow solid | 12.9 g; 34 |

TABLE 29-1

The NMR, MS and specific rotation datum of the compound TT

| No. | ¹H NMR | MS | specific rotation |
|---|---|---|---|
| TT1 | ¹H NMR (400 MHz, DMSO-$d_6$): δ 9.93 (s, 1H), 7.97 (d, 1H), 7.90 (d, 1H), 7.58 (d, 1H), 7.41 (dd, 1H), 7.35 (d, 1H), 6.00 (s, 1H), 3.93 (q, 2H), 2.46 (s, 3H), 1.03 (t, 3H). | MS (ESI, pos. ion) m/z: 396.1 [M + H]⁺; | $[\alpha]_D^{25}$ = −39.07 (c = 0.3032 g/100 mL, MeOH); |
| TT2 | ¹H NMR (400 MHz, DMSO-$d_6$): δ 9.99 (s, 1H), 7.98 (d, 1H), 7.90 (d, 1H), 7.59 (d, 1H), 7.40 (dd, 1H), 7.33 (d, 1H), 5.98 (s, 1H), 3.49 (s, 3H), 2.47 (s, 3H). | MS (ESI, pos. ion) m/z: 382.1 [M + H]⁺ | $[\alpha]_D^{25}$ = −46.08 (c = 0.3038 g/100 mL, MeOH); |

Step 2) (R)-ethyl 4-(2,4-dichlorophenyl)-6-(bromomethyl)-2-(thiazol-2-yl)-1,4-dihydropyrimidine-5-carboxylate

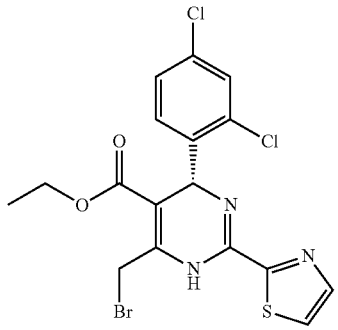

To a flask were added (R)-ethyl 4-(2,4-chlorophenyl)-6-methyl-2-(thiazol-2-yl)-1,4-dihydropyrimidine-5-carboxylate (39.6 g, 0.1 mol) and CCl$_4$ (800 mL), followed by NBS (19.6 g, 0.11 mol) at 70° C. The mixture was stirred for 30 min After the reaction, the mixture was cooled and filtered. The filtrate was concentrated to obtain the product as a yellow solid (37.1 g, 78%).

MS (ESI, pos.ion) m/z: 475.6 [M+H]$^+$;

$^1$H NMR (600 MHz, DMSO-d$_6$): δ 8.03 (d, 1H), 7.98 (d, 1H), 7.66-7.62 (m, 1H), 7.47-7.35 (m, 2H), 5.99 (s, 1H), 4.82 (br, 2H), 4.02 (q, 2H), 1.09 (t, 3H).

The compound WW can be prepared under the reaction conditions shown in table 30 according to the procedure described in step 2 of Example 16.

TABLE 30

The reaction conditions for preparation of compound WW

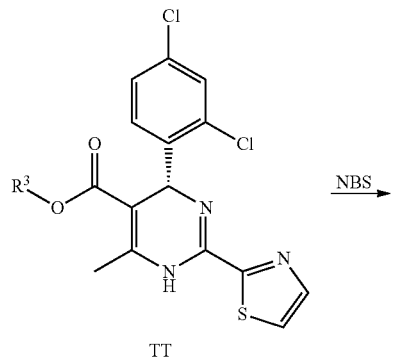

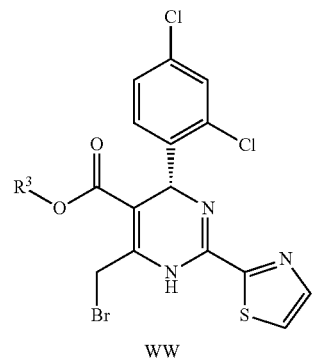

TABLE 30-continued

| No. | R$^3$ | The mole ratio of NBS to compound TT; the amount of compound TT | Reaction solvent | The mass ratio of reaction solvent to compound (TT) | Reaction temperature (° C.) | Product character | Quality; yield (%) of product |
|---|---|---|---|---|---|---|---|
| WW1 | ethyl | 1.0; 39.6 g | DCM | 10 | 39 | yellow solid | 35.2 g; 72 |
| WW1 | ethyl | 1.0; 39.6 g | CHCl$_3$ | 20 | 61 | yellow solid | 36.3 g; 75 |
| WW1 | ethyl | 1.1; 39.6 g | CCl$_4$ | 30 | 76 39 | yellow solid | 44.3 g; 80 |
| WW2 | methyl | 1.0; 38.2 g | DCM | 10 | 39 | yellow solid | 29.9 g; 70 |
| WW2 | methyl | 1.1; 38.2 g | CHCl$_3$ | 20 | 61 | yellow solid | 30.8 g; 72 |
| WW2 | methyl | 1.1; 38.2 g | CCl$_4$ | 30 | 76 | yellow solid | 34.9 g; 79 |

TABLE 30-1

The NMR and MS datum of compound WW

| No. | $^1$H NMR | MS |
|---|---|---|
| WW1 | $^1$H NMR (600 MHz, DMSO-d$_6$): δ 8.03 (d, 1H), 7.98 (d, 1H), 7.66-7.62 (m, 1H), 7.47-7.35 (m, 2H), 5.99 (s, 1H), 4.82 (br, 2H), 4.02 (q, 2H), 1.09 (t, 3H). | MS (ESI, pos. ion) m/z: 475.6 [M + H]$^+$; |
| WW2 | $^1$H NMR (600 MHz, DMSO-d$_6$): δ 9.91 (s, 1H), 8.01 (d, 1H), 7.96 (d, 1H), 7.62 (br, 1H), 7.40 (br, 2H), 6.01 (s, 1H), 4.86 (br, 2H), 3.56 (s, 3H). | MS (ESI, pos. ion) m/z: 459.9 [M + H]$^+$; |

Step 3) (R)-ethyl 4-(2,4-dichlorophenyl)-6-(morpholinomethyl)-2-(thiazol-2-yl)-1,4-dihydropyrimidine-5-carboxylate

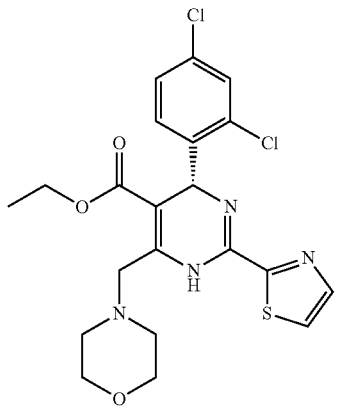

To a flask were added (R)-ethyl 4-(2,4-dichlorophenyl)-6-(bromomethyl)-2-(thiazol-2-yl)-1,4-dihydropyrimidine-5-carboxylate (47.5 g, 0.1 mol), anhydrous ethanol (285 g) and morpholine (34.8 g, 0.4 mol). The mixture was stirred at 25° C. for 6 hours. After the reaction, the mixture was concentrated. To the residue was added ethyl acetate (475 g), the resulting mixture was washed with water (250 mL×2). The organic layer was concentrated to give the product as tawny oil (37.5 g, 78%)

MS (ESI, pos.ion) m/z: 480.7 [M+H]$^+$;

$^1$H NMR (600 MHz, DMSO-d$_6$): δ 9.69 (s, 1H), 8.03 (d, 1H), 7.94 (d, 1H), 7.60 (s, 1H), 7.39 (s, 2H), 6.06 (s, 1H), 3.97 (q, 2H), 3.92 (dd, 2H), 3.67 (br, 4H), 2.56 (br, 4H), 1.06 (t, 3H).

The compound UU can be prepared under the reaction conditions shown in table 31 according to the procedure described in step 3 of Example 16.

TABLE 31

The reaction conditions for preparation of compound UU

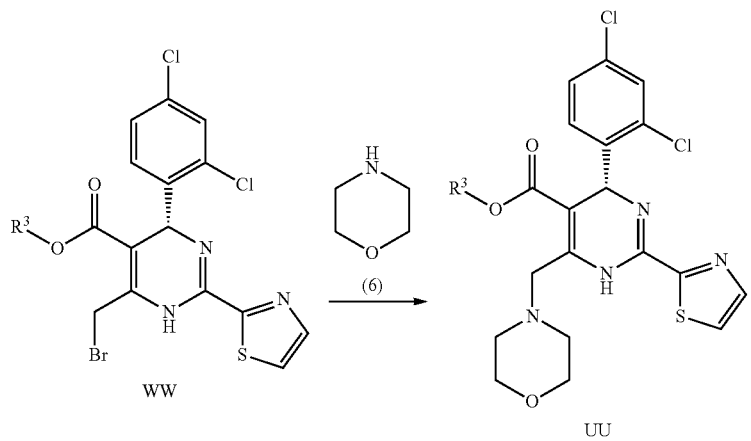

| No. | R$^3$ | The mole ratio of compound (6) to compound WW; the amount of compound WW | Reaction solvent | The mass ratio of reaction solvent to compound (WW) | Reaction temperature (° C.) | Reaction time (h) | Product character | Quality; yield (%) of product |
|---|---|---|---|---|---|---|---|---|
| UU1 | ethyl | 2; 47.5 g | ethanol | 20 | 25 | 2 | tawny oil | 36.6 g; 76 |
| UU1 | ethyl | 3; 47.5 g | acetone | 10 | 40 | 10 | tawny oil | 35.1 g; 73 |
| UU1 | ethyl | 4; 47.5 g | methanol | 10 | 30 | 6 | tawny oil | 34.6 g; 72 |
| UU1 | ethyl | 5; 47.5 g | ethyl acetate | 20 | 50 | 24 | tawny oil | 34.2 g; 71 |
| UU1 | ethyl | 6; 47.5 g | DCM | 8 | 39 | 6 | tawny oil | 31.7 g; 66 |
| UU1 | ethyl | 3; 47.5 g | DMF | 4 | 60 | 1 | tawny oil | 33.2 g; 69 |

TABLE 31-continued

The reaction conditions for preparation of compound UU

| No. | R³ | The mole ratio of compound (6) to compound WW; the amount of compound WW | Reaction solvent | The mass ratio of reaction solvent to compound (WW) | Reaction temperature (° C.) | Reaction time (h) | Product character | Quality; yield (%) of product |
|---|---|---|---|---|---|---|---|---|
| UU1 | ethyl | 4; 47.5 g | THF | 6 | 50 | 8 | tawny oil | 34.6 g; 72 |
| UU2 | methyl | 2; 46.1 g | ethanol | 20 | 25 | 2 | tawny oil | 33.2 g; 71 |
| UU2 | methyl | 3; 46.1 g | acetone | 10 | 40 | 10 | tawny oil | 36.9 g; 79 |
| UU2 | methyl | 4; 46.1 g | methanol | 10 | 30 | 6 | tawny oil | 36 g; 77 |
| UU2 | methyl | 5; 46.1 g | ethyl acetate | 20 | 50 | 24 | tawny oil | 34.1 g; 73 |
| UU2 | methyl | 6; 46.1 g | DCM | 8 | 39 | 6 | tawny oil | 31.3 g; 67 |
| UU2 | methyl | 3; 46.1 g | DMF | 4 | 60 | 1 | tawny oil | 33.2 g; 71 |
| UU2 | methyl | 4; 46.1 g | THF | 6 | 50 | 8 | tawny oil | 31.8 g; 68 |

TABLE 31-1

The NMR and MS datum of compound UU

| No. | ¹H NMR | MS |
|---|---|---|
| UU1 | ¹H NMR (600 MHz, DMSO-d₆): δ 9.69 (s, 1H), 8.03 (d, 1H), 7.94 (d, 1H), 7.60 (s, 1H), 7.39 (s, 2H), 6.06 (s, 1H), 3.97 (q, 2H), 3.92 (dd, 2H), 3.67 (br, 4H), 2.56 (br, 4H), 1.06 (t, 3H). | MS (ESI, pos. ion) m/z: 480.7 [M + H]⁺; |
| UU2 | ¹H NMR (400 MHz, CDCl₃): δ 9.73 (s, 1H), 7.87 (d, 1H), 7.47 (d, 1H), 7.42 (d, 1H), 7.24 (d, 1H), 7.18 (dd, 1H), 6.21 (s, 1H), 4.02 (d, 1H), 3.89 (d, 1H), 3.85 (t, 4H), 3.62 (s, 3H), 2.65 (t, 4H). | MS (ESI, pos. ion) m/z: 467.1 [M + H]⁺; |

Example 17: The Preparation of (S)-4-(((R)-6-(2,4-dichlorophenyl)-5-(ethoxycarbonyl)-2-(thiazol-2-yl)-3,6-dihydropyrimidin-4-yl)methyl)morpholine-3-carboxylic acid

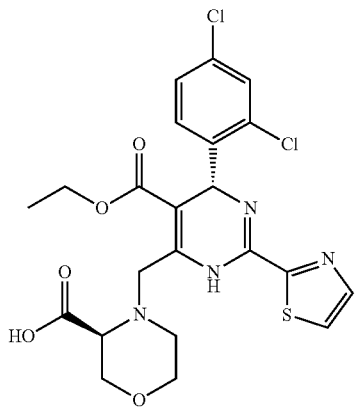 [SMILES: CCOC(=O)C1=C(CN2CCOC[C@H]2C(=O)O)NC(c2nccs2)=N[C@H]1c1ccc(Cl)cc1Cl]

To a flask were added (R)-ethyl 4-(2,4-dichlorophenyl)-6-(bromomethyl)-2-(thiazol-2-yl)-1,4-dihydropyrimidine-5-carboxylate (4.75 g, 10 mmol), (S)-morpholine-3-carboxylic acid (1.31 g, 10 mmol), potassium carbonate (2.76 g, 20 mmol) and ethanol (95 mL). The mixture was stirred at 30° C. for 12 hours. After the reaction, the mixture was filtered. The filtrate was concentrated. To the residue was added water (100 mL), the resulting mixture was extracted with ethyl acetate (100 mL). The organic layer was discarded. To the aqueous layer was added ethyl acetate (100 mL), the mixture was adjusted to pH 3-6 with concentrated hydrochloric acid. The organic layer was dried over anhydrous sodium sulfate and concentrated to give the product as a yellow solid (4.1 g, 78%).

MS (ESI, pos.ion) m/z: 524.7 [M+H]$^+$;

$^1$H NMR (400 MHz, DMSO-$d_6$): δ 12.86 (br, 1H), 9.84 (s, 1H), 8.03 (d, 1H), 7.94 (d, 1H), 7.60 (br, 1H), 7.42-7.36 (m, 2H), 6.05 (s, 1H), 4.25 (d, 1H), 4.09-3.91 (m, 4H), 3.83 (dd, 1H), 3.75-3.58 (m, 3H), 3.12-3.03 (m, 1H), 2.43-2.36 (m, 1H), 1.06 (t, 3H).

The compound XX can be prepared under the reaction conditions shown in table 32 according to the procedure described in Example 17.

TABLE 32

The reaction conditions for preparation of compound XX

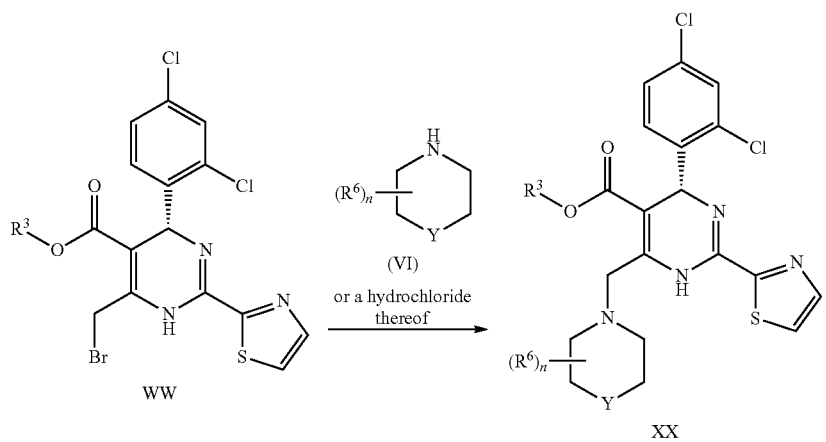

| No. | R$^3$ | (VI) or a hydrochloride thereof | The mole ratio of compound WW to compound (VI); the amount of compound WW | Reaction solvent | The mass ratio of reaction solvent to compound WW | Reaction temperature (° C.) | Reaction time (h) | Product character | Quality; yield (%) of product |
|---|---|---|---|---|---|---|---|---|---|
| XX1 | ethyl | (structure) HCl | 1; 4.75 g | ethanol | 8 | 30 | 4 | yellow solid | 3.76 g; 68 |
| XX2 | ethyl | (structure) HCl | 1; 4.75 g | ethanol | 4 | 30 | 8 | yellow solid | 3.65 g; 66 |

TABLE 32-continued

The reaction conditions for preparation of compound XX

| No. | R³ | (VI) or a hydrochloride thereof | The mole ratio of compound WW to compound (VI); the amount of compound WW | Reaction solvent | The mass ratio of reaction solvent to compound WW | Reaction temperature (° C.) | Reaction time (h) | Product character | Quality; yield (%) of product |
|---|---|---|---|---|---|---|---|---|---|
| XX3 | ethyl | (3-morpholinyl propanoic acid·HCl) | 1; 4.75 g | ethanol | 20 | 30 | 24 | yellow solid | 2.38 g; 43 |
| XX4 | ethyl | (2-methyl-morpholine-3-carboxylic acid) | 1; 4.75 g | ethanol | 30 | 30 | 6 | yellow solid | 4.2 g; 78 |
| XX5 | ethyl | (2-methyl-3-morpholinyl propanoic acid·HCl) | 1; 4.75 g | ethanol | 15 | 30 | 24 | yellow solid | 3.12 g; 55 |
| XX6 | ethyl | (4,4-difluoro-pyrrolidine-2-carboxylic acid) | 1; 4.75 g | ethanol | 20 | 30 | 6 | yellow solid | 3.98 g; 73 |
| XX7 | ethyl | (4,4-difluoro-2-pyrrolidinyl propanoic acid·HCl) | 1; 4.75 g | ethanol | 25 | 30 | 12 | yellow solid | 3.55 g; 62 |
| XX8 | ethyl | (4,4-difluoro-2-pyrrolidinyl propanoic acid·HCl) | 1; 4.75 g | ethanol | 14 | 30 | 12 | yellow solid | 3.67 g; 64 |

TABLE 32-continued

The reaction conditions for preparation of compound XX

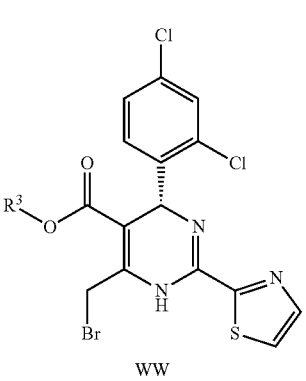

| No. | R³ | (VI) or a hydrochloride thereof | The mole ratio of compound WW to compound (VI); the amount of compound WW | Reaction solvent | The mass ratio of reaction solvent to compound WW | Reaction temperature (° C.) | Reaction time (h) | Product character | Quality; yield (%) of product |
|---|---|---|---|---|---|---|---|---|---|
| XX9 | methyl | 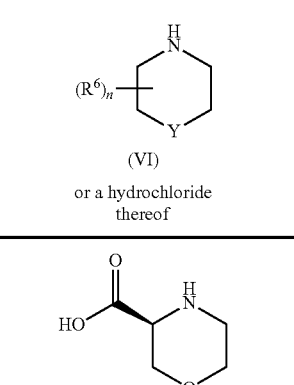 | 1; 4.61 g | ethanol | 8 | 30 | 4 | yellow solid | 3.73 g; 73 |
| XX10 | methyl | 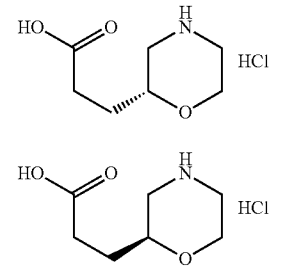 | 1; 4.61 g | ethanol | 4 | 30 | 8 | yellow solid | 3.4 g; 63 |
| XX11 | methyl | 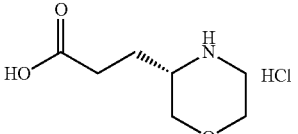 | 1; 4.61 g | ethanol | 10 | 30 | 12 | yellow solid | 3.34 g; 62 |
| XX12 | methyl | 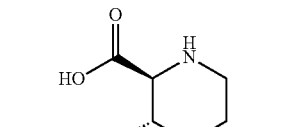 | 1; 4.61 g | ethanol | 30 | 30 | 6 | yellow solid | 2.2 g; 41 |
| XX13 | methyl | 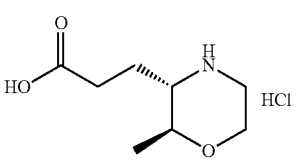 | 1; 4.61 g | ethanol | 8 | 30 | 12 | yellow solid | 3.83 g; 73 |
| XX14 | methyl |  | 1; 4.61 g | ethanol | 20 | 30 | 6 | yellow solid | 2.49 g; 45 |

TABLE 32-continued

The reaction conditions for preparation of compound XX

| No. | R³ | (VI) or a hydrochloride thereof | The mole ratio of compound WW to compound (VI); the amount of compound WW | Reaction solvent | The mass ratio of reaction solvent to compound WW | Reaction temperature (° C.) | Reaction time (h) | Product character | Quality; yield (%) of product |
|---|---|---|---|---|---|---|---|---|---|
| XX15 | methyl | (4,4-difluoro-pyrrolidine-2-carboxylic acid) | 1; 4.61 g | ethanol | 25 | 30 | 12 | yellow solid | 3.77 g; 71 |
| XX16 | methyl | (3-(4,4-difluoropyrrolidin-2-yl)propanoic acid·HCl) | 1; 4.61 g | ethanol | 14 | 30 | 12 | yellow solid | 3.3 g; 59 |
| XX17 | methyl | (3-(4,4-difluoropyrrolidin-2-yl)propanoic acid·HCl) | 1; 4.61 g | ethanol | 15 | 30 | 24 | yellow solid | 3.63 g; 65 |

TABLE 32-1

The NMR and MS datum of compound XX

| No. | ¹H NMR | MS |
|---|---|---|
| XX1 | ¹H NMR (400 MHz, DMSO-$d_6$): δ 12.04 (s, 1H), 9.66 (s, 1H), 8.02 (d, 1H), 7.95 (d, 1H), 7.61 (br, 1H), 7.38 (br, 2H), 6.05 (s, 1H), 3.96 (q, 2H), 3.89-3.86 (m, 3H), 3.61-3.46 (m, 2H), 2.77 (t, 2H), 2.36-2.23 (m, 3H), 2.02 (t, 1H), 1.63 (dd, 2H), 1.05 (t, 3H). | MS (ESI, pos. ion) m/z: 553.2 [M + H]⁺; |
| XX2 | ¹H NMR (400 MHz, DMSO-$d_6$): δ 12.08 (s, 1H), 9.66 (s, 1H), 8.03 (d, 1H), 7.95 (d, 1H), 7.61 (br, 1H), 7.40 (br, 2H), 6.06 (s, 1H), 3.98-3.93 (m, 3H), 3.86-3.82 (m, 2H), 3.58-3.48 (m, 2H), 2.87 (d, 1H), 2.63 (d, 1H), 2.36-2.23 (m, 3H), 2.10 (t, 1H), 1.72-1.63 (m, 2H), 1.06 (t, 3H). | MS (ESI, pos. ion) m/z: 552.9 [M + H]⁺; |
| XX3 | ¹H NMR (400 MHz, DMSO-$d_6$): δ 9.84 (s, 1H), 8.03 (d, 1H), 7.95 (d, 1H), 7.60 (br, 1H), 7.40 (br, 2H), 6.05 (s, 1H), 4.18 (d, 1H), 3.97 (q, 2H), 3.90 (d, 1H), 3.82-3.80 (m, 1H), 3.74-3.72 (m, 1H), 3.61-3.55 (m, 1H), 3.37-3.35 (m, 1H), 2.78-2.76 (m, 1H), 2.56-2.54 (m, 1H), 2.49-2.46 (m, 1H), 2.35-2.20 (m, 2H), 1.88-1.83 (m, 1H), 1.64-1.54 (m, 1H), 1.07 (t, 3H). | MS (ESI, pos. ion) m/z: 552.9 [M + H]⁺; |

TABLE 32-1-continued

The NMR and MS datum of compound XX

| No. | $^1$H NMR | MS |
|---|---|---|
| XX4 | $^1$H NMR (400 MHz, DMSO-$d_6$): δ 13.12 (s, 1H), 9.79 (s, 1H), 8.02 (d, 1H), 7.94 (d, 1H), 7.60 (br, 1H), 7.39 (br, 2H), 6.03 (s, 1H), 4.06 (d, 1H), 3.96 (q, 2H), 3.90-3.87 (m, 1H), 3.74-3.59 (m, 3H), 3.47-3.43 (m, 1H), 2.98 (d, 1H), 2.90 (d, 1H), 1.20 (d, 3H), 1.04 (t, 3H). | MS (ESI, pos. ion) m/z: 539.2 [M + H]$^+$; |
| XX5 | $^1$H NMR (400 MHz, DMSO-$d_6$): δ 12.09 (s, 1H), 9.76 (s, 1H), 8.03 (d, 1H), 7.96 (d, 1H), 7.59 (br, 1H), 7.38 (br, 2H), 6.06 (s, 1H), 4.15 (d, 1H), 4.02-3.93 (m, 2H), 3.87 (d, 1H), 3.78-3.73 (m, 1H), 3.60-3.54 (m, 1H), 3.51-3.46 (m, 1H), 2.67 (d, 1H), 2.45-2.41 (m, 1H), 2.38-2.30 (m, 3H), 2.04 -1.92 (m, 1H), 1.81-1.73 (m, 1H), 1.21 (d, 3H), 1.08 (t, 3H). | MS (ESI, pos. ion) m/z: 567.1 [M + H]$^+$; |
| XX6 | $^1$H NMR (600 MHz, DMSO-$d_6$): δ 12.90 (s, 1H), 9.67 (s, 1H), 7.98 (d, 1H), 7.92 (d, 1H), 7.60 (br, 1H), 7.42 (br, 2H), 6.03 (s, 1H), 4.33 (d, 1H), 4.08 (d, 1H), 3.96 (q, 2H), 3.92-3.89 (m, 1H), 3.53-3.48 (m, 1H), 3.19-3.13 (m, 1H), 2.79-2.73 (m, 1H), 2.47-2.45 (m, 1H), 1.06 (t, 3H). | MS (ESI, pos. ion) m/z: 545.1 [M + H]$^+$; |
| XX7 | $^1$H NMR (400 MHz, DMSO-$d_6$): δ 12.05 (s, 1H), 9.52 (s, 1H), 8.00 (d, 1H), 7.94 (d, 1H), 7.60 (br, 1H), 7.41 (br, 2H), 6.04 (s, 1H), 4.14 (dd, 2H), 3.97 (q, 2H), 3.57-3.49 (m, 1H), 3.07-2.97 (m, 2H), 2.58-2.54 (m, 1H), 2.34-2.21 (m, 2H), 2.18-2.03 (m, 1H), 1.95-1.91 (m, 1H), 1.60-1.49 (m, 1H), 1.06 (t, 3H). | MS (ESI, pos. ion) m/z: 573.3 [M + H]$^+$; |
| XX8 | $^1$H NMR (400 MHz, DMSO-$d_6$): δ 12.17 (s, 1H), 9.47 (s, 1H), 8.00 (d, 1H), 7.94 (d, 1H), 7.60 (br, 1H), 7.45-7.37 (m, 2H), 6.06 (s, 1H), 4.15 (dd, 2H), 3.96 (q, 2H), 3.47-3.39 (m, 1H), 3.01-2.86 (m, 2H), 2.59-2.53 (m, 1H), 2.38-2.25 (m, 2H), 2.15-2.01 (m, 2H), 1.65-1.55 (m, 1H), 1.05 (t, 3H). | MS (ESI, pos. ion) m/z: 573.2 [M + H]$^+$; |
| XX9 | $^1$H NMR (400 MHz, CDCl$_3$): δ 8.42 (s, 1H), 7.87 (d, 1H), 7.50 (d, 1H), 7.42 (d, 1H), 7.28 (br, 1H), 7.20 (dd, 1H), 6.20 (s, 1H), 4.23-4.15 (m, 2H), 4.13-4.05 (m, 2H), 3.90-3.80 (m, 2H), 3.61 (s, 3H), 3.59-3.57 (m, 1H), 3.27-3.23 (m, 1H), 2.62-2.54 (m, 1H). | MS (ESI, pos. ion) m/z: 511.1 [M + H]$^+$; |
| XX10 | $^1$H NMR (400 MHz, DMSO-$d_6$): δ 12.03 (s, 1H), 9.70 (s, 1H), 8.01 (d, 1H), 7.94 (d, 1H), 7.59 (br, 1H), 7.37 (br, 2H), 6.04 (s, 1H), 3.89-3.86 (m, 3H), 3.63-3.57 (m, 1H), 3.52 (s, 3H), 3.49-3.47 (m, 2H), 2.76 (t, 2H), 2.39-2.24 (m, 3H), 2.04 (t, 1H), 1.63 (dd, 2H). | MS (ESI, pos. ion) m/z: 538.8 [M + H]$^+$; |
| XX11 | $^1$H NMR (600 MHz, DMSO-$d_6$): δ 12.06 (s, 1H), 9.70 (s, 1H), 8.03 (d, 1H), 7.94 (d, 1H), 7.59 (br, 1H), 7.40 (br, 2H), 6.03 (s, 1H), 3.96 (d, 1H), 3.85-3.80 (m, 2H), 3.57-3.55 (m, 1H), 3.52 (s, 3H), 3.51-3.48 (m, 1H), 2.88 (d, 1H), 2.61 (d, 1H), 2.38-2.21 (m, 3H), 2.16-2.09 (m, 1H), 1.72-1.65 (m, 2H). | MS (ESI, pos. ion) m/z: 539.1 [M + H]$^+$; |
| XX12 | $^1$H NMR (400 MHz, DMSO-$d_6$): δ 12.17 (s, 1H), 9.89 (s, 1H), 8.04 (d, 1H), 7.95 (d, 1H), 7.60 (br, 1H), 7.42-7.37 (m, 2H), 6.04 (s, 1H), 4.18 (d, 1H), 3.90 (d, 1H), 3.84-3.80 (m, 1H), 3.76-3.72 (m, 1H), 3.61-3.56 (m, 1H), 3.53 (s, 3H), 3.46-3.42 (m, 1H), 3.30-3.26 (m, 1H), 2.80-2.75 (m, 1H), 2.56-2.53 (m, 1H), 2.37-2.22 (m, 2H), 1.93-1.83 (m, 1H), 1.62-1.58 (m, 1H). | MS (ESI, pos. ion) m/z: 538.9 [M + H]$^+$; |
| XX13 | $^1$H NMR (600 MHz, DMSO-$d_6$): δ 13.00 (s, 1H), 9.83 (s, 1H), 8.03 (d, 1H), 7.94 (d, 1H), 7.60 (br, 1H), 7.39-7.36 (m, 2H), 6.02 (s, 1H), 4.05 (d, 1H), 3.90-3.86 (m, 1H), 3.74 (d, 1H), 3.70-3.68 (m, 1H), 3.65-3.60 (m, 1H), 3.51 (s, 3H), 3.42-3.36 (m, 1H), 2.99 (d, 1H), 2.89 (d, 1H), 1.20 (d, 3H). | MS (ESI, pos. ion) m/z: 524.7 [M + H]$^+$; |
| XX14 | $^1$H NMR (400 MHz, DMSO-$d_6$): δ 12.09 (s, 1H), 9.76 (s, 1H), 8.03 (d, 1H), 7.94 (d, 1H), 7.60 (br, 1H), 7.39 (br, 1H), 6.03 (s, 1H), 4.17 (d, 1H), 3.89 (d, 1H), 3.78-3.74 (m, 1H), 3.61-3.55 (m, 1H), 3.53 (s, 3H), 3.50-3.46 (m, 1H), 2.67 (d, 1H), 2.48-2.42 (m, 1H), 2.37-2.31 (m, 3H), 2.03 -1.93 (m, 1H), 1.82-1.73 (m, 1H), 1.21 (d, 3H). | MS (ESI, pos. ion) m/z: 553.1 [M + H]$^+$; |
| XX15 | $^1$H NMR (400 MHz, CDCl$_3$): δ 8.19 (s, 1H), 7.88 (d, 1H), 7.57 (d, 1H), 7.45 (br, 1H), 7.28 (br, 2H), 6.15 (s, 1H), 4.67 (d, 1H), 3.98-3.93 (m, 1H), 3.76 (d, 1H), 3.64 (s, 3H), 3.60-3.55 (m, 1H), 3.34-3.24 (m, 1H), 2.86-2.76 (m, 1H), 2.68-2.54 (m, 1H). | MS (ESI, pos. ion) m/z: 531.1 [M + H]$^+$; |
| XX16 | $^1$H NMR (400 MHz, DMSO-$d_6$): δ 11.07 (br, 1H), 9.56 (s, 1H), 7.99 (d, 1H), 7.92 (d, 1H), 7.60 (br, 1H), 7.39 (br, 2H), 6.02 (s, 1H), 4.14 (dd, 2H), 3.52 (s, 3H), 3.08-2.94 (m, 3H), 2.55-2.53 (m, 1H), 2.30-2.19 (m, 2H), 2.12-1.99 (m, 1H), 1.95-1.84 (m, 1H), 1.60-1.46 (m, 1H). | MS (ESI, pos. ion) m/z: 559.0 [M + H]$^+$; |
| XX17 | $^1$H NMR (400 MHz, DMSO-$d_6$): δ 12.15 (s, 1H), 9.52 (s, 1H), 8.00 (d, 1H), 7.94 (d, 1H), 7.60 (s, 1H), 7.41 (br, 2H), 6.05 (s, 1H), 4.13 (dd, 2H), 3.52 (s, 3H), 3.47-3.39 (m, 1H), 3.01-2.87 (m, 2H), 2.59-2.53 (m, 1H), 2.37-2.25 (m, 2H), 2.15-2.02 (m, 2H), 1.64-1.55 (m, 1H). | MS (ESI, pos. ion) m/z: 558.6 [M + H]$^+$; |

In the specification, Unless specified or limited otherwise, terms such as "first" and "second" are used herein for purposes of description and are not intended to indicate or imply relative importance or significance.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example", "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A process for preparing a dihydropyrimidine compound having Formula (I), or a tautomer thereof having Formula (Ia),

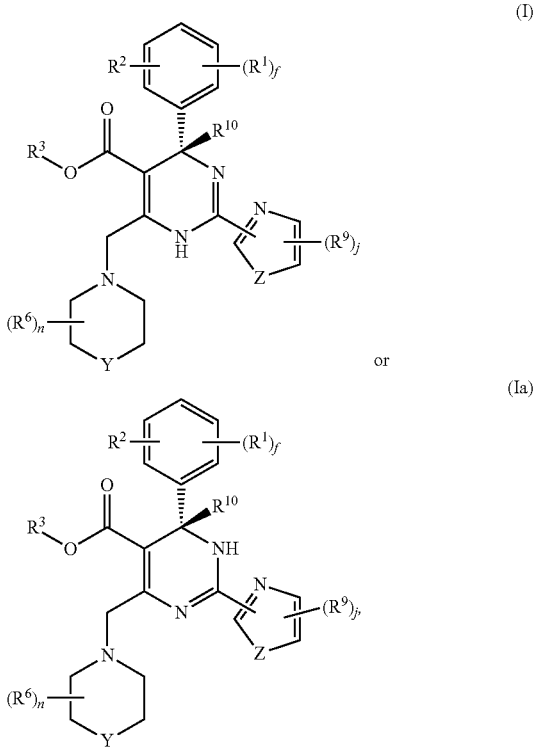

wherein each $R^1$ and $R^2$ is independently F, Cl, or Br;
$R^3$ is $C_{1-4}$ alkyl;
Z is —O—, —S—, —S(=O)$_t$, or —N($R^4$)—;
Y is —O—, —S—, —S(=O)$_t$, —(CH$_2$)$_q$—, or —N($R^5$)—;
each t and q is independently 0, 1, or 2;
each of $R^4$ and $R^5$ is independently H or $C_{1-4}$ alkyl;
each $R^6$ is independently H, deuterium, halo, $C_{1-4}$ alkyl, $C_{1-4}$ haloalkyl, amino, $C_{1-4}$ alkylamino, $C_{1-4}$ alkoxy, nitro, triazolyl, tetrazyl, —(CR$^7$R$^{7a}$)$_m$—OH, —S(=O)$_q$OR$^{8a}$, —(CR$^7$R$^{7a}$)$_m$—S(=O)$_q$N(R$^{8a}$)$_2$, —(CR$^7$R$^{7a}$)$_t$—N(R$^{8a}$)$_2$, —(CR$^7$R$^{7a}$)$_m$—C(=O)O—R$^8$, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_m$—C(=O)O—(CR$^7$R$^{7a}$)$_m$—C(=O)O—R$^8$, —(CR$^7$R$^{7a}$)$_m$—OC(=O)—R$^8$, or —(CR$^7$R$^{7a}$)$_m$—C(=O)—N(R$^8$R$^{8a}$);
each $R^{7a}$ and $R^7$ is independently H, halo, $C_{1-4}$ alkyl, $C_{1-4}$ haloalkyl, —(CH$_2$)$_m$—OH, or —(CH$_2$)$_m$—C(=O)O—R$^8$; or $R^{7a}$ and $R^7$, together with the carbon atom to which they are attached, form a $C_{3-6}$ cycloalkyl group, $C_{2-9}$ heterocyclyl group, or —(C=O)—;
each $R^8$ and $R^{8a}$ is independently H, $C_{1-4}$ alkyl, amino-$C_{1-4}$-alkyl, $C_{1-4}$ alkoxy, $C_{1-6}$ alkyl-S(=O)$_q$—, $C_{6-10}$ aryl, $C_{1-9}$ heteroaryl, $C_{3-6}$ cycloalkyl, $C_{2-9}$ heterocyclyl, $C_{6-10}$ aryl-$C_{1-6}$-alkyl, $C_{1-9}$ heteroaryl-$C_{1-6}$-alkyl, $C_{3-6}$ cycloalkyl-$C_{1-4}$-alkyl, $C_{2-9}$ heterocyclyl-$C_{1-6}$-alkyl, $C_{2-9}$ heterocyclyl-S(=O)$_q$—, $C_{1-9}$ heteroaryl-S(=O)$_q$—, $C_{3-6}$ cycloalkyl-S(=O)$_q$—, $C_{6-10}$ aryl-S(=O)$_q$—, —(CH$_2$)$_m$—OH, —(CH$_2$)$_m$—C(=O)O—(CH$_2$)$_m$—H, or —(CH$_2$)$_m$—OC(=O)—(CH$_2$)$_m$—H;
each $R^9$ is independently H, halo, $C_{1-4}$ alkyl, $C_{1-4}$ haloalkyl, $C_{1-4}$ alkylthio, $C_{3-6}$ cycloalkyl, —(CR$^7$R$^{7a}$)$_m$—C(=O)—N(R$^8$R$^{8a}$), or —(CR$^{7a}$)$_m$—C(=O)O—R$^8$;
$R^{10}$ is H or deuterium;
n is 0, 1, 2, 3, 4, or 5;
each m is independently 0, 1, 2, 3, or 4;
f is 1, 2, 3, or 4; and
j is 0, 1, or 2;
wherein the process comprises the steps of:
step (A): reacting an amidine compound of Formula (II), or a salt thereof

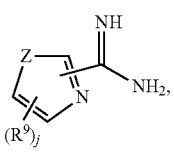

with an aldehyde compound of Formula (III)

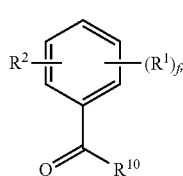

and a compound of Formula (IVa)

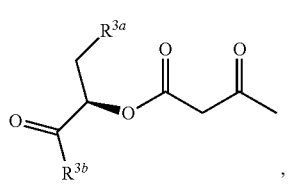

in a first organic solvent to obtain a compound of Formula (Va), (Va)

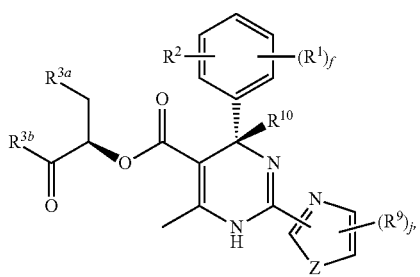

wherein R[3b] is methoxy or ethoxy; and
R[3a] is H or $C_{1-3}$ alkyl;

step (B): halogenating the compound of Formula (Va) in a third organic solvent to form a halide; and then reacting the halide with a compound of Formula (VI), or a salt thereof to obtain a compound of Formula (VIIa), (VI)

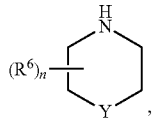

(VIIa)

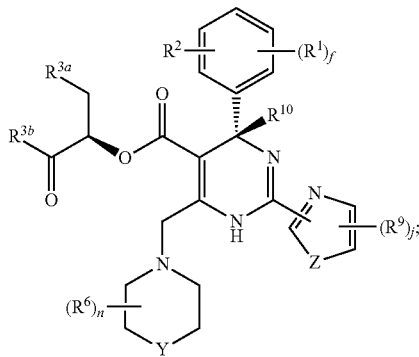

and step (C): forming the compound of Formula (I) or Formula (Ia) from the compound of Formula (VIIa) by means of a transesterification.

2. The process of claim 1, wherein the dihydropyrimidine compound has Formula (I-1), or a tautomer thereof having Formula (Ia-1), (I-1)

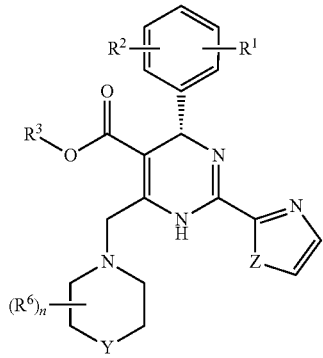

or (Ia-1)

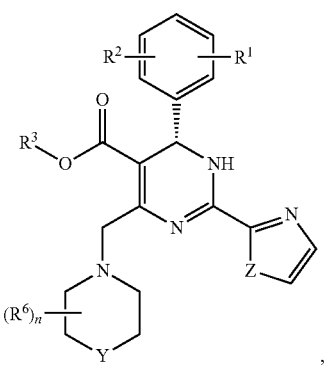

, wherein, each R[6] is independently H, halo, $C_{1-4}$ alkyl, $C_{1-4}$ haloalkyl, amino, $C_{1-4}$ alkylamino, $C_{1-4}$ alkoxy, nitro, triazolyl, tetrazyl, $-(CR^7R^{7a})_m-OH$, $-S(=O)_q OR^{8a}$, $-(CR^7R^{7a})_m-S(=O)_g N(R^{8a})_2$, $-(CR^7 R^{7a})_t-N(R^{8a})_2$, $-(CR^7R^{7a})_m-C(=O)O-R^8$, $-(CR^7R^{7a})_m-C(=O)O-(CR^7R^{7a})_m-OC(=O) O-R^8$, $-(CR^7R^{7a})_m-C(=O)O-(CR^7R^{7a})_m-OC (=O)-R^8$, $-(CR^7R^{7a})_m-C(=O)O-(CR^7R^{7a})_m-C(=O)O-R^8$, $-(CR^7R^{7a})_m-OC(=O)-R^8$, or $-(CR^7R^{7a})_m-C(=O)-N(R^8R^{8a})$; and each R[7a] and R[7] is independently H, $C_{1-4}$ alkyl, $C_{1-4}$ haloalkyl, $-(CH_2)_m-OH$, or $-(CH_2)_m-C(=O)O-R^8$.

3. The process of claim 2, wherein the dihydropyrimidine compound has Formula (I-2), or a tautomer thereof having Formula (Ia-2), (I-2)

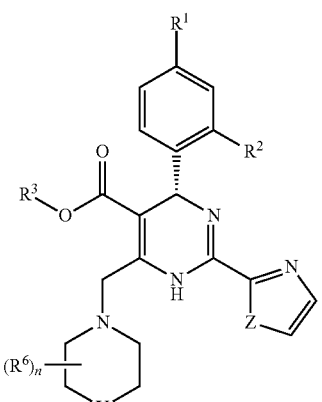

or (Ia-2)

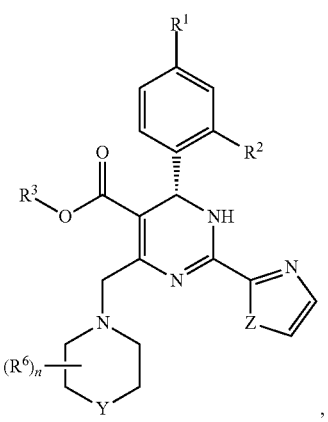

, wherein R[1] is F or Cl; and R[2] is Cl or Br.

4. The process of claim 1, wherein
$R^3$ is methyl, ethyl, propyl, isopropyl, tert-butyl, or butyl;
Z is —O—, —S—, or —N(CH$_3$)—;
Y is —O—, —S—, —S(=O)$_2$—, or —(CH$_2$)$_q$—;
each $R^6$ is independently H, halo, $C_{1-4}$ alkyl, $C_{1-4}$ haloalkyl, amino, $C_{1-4}$ alkylamino, $C_{1-4}$ alkoxy, nitro, triazolyl, tetrazyl, —(CR$^7$R$^{7a}$)$_m$—OH, —(CR$^7$R$^{7a}$)$_m$—C(=O)O—R$^8$, —(CR$^7$R$^{7a}$)$_t$—N(R$^{8a}$)$_2$, —S(=O)$_q$OR$^{8a}$, —(CR$^7$R$^{7a}$)$_m$—S(=O)$_q$N(R$^{8a}$)$_2$, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_m$—C(=O)O—(CR$^7$R$^{7a}$)$_m$—C(=O)O—R$^8$, —(CR$^7$R$^{7a}$)$_m$—OC(=O)—R$^8$, or —(CR$^7$R$^{7a}$)$_m$—C(=O)N(R$^8$R$^{8a}$);
each $R^{7a}$ and $R^7$ is independently H, methyl, ethyl, trifluoromethyl, —(CH$_2$)$_m$—OH, or —(CH$_2$)$_m$—C(=O)O—R$^8$;
each $R^8$ and $R^{8a}$ is independently H, methyl, ethyl, propyl, isopropyl, aminomethyl, methoxy, $C_{1-4}$ alkyl-S(=O)$_2$—, phenyl, pyridyl, thiazolyl, furanyl, imidazolyl, isoxazolyl, oxazolyl, pyrrolyl, pyrimidinyl, pyridazinyl, diazolyl, triazolyl, tetrazolyl, thienyl, pyrazolyl, isothiazolyl, oxadiazolyl, thiadiazolyl, pyrazinyl, pyranyl, triazinyl, cyclopropyl, cyclobutyl, cyclopentyl, cyclohexyl, cyclopropyl-S(=O)$_2$—, cyclobutyl-S(=O)$_2$—, cyclopentyl-S(=O)$_2$—, cyclohexyl-S(=O)$_2$—, naphthyl-S(=O)$_2$—, phenyl-S(=O)$_2$—, —(CH$_2$)$_m$—OH, —(CH$_2$)$_m$—C(=O)O—(CH$_2$)$_m$—H, or —(CH$_2$)$_m$—OC(=O)—(CH$_2$)$_m$—H;
$R^{3b}$ is methoxy or ethoxy; and
$R^{3a}$ is H, methyl, ethyl, isopropyl, or propyl.

5. The process of claim 1, wherein the reaction in step (A) is performed at a temperature from 25° C. to 154° C. or from 60° C. to 100° C.

6. The process of claim 1, wherein the step (A) further comprises a step of cooling the resulting compound of Formula (Va) of step (A) to obtain a solid compound of Formula (Va) at a cooling temperature from −40° C. to 40° C. or from 25° C. to 40° C.

7. The process of claim 6, wherein the cooling is performed for a period of from 0 hour to 24 hours, or from 1 minute to 24 hours, or from 1 hour to 8 hours.

8. The process of claim 1, wherein the first organic solvent is applied in an amount of 0 equivalent to 80 equivalents, or 1 equivalent to 20 equivalents per 1 equivalent by weight of the amidine compound of Formula (II), or a salt thereof.

9. The process of claim 1, wherein step (A) further comprises a step of purifying the compound of Formula (Va) in a second organic solvent, wherein the compound of Formula (Va) is purified by at least one of the following methods:
(1) trituration, wherein the trituration is carried out at a temperature from −20° C. to 50° C. or from 0° C. to 40° C.;
(2) recrystallization, wherein the recrystallization comprises a crystallization process at a temperature from −30° C. to 40° C. or from 0° C. to 40° C., and wherein the recrystallization comprises a crystallization process of from 1 hour to 20 hours or from 1 hour to 10 hours; or
(3) washing, wherein the washing is performed at a temperature from 0° C. to 30° C.

10. The process of claim 9, wherein the second organic solvent is applied in an amount of 2 equivalent to 20 equivalents per 1 equivalent by weight of the amidine compound of Formula (II), or a salt thereof.

11. The process of claim 9, wherein each of the first organic solvent and the second organic solvent is independently a $C_{1-4}$ alcohol, a $C_{1-4}$ alcohol-water mixture, acetone, diethyl ether, isopropyl ether, petroleum ether, tetrahydrofuran, acetonitrile, cyclopentane, cyclohexane, n-hexane, a $C_{1-4}$ haloalkane solvent, ethyl acetate, trifluoroethanol, 2-methoxyethanol, 1,2-dimethoxyethane, 2-methoxyethyl ether, N,N-dimethyl formamide, N-methylpyrolidone, or a combination thereof, or wherein each of the first organic solvent and the second organic solvent is independently methanol, ethanol, n-propanol, i-propanol, n-butanol, tert-butanol, an ethanol-water mixture at a volume ratio of from 10:90 to 90:10, acetone, tetrahydrofuran, N-methylpyrolidone, trifluoroethanol, 2-methoxyethanol, 1,2-dimethoxyethane, 2-methoxyethyl ether, ethyl acetate, glycol, N,N-dimethyl formamide, or a combination thereof.

12. The process of claim 1, wherein the third organic solvent is one or more $C_{1-4}$ alcohols, one or more $C_{1-4}$ haloalkanes, acetonitrile, isopropyl ether, petroleum ether, toluene, xylene, tetrahydrofuran, ethyl acetate, acetone, or a combination thereof, or wherein the third organic solvent is dichloromethane, chloroform, tetrachloromethane, acetonitrile, isopropyl ether, petroleum ether, tetrahydrofuran, methanol, ethanol, propanol, i-propanol, n-butanol, tert-butanol, ethyl acetate, acetone, or a combination thereof.

13. The process of claim 1, wherein the halogenating reaction in step (B) is carried out in the presence of a halogenating agent, and wherein the halogenating agent is N-bromosuccinimide, N-chlorosuccinimide, N-iodosuccinimide, 1,3-dibromo-5,5-dimethylhydantoin, or 1,3-dichloro-5,5-dimethylhydantoin, or a combination thereof.

14. The process of claim 1, wherein the transesterification in step (C) is performed in the presence of a base, and wherein the base is formed by reacting lithium, sodium, or potassium or a combination thereof with a $C_{1-4}$ alcohol.

15. The process of claim 14, wherein the $C_{1-4}$ alcohol is methanol, ethanol, propanol, i-propanol, n-butanol, i-butanol, or tert-butanol, and wherein the lithium, sodium or potassium or a combination thereof is applied in an amount of 2 equivalents to 6 equivalents per 1 equivalent by mole of the compound of Formula (VIIa).

16. The process of claim 1, wherein the compound of Formula (IVa) in step (A) is prepared by a process comprising reacting a compound of Formula (VIIIa) with a compound of Formula (IX), (VIIIa)

(IX)

17. A compound having Formula (Va), or a tautomer thereof having Formula (Va1), or a salt thereof, or a combination thereof, (Va)
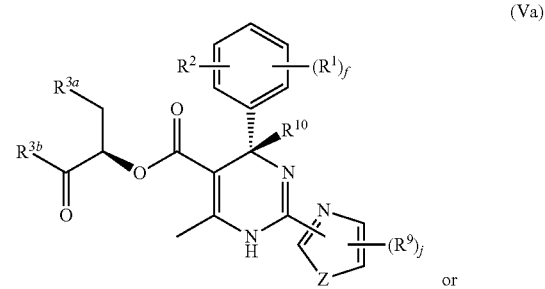

or (Va1)

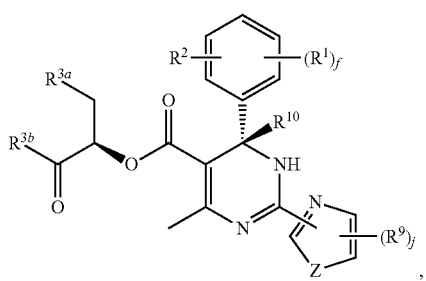

wherein each $R^1$ and $R^2$ is independently F, Cl, or Br;
$R^{3b}$ is methoxy or ethoxy;
$R^{3a}$ is H or $C_{1-3}$ alkyl;
each $R^9$ is independently H, halo, $C_{1-4}$ alkyl, $C_{1-4}$ alkyl-thio, $C_{1-4}$ haloalkyl, $C_{3-6}$ cycloalkyl, —(CR$^7$R$^{7a}$)$_m$—C(=O)—N(R$^8$R$^{8a}$), or —(CR$^7$R$^{7a}$)$_m$—C(=O)O—R$^8$;
each $R^{7a}$ and $R^7$ is independently H, halo, $C_{1-4}$ alkyl, $C_{1-4}$ haloalkyl, —(CH$_2$)$_m$—OH, or —(CH$_2$)$_m$—C(=O)O—R$^8$; or $R^{7a}$ and $R^7$, together with the carbon atom to which they are attached, form a $C_{3-6}$ cycloalkyl group, $C_{2-9}$ heterocyclyl group, or —(C=O)—;
each $R^8$ and $R^{8a}$ is independently H, $C_{1-4}$ alkyl, amino-$C_{1-4}$-alkyl, $C_{1-4}$ alkoxy, $C_{1-6}$ alkyl-S(=O)$_q$—, $C_{6-10}$ aryl, $C_{1-9}$ heteroaryl, $C_{3-6}$ cycloalkyl, $C_{2-9}$ heterocyclyl, $C_{6-10}$ aryl-$C_{1-6}$-alkyl, $C_{1-9}$ heteroaryl-$C_{1-6}$-alkyl, $C_{3-6}$ cycloalkyl-$C_{1-4}$-alkyl, $C_{2-9}$ heterocyclyl-$C_{1-6}$-alkyl, $C_{2-9}$ heterocyclyl-S(=O)$_q$—, $C_{1-9}$ heteroaryl-S(=O)$_q$—, $C_{3-6}$ cycloalkyl-S(=O)$_q$—, $C_{6-10}$ aryl-S(=O)$_q$—, —(CH$_2$)$_m$—OH, —(CH$_2$)$_m$—C(=O)O—(CH$_2$)$_m$—H, or —(CH$_2$)$_m$—OC(=O)—(CH$_2$)$_m$—H;
each m is independently 0, 1, 2, 3, or 4;
$R^{10}$ is H or deuterium;
f is 1, 2, 3, or 4;
j is 0, 1, or 2;
Z is —O—, —S—, —S(=O)$_t$, or —N(R$^4$)—;
t is 0, 1, or 2; and
$R^4$ is H or $C_{1-4}$ alkyl.

18. The compound of claim 17 having Formula (Va-1), or a tautomer thereof having Formula (Va1-1), or a salt thereof, or a combination thereof, (Va-1)

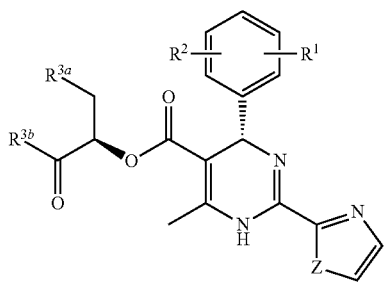

or (Va1-1)

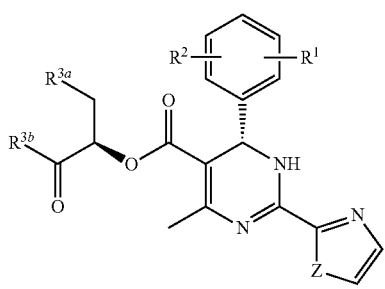

19. The compound of claim 17 having Formula (Va-2), or a tautomer thereof having Formula (Va1-2), or a salt thereof, or a combination thereof, (Va-2)

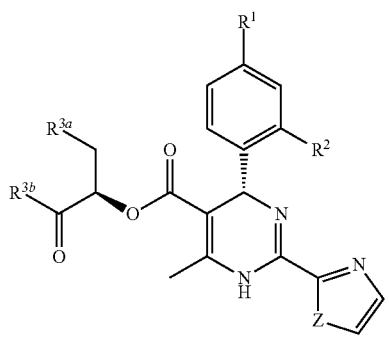

or (Va1-2)

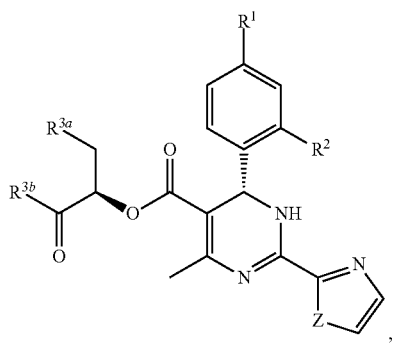

wherein $R^1$ is F or Cl; and $R^2$ is Cl or Br;
Z is —O—, —S—, or —N(CH$_3$)—;
$R^{3b}$ is methoxy or ethoxy; and
$R^{3a}$ is H, methyl, ethyl, isopropyl, or propyl.

20. A process for preparing a dihydropyrimidine compound having Formula (I), or a tautomer thereof having Formula (Ia), (I)

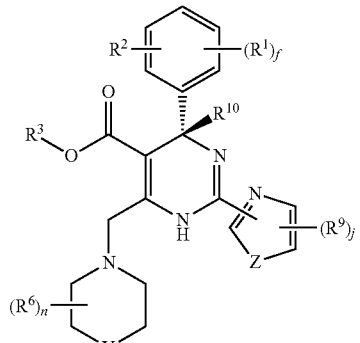

or (Ia)

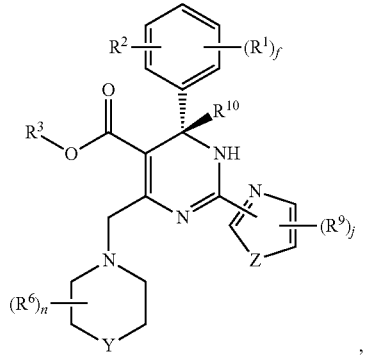

wherein each $R^1$ and $R^2$ is independently F, Cl, or Br;
$R^3$ is $C_{1-4}$ alkyl;
Z is —O—, —S—, —S(=O)$_t$, or —N(R$^4$)—;

Y is —O—, —S—, —S(=O)$_t$-, —(CH$_2$)q-, or —N(R$^5$)—;

each t and q is independently 0, 1, or 2;

each of R$^4$ and R$^5$ is independently H or C$_{1-4}$ alkyl;

each R$^6$ is independently H, deuterium, halo, C$_{1-4}$ alkyl, C$_{1-4}$ haloalkyl, amino, C$_{1-4}$ alkylamino, C$_{1-4}$ alkoxy, nitro, triazolyl, tetrazyl, —(CR$^7$R$^{7a}$)$_m$—OH, —(CR$^7$R$^{7a}$)$_m$—C(=O)O—R$^8$, —(CR$^7$R$^{7a}$)$_t$—N(R$^{8a}$)$_2$, —S(=O)$_q$OR$^{8a}$, —(CR$^7$R$^{7a}$)$_m$—S(=O)$_q$N(R$^{8a}$)$_2$, —(CR$^7$R$^{7a}$)$_m$—C(=O)O—(CR$^7$R$^{7a}$)$_m$—OC(=O)O—R$^8$, —(CR$^7$R$^{7a}$)$_m$—C(=O)O—(CR$^7$R$^{7a}$)$_m$—OC(=O)—R$^8$, —(CR$^7$R$^{7a}$)$_m$—C(=O)O—(CR$^7$R$^{7a}$)$_m$—C(=O)O—R$^8$, —(CR$^7$R$^{7a}$)$_m$—OC(=O)—R$^8$, or —(CR$^7$R$^{7a}$)$_m$—C(=O)N(R$^8$R$^{8a}$);

each R$^{7a}$ and R$^7$ is independently H, halo, C$_{1-4}$ alkyl, C$_{1-4}$ haloalkyl, or —(CH$_2$)$_m$—C(=O)O—R$^8$; or R$^{7a}$ and R$^7$, together with the carbon atom to which they are attached, form a C$_{3-6}$ cycloalkyl group, C$_{2-9}$ heterocyclyl group, or —(C=O)—;

each R$^8$ and R$^{8a}$ is independently H, C$_{1-4}$ alkyl, amino-C$_{1-4}$-alkyl, C$_{1-4}$ alkoxy, C$_{1-6}$ alkyl-S(=O)$_q$—, C$_{6-10}$ aryl, C$_{1-9}$ heteroaryl, C$_{3-6}$ cycloalkyl, C$_{2-9}$ heterocyclyl, C$_{6-10}$ aryl-C$_{1-6}$-alkyl, C$_{1-9}$ heteroaryl-C$_{1-6}$-alkyl, C$_{3-6}$ cycloalkyl-C$_{1-4}$-alkyl, C$_{2-9}$ heterocyclyl-C$_{1-6}$-alkyl, C$_{2-9}$ heterocyclyl-S(=O)$_q$—, C$_{1-9}$ heteroaryl-S(=O)$_q$—, C$_{3-6}$ cycloalkyl-S(=O)$_q$—, C$_{6-10}$ aryl-S(=O)$_q$—, —(CH$_2$)$_m$—OH, —(CH$_2$)$_m$—C(=O)O—(CH$_2$)$_m$—H, or —(CH$_2$)$_m$—OC(=O)—(CH$_2$)$_m$—H;

each R$^9$ is independently H, halo, C$_{1-4}$ alkyl, C$_{1-4}$ alkyl-thio, C$_{1-4}$ haloalkyl, C$_{3-6}$ cycloalkyl, —(CR$^7$R$^{7a}$)$_m$—C(=O)—N(R$^8$R$^{8a}$), or —(CR$^7$R$^{7a}$)$_m$—C(=O)O—R$^8$;

R$^{10}$ is H or deuterium;

n is 0, 1, 2, 3, 4, or 5;

each m is independently 0, 1, 2, 3, or 4;

f is 1, 2, 3, or 4; and j is 0, 1, or 2;

wherein the process comprises the steps of:

step (1): reacting an amidine compound of Formula (II), or a salt thereof

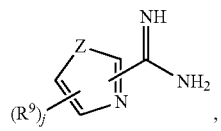

(II)

with an aldehyde compound of Formula (III)

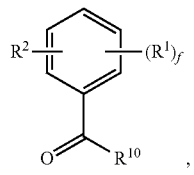

(III)

and a compound of Formula (IVa)

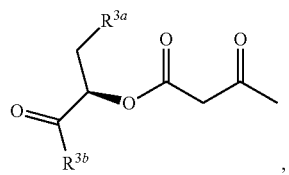

(IVa)

to obtain a compound (Va),

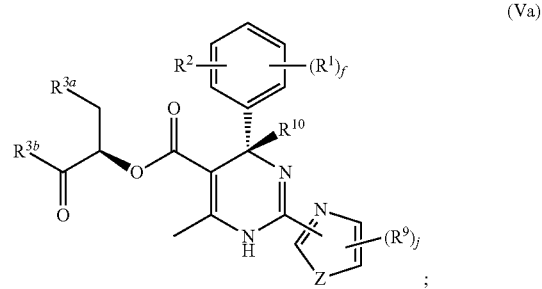

(Va)

step (2): forming a compound of Formula (X) from a compound of Formula (Va) by means of a transesterification,

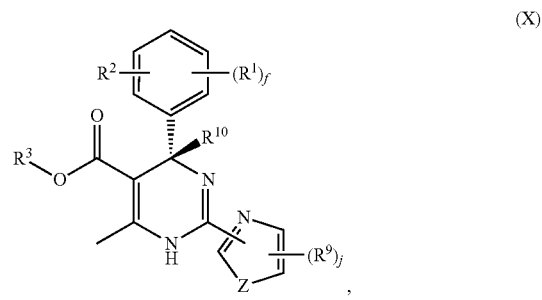

(X)

wherein R$^{3b}$ is methoxy or ethoxy; and

R$^{3a}$ is H or C$_{1-3}$ alkyl; and step (3): halogenating the compound of Formula (X) in a fourth organic solvent to form a halide; and then reacting the halide with a compound of Formula (VI), or a salt thereof to obtain a compound of Formula (I) or Formula (Ia),

(VI)

21. The process of claim 20, wherein the dihydropyrimidine compound has Formula (I-1), or a tautomer thereof having Formula (Ia-1),

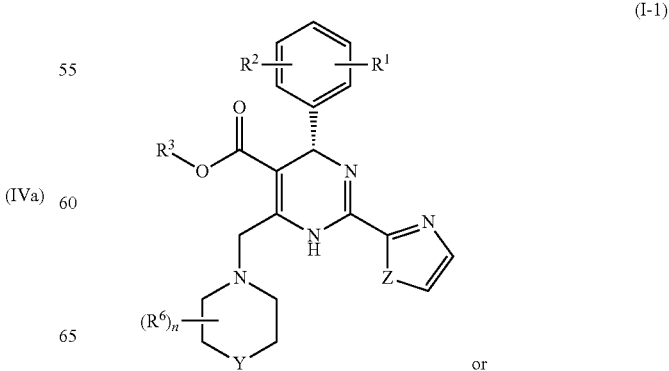

(I-1)

or

-continued

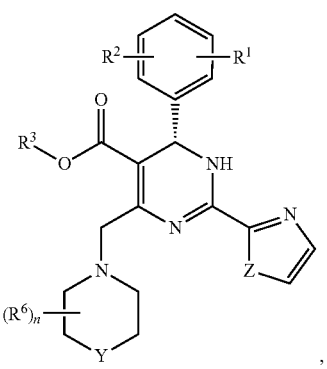

(Ia-1)

wherein, each $R^6$ is independently H, halo, $C_{1-4}$ alkyl, $C_{1-4}$ haloalkyl, amino, $C_{1-4}$ alkylamino, $C_{1-4}$ alkoxy, nitro, triazolyl, tetrazyl, $-(CR^7R^{7a})_m-OH$, $-(CR^7R^{7a})_m-C(=O)O-R^8$, $-(CR^7R^{7a})_t-N(R^{8a})_2$, $-S(=O)_qOR^{8a}$, $-(CR^7R^{7a})_m-S(=O)_qN(R^{8a})_2$, $-(CR^7R^{7a})_m-C(=O)O-(CR^7R^{7a})_m-OC(=O)O-R^8$, $-(CR^7R^{7a})_m-C(=O)O-(CR^7R^{7a})_m-OC(=O)-R^8$, $-(CR^7R^{7a})_m-C(=O)O-(CR^7R^{7a})_m-C(=O)O-R^8$, $-(CR^7R^{7a})_m-OC(=O)-R^8$, or $-(CR^7R^{7a})_m-C(=O)N(R^8R^{8a})$; and each $R^{7a}$ and $R^7$ is independently H, $C_{1-4}$ alkyl, $C_{1-4}$ haloalkyl, $-(CH_2)_m-OH$, or $-(CH_2)_m-C(=O)O-R^8$.

22. The process of claim 21, wherein the dihydropyrimidine compound has Formula (I-2), or a tautomer thereof having Formula (Ia-2),

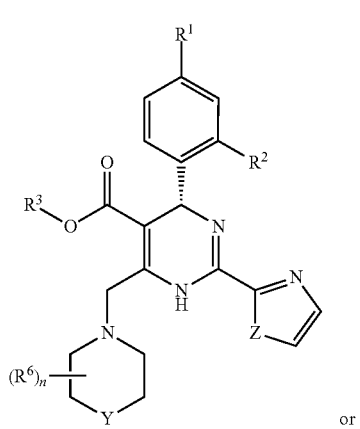

(I-2)

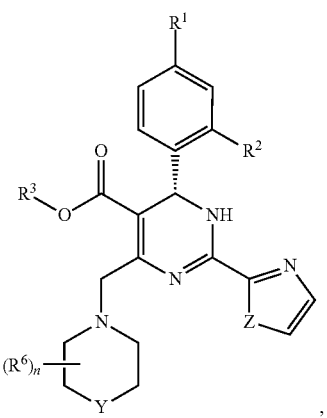

(Ia-2)

wherein $R^1$ is F or Cl; and $R^2$ is Cl or Br.

23. The process of claim 20, wherein
$R^3$ is methyl, ethyl, propyl, isopropyl, tert-butyl, or butyl;
Z is $-O-$, $-S-$, or $-N(CH_3)-$;
Y is $-O-$, $-S-$, $-S(=O)_2-$, or $-(CH_2)_q-$;
each $R^6$ is independently H, halo, $C_{1-4}$ alkyl, $C_{1-4}$ haloalkyl, amino, $C_{1-4}$ alkylamino, $C_{1-4}$ alkoxy, nitro, triazolyl, tetrazyl, $-(CR^7R^{7a})_m-OH$, $-S(=O)_qOR^{8a}$, $-(CR^7R^{7a})_m-S(=O)_qN(R^{8a})_2$, $-(CR^7R^{7a})_t-N(R^{8a})_2$, $-(CR^7R^{7a})_m-C(=O)O-R^8$, $-(CR^7R^{7a})_m-C(=O)O-(CR^7R^{7a})_m-OC(=O)O-R^8$, $-(CR^7R^{7a})_m-C(=O)O-(CR^7R^{7a})_m-OC(=O)-R^8$, $-(CR^7R^{7a})_m-C(=O)O-(CR^7R^{7a})_m-C(=O)O-R^8$, $-(CR^7R^{7a})_m-OC(=O)-R^8$, or $-(CR^7R^{7a})_m-C(=O)-N(R^8R^{8a})$;

each $R^{7a}$ and $R^7$ is independently H, methyl, ethyl, trifluoromethyl, or $-(CH_2)_m-C(=O)O-R^8$;

each $R^8$ and $R^{8a}$ is independently H, methyl, ethyl, propyl, isopropyl, aminomethyl, methoxy, $C_{1-4}$ alkyl-$S(=O)_2-$, phenyl, pyridyl, thiazolyl, furanyl, imidazolyl, isoxazolyl, oxazolyl, pyrrolyl, pyrimidinyl, pyridazinyl, diazolyl, triazolyl, tetrazolyl, thienyl, pyrazolyl, isothiazolyl, oxadiazolyl, thiadiazolyl, pyrazinyl, pyranyl, triazinyl, cyclopropyl, cyclobutyl, cyclopentyl, cyclohexyl, cyclopropyl-$S(=O)_2-$, cyclobutyl-$S(=O)_2-$, cyclopentyl-$S(=O)_2-$, cyclohexyl-$S(=O)_2-$, naphthyl-$S(=O)_2-$, phenyl-$S(=O)_2-$, $-(CH_2)_m-OH$, $-(CH_2)_m-C(=O)O-(CH_2)_m-H$, or $-(CH_2)_m-OC(=O)-(CH_2)_m-H$;

$R^{3b}$ is methoxy or ethoxy; and
$R^{3a}$ is H, methyl, ethyl, isopropyl, or propyl.

24. The process of claim 20, wherein the transesterification in step (2) is performed in the present of a base, wherein the base is formed by reacting lithium, sodium, or potassium or a combination thereof with a $C_{1-4}$ alcohol, wherein the $C_{1-4}$ alcohol is methanol, ethanol, propanol, i-propanol, n-butanol, i-butanol, or tert-butanol, and wherein the lithium, sodium, potassium or a combination thereof is applied in an amount of 2 equivalents to 8 equivalents per 1 equivalent by mole of the compound of Formula (Va).

25. The process of claim 20, wherein the fourth organic solvent is one or more $C_{1-4}$ alcohols, one or more $C_{1-4}$ haloalkanes, ethyl acetate, acetonitrile, isopropyl ether, petroleum ether, toluene, xylene, tetrahydrofuran, acetone, or a combination thereof, or the forth organic solvent is methanol, ethanol, propanol, i-propanol, n-butanol, tert-butanol, dichloromethane, chloroform, tetrachloromethane, ethyl acetate, acetonitrile, isopropyl ether, petroleum ether, tetrahydrofuran, acetone, or a combination thereof.

26. The process of claim 20, wherein the halogenating reaction in step (3) is carried out in the presence of a halogenating agent, and wherein the halogenating agent is N-bromosuccinimide, N-chlorosuccinimide, N-iodosuccinimide, 1,3-dibromo-5,5-dimethylhydantoin, 1,3-dichloro-5,5-dimethylhydantoin, or a combination thereof.

27. The process of claim 10, wherein each of the first organic solvent and the second organic solvent is independently a $C_{1-4}$ alcohol, a $C_{1-4}$ alcohol-water mixture, acetone, diethyl ether, isopropyl ether, petroleum ether, tetrahydrofuran, acetonitrile, cyclopentane, cyclohexane, n-hexane, a $C_{1-4}$ haloalkane solvent, ethyl acetate, trifluoroethanol, 2-methoxyethanol, 1,2-dimethoxyethane, 2-methoxyethyl ether, N,N-dimethyl formamide, N-methylpyrolidone, or a combination thereof, or wherein each of the first organic solvent and the second organic solvent is independently methanol, ethanol, n-propanol, i-propanol, n-butanol, tert-butanol, an ethanol-water mixture at a volume ratio of from 10:90 to 90:10, acetone, tetrahydrofuran, N-methylpyrolidone, trifluoroethanol, 2-methoxyethanol, 1,2-dimethoxyethane, 2-methoxyethyl ether, ethyl acetate, glycol, N,N-dimethyl formamide, or a combination thereof.

* * * * *